US011186591B2

United States Patent
Cmiljanovic et al.

(10) Patent No.: US 11,186,591 B2
(45) Date of Patent: Nov. 30, 2021

(54) DIFLUOROMETHYL-AMINOPYRIDINES AND DIFLUOROMETHYL-AMINOPYRIMIDINES

(71) Applicants: TORQUR AG, Basel (CH); UNIVERSITÄT BASEL, Basel (CH)

(72) Inventors: Vladimir Cmiljanovic, Basel (CH); Paul Hebeisen, Basel (CH); Florent Beaufils, Bartenheim (FR); Thomas Bohnacker, Basel (CH); Denise Rageot, Saint-Louis (FR); Alexander Sele, Basel (CH); Matthias Wymann, Bern (CH); Jean-Baptiste Langlois, Sierentz (FR)

(73) Assignees: UNIVERSITÄT BASEL, Basel (CH); TORQUR AG, Basel (CH)

( * ) Notice: Subject to any disclaimer, the term of this patent is extended or adjusted under 35 U.S.C. 154(b) by 0 days.

(21) Appl. No.: 16/818,512

(22) Filed: Mar. 13, 2020

(65) Prior Publication Data
US 2020/0277304 A1    Sep. 3, 2020

Related U.S. Application Data

(62) Division of application No. 15/525,779, filed as application No. PCT/EP2015/076192 on Nov. 10, 2015, now Pat. No. 10,640,516.

(30) Foreign Application Priority Data

Nov. 11, 2014 (EP) ..................... 14192617

(51) Int. Cl.

| | | |
|---|---|---|
| C07D 413/14 | (2006.01) | |
| C07D 498/08 | (2006.01) | |
| A61K 31/53 | (2006.01) | |
| C07D 401/14 | (2006.01) | |
| C07D 405/14 | (2006.01) | |
| C07D 401/04 | (2006.01) | |
| C07D 403/04 | (2006.01) | |
| C07D 239/48 | (2006.01) | |
| C07D 491/048 | (2006.01) | |
| C07D 491/056 | (2006.01) | |
| C07D 491/20 | (2006.01) | |
| C07D 519/00 | (2006.01) | |
| A61P 35/00 | (2006.01) | |
| C07D 417/14 | (2006.01) | |
| C07D 491/107 | (2006.01) | |
| C07D 491/18 | (2006.01) | |

(52) U.S. Cl.
CPC ............ *C07D 498/08* (2013.01); *A61K 31/53* (2013.01); *A61P 35/00* (2018.01); *C07D 239/48* (2013.01); *C07D 401/04* (2013.01); *C07D 401/14* (2013.01); *C07D 403/04* (2013.01); *C07D 405/14* (2013.01); *C07D 413/14* (2013.01); *C07D 417/14* (2013.01); *C07D 491/048* (2013.01); *C07D 491/056* (2013.01); *C07D 491/107* (2013.01); *C07D 491/18* (2013.01); *C07D 491/20* (2013.01); *C07D 519/00* (2013.01)

(58) Field of Classification Search
CPC .................................................. C07D 413/14
See application file for complete search history.

(56) References Cited

FOREIGN PATENT DOCUMENTS

| WO | 02/088112 A1 | 7/2002 |
|---|---|---|
| WO | 2006/095906 A1 | 9/2006 |
| WO | 2007/084786 A1 | 7/2007 |
| WO | 2008/098058 A1 | 8/2008 |
| WO | 2010/052569 A2 | 5/2010 |

OTHER PUBLICATIONS

Burger, et al., "Identification of NVP-BKM120 as a Potent, Selective, Orally Bioavailable Class I PI3 Kinase Inhibitor for Treating Cancer," *ACS Med Chem Lett* 2:774-779 (2011).
Kong, et al., "In vitro multifaceted activities of a specific group of novel phosphatidylinositol 3-kinase inhibitors on hotspot mutant PIK3CA," *Invest New Drugs* 32:1134-1143 (2014).
Rewcastle., et al., "Synthesis and Biological Evaluation of Novel Analogues of the Pan Class I Phosphatidylinositol 3-Kinase (PI3K) Inhibitor 2-(Difluoromethyl)-1-[4,6-di(4-morpholinyl)-1,3,5-triazin-2-yl]-1H-benzimidazole (ZSTK474)," *J Med Chem* 54:7105-7126 (2011).
International Search Report for PCT/EP2015/076192, dated Jan. 7, 2016.

*Primary Examiner* — Brian E McDowell
(74) *Attorney, Agent, or Firm* — Medler Ferro Woodhouse & Mills PLLC

(57) ABSTRACT

The invention relates to novel phosphoinositide 3-kinase (PI3K), mammalian target of rapamycin (mTOR) and PI3K-related kinase (PIKKs) inhibitor compounds of formula (I), wherein $X^1$, $X^2$ and $X^3$ are N or CH, with the proviso that at least two of $X^1$, $X^2$ and $X^3$ are N; Y is N or CH, These compounds are useful, either alone or in combination with further therapeutic agents, for treating disorders mediated by lipid kinases.

14 Claims, No Drawings

DIFLUOROMETHYL-AMINOPYRIDINES AND DIFLUOROMETHYL-AMINOPYRIMIDINES

FIELD OF THE INVENTION

The invention relates to new difluoromethyl-aminopyridyl- and difluoromethyl-aminopyrimidinyl-substituted triazines and pyrimidines as therapeutic agents and diagnostic probes useful for modulating cellular activities such as signal transduction, proliferation, differentiation, cell death, migration, and control, release and action of inflammatory mediators, chemokines and cytokines. The compounds of the invention modulate kinase activities, in particular those of phosphoinositide 3-kinase (PI3K), phosphoinositide 4-kinase (PI4K), mammalian target of rapamycin (mTOR), Vps34 and PI3K-related kinases (PIKKs).

BACKGROUND OF THE INVENTION

Protein kinases participate in the signaling events and control cellular activation, growth, differentiation, survival and migration in response to extracellular mediators or stimuli including growth factors, cytokines or chemokines. In general, these kinases are classified in two groups, those that preferentially phosphorylate tyrosine residues and those that preferentially phosphorylate serine and/or threonine residues. Tyrosine kinases include membrane-spanning growth factor receptors, for example the epidermal growth factor receptor (EGFR) and cytosolic non-receptor kinases including Src family kinases, the Syk family kinases and the Tec family kinases.

Increased protein kinase activities are involved in many diseases including cancer, metabolic diseases, immunological diseases and inflammatory disorders. These can be caused either directly or indirectly by the failure of control mechanisms due to mutation(s), overexpression or inappropriate control of enzyme activity.

Protein tyrosine kinases—both receptor tyrosine kinases and non-receptor kinases—are essential for the activation and proliferation of cells of the immune system. Among the earliest detectable events upon immunoreceptor activation in mast cells, T cells and B cells is the stimulation of non-receptor tyrosine kinases.

Phosphoinositide 3-kinases (PI3Ks) were early on identified as lipid kinases associated with viral oncogenes [Whitman et al., Nature 315:239-242 (1985)], and for the last 20 years, the connection between cancer and PI3K has been further substantiated [Wymann et al., Curr. Opin. Cell Biol. 17:141-149 (2005)]. PI3Ks have since been recognized to modulate a wide range of cellular activities, and to be central to the growth and metabolic control. Genetically modified mice targeting the PI3K pathway, and the elucidation of human hereditary disease like Cowden's syndrome, tuberous sclerosis, ataxia telangiectasia, X-linked myotubular myopathy and Charcot-Marie-Tooth neuropathy, have provided further insight into the cellular and systemic role of phosphoinositide signaling. Deregulation of phosphoinositide levels, and in particular the product of class I PI3Ks, PtdIns (3,4,5)P$_3$, is involved in the pathogenesis of cancer, chronic inflammation, allergy, metabolic disease, diabetes and cardiovascular problems.

PI3Ks are a family of enzymes, which phosphorylate the 3'-OH position of the inositol ring of phosphoinositides. They have been divided into three classes on the basis of structural features and in vitro lipid substrate specificity [Marone et al., Biochimica et Biophysica Acta 1784:159-185 (2008)]. Class I PI3Ks form heterodimers, which consist of one of the four closely related catalytic subunits of approx. 110 kDa, and an associated regulatory subunit belonging to two distinct families. In vitro they are capable to convert PtdIns to PtdIns-3-P, PtdIns-4-P to PtdIns(3,4)P$_2$, and PtdIns (4,5)P$_2$ to PtdIns(3,4,5)P$_3$, but the in vivo substrate is PtdIns (4,5)P$_2$ [Cantley et al., Science 296:1655-1657 (2002)]. Class I PI3Ks are activated by a large variety of cell-surface receptors, comprising growth factor receptors as well as G protein-coupled receptors.

Class II PI3Ks are capable to phosphorylate PtdIns and PtdIns-4-P in vitro, but their relevant in vivo substrates are still under investigation. This class of large (170-200 kDa) enzymes has three members, all characterized by a C-terminal C2 homology domain. No adaptor molecules for class II PI3Ks have been identified so far. Class III PI3Ks are solely able to phosphorylate PtdIns, and thus generate only PtdIns-3-P. The single member of this class is Vps34, of which the S. cerevisiae Vps34p (vacuolar protein sorting mutant 34 protein) is the prototype, and has been shown to play an essential role in trafficking of newly synthesized proteins from the Golgi to the yeast vacuole, an organelle equivalent to lysosomes in mammals [Schu et al., Science 260:88-91 (1993)].

Phosphoinositide 4-kinases (PI4Ks) phosphorylate the 4'-OH position of the inositol ring of PtdIns, and thereby generate PtdIns-4-P. This lipid can then be further phosphorylated by PtdIns-4-P 5-kinases to generate PtdIns (4,5)P$_2$, which is the main source for phospholipase C and PI3K signaling at the plasma membrane. Four PI4Ks isoforms are known: PI4KIIα and β and PI4KIIIα and β. The PI4KIIIs are most closely related to PI3Ks. The class of PI3K-related proteins, referred to as class IV PI3Ks, consists of high molecular weight enzymes with a catalytic core similar to PI3Ks and PI4Ks and include the mammalian target of rapamycin (mTOR, also known as FRAP), DNA-dependent protein kinase (DNA-PKcs), the ataxia telangiectasia mutated gene product (ATM), ataxia telangiectasia related (ATR), SMG-1 and transformation/transcription domain-associated protein (TRRAP). The first five members are active protein serine-threonine kinases that are involved in cell growth control and genome/transcriptome surveillance [Marone et al., Biochimica et Biophysica Acta 1784:159-185 (2008)]. DNA-PKcs, ATM, ATR and SMG-1 are involved in DNA damage responses. The only active kinase not involved in DNA damage is mTOR, which is regulated by growth factors and nutrient availability, and coordinates protein synthesis, cell growth and proliferation. Target of rapamycin (mTOR) complexes 1 and 2 integrate growth factor signaling (via PI3K/PKB and the Ras/MAPK cascade), energy status (LKB1 and AMPK) and nutrient detection. TOR is positively regulated by PKB/Akt, which phosphorylates the negative regulator TSC2 in the tuberous sclerosis complex (TSC), resulting in activation of the GTPase Rheb and mTOR. In parallel, mTOR stimulates translation of ribosomal proteins and therefore ribosome biogenesis via the activation [Wullschleger et al., Cell 124:471 (2006)]. Rapamycin and its derivatives, RAD001 and CCI-779, bind to FKBP12, and the complex blocks mTOR complex 1 (mTORC1) activity very selectively. Various clinical trials were initiated using rapamycin and derivatives, mostly in patients with tumors displaying elevated PI3K signaling and hyperactive mTOR.

The PI3K pathway is a key signaling transduction cascade controlling the regulation of cell growth, proliferation, survival as well as cell migration. PI3Ks are activated by a wide variety of different stimuli including growth factors, inflammatory mediators, hormones, neurotransmitters, and immunoglobulins and antigens [Wymann et al., *Trends Pharmacol. Sci.* 24:366-376 (2003)]. The class IA PI3K isoforms PI3Kα, β and δ are all bound to one of the p85/p55/p50 regulatory subunits, which all harbor two SH2 domains that bind with high affinity to phosphorylated Tyr-X-X-Met motifs. These motifs are present in activated growth factor receptors, their substrates and numerous adaptor proteins. As described above, activation of the PI3K/PKB signaling cascade has a positive effect on cell growth, survival and proliferation. Constitutive up-regulation of PI3K signaling can have a deleterious effect on cells leading to uncontrolled proliferation, enhanced migration and adhesion-independent growth. These events favor not only the formation of malignant tumors, but also the development of inflammatory and autoimmune disease.

The patent applications WO2010/052569, WO2007/084786 and WO2008/098058 describe certain analogous triazines and pyrimidines derivatives having PI3K and mTOR inhibiting properties, and their use as pharmaceuticals.

SUMMARY OF THE INVENTION

The invention relates in a first aspect to difluoromethyl-substituted heteroaromatic compounds of formula (I),

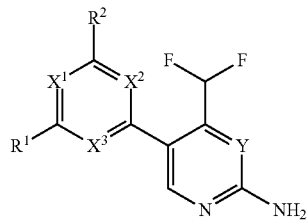

wherein $X^1$, $X^2$ and $X^3$ are, independently of each other, N or CH; with the proviso that at least two of $X^1$, $X^2$ and $X^3$ are N;

Y is N or CH;

$R^1$ and $R^2$ are independently of each other (i) a morpholinyl of formula (1)

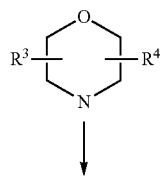

wherein the arrow denotes the bond in formula (I); and wherein $R^3$ and $R^4$ are independently of each other H, $C_1$-$C_3$alkyl optionally substituted with one or two OH, $C_1$-$C_2$fluoroalkyl, $C_1$-$C_2$alkoxy, $C_1$-$C_2$alkoxyC$_1$-$C_3$alkyl, CN, or C(O)O—$C_1$-$C_2$alkyl; or $R^3$ and $R^4$ form together a bivalent residue —$R^5R^6$— selected from $C_1$-$C_3$alkylene optionally substituted with 1 to 4 F, —CH$_2$—O—CH$_2$—, —CH$_2$—NH—CH$_2$—, or any of the structures

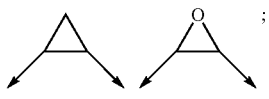

wherein the arrows denote the bonds in formula (II);

(ii) phenyl optionally substituted with 1 to 3 $R^7$, wherein $R^7$ is independently at each occurrence halogen, —OH, $C_1$-$C_3$alkyl optionally substituted with one or two OH, $C_1$-$C_2$fluoroalkyl, $C_1$-$C_2$alkoxy, $C_1$-$C_2$alkoxyC$_1$-$C_3$alkyl, $C_3$-$C_6$cycloalkyl, —NH$_2$, NHCH$_3$ or N(CH$_3$)$_2$;

(iii) a 5- to 6-membered heteroaryl ring W containing one to four heteroatoms independently selected from N, O and S, optionally substituted by 1 to 3 $R^8$, wherein $R^8$ is independently at each occurrence halogen, —OH, $C_1$-$C_3$alkyl optionally substituted with one or two OH, $C_1$-$C_2$fluoroalkyl, $C_1$-$C_2$alkoxy, $C_1$-$C_2$alkoxyC$_1$-$C_3$alkyl, $C_3$-$C_6$cycloalkyl, —NH$_2$, NHCH$_3$ or N(CH$_3$)$_2$;

(iv) a saturated 4- to 6-membered heterocyclic ring Z containing 1 to 3 heteroatoms independently selected from N, O and S, optionally substituted by 1 to 3 $R^9$; wherein $R^9$ is independently at each occurrence halogen, —OH, $C_1$-$C_3$alkyl optionally substituted with one or two OH, $C_1$-$C_2$fluoroalkyl, $C_1$-$C_2$alkoxy, $C_1$-$C_2$alkoxyC$_1$-$C_3$alkyl, $C_3$-$C_6$cycloalkyl, =O, —NH$_2$, NHCH$_3$ or N(CH$_3$)$_2$; or two $R^9$ substituents form together a bivalent residue —$R^{10}R^{11}$— selected from $C_1$-$C_3$alkylene optionally substituted with 1 to 4 F, —CH$_2$—O—CH$_2$— or —O—CH$_2$CH$_2$—O—;

(v) OR$^{12}$, wherein R$^{12}$ is $C_1$-$C_3$alkyl, $C_1$-$C_3$haloalkyl, $C_1$-$C_3$alkoxy, $C_3$-$C_6$cycloalkyl, $C_1$-$C_2$alkyleneC$_3$-$C_6$cycloalkyl; Cycle-P or $C_1$-$C_2$alkyleneCycle-P, wherein Cycle-P represents a saturated 4- to 6-membered heterocyclic ring containing 1 to 3 heteroatoms independently selected from N, O and S, optionally substituted by 1 to 3 R$^{13}$, wherein R$^{13}$ is independently at each occurrence halogen, —OH, $C_1$-$C_3$alkyl optionally substituted with one or two OH, $C_1$-$C_2$fluoroalkyl, $C_1$-$C_2$alkoxy, $C_1$-$C_2$alkoxyC$_1$-$C_3$alkyl, $C_3$-$C_6$cycloalkyl, —NH$_2$, NHCH$_3$ or N(CH$_3$); Cycle-Q or $C_1$-$C_2$alkyleneCycle-Q, wherein Cycle-Q represents 5- to 6-membered heteroaryl ring containing one to four heteroatoms independently selected from N, O and S, optionally substituted by 1 to 3 R$^{14}$, wherein R$^{14}$ is independently at each occurrence halogen, —OH, $C_1$-$C_3$alkyl optionally substituted with one or two OH, $C_1$-$C_2$fluoroalkyl, $C_1$-$C_2$alkoxy, $C_1$-$C_2$alkoxyC$_1$-$C_3$alkyl, $C_3$-$C_6$cycloalkyl, —NH$_2$, NHCH$_3$ or N(CH$_3$); or (vi) NR$^{15}$R$^{16}$; wherein R$^{15}$ and R$^{16}$ are independently of each other H, $C_1$-$C_3$alkyl optionally substituted with one or two OH, $C_1$-$C_2$fluoroalkyl, $C_1$-$C_2$alkoxy, $C_1$-$C_2$alkoxyC$_1$-$C_3$alkyl; Cycle-P or $C_1$-$C_2$alkyleneCycle-P, wherein Cycle-P represents a saturated 4- to 6-membered heterocyclic ring containing 1 to 3 heteroatoms independently selected from N, O and S, optionally substituted by 1 to 3 R$^{13}$, wherein R$^{13}$ is independently at each occurrence halogen, —OH, $C_1$-$C_3$alkyl optionally substituted with one or two OH, $C_1$-$C_2$fluoroalkyl, $C_1$-$C_2$alkoxy, $C_1$-$C_2$alkoxyC$_1$-$C_3$alkyl, $C_3$-$C_6$cycloalkyl, —NH$_2$, NHCH$_3$ or N(CH$_3$); Cycle-Q or $C_1$-$C_2$alkyleneCycle-Q, wherein Cycle-Q represents 5- to 6-membered heteroaryl ring containing one to four heteroatoms independently selected from N, O and S, optionally substituted by 1 to 3 $R^{14}$, wherein $R^{14}$ is independently at each occurrence halogen, —OH, $C_1$-$C_3$alkyl optionally substituted with one or two OH, $C_1$-$C_2$fluoroalkyl, $C_1$-$C_2$alkoxy, $C_1$-$C_2$alkoxyC$_1$-$C_3$alkyl, $C_3$-$C_6$cycloalkyl, —NH$_2$, NHCH$_3$ or N(CH$_3$);

with the proviso that at least one of $R^1$ and $R^2$ is a morpholinyl of formula II; and prodrugs, metabolites, tautomers, solvates and pharmaceutically acceptable salts thereof.

In further aspects, the invention relates to pharmaceutical compositions comprising a compound of formula (I) as defined hereinbefore, and to methods of preventing or treating a disease or disorder modulated by PI3Ks, mTOR and PIKKs, in particular treating a hyperproliferative disorder, comprising administering to a mammal in need of such treatment an effective amount of a compound of formula (I) as defined hereinbefore. An additional aspect of the invention is the use of a compound of formula (I) as defined hereinbefore for the treatment or prevention of a disease or condition modulated by PI3Ks, mTOR and PIKKs in a mammal, and the use of a compound of formula (I) as defined hereinbefore in the preparation of a medicament for the treatment or prevention of a disease or condition modulated by PI3Ks, mTOR and PIKKs, in a mammal.

In again further aspects, the invention relates to the use of an effective amount of compounds of formula (I) as defined hereinbefore in combination with standard treatment, such as chemotherapy, radiotherapy, targeted therapy or immunotherapy of a disease or disorder modulated by PI3Ks, mTOR and PIKKs, in particular hyperproliferative disorders.

Further the invention relates to the synthesis of compounds of formula (I) as defined hereinbefore including tautomers, solvates, intermediates, prodrugs and salts of said compounds.

Further aspects and embodiments of the present invention will be become apparent as this description continues.

DETAILED DESCRIPTION OF THE INVENTION

Reference will now be made in detail to the presented and further aspects and the presented and further embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the aspects of the present invention and, in particular the claims. One skilled in the art will recognize many methods and materials similar or equivalent to those described herein, which could be used in the practice of the present invention. The present invention is in no way limited to the methods and materials herein described.

Definitions

The terms "treat" and "treatment" refer to both therapeutic treatment and prophylactic or preventative measures, wherein the object is to prevent or slow down (lessen) an undesired pathological change or disorder, such as the development or spread of cancer. For purpose of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The phrase "effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TIP) and/or determining the response rate (RR).

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukaemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, bile duct cancer, mantle cell lymphoma, CNS lymphoma, chronic lymphocytic leukemia, non-Hodgkin's lymphoma, as well as head and neck cancer.

A "chemotherapeutic agent" is a chemical compound useful in the treatment of cancer. Examples of known chemotherapeutic agents include trastuzumab, pertuzumab, erlotinib (TARCEVA®, Genentech/Roche/OSI Pharm.), bortezomib (VELCADE®, Millennium Pharm.), fulvestrant (FASLODEX®, AstraZeneca), sunitib (SUTENT®, Pfizer/Sugen), letrozole (FEMARA®, Novartis), imatinib mesylate (GLEEVEC®, Novartis), finasunate (VATALANIB®, Novartis), oxaliplatin (ELOXATIN®, Sanofi), 5-FU (5-fluorouracil), leucovorin, rapamycin (Sirolimus, RAPAMUNE®, Wyeth), lapatinib (TYKERB®, GSK572016, Glaxo Smith Kline), lonafarnib (SCH 66336), sorafenib (NEXAVAR, Bayer Labs), and gefitinib (IRESSA®, AstraZeneca), AG1478, alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and melamines including altretamine, triethylenemelamine, triethylenephosphoramide, triethylenethiophosphoramide and trimethylomelamine; acetogenins; a camptothecin (including the synthetic analog topotecan); bryostatin; callystatin; CC-1065 (including its adozelesin, carzelesin and bizelesin synthetic analogs); cryptophycins; dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammal 1 and calicheamicin omegal 1; dynemicin, including dynemicin A; biphosphonates, such as clodronate; an esperamicin; as well as neocarzinostatin chromophore and related chromoprotein enediyne antibiotic chromophores, aclacinomysins, actinomycin, authramycin, azaserine, bleomycins, cactinomycin, carabicin, carminomycin, carzinophillin, chromomycinis, dactinomycin, daunorubicin, detorubicin, 6-diazol-5-oxo-L-norleucine, ADRIAMYCIN® (doxorubicin), morpholino-doxorubicin, cyanomorpholino-doxorubicin, 2-pyrrolino-doxorubicin and deoxydoxorubicin, epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex; razoxane; rhizoxin; sizofiran; spirogermanium; tenuazonic acid; triaziquone; trichothecenes; urethane; indesine; dacarbazine; mannomustine; mitobronitol; mitolactol; pipobroman; gacytosine; arabinoside; taxoids, e.g., TAXOL® (paclitaxel; Bristol-Myers Squibb), ABRAXANE™ (Cremophor-free), albumin-engineered nanoparticle formulations of paclitaxel, and TAXOTERE® (docetaxel, doxetaxel; Sanofi-Aventis); chlorambucil; GEMZAR® (gemcitabine); 6-thioguanine; mercaptopurine; methotrexate; platinum analogs such as cisplatin and carboplatin; vinblastine; etoposide; ifosfamide; mitoxantrone; vincristine; NAVELBINE® (vinorelbine); novantrone; teniposide; edatrexate; daunomycin; aminopterin; capecitabine (XELODA®); ibandronate; CP-11; topoisomerase inhibitor RFS 2000; difluoromethylornithine (DMFO); retinoids such as retinoic acid; and pharmaceutically acceptable salts; acids and derivatives of any of the above.

Also included in the definition of "chemotherapeutic agent" are: (i) anti-hormonal agents that act to regulate or inhibit hormone action on tumors such as anti-estrogens and selective receptor modulators (SERMs), including, for example, tamoxifen (including NOLVADEX®; tamoxifen citrate), raloxifene, droloxifene, and FARESTON® (toremifine citrate); (ii) aromatase inhibitors that inhibit the enzyme aromatase, which regulates estrogen production in the adrenal glands, such as, for example, 4(5)-imidazoles, MEGASE® (megestrol acetate); AROMASIN® (exemestane; Pfizer), formestanie, fadrazole, RIVISOR® (vorozole), FEMARA® (letrozole; Novartis), and ARIMIDEX® (anastrozole; AstraZeneca); (iii) anti-androgens such as flutamide, nilutamide; (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Raf I and H-Ras; (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rll-2; a topoisomerase 1 inhibitor such as LURTOTECANE®; ABARELIX® rmRH; (ix) anti-angiogenic agents such as bevacizumab (AVASTIN®, Genentech/Roche); and (x) pharmaceutically acceptable salts, acids and derivatives of any of the above.

The term "prodrug" as used in this application refers to a precursor or derivative form of a compound of the invention that may have improved properties such as better solubility, reduced cytotoxicity or increased bioavailability compared to the parent compound or drug and is capable of being activated or converted into the more active parent form. The prodrugs of this invention include, but are not limited to, derivatives of the amino group connected to the pyridine or pyrimidine nucleus in which one or two hydrogens are replaced by a suitable substituent, or derivatives of the ring amino function if $R^2$ is piperazin-1-yl. Examples of such prodrugs are compounds acylated by an amino acid selected from the 20 most often occurring natural L-alpha-amino acids, acylated by a dipeptide such as L-Ala-L-Ala, by carbonic acid, sulfuric acid or phosphoric acid, as well as pharmaceutically acceptable salts thereof.

A "metabolite" is a product produced through metabolism in the body of a specified compound or salt thereof. Metabolites of a compound may be identified using routine techniques known in the art and their activities determined using tests such as those described herein. Such products may result for example from the oxidation, reduction, hydrolysis, amidation, deamidation, esterification, deesterification, enzymatic cleavage, and the like, of the administered compound. In particular, compounds of formula (I) as defined hereinbefore, which are oxygenated or hydroxylated at any one position in the morpholine, piperazine or thiomorpholine ring $R^1$ and/or $R^2$ are considered metabolites. Further metabolites considered are thiomorpholine S-oxides and thiomorpholine S,S-dioxides. Accordingly, the invention is also directed to metabolites of compounds of the invention, including compounds produced by a process comprising contacting a compound of this invention with a mammal for a period of time sufficient to yield a metabolic product thereof.

A "liposome" is a small vesicle composed of various types of lipids, phospholipids and/or surfactants, which is useful for delivery of a drug (such as the PI3K and mTOR kinase inhibitors disclosed herein and, optionally, a chemotherapeutic agent) to a mammal. The components of the liposome are commonly arranged in a bilayer formation, similar to the lipid arrangement of biological membranes.

The term "chiral" refers to molecules, which have the property of non-superimposability of the mirror image partner, while the term "achiral" refers to molecules, which are superimposable on their mirror image partner.

The term "stereoisomers" refers to compounds, which have identical chemical constitution, but differ with regard to the arrangement of the atoms or groups in space.

"Diastereomer" refers to a stereoisomer with two or more centers of chirality in which the compounds are not mirror images of one another. Diastereomers have different physical properties, e.g. melting points, boiling points, spectral properties, and chemical and biological reactivities. Mixtures of diastereomers may be separated under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McRaw-Hiff Dictionary of Chemical Terms* (1984), McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric or a scalemic mixture. A 50:50 mixture of enantiomers is referred to as a racemic mixture or a racemate. The term "tautomer" or "tautomeric form" refers to structural isomers of different energies, which are interconvertible via a low energy barrier. For example, proton tautomers include interconversions via migration of a proton, such as keto-enol and imine-enamine isomerizations.

The phrase "pharmaceutically acceptable salt" as used herein, refers to pharmaceutically acceptable organic or inorganic salts of a compound of the invention, in particular acid addition salts. Exemplary salts include, but are not limited to, sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate (mesylate), ethane-sulfonate, benzenesulfonate, p-toluenesulfonate, and pamoate salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, trifluoroacetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

The phrase "pharmaceutically acceptable" indicates that the substance or composition must be compatible chemically and/or toxicologically, with the other ingredients comprising a formulation, and/or the mammal being treated therewith.

A "solvate" refers to an association or complex of one or more solvent molecules and a compound of the invention. Examples of solvents that form solvates include, but are not limited to, water, isopropanol, ethanol, methanol, dimethyl sulfoxide (DMSO), ethyl acetate, acetic acid, and ethanolamine. The term "hydrate" refers to the complex where the solvent molecule is water.

The term "protecting group" refers to a substituent that is commonly employed to block or protect a particular functionality during the reaction of other functional groups on the compound. For example, an "amino-protecting group" is a substituent attached to an amino group that blocks or protects the amino functionality in the compound. Suitable amino-protecting groups include acetyl, trifluoroacetyl, tert-butoxycarbonyl (BOC), benzyloxycarbonyl and 9-fluorenylmethylenoxycarbonyl (Fmoc). For a general description of protecting groups and their use, see T. W. Greene, Protective Groups in Organic Synthesis, John Wiley & Sons, New York, 1991.

The terms "compound of this invention" and "compounds of the present invention" and "compounds of formula (I)" include stereoisomers, geometric isomers, tautomers, solvates, pharmaceutically acceptable salts, and solvates of the salts thereof.

The term "mammal" includes, but is not limited to, humans, mice, rats, guinea pigs, monkeys, dogs, cats, horses, cows, pigs, and sheep. The term "mammal", as used herein, preferably refers to humans.

The present invention provides new difluoromethyl-aminopyridyl- and difluoromethyl-aminopyrimidinyl-substituted triazines and pyrimidines, and pharmaceutical formulations thereof, which are useful as therapeutic agents and novel diagnostic probes. Moreover, these compounds are potentially useful in the treatment of diseases, conditions and/or disorders modulated by protein kinases and lipid kinases.

More specifically, in a first aspect, the present invention provides a compound of formula (I),

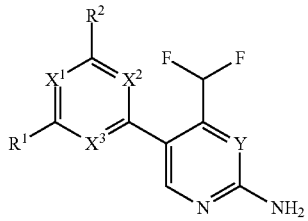

wherein
$X^1$, $X^2$ and $X^3$ are, independently of each other, N or CH; with the proviso that at least two of $X^1$, $X^2$ and $X^3$ are N;
Y is N or CH;
$R^1$ and $R^2$ are independently of each other
(i) a morpholinyl of formula (II)

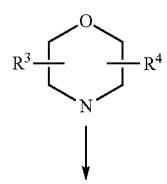

wherein the arrow denotes the bond in formula (I); and wherein $R^3$ and $R^4$ are independently of each other H, $C_1$-$C_3$alkyl optionally substituted with one or two OH, $C_1$-$C_2$fluoroalkyl, $C_1$-$C_2$alkoxy, $C_1$-$C_2$alkoxyC_1$-$C_3$alkyl, CN, or C(O)O—$C_1$-$C_2$alkyl; or $R^3$ and $R^4$ form together a bivalent residue —$R^5R^6$— selected from $C_1$-$C_3$alkylene optionally substituted with 1 to 4 F, —CH$_2$—O—CH$_2$—, —CH$_2$—NH—CH$_2$—, or any of the structures

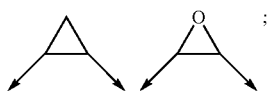

wherein the arrows denote the bonds in formula (II);
(ii) phenyl optionally substituted with 1 to 3 $R^7$, wherein $R^7$ is independently at each occurrence halogen, —OH, $C_1$-$C_3$alkyl optionally substituted with one or two OH, $C_1$-$C_2$fluoroalkyl, $C_1$-$C_2$alkoxy, $C_1$-$C_2$alkoxyC_1$-$C_3$alkyl, $C_3$-$C_6$cycloalkyl, —NH$_2$, NHCH$_3$ or N(CH$_3$)$_2$;
(iii) a 5- to 6-membered heteroaryl ring W containing one to four heteroatoms independently selected from N, O and S, optionally substituted by 1 to 3 $R^8$, wherein $R^8$ is independently at each occurrence halogen, —OH, $C_1$-$C_3$alkyl optionally substituted with one or two OH, $C_1$-$C_2$fluoroalkyl, $C_1$-$C_2$alkoxy, $C_1$-$C_2$alkoxyC_1$-$C_3$alkyl, $C_3$-$C_6$cycloalkyl, —NH$_2$, NHCH$_3$ or N(CH$_3$)$_2$;
(iv) a saturated 4- to 6-membered heterocyclic ring Z containing 1 to 3 heteroatoms independently selected from N, O and S, optionally substituted by 1 to 3 $R^9$; wherein $R^9$ is independently at each occurrence halogen, —OH, $C_1$-$C_3$alkyl optionally substituted with one or two OH, $C_1$-$C_2$fluoroalkyl, $C_1$-$C_2$alkoxy, $C_1$-$C_2$alkoxyC_1$-$C_3$alkyl, $C_3$-$C_6$cycloalkyl, =O, —NH$_2$, NHCH$_3$ or N(CH$_3$)$_2$; or two $R^9$ substituents form together a bivalent residue —$R^{10}R^{11}$— selected from $C_1$-$C_3$alkylene optionally substituted with 1 to 4 F, —CH$_2$—O—CH$_2$— or —O—CH$_2$CH$_2$—O—;
(v) OR$^{12}$, wherein R$^{12}$ is $C_1$-$C_3$alkyl, $C_1$-$C_3$haloalkyl, $C_1$-$C_3$alkoxy, $C_3$-$C_6$cycloalkyl, $C_1$-$C_2$alkyleneC_3$-$C_6$cycloalkyl; Cycle-P or $C_1$-$C_2$alkyleneCycle-P, wherein Cycle-P represents a saturated 4- to 6-membered heterocyclic ring containing 1 to 3 heteroatoms independently selected from N, O and S, optionally substituted by 1 to 3 $R^{13}$, wherein $R^{13}$ is independently at each occurrence halogen, —OH, $C_1$-$C_3$alkyl optionally substituted with one or two OH, $C_1$-$C_2$fluoroalkyl, $C_1$-$C_2$alkoxy, $C_1$-$C_2$alkoxyC_1$-$C_3$alkyl, $C_3$-$C_6$cycloalkyl, —NH$_2$, NHCH$_3$ or N(CH$_3$); Cycle-Q or $C_1$-$C_2$alkyleneCycle-Q, wherein Cycle-Q represents 5- to 6-membered heteroaryl ring containing one to four heteroatoms independently selected from N, O and S, optionally substituted by 1 to 3 $R^{14}$, wherein $R^{14}$ is independently at each occurrence halogen, —OH, $C_1$-$C_3$alkyl optionally substituted with one or two OH, $C_1$-$C_2$fluoroalkyl, $C_1$-$C_2$alkoxy, $C_1$-$C_2$alkoxyC_1$-$C_3$alkyl, $C_3$-$C_6$cycloalkyl, —NH$_2$, NHCH$_3$ or N(CH$_3$); or
(vi) NR$^{15}$R$^{16}$; wherein R$^{15}$ and R$^{16}$ are independently of each other H, $C_1$-$C_3$alkyl optionally substituted with one or two OH, $C_1$-$C_2$fluoroalkyl, $C_1$-$C_2$alkoxy, $C_1$-$C_2$alkoxyC_1$-$C_3$alkyl; Cycle-P or $C_1$-$C_2$alkyleneCycle-P, wherein Cycle-P represents a saturated 4- to 6-membered heterocyclic ring containing 1 to 3 heteroatoms independently selected from N, O and S, optionally substituted by 1 to 3 $R^{13}$, wherein $R^{13}$ is independently at each occurrence halogen, —OH, $C_1$-$C_3$alkyl optionally substituted with one or two OH, $C_1$-$C_2$fluoroalkyl, $C_1$-$C_2$alkoxy, $C_1$-$C_2$alkoxyC_1$-$C_3$alkyl, $C_3$-$C_6$cycloalkyl, —NH$_2$, NHCH$_3$ or N(CH$_3$); Cycle-Q or $C_1$-$C_2$alkyleneCycle-Q, wherein Cycle-Q represents 5- to 6-membered heteroaryl ring containing one to four heteroatoms independently selected from N, O and S, optionally substituted by 1 to 3 $R^{14}$, wherein $R^{14}$ is independently at each occurrence halogen, —OH, $C_1$-$C_3$alkyl optionally substituted with one or two OH, $C_1$-$C_2$fluoroalkyl, $C_1$-$C_2$alkoxy, $C_1$-$C_2$alkoxyC_1$-$C_3$alkyl, $C_3$-$C_6$cycloalkyl, —NH$_2$, NHCH$_3$ or N(CH$_3$);
with the proviso that at least one of $R^1$ and $R^2$ is a morpholinyl of formula II; and prodrugs, metabolites, tautomers, solvates and pharmaceutically acceptable salts thereof.

In another aspect, the present invention provides for a compound of formula (I),

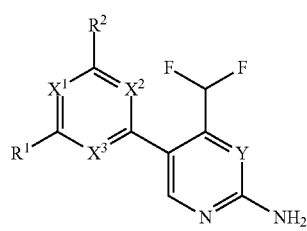

wherein
X¹, X² and X³ are, independently of each other, N or CH; with the proviso that at least two of X¹, X² and X³ are N;
Y is N or CH;
R¹ and R² are independently of each other
(i) a morpholinyl of formula (II)

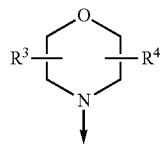

wherein the arrow denotes the bond in formula (I); and wherein R³ and R⁴ are independently of each other H, $C_1$-$C_3$alkyl optionally substituted with one or two OH, $C_1$-$C_2$fluoroalkyl, $C_1$-$C_2$alkoxy, $C_1$-$C_2$alkoxyC$_1$-$C_3$alkyl, CN, or C(O)O—$C_1$-$C_2$alkyl; or R³ and R⁴ form together a bivalent residue —R⁵R⁶— selected from $C_1$-$C_3$alkylene optionally substituted with 1 to 4 F, —CH$_2$—O—CH$_2$—, —CH$_2$—NH—CH$_2$—, or any of the structures

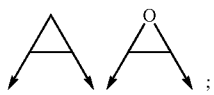

wherein the arrows denote the bonds in formula (II);
(ii) phenyl optionally substituted with 1 to 3 R⁷, wherein R⁷ is independently at each occurrence halogen, —OH, $C_1$-$C_3$alkyl optionally substituted with one or two OH, $C_1$-$C_2$fluoroalkyl, $C_1$-$C_2$alkoxy, $C_1$-$C_2$alkoxyC$_1$-$C_3$alkyl, $C_3$-$C_6$cycloalkyl, —NH$_2$, NHCH$_3$ or N(CH$_3$)$_2$;
(iii) a 5- to 6-membered heteroaryl ring W containing one to four heteroatoms independently selected from N, O and S, optionally substituted by 1 to 3 R⁸, wherein R⁸ is independently at each occurrence halogen, —OH, $C_1$-$C_3$alkyl optionally substituted with one or two OH, $C_1$-$C_2$fluoroalkyl, $C_1$-$C_2$alkoxy, $C_1$-$C_2$alkoxyC$_1$-$C_3$alkyl, $C_3$-$C_6$cycloalkyl, —NH$_2$, NHCH$_3$ or N(CH$_3$)$_2$;
(iv) a saturated 4- to 6-membered heterocyclic ring Z containing 1 to 3 heteroatoms independently selected from N, O and S, optionally substituted by 1 to 3 R⁹; wherein R⁹ is independently at each occurrence halogen, —OH, $C_1$-$C_3$alkyl optionally substituted with one or two OH, $C_1$-$C_2$fluoroalkyl, $C_1$-$C_2$alkoxy, $C_1$-$C_2$alkoxyC$_1$-$C_3$alkyl, $C_3$-$C_6$cycloalkyl, =O, —NH$_2$, NHCH$_3$ or N(CH$_3$)$_2$; or two R⁹ substituents form together a bivalent residue —R¹⁰R¹¹— selected from $C_1$-$C_3$alkylene optionally substituted with 1 to 4 F, —CH$_2$—O—CH$_2$— or —O—CH$_2$CH$_2$—O—;
(v) OR¹², wherein R¹² is $C_1$-$C_3$alkyl, $C_1$-$C_3$haloalkyl, $C_1$-$C_3$alkoxy, $C_3$-$C_6$cycloalkyl, $C_1$-$C_2$alkyleneC$_3$-$C_6$cycloalkyl; Cycle-P or $C_1$-$C_2$alkyleneCycle-P, wherein Cycle-P represents a saturated 4- to 6-membered heterocyclic ring containing 1 to 3 heteroatoms independently selected from N, O and S, optionally substituted by 1 to 3 R¹³, wherein R¹³ is independently at each occurrence halogen, —OH, $C_1$-$C_3$alkyl optionally substituted with one or two OH, $C_1$-$C_2$fluoroalkyl, $C_1$-$C_2$alkoxy, $C_1$-$C_2$alkoxyC$_1$-$C_3$alkyl, $C_3$-$C_6$cycloalkyl, —NH$_2$, NHCH$_3$ or N(CH$_3$); Cycle-Q or $C_1$-$C_2$alkyleneCycle-Q, wherein Cycle-Q represents 5- to 6-membered heteroaryl ring containing one to four heteroatoms independently selected from N, O and S, optionally substituted by 1 to 3 R¹⁴, wherein R¹⁴ is independently at each occurrence halogen, —OH, $C_1$-$C_3$alkyl optionally substituted with one or two OH, $C_1$-$C_2$fluoroalkyl, $C_1$-$C_2$alkoxy, $C_1$-$C_2$alkoxyC$_1$-$C_3$alkyl, $C_3$-$C_6$cycloalkyl, —NH$_2$, NHCH$_3$ or N(CH$_3$); or
(vi) NR¹⁵R¹⁶; wherein R¹⁵ and R¹⁶ are independently of each other H, $C_1$-$C_3$alkyl optionally substituted with one or two OH, $C_1$-$C_2$fluoroalkyl, $C_1$-$C_2$alkoxy, $C_1$-$C_2$alkoxyC$_1$-$C_3$alkyl; Cycle-P or $C_1$-$C_2$alkyleneCycle-P, wherein Cycle-P represents a saturated 4- to 6-membered heterocyclic ring containing 1 to 3 heteroatoms independently selected from N, O and S, optionally substituted by 1 to 3 R¹³, wherein R¹³ is independently at each occurrence halogen, —OH, $C_1$-$C_3$alkyl optionally substituted with one or two OH, $C_1$-$C_2$fluoroalkyl, $C_1$-$C_2$alkoxy, $C_1$-$C_2$alkoxyC$_1$-$C_3$alkyl, $C_3$-$C_6$cycloalkyl, —NH$_2$, NHCH$_3$ or N(CH$_3$); Cycle-Q or $C_1$-$C_2$alkyleneCycle-Q, wherein Cycle-Q represents 5- to 6-membered heteroaryl ring containing one to four heteroatoms independently selected from N, O and S, optionally substituted by 1 to 3 R¹⁴, wherein R¹⁴ is independently at each occurrence halogen, —OH, $C_1$-$C_3$alkyl optionally substituted with one or two OH, $C_1$-$C_2$fluoroalkyl, $C_1$-$C_2$alkoxy, $C_1$-$C_2$alkoxyC$_1$-$C_3$alkyl, $C_3$-$C_6$cycloalkyl, —NH$_2$, NHCH$_3$ or N(CH$_3$);
with the proviso that at least one of R¹ and R² is a morpholinyl of formula II; and prodrugs, metabolites, tautomers, solvates and pharmaceutically acceptable salts thereof, and further
with the provisos that
(a) when R¹ is 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl; then R² is not 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl;
(b) when R² is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl; then R¹ is not 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl.

In another aspect, the present invention provides for a compound of formula (I),

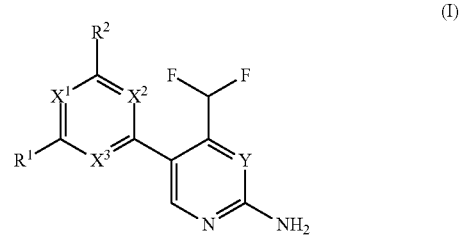

wherein

X$^1$, X$^2$ and X$^3$ are, independently of each other, N or CH; with the proviso that at least two of X$^1$, X$^2$ and X$^3$ are N;

Y is N or CH;

R$^1$ and R$^2$ are independently of each other (vii) a morpholinyl of formula (II)

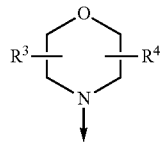

(II)

wherein the arrow denotes the bond in formula (I); and wherein R$^3$ and R$^4$ are independently of each other H, C$_1$-C$_3$alkyl optionally substituted with one or two OH, C$_1$-C$_2$fluoroalkyl, C$_1$-C$_2$alkoxy, C$_1$-C$_2$alkoxyC$_1$-C$_3$alkyl, CN, or C(O)O—C$_1$-C$_2$alkyl; or R$^3$ and R$^4$ form together a bivalent residue —R$^5$R$^6$— selected from C$_1$-C$_3$alkylene optionally substituted with 1 to 4 F, —CH$_2$—O—CH$_2$—, —CH$_2$—NH—CH$_2$—, or any of the structures

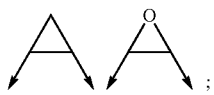

wherein the arrows denote the bonds in formula (II);

(viii) phenyl optionally substituted with 1 to 3 R$^7$, wherein R$^7$ is independently at each occurrence halogen, —OH, C$_1$-C$_3$alkyl optionally substituted with one or two OH, C$_1$-C$_2$fluoroalkyl, C$_1$-C$_2$alkoxy, C$_1$-C$_2$alkoxyC$_1$-C$_3$alkyl, C$_3$-C$_6$cycloalkyl, —NH$_2$, NHCH$_3$ or N(CH$_3$)$_2$;

(ix) a 5- to 6-membered heteroaryl ring W containing one to four heteroatoms independently selected from N, O and S, optionally substituted by 1 to 3 R$^8$, wherein R$^8$ is independently at each occurrence halogen, —OH, C$_1$-C$_3$alkyl optionally substituted with one or two OH, C$_1$-C$_2$fluoroalkyl, C$_1$-C$_2$alkoxy, C$_1$-C$_2$alkoxyC$_1$-C$_3$alkyl, C$_3$-C$_6$cycloalkyl, —NH$_2$, NHCH$_3$ or N(CH$_3$)$_2$;

(x) a saturated 4- to 6-membered heterocyclic ring Z containing 1 to 3 heteroatoms independently selected from N, O and S, optionally substituted by 1 to 3 R$^9$; wherein R$^9$ is independently at each occurrence halogen, —OH, C$_1$-C$_3$alkyl optionally substituted with one or two OH, C$_1$-C$_2$fluoroalkyl, C$_1$-C$_2$alkoxy, C$_1$-C$_2$alkoxyC$_1$-C$_3$alkyl, C$_3$-C$_6$cycloalkyl, =O, —NH$_2$, NHCH$_3$ or N(CH$_3$)$_2$; or two R$^9$ substituents form together a bivalent residue —R$^{10}$R$^{11}$— selected from C$_1$-C$_3$alkylene optionally substituted with 1 to 4 F, —CH$_2$—O—CH$_2$— or —O—CH$_2$CH$_2$—O—;

(xi) OR$^{12}$, wherein R$^{12}$ is C$_1$-C$_3$alkyl, C$_1$-C$_3$haloalkyl, C$_1$-C$_3$alkoxy, C$_3$-C$_6$cycloalkyl, C$_1$-C$_2$alkyleneC$_3$-C$_6$cycloalkyl; Cycle-P or C$_1$-C$_2$alkyleneCycle-P, wherein Cycle-P represents a saturated 4- to 6-membered heterocyclic ring containing 1 to 3 heteroatoms independently selected from N, O and S, optionally substituted by 1 to 3 R$^{13}$, wherein R$^{13}$ is independently at each occurrence halogen, —OH, C$_1$-C$_3$alkyl optionally substituted with one or two OH, C$_1$-C$_2$fluoroalkyl, C$_1$-C$_2$alkoxy, C$_1$-C$_2$alkoxyC$_1$-C$_3$alkyl, C$_3$-C$_6$cycloalkyl, —NH$_2$, NHCH$_3$ or N(CH$_3$); Cycle-Q or C$_1$-C$_2$alkyleneCycle-Q, wherein Cycle-Q represents 5- to 6-membered heteroaryl ring containing one to four heteroatoms independently selected from N, O and S, optionally substituted by 1 to 3 R$^{14}$, wherein R$^{14}$ is independently at each occurrence halogen, —OH, C$_1$-C$_3$alkyl optionally substituted with one or two OH, C$_1$-C$_2$fluoroalkyl, C$_1$-C$_2$alkoxy, C$_1$-C$_2$alkoxyC$_1$-C$_3$alkyl, C$_3$-C$_6$cycloalkyl, —NH$_2$, NHCH$_3$ or N(CH$_3$); or (xii) NR$^{15}$R$^{16}$; wherein R$^{15}$ and R$^{16}$ are independently of each other H, C$_1$-C$_3$alkyl optionally substituted with one or two OH, C$_1$-C$_2$fluoroalkyl, C$_1$-C$_2$alkoxy, C$_1$-C$_2$alkoxyC$_1$-C$_3$alkyl; Cycle-P or C$_1$-C$_2$alkyleneCycle-P, wherein Cycle-P represents a saturated 4- to 6-membered heterocyclic ring containing 1 to 3 heteroatoms independently selected from N, O and S, optionally substituted by 1 to 3 R$^{13}$, wherein R$^{13}$ is independently at each occurrence halogen, —OH, C$_1$-C$_3$alkyl optionally substituted with one or two OH, C$_1$-C$_2$fluoroalkyl, C$_1$-C$_2$alkoxy, C$_1$-C$_2$alkoxyC$_1$-C$_3$alkyl, C$_3$-C$_6$cycloalkyl, —NH$_2$, NHCH$_3$ or N(CH$_3$); Cycle-Q or C$_1$-C$_2$alkyleneCycle-Q, wherein Cycle-Q represents 5- to 6-membered heteroaryl ring containing one to four heteroatoms independently selected from N, O and S, optionally substituted by 1 to 3 R$^{14}$, wherein R$^{14}$ is independently at each occurrence halogen, —OH, C$_1$-C$_3$alkyl optionally substituted with one or two OH, C$_1$-C$_2$fluoroalkyl, C$_1$-C$_2$alkoxy, C$_1$-C$_2$alkoxyC$_1$-C$_3$alkyl, C$_3$-C$_6$cycloalkyl, —NH$_2$, NHCH$_3$ or N(CH$_3$);

with the proviso that at least one of R$^1$ and R$^2$ is a morpholinyl of formula II; and prodrugs, metabolites, tautomers, solvates and pharmaceutically acceptable salts thereof, and further with the proviso that R$^1$ is not 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl; and R$^2$ is not 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl.

In another aspect, the invention provides for a compound of formula (I),

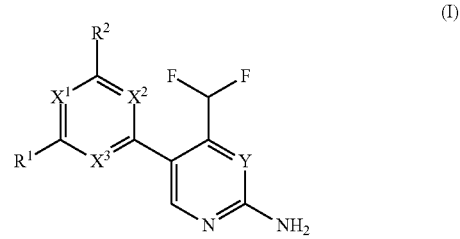

(I)

wherein

X$^1$, X$^2$ and X$^3$ are, independently of each other, N or CH; with the proviso that at least two of X$^1$, X$^2$ and X$^3$ are N; Y is N or CH;

R$^1$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl; and $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, piperazin-1-yl, 4-methylpiperazin-1-yl, or 4-thiomorpholinyl.

In again another aspect, the present invention provides for a compound of formula (I) as defined herein for use in a method of preventing or treating a disease or disorder modulated by any one of PI3Ks, mTOR and PIKKs either individually or in any combination, wherein said method comprises administering to a mammal in need of such prevention or treatment an effective amount of said a compound of formula (I). Preferably, said disease or disorder is a hyperproliferative disorder.

In again a further aspect, the present invention provides for a use of a compound of formula (I) as defined herein in the preparation of a medicament for the treatment or prevention of a disease or condition modulated by any one of PI3Ks, mTOR and PIKKs either individually or in any combination, in a mammal, preferably in a human. Preferably, said disease or disorder is a hyperproliferative disorder.

In again a further aspect, the present invention provides for a use of a compound of formula (I) as defined herein in the manufacture of a medicament for the treatment or prevention of a disease or condition modulated any one of PI3Ks, mTOR and PIKKs either individually or in any combination, in a mammal, preferably in a human. Preferably, said disease or disorder is a hyperproliferative disorder.

In again another aspect, the present invention provides for a method of preventing or treating a disease or disorder modulated any one of PI3Ks, mTOR and PIKKs either individually or in any combination, wherein said method comprises administering to a mammal in need of such prevention or treatment an effective amount of a compound of formula (I) as defined herein.

Each alkyl moiety either alone or as part of a larger group such as alkoxy is a straight or branched chain and is preferably $C_1$-$C_3$alkyl, more preferably $C_1$-$C_2$alkyl. Examples include in particular methyl, ethyl, n-propyl and prop-2-yl (iso-propyl). Examples of an alkoxy include in particular methoxy, ethoxy, n-propoxy and iso-propoxy. As described herein, alkoxy may include further substitutents such as halogen atoms leading to haloalkoxy moieties.

The term "alkoxyalkyl" refers to a R—O—R' moiety in which the R and R' groups are alkyl groups as defined herein. Examples include methoxymethyl, methoxyethyl, ethoxyethyl and methoxypropyl.

Each alkylene moiety is a straight or branched chain and is, particularly for example, —$CH_2$—, —$CH_2$—$CH_2$—, —$CH(CH_3)$—, —$CH_2$—$CH_2$—$CH_2$—, —$CH(CH_3)$—$CH_2$—, or —$CH(CH_2CH_3)$—, preferably —$CH_2$—, —$CH_2$—$CH_2$— or —$CH(CH_3)$—.

Each haloalkyl moiety either alone or as part of a larger group such as haloalkoxy is an alkyl group substituted by one or more of the same or different halogen atoms. Haloalkyl moieties include for example 1 to 5 halo substituents, or 1 to 3 halo substituents.

Examples include in particular fluoromethyl, difluoromethyl, trifluoromethyl, chlorodifluoromethyl and 2,2,2-trifluoro-ethyl.

Each haloalkenyl moiety either alone or as part of a larger group such as haloalkenyloxy is an alkenyl group substituted by one or more of the same or different halogen atoms. Examples include, 2-difluoro-vinyl and 1,2-dichloro-2-fluoro-vinyl. Haloalkenyl moieties include for example 1 to 5 halo substituents, or 1 to 3 halo substituents.

Each cycloalkyl moiety can be in mono- or bi-cyclic form, typically and preferably in monocyclic form, and preferably contains 3 to 6 carbon atoms. Preferred examples of monocyclic cycloalkyl groups include in particular cyclopropyl, cyclobutyl, cyclopentyl and cyclohexyl.

Halogen is fluorine, chlorine, bromine, or iodine, preferably fluorine.

The term "heteroaryl" refers to an aromatic ring system containing at least one heteroatom, and preferably up to four heteroatoms selected from nitrogen, oxygen and sulfur as ring members. Heteroaryl rings do not contain adjacent oxygen atoms, adjacent sulfur atoms, or adjacent oxygen and sulfur atoms within the ring. Preferred examples include in particular pyridinyl, pyrimidinyl, pyrazinyl, pyridazinyl, pyrrolyl, pyrazolyl, imidazolyl, triazolyl, tetrazolyl, isoxazolyl, oxazolyl, isothiazolyl, thiazolyl, furanyl, and thiophenyl The term "heterocyclic ring" refers to a saturated or partially unsaturated carbocyclic ring containing one to three heteroatoms selected from nitrogen, oxygen and sulfur as ring members. Such rings do not contain adjacent oxygen atoms, adjacent sulfur atoms, or adjacent oxygen and sulfur atoms within the ring. Preferred examples include in particular tetrahydrofuranyl, pyrrolidinyl, pyrazolidinyl, imidazolidinyl, piperidinyl, piperazinyl, dioxanyl, morpholinyl, oxazolidinyl and isooxazolidinyl.

Where a group is said to be optionally substituted, preferably there are optionally 1-3 substituents, more preferably optionally 1-2 substituents.

Certain compounds of formula (I) may contain one or two or more centers of chirality and such compounds may be provided as pure enantiomers or pure diastereoisomers as well as mixtures thereof in any ratio. The compounds of the invention also include all tautomeric forms of the compounds of formula (I).

In a preferred embodiment, the present invention provides for the compound of formula (I) as defined herein and tautomers, solvates and pharmaceutically acceptable salts thereof.

In another preferred embodiment, the present invention provides for the compound of formula (I), wherein $X^1$, $X^2$ and $X^3$ are N.

In another preferred embodiment, (i) said $X^1$ and said $X^2$ are N, and said $X^3$ is CH; (ii) said $X^1$ and said $X^3$ are N, and said $X^2$ is CH; or (iii) said $X^2$ and said $X^3$ are N, and said $X^1$ is CH, and preferably tautomers, solvates and pharmaceutically acceptable salts thereof. In another embodiment, (i) said $X^1$ and said $X^2$ are N, and said $X^3$ is CH; or (ii) said $X^2$ and said $X^3$ are N, and said $X^1$ is CH, and preferably tautomers, solvates and pharmaceutically acceptable salts thereof. In another preferred embodiment, said $X^1$ and said $X^3$ are N, and said $X^2$ is CH; and preferably tautomers, solvates and pharmaceutically acceptable salts thereof.

In another preferred embodiment, said Y is N, and preferably tautomers, solvates and pharmaceutically acceptable salts thereof. In another preferred embodiment, said Y is CH, and preferably tautomers, solvates and pharmaceutically acceptable salts thereof.

In another preferred embodiment, said $R^1$ and said $R^2$ are independently of each other (i) a morpholinyl of formula (II); (ii) said 5- to 6-membered heteroaryl ring W; (iii) said saturated 4- to 6-membered heterocyclic ring Z; (iv) said $OR^{12}$; or (v) said $NR^{15}R^{16}$.

In another preferred embodiment, said $R^1$ and said $R^2$ are independently of each other selected from
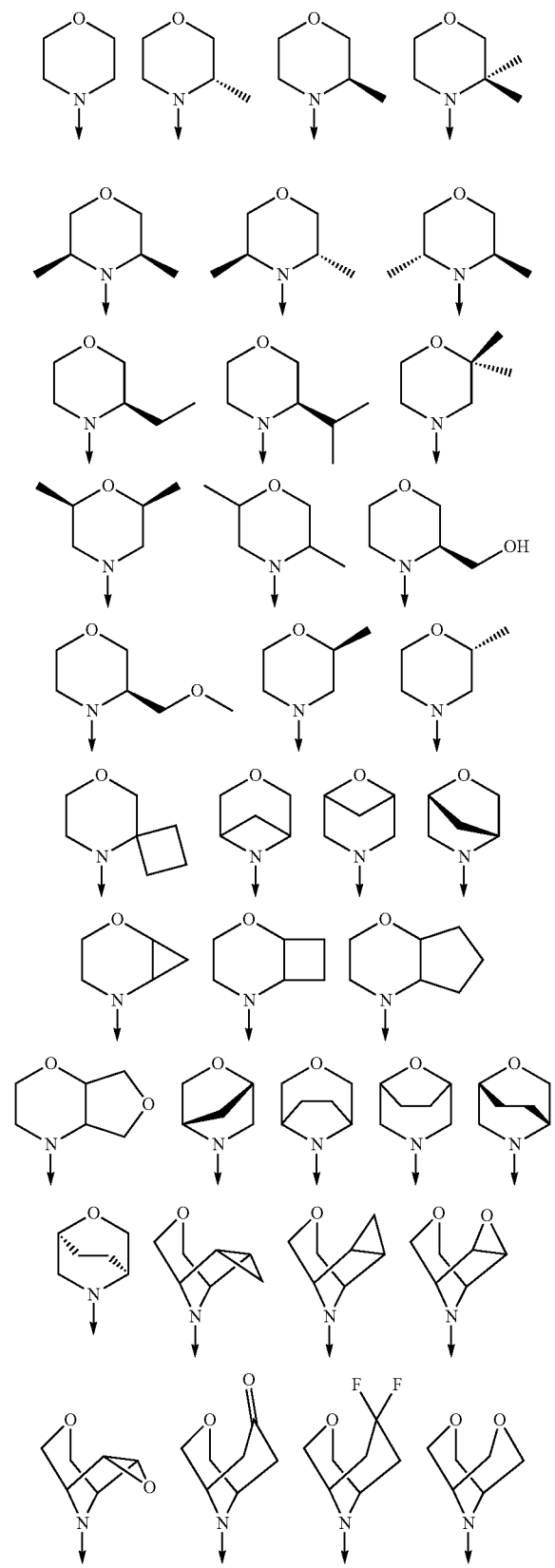
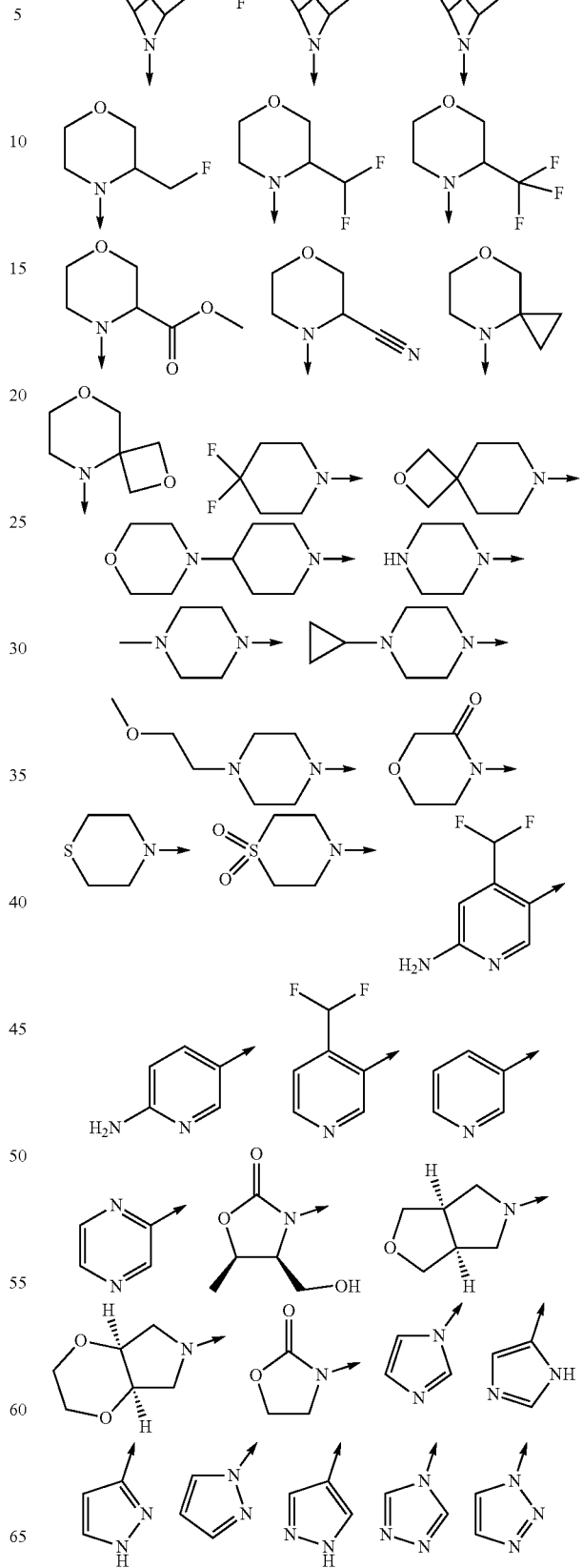

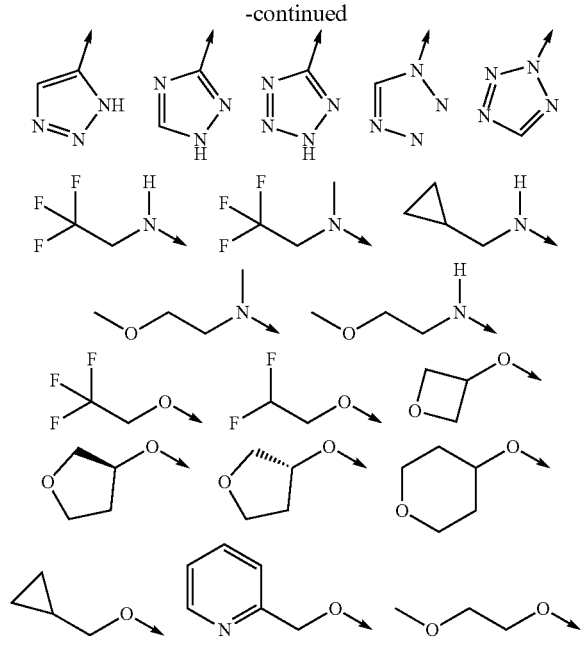
In another preferred embodiment, said $R^1$ and said $R^2$ are independently of each other selected from
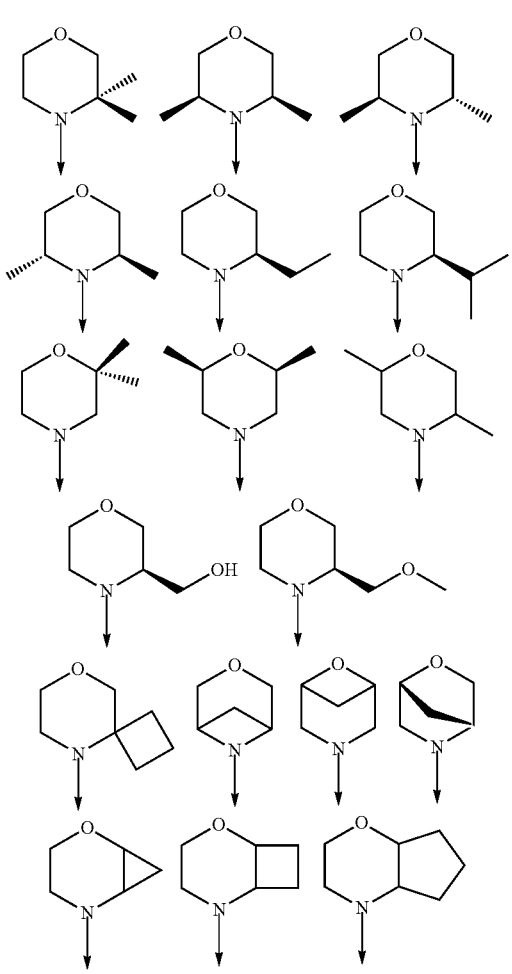
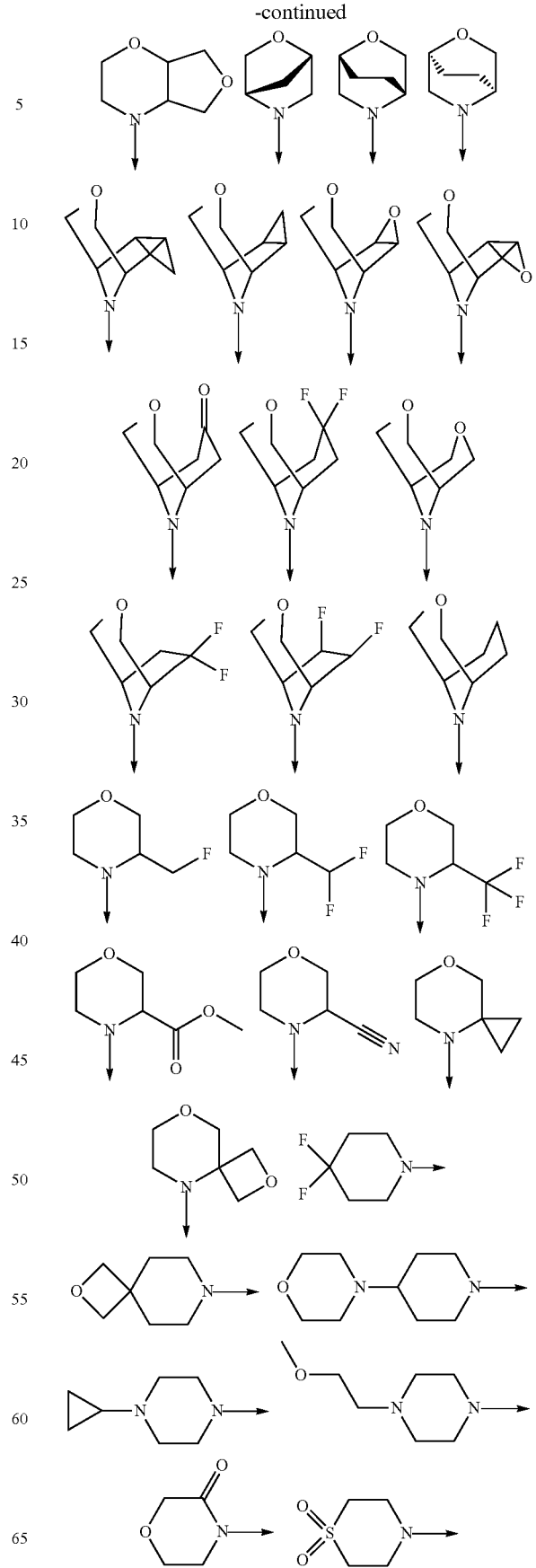

-continued

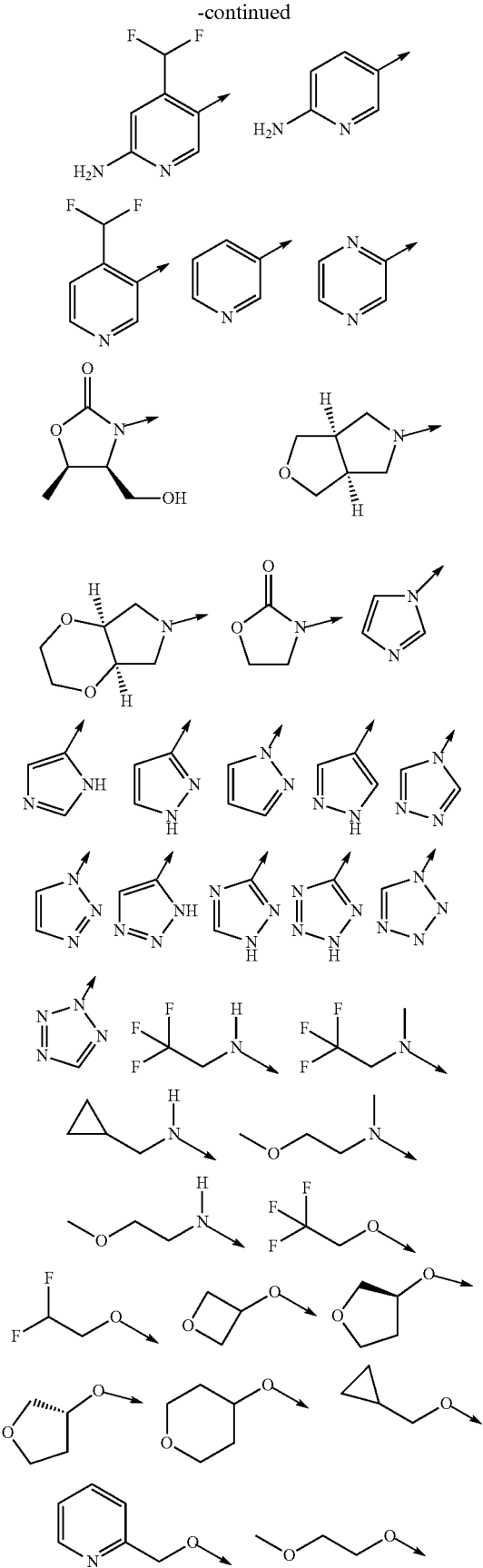

In another preferred embodiment, $R^1$ and $R^2$ are independently of each other selected from

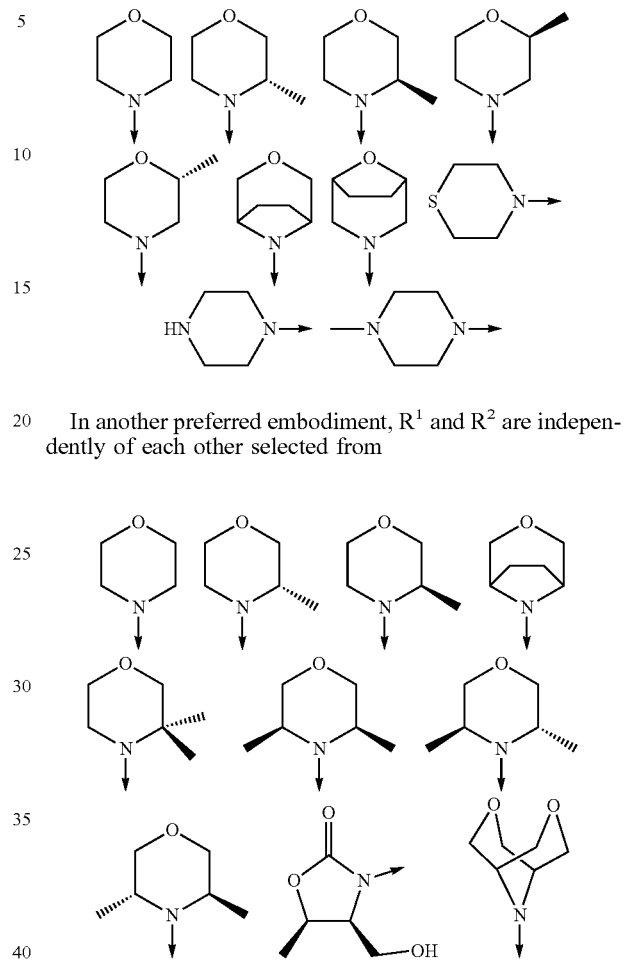

In another preferred embodiment, $R^1$ and $R^2$ are independently of each other selected from In another preferred embodiment, said compound of formula (I) is selected from
4-(difluoromethyl)-5-(4,6-dimorpholino-1,3,5-triazin-2-yl) pyridin-2-amine;
4-(difluoromethyl)-5-(4,6-dimorpholino-1,3,5-triazin-2-yl) pyrimidin-2-amine;
5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine;
5-(4-(3-oxa-8-azabicyclo[3.2.1]octan-8-yl)-6-morpholino-1,3,5-triazin-2-yl)-4-(difluoromethyl)pyridin-2-amine;
5-(4-(3-oxa-8-azabicyclo[3.2.1]octan-8-yl)-6-morpholino-1,3,5-triazin-2-yl)-4-(difluoromethyl)pyrimidin-2-amine;
5-(4,6-bis((S)-3-methylmorpholino)-1,3,5-triazin-2-yl)-4-(difluoromethyl)pyridin-2-amine;
5-(4,6-bis((S)-3-methylmorpholino)-1,3,5-triazin-2-yl)-4-(difluoromethyl)pyrimidin-2-amine;
(S)-4-(difluoromethyl)-5-(4-(3-methylmorpholino)-6-morpholino-1,3,5-triazin-2-yl)pyridin-2-amine;
(S)-4-(difluoromethyl)-5-(4-(3-methylmorpholino)-6-morpholino-1,3,5-triazin-2-yl)pyrimidin-2-amine;
5-(4-(3-oxa-8-azabicyclo[3.2.1]octan-8-yl)-6-((S)-3-methylmorpholino)-1,3,5-triazin-2-yl)-4-(difluoromethyl) pyridin-2-amine;
5-(4-(3-oxa-8-azabicyclo[3.2.1]octan-8-yl)-6-((S)-3-methylmorpholino)-1,3,5-triazin-2-yl)-4-(difluoromethyl)pyrimidin-2-amine;

4-(difluoromethyl)-5-(4-morpholino-6-(piperazin-1-yl)-1,3,5-triazin-2-yl)pyridin-2-amine;

4-(difluoromethyl)-5-(4-morpholino-6-(piperazin-1-yl)-1,3,5-triazin-2-yl)pyrimidin-2-amine;

(S)-4-(difluoromethyl)-5-(4-(3-methylmorpholino)-6-(piperazin-1-yl)-1,3,5-triazin-2-yl)pyridin-2-amine;

(S)-4-(difluoromethyl)-5-(4-(3-methylmorpholino)-6-(piperazin-1-yl)-1,3,5-triazin-2-yl)pyrimidin-2-amine;

4-(difluoromethyl)-5-(2,6-dimorpholinopyrimidin-4-yl)pyridin-2-amine;

4'-(difluoromethyl)-2,6-dimorpholino-[4,5'-bipyrimidin]-2'-amine;

4-(difluoromethyl)-5-(4,6-dimorpholinopyrimidin-2-yl)pyridin-2-amine;

4'-(difluoromethyl)-4,6-dimorpholino-[2,5'-bipyrimidin]-2'-amine;

4-(difluoromethyl)-5-(4-morpholino-6-thiomorpholino-1,3,5-triazin-2-yl)pyridin-2-amine;

4-(difluoromethyl)-5-(4-morpholino-6-thiomorpholino-1,3,5-triazin-2-yl)pyrimidin-2-amine;

5-(6-(3-oxa-8-azabicyclo[3.2.1]octan-8-yl)-2-(3-oxa-8-azabicyclo[3.2.1]octan-8-yl)pyrimidin-4-yl)-4-(difluoromethyl)pyridin-2-amine;

5-(2-(3-oxa-8-azabicyclo[3.2.1]octan-8-yl)-6-morpholinopyrimidin-4-yl)-4-(difluoromethyl)pyridin-2-amine;

2-(3-oxa-8-azabicyclo[3.2.1]octan-8-yl)-4'-(difluoromethyl)-6-morpholino-[4,5'-bipyrimidin]-2'-amine;

5-(2,6-bis((S)-3-methylmorpholino)pyrimidin-4-yl)-4-(difluoromethyl)pyridin-2-amine;

4'-(difluoromethyl)-2,6-bis((S)-3-methylmorpholino)-[4,5'-bipyrimidin]-2'-amine;

(S)-4-(difluoromethyl)-5-(6-(3-methylmorpholino)-2-morpholinopyrimidin-4-yl)pyridin-2-amine;

(S)-4'-(difluoromethyl)-6-(3-methylmorpholino)-2-morpholino-[4,5'-bipyrimidin]-2'-amine;

5-(4-(8-Oxa-3-azabicyclo[3.2.1]octan-3-yl)-6-(8-oxa-3-azabicyclo[3.2.1]octan-3-yl)-1,3,5-triazin-2-yl)-4-(difluoromethyl)pyridin-2-amine;

5-[4,6-bis(2,2-dimethylmorpholin-4-yl)-1,3,5-triazin-2-yl]-4-(difluoromethyl)pyridin-2-amine;

(S)-4-(difluoromethyl)-5-(2-(3-methylmorpholino)-6-morpholinopyrimidin-4-yl)pyridin-2-amine;

(S)-4'-(difluoromethyl)-2-(3-methylmorpholino)-6-morpholino-[4,5'-bipyrimidin]-2'-amine;

4-(difluoromethyl)-5-[4-[(2S,6R)-2,6-dimethylmorpholin-4-yl]-6-[(3R)-3-methylmorpholin-4-yl]-1,3,5-triazin-2-yl]pyridin-2-amine;

5-[4,6-bis[(2R,6S)-2,6-dimethylmorpholin-4-yl]-1,3,5-triazin-2-yl]-4-(difluoromethyl)pyridin-2-amine;

4-[4-[6-amino-4-(difluoromethyl)-3-pyridyl]-6-morpholino-1,3,5-triazin-2-yl]morpholin-3-one;

4-[4-[2-amino-4-(difluoromethyl)pyrimidin-5-yl]-6-morpholino-1,3,5-triazin-2-yl]morpholin-3-one;

5-[4,6-bis(3,7-dioxa-9-azabicyclo[3.3.1]nonan-9-yl)-1,3,5-triazin-2-yl]-4-(difluoromethyl)pyridin-2-amine;

4-(difluoromethyl)-5-[4-(3,7-dioxa-9-azabicyclo[3.3.1]nonan-9-yl)-6-(3-oxa-8-azabicyclo[3.2.1]octan-8-yl)-1,3,5-triazin-2-yl]pyridin-2-amine;

5-[4,6-bis(3,3-dimethylmorpholin-4-yl)-1,3,5-triazin-2-yl]-4-(difluoromethyl)pyridin-2-amine;

5-[4,6-bis[(3R,5S)-3,5-dimethylmorpholin-4-yl]-1,3,5-triazin-2-yl]-4-(difluoromethyl)pyridin-2-amine;

5-[4,6-bis[(3R)-3-methylmorpholin-4-yl]-1,3,5-triazin-2-yl]-4-(difluoromethyl)pyridin-2-amine;

4-(difluoromethyl)-5-[4-(3,3-dimethylmorpholin-4-yl)-6-morpholino-1,3,5-triazin-2-yl]pyridin-2-amine;

5-[4-[6-amino-4-(difluoromethyl)-3-pyridyl]-6-[(3R)-3-methylmorpholin-4-yl]-1,3,5-triazin-2-yl]-4-(difluoromethyl)pyridin-2-amine;

4-(difluoromethyl)-5-[4-[(3R,5S)-3,5-dimethylmorpholin-4-yl]-6-[(3R)-3-methylmorpholin-4-yl]-1,3,5-triazin-2-yl]pyridin-2-amine;

4-(difluoromethyl)-5-[4-(3,3-dimethylmorpholin-4-yl)-6-[(3R)-3-methyl morpholin-4-yl]-1,3,5-triazin-2-yl]pyridin-2-amine;

4-(difluoromethyl)-5-[4-[(3R)-3-(methoxymethyl)morpholin-4-yl]-6-[(3R)-3-methylmorpholin-4-yl]-1,3,5-triazin-2-yl]pyridin-2-amine;

4-(difluoromethyl)-5-[4-(3,7-dioxa-9-azabicyclo[3.3.1]nonan-9-yl)-6-[(3R)-3-methylmorpholin-4-yl]-1,3,5-triazin-2-yl]pyridin-2-amine;

(4S,5R)-3-[4-[2-amino-4-(difluoromethyl)pyrimidin-5-yl]-6-morpholino-1,3,5-triazin-2-yl]-4-(hydroxymethyl)-5-methyl-oxazolidin-2-one;

(4S,5R)-3-[6-[2-amino-4-(difluoromethyl)pyrimidin-5-yl]-2-morpholino-pyrimidin-4-yl]-4-(hydroxymethyl)-5-methyl-oxazolidin-2-one;

4-(difluoromethyl)-5-[4-[(3R)-3-methylmorpholin-4-yl]-6-(3-oxa-6-azabicyclo[3.1.1]heptan-6-yl)-1,3,5-triazin-2-yl]pyridin-2-amine;

4-(difluoromethyl)-5-[4-[(3R)-3-methylmorpholin-4-yl]-6-(6-oxa-3-azabicyclo[3.1.1]heptan-3-yl)-1,3,5-triazin-2-yl]pyridin-2-amine;

4-(difluoromethyl)-5-[4-[(3R)-3-methylmorpholin-4-yl]-6-[(1R,4R)-2-oxa-5-azabicyclo[2.2.1]heptan-5-yl]-1,3,5-triazin-2-yl]pyridin-2-amine;

4-(difluoromethyl)-5-[4-[(3R)-3-methylmorpholin-4-yl]-6-[(1S,4S)-2-oxa-5-azabicyclo[2.2.1]heptan-5-yl]-1,3,5-triazin-2-yl]pyridin-2-amine;

5-[4,6-bis[(3R)-3-ethylmorpholin-4-yl]-1,3,5-triazin-2-yl]-4-(difluoromethyl)pyridin-2-amine;

5-[4,6-bis(8-oxa-5-azaspiro[3.5]nonan-5-yl)-1,3,5-triazin-2-yl]-4-(difluoromethyl)pyridin-2-amine;

5-[4,6-bis[(3R)-3-isopropylmorpholin-4-yl]-1,3,5-triazin-2-yl]-4-(difluoromethyl)pyridin-2-amine;

4-[6-amino-4-(difluoromethyl)-3-pyridyl]-N-methyl-6-[(3R)-3-methylmorpholin-4-yl]-N-(2,2,2-trifluoroethyl)-1,3,5-triazin-2-amine;

4-[6-amino-4-(difluoromethyl)-3-pyridyl]-6-[(3R)-3-methylmorpholin-4-yl]-N-(2,2,2-trifluoroethyl)-1,3,5-triazin-2-amine;

4-[6-amino-4-(difluoromethyl)-3-pyridyl]-N-(cyclopropylmethyl)-6-[(3R)-3-methylmorpholin-4-yl]-1,3,5-triazin-2-amine;

4-(difluoromethyl)-5-[4-[(3R)-3-methylmorpholin-4-yl]-6-(2,2,2-trifluoroethoxy)-1,3,5-triazin-2-yl]pyridin-2-amine;

5-[4-(2,2-difluoroethoxy)-6-[(3R)-3-methyl morpholin-4-yl]-1,3,5-triazin-2-yl]-4-(difluoromethyl)pyridin-2-amine;

5-[4-[(3aR,6aS)-1,3,3a,4,6,6a-hexahydrofuro[3,4-c]pyrrol-5-yl]-6-[(3R)-3-methylmorpholin-4-yl]-1,3,5-triazin-2-yl]-4-(difluoromethyl)pyridin-2-amine;

5-[4-[(4aS,7aR)-2,3,4a,5,7,7a-hexahydro-[1,4]dioxino[2,3-c]pyrrol-6-yl]-6-[(3R)-3-methylmorpholin-4-yl]-1,3,5-triazin-2-yl]-4-(difluoromethyl)pyridin-2-amine;

4-(difluoromethyl)-5-[4-(4,4-difluoro-1-piperidyl)-6-[(3R)-3-methylmorpholin-4-yl]-1,3,5-triazin-2-yl]pyridin-2-amine;

4-(difluoromethyl)-5-[4-[(3R)-3-methylmorpholin-4-yl]-6-(2-oxa-7-azaspiro[3.5]nonan-7-yl)-1,3,5-triazin-2-yl]pyridin-2-amine;

4-(difluoromethyl)-5-[4-(3,3-dimethylmorpholin-4-yl)-6-[(3R,5S)-3,5-dimethylmorpholin-4-yl]-1,3,5-triazin-2-yl]pyridin-2-amine;

4-(difluoromethyl)-5-[4-(3,3-dimethylmorpholin-4-yl)-6-[(3R)-3-(methoxymethyl)morpholin-4-yl]-1,3,5-triazin-2-yl]pyridin-2-amine;

[(3R)-4-[4-[6-amino-4-(difluoromethyl)-3-pyridyl]-6-(3,3-dimethylmorpholin-4-yl)-1,3,5-triazin-2-yl]morpholin-3-yl]methanol;

4-(difluoromethyl)-5-[4-(3,3-dimethylmorpholin-4-yl)-6-(3,7-dioxa-9-azabicyclo[3.3.1]nonan-9-yl)-1,3,5-triazin-2-yl]pyridin-2-amine;

5-[4-(4-cyclopropylpiperazin-1-yl)-6-(3,3-dimethylmorpholin-4-yl)-1,3,5-triazin-2-yl]-4-(difluoromethyl)pyridin-2-amine;

4-(difluoromethyl)-5-[4-(3,3-dimethylmorpholin-4-yl)-6-[4-(2-methoxyethyl)piperazin-1-yl]-1,3,5-triazin-2-yl]pyridin-2-amine;

4-(difluoromethyl)-5-[4-(3,3-dimethylmorpholin-4-yl)-6-(oxetan-3-yloxy)-1,3,5-triazin-2-yl]pyridin-2-amine;

4-(difluoromethyl)-5-[4-(3,3-dimethylmorpholin-4-yl)-6-[(3S)-tetrahydrofuran-3-yl]oxy-1,3,5-triazin-2-yl]pyridin-2-amine;

4-(difluoromethyl)-5-[4-(3,3-dimethylmorpholin-4-yl)-6-[(3R)-tetrahydrofuran-3-yl]oxy-1,3,5-triazin-2-yl]pyridin-2-amine;

4-(difluoromethyl)-5-[4-(3,3-dimethyl morpholin-4-yl)-6-tetrahydropyran-4-yloxy-1,3,5-triazin-2-yl]pyridin-2-amine;

4-(difluoromethyl)-5-[4-(3,3-dimethylmorpholin-4-yl)-6-(1,1-dioxo-1,4-thiazinan-4-yl)-1,3,5-triazin-2-yl]pyridin-2-amine;

[(3R)-4-[4-[6-amino-4-(difluoromethyl)-3-pyridyl]-6-[(3R)-3-methylmorpholin-4-yl]-1,3,5-triazin-2-yl]morpholin-3-yl]methanol;

4-(difluoromethyl)-5-[4-[(3R,5R)-3,5-dimethylmorpholin-4-yl]-6-[(3R)-3-methylmorpholin-4-yl]-1,3,5-triazin-2-yl]pyridin-2-amine;

4-(difluoromethyl)-5-[4-[(3S,5S)-3,5-dimethylmorpholin-4-yl]-6-[(3R)-3-methylmorpholin-4-yl]-1,3,5-triazin-2-yl]pyridin-2-amine;

4-(difluoromethyl)-5-[4-morpholino-6-(3-oxa-9-azabicyclo[3.3.1]nonan-9-yl)-1,3,5-triazin-2-yl]pyridin-2-amine;

5-[4,6-bis(3-oxa-9-azabicyclo[3.3.1]nonan-9-yl)-1,3,5-triazin-2-yl]-4-(difluoromethyl)pyridin-2-amine;

5-[4-[6-amino-4-(difluoromethyl)-3-pyridyl]-6-(3,7-dioxa-9-azabicyclo[3.3.1]nonan-9-yl)-1,3,5-triazin-2-yl]-4-(difluoromethyl)pyridin-2-amine;

4-(difluoromethyl)-5-[4-[(3R)-3-methylmorpholin-4-yl]-6-(4-morpholino-1-piperidyl)-1,3,5-triazin-2-yl]pyridin-2-amine;

5-[4-(4-cyclopropylpiperazin-1-yl)-6-[(3R)-3-methylmorpholin-4-yl]-1,3,5-triazin-2-yl]-4-(difluoromethyl)pyridin-2-amine;

5-[4-(4-cyclopropylpiperazin-1-yl)-6-[(3S,5R)-3,5-dimethylmorpholin-4-yl]-1,3,5-triazin-2-yl]-4-(difluoromethyl)pyridin-2-amine;

4-(difluoromethyl)-5-[4-[4-(2-methoxyethyl)piperazin-1-yl]-6-[(3R)-3-methylmorpholin-4-yl]-1,3,5-triazin-2-yl]pyridin-2-amine;

4-(difluoromethyl)-5-[4-[(3S,5R)-3,5-dimethylmorpholin-4-yl]-6-[4-(2-methoxyethyl) piperazin-1-yl]-1,3,5-triazin-2-yl]pyridin-2-amine;

4-(difluoromethyl)-5-[4-[(3R,5S)-3,5-dimethylmorpholin-4-yl]-6-(4-morpholino-1-piperidyl)-1,3,5-triazin-2-yl]pyridin-2-amine;

4-(difluoromethyl)-5-[4-(1,1-dioxo-1,4-thiazinan-4-yl)-6-[(3R)-3-methylmorpholin-4-yl]-1,3,5-triazin-2-yl]pyridin-2-amine;

4-(difluoromethyl)-5-[4-[(3S,5R)-3,5-dimethylmorpholin-4-yl]-6-(1,1-dioxo-1,4-thiazinan-4-yl)-1,3,5-triazin-2-yl]pyridin-2-amine;

4-(difluoromethyl)-5-[4-[(3R)-3-methylmorpholin-4-yl]-6-tetrahydropyran-4-yloxy-1,3,5-triazin-2-yl]pyridin-2-amine;

4-(difluoromethyl)-5-[4-[(3S,5R)-3,5-dimethylmorpholin-4-yl]-6-tetrahydropyran-4-yloxy-1,3,5-triazin-2-yl]pyridin-2-amine;

4-(difluoromethyl)-5-[4-[(3R)-3-methylmorpholin-4-yl]-6-[(3S)-tetrahydrofuran-3-yl]oxy-1,3,5-triazin-2-yl]pyridin-2-amine;

4-(difluoromethyl)-5-[4-[(3R)-3-methylmorpholin-4-yl]-6-[(3R)-tetrahydrofuran-3-yl]oxy-1,3,5-triazin-2-yl]pyridin-2-amine;

4-(difluoromethyl)-5-[4-[(3S,5R)-3,5-dimethylmorpholin-4-yl]-6-[(3S)-tetrahydrofuran-3-yl]oxy-1,3,5-triazin-2-yl]pyridin-2-amine;

4-(difluoromethyl)-5-[4-[(3S,5R)-3,5-dimethylmorpholin-4-yl]-6-[(3R)-tetrahydrofuran-3-yl]oxy-1,3,5-triazin-2-yl]pyridin-2-amine;

4-(difluoromethyl)-5-[4-[(3R)-3-methylmorpholin-4-yl]-6-(oxetan-3-yloxy)-1,3,5-triazin-2-yl]pyridin-2-amine;

4-(difluoromethyl)-5-[4-[(3S,5R)-3,5-dimethylmorpholin-4-yl]-6-(oxetan-3-yloxy)-1,3,5-triazin-2-yl]pyridin-2-amine;

4-(difluoromethyl)-5-[4-[(3R,5S)-3,5-dimethylmorpholin-4-yl]-6-(3,7-dioxa-9-azabicyclo[3.3.1]nonan-9-yl)-1,3,5-triazin-2-yl]pyridin-2-amine;

3-[4-[6-amino-4-(difluoromethyl)-3-pyridyl]-6-[(3R,5S)-3,5-dimethylmorpholin-4-yl]-1,3,5-triazin-2-yl]oxazolidin-2-one;

5-(4-((1R,2R,4S,5S)-7-oxa-9-azatricyclo[3.3.1.0$^{2,4}$]nonan-9-yl)-6-((2R,4S)-7-oxa-9-azatricyclo[3.3.1.0$^{2,4}$]nonan-9-yl)-1,3,5-triazin-2-yl)-4-(difluoromethyl)pyridin-2-amine;

5-[4,6-bis(6,6-difluoro-3-oxa-8-azabicyclo[3.2.1]octan-8-yl)-1,3,5-triazin-2-yl]-4-(difluoromethyl)pyridin-2-amine;

5-[4,6-bis(6,7-difluoro-3-oxa-8-azabicyclo[3.2.1]octan-8-yl)-1,3,5-triazin-2-yl]-4-(difluoromethyl)pyridin-2-amine;

5-[4-(6-amino-3-pyridyl)-6-[(3R)-3-methylmorpholin-4-yl]-1,3,5-triazin-2-yl]-4-(difluoromethyl)pyridin-2-amine;

4-(difluoromethyl)-5-[4-[4-(difluoromethyl)-3-pyridyl]-6-[(3R)-3-methylmorpholin-4-yl]-1,3,5-triazin-2-yl]pyridin-2-amine;

4-(difluoromethyl)-5-[4-[(3R)-3-methylmorpholin-4-yl]-6-(3-pyridyl)-1,3,5-triazin-2-yl]pyridin-2-amine;

4-(difluoromethyl)-5-[4-[(3R)-3-methylmorpholin-4-yl]-6-pyrazin-2-yl-1,3,5-triazin-2-yl]pyridin-2-amine;

4-(difluoromethyl)-5-[4-[(3R)-3-methylmorpholin-4-yl]-6-(1H-pyrazol-3-yl)-1,3,5-triazin-2-yl]pyridin-2-amine;

4-(difluoromethyl)-5-[4-[(3R)-3-methylmorpholin-4-yl]-6-(1H-pyrazol-4-yl)-1,3,5-triazin-2-yl]pyridin-2-amine;

4-(difluoromethyl)-5-[4-[(3R)-3-methylmorpholin-4-yl]-6-(1,2,4-triazol-1-yl)-1,3,5-triazin-2-yl]pyridin-2-amine;

4-(difluoromethyl)-5-[4-[(3R)-3-methylmorpholin-4-yl]-6-(1H-1,2,4-triazol-3-yl)-1,3,5-triazin-2-yl]pyridin-2-amine;

4-(difluoromethyl)-5-[4-[(3R)-3-methylmorpholin-4-yl]-6-(2H-tetrazol-5-yl)-1,3,5-triazin-2-yl]pyridin-2-amine.

In another preferred embodiment, said compound of formula (I) is selected from 4-(difluoromethyl)-5-(4,6-dimorpholino-1,3,5-triazin-2-yl)pyridin-2-amine;
4-(difluoromethyl)-5-(4,6-dimorpholino-1,3,5-triazin-2-yl)pyrimidin-2-amine;
5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine;
5-(4-(3-oxa-8-azabicyclo[3.2.1]octan-8-yl)-6-morpholino-1,3,5-triazin-2-yl)-4-(difluoromethyl)pyridin-2-amine;
5-(4-(3-oxa-8-azabicyclo[3.2.1]octan-8-yl)-6-morpholino-1,3,5-triazin-2-yl)-4-(difluoromethyl)pyrimidin-2-amine;
5-(4,6-bis((S)-3-methylmorpholino)-1,3,5-triazin-2-yl)-4-(difluoromethyl)pyridin-2-amine;
5-(4,6-bis((S)-3-methylmorpholino)-1,3,5-triazin-2-yl)-4-(difluoromethyl)pyrimidin-2-amine;
(S)-4-(difluoromethyl)-5-(4-(3-methylmorpholino)-6-morpholino-1,3,5-triazin-2-yl)pyridin-2-amine;
(S)-4-(difluoromethyl)-5-(4-(3-methylmorpholino)-6-morpholino-1,3,5-triazin-2-yl)pyrimidin-2-amine;
5-(4-(3-oxa-8-azabicyclo[3.2.1]octan-8-yl)-6-((S)-3-methylmorpholino)-1,3,5-triazin-2-yl)-4-(difluoromethyl)pyridin-2-amine;
5-(4-(3-oxa-8-azabicyclo[3.2.1]octan-8-yl)-6-((S)-3-methylmorpholino)-1,3,5-triazin-2-yl)-4-(difluoromethyl)pyrimidin-2-amine;
4-(difluoromethyl)-5-(4-morpholino-6-(piperazin-1-yl)-1,3,5-triazin-2-yl)pyridin-2-amine;
4-(difluoromethyl)-5-(4-morpholino-6-(piperazin-1-yl)-1,3,5-triazin-2-yl)pyrimidin-2-amine;
(S)-4-(difluoromethyl)-5-(4-(3-methylmorpholino)-6-(piperazin-1-yl)-1,3,5-triazin-2-yl)pyridin-2-amine;
(S)-4-(difluoromethyl)-5-(4-(3-methylmorpholino)-6-(piperazin-1-yl)-1,3,5-triazin-2-yl)pyrimidin-2-amine;
4-(difluoromethyl)-5-(2,6-dimorpholinopyrimidin-4-yl)pyridin-2-amine;
4'-(difluoromethyl)-2,6-dimorpholino-[4,5'-bipyrimidin]-2'-amine;
4-(difluoromethyl)-5-(4,6-dimorpholinopyrimidin-2-yl)pyridin-2-amine;
4'-(difluoromethyl)-4,6-dimorpholino-[2,5'-bipyrimidin]-2'-amine;
4-(difluoromethyl)-5-(4-morpholino-6-thiomorpholino-1,3,5-triazin-2-yl)pyridin-2-amine;
4-(difluoromethyl)-5-(4-morpholino-6-thiomorpholino-1,3,5-triazin-2-yl)pyrimidin-2-amine;
5-(6-(3-oxa-8-azabicyclo[3.2.1]octan-8-yl)-2-(3-oxa-8-azabicyclo[3.2.1]octan-8-yl)pyrimidin-4-yl)-4-(difluoromethyl)pyridin-2-amine;
5-(2-(3-oxa-8-azabicyclo[3.2.1]octan-8-yl)-6-morpholinopyrimidin-4-yl)-4-(difluoromethyl)pyridin-2-amine;
2-(3-oxa-8-azabicyclo[3.2.1]octan-8-yl)-4'-(difluoromethyl)-6-morpholino-[4,5'-bipyrimidin]-2'-amine;
5-(2,6-bis((S)-3-methylmorpholino)pyrimidin-4-yl)-4-(difluoromethyl)pyridin-2-amine;
4'-(difluoromethyl)-2,6-bis((S)-3-methylmorpholino)-[4,5'-bipyrimidin]-2'-amine;
(S)-4-(difluoromethyl)-5-(6-(3-methylmorpholino)-2-morpholinopyrimidin-4-yl)pyridin-2-amine;
(S)-4'-(difluoromethyl)-6-(3-methylmorpholino)-2-morpholino-[4,5'-bipyrimidin]-2'-amine;
5-(4-(8-Oxa-3-azabicyclo[3.2.1]octan-3-yl)-6-(8-oxa-3-azabicyclo[3.2.1]octan-3-yl)-1,3,5-triazin-2-yl)-4-(difluoromethyl)pyridin-2-amine;
5-[4,6-bis(2,2-dimethylmorpholin-4-yl)-1,3,5-triazin-2-yl]-4-(difluoromethyl)pyridin-2-amine;
(S)-4-(difluoromethyl)-5-(2-(3-methylmorpholino)-6-morpholinopyrimidin-4-yl)pyridin-2-amine;
(S)-4'-(difluoromethyl)-2-(3-methylmorpholino)-6-morpholino-[4,5'-bipyrimidin]-2'-amine;
4-(difluoromethyl)-5-[4-[(2S,6R)-2,6-dimethylmorpholin-4-yl]-6-[(3R)-3-methylmorpholin-4-yl]-1,3,5-triazin-2-yl]pyridin-2-amine;
5-[4,6-bis[(2R,6S)-2,6-dimethylmorpholin-4-yl]-1,3,5-triazin-2-yl]-4-(difluoromethyl)pyridin-2-amine.

In another preferred embodiment, said compound of formula (I) is selected from

4-[4-[6-amino-4-(difluoromethyl)-3-pyridyl]-6-morpholino-1,3,5-triazin-2-yl]morpholin-3-one;
4-[4-[2-amino-4-(difluoromethyl)pyrimidin-5-yl]-6-morpholino-1,3,5-triazin-2-yl]morpholin-3-one;
5-[4,6-bis(3,7-dioxa-9-azabicyclo[3.3.1]nonan-9-yl)-1,3,5-triazin-2-yl]-4-(difluoromethyl)pyridin-2-amine;
4-(difluoromethyl)-5-[4-(3,7-dioxa-9-azabicyclo[3.3.1]nonan-9-yl)-6-(3-oxa-8-azabicyclo[3.2.1]octan-8-yl)-1,3,5-triazin-2-yl]pyridin-2-amine;
5-[4,6-bis(3,3-dimethylmorpholin-4-yl)-1,3,5-triazin-2-yl]-4-(difluoromethyl)pyridin-2-amine;
5-[4,6-bis[(3R,5S)-3,5-dimethylmorpholin-4-yl]-1,3,5-triazin-2-yl]-4-(difluoromethyl)pyridin-2-amine;
5-[4,6-bis[(3R)-3-methylmorpholin-4-yl]-1,3,5-triazin-2-yl]-4-(difluoromethyl)pyridin-2-amine;
4-(difluoromethyl)-5-[4-(3,3-dimethylmorpholin-4-yl)-6-morpholino-1,3,5-triazin-2-yl]pyridin-2-amine;
5-[4-[6-amino-4-(difluoromethyl)-3-pyridyl]-6-[(3R)-3-methylmorpholin-4-yl]-1,3,5-triazin-2-yl]-4-(difluoromethyl)pyridin-2-amine;
4-(difluoromethyl)-5-[4-[(3R,5S)-3,5-dimethylmorpholin-4-yl]-6-[(3R)-3-methylmorpholin-4-yl]-1,3,5-triazin-2-yl]pyridin-2-amine;
4-(difluoromethyl)-5-[4-(3,3-dimethylmorpholin-4-yl)-6-[(3R)-3-methylmorpholin-4-yl]-1,3,5-triazin-2-yl]pyridin-2-amine;
4-(difluoromethyl)-5-[4-[(3R)-3-(methoxymethyl)morpholin-4-yl]-6-[(3R)-3-methylmorpholin-4-yl]-1,3,5-triazin-2-yl]pyridin-2-amine;
4-(difluoromethyl)-5-[4-(3,7-dioxa-9-azabicyclo[3.3.1]nonan-9-yl)-6-[(3R)-3-methylmorpholin-4-yl]-1,3,5-triazin-2-yl]pyridin-2-amine;
(4S,5R)-3-[4-[2-amino-4-(difluoromethyl)pyrimidin-5-yl]-6-morpholino-1,3,5-triazin-2-yl]-4-(hydroxymethyl)-5-methyl-oxazolidin-2-one;
(4S,5R)-3-[6-[2-amino-4-(difluoromethyl)pyrimidin-5-yl]-2-morpholino-pyrimidin-4-yl]-4-(hydroxymethyl)-5-methyl-oxazolidin-2-one;
4-(difluoromethyl)-5-[4-[(3R)-3-methylmorpholin-4-yl]-6-(3-oxa-6-azabicyclo[3.1.1]heptan-6-yl)-1,3,5-triazin-2-yl]pyridin-2-amine;
4-(difluoromethyl)-5-[4-[(3R)-3-methylmorpholin-4-yl]-6-(6-oxa-3-azabicyclo[3.1.1]heptan-3-yl)-1,3,5-triazin-2-yl]pyridin-2-amine;
4-(difluoromethyl)-5-[4-[(3R)-3-methylmorpholin-4-yl]-6-[(1R,4R)-2-oxa-5-azabicyclo[2.2.1]heptan-5-yl]-1,3,5-triazin-2-yl]pyridin-2-amine;
4-(difluoromethyl)-5-[4-[(3R)-3-methylmorpholin-4-yl]-6-[(1 S,4S)-2-oxa-5-azabicyclo[2.2.1]heptan-5-yl]-1,3,5-triazin-2-yl]pyridin-2-amine;
5-[4,6-bis[(3R)-3-ethylmorpholin-4-yl]-1,3,5-triazin-2-yl]-4-(difluoromethyl)pyridin-2-amine;
5-[4,6-bis(8-oxa-5-azaspiro[3.5]nonan-5-yl)-1,3,5-triazin-2-yl]-4-(difluoromethyl)pyridin-2-amine;
5-[4,6-bis[(3R)-3-isopropylmorpholin-4-yl]-1,3,5-triazin-2-yl]-4-(difluoromethyl)pyridin-2-amine;

4-[6-amino-4-(difluoromethyl)-3-pyridyl]-N-methyl-6-[(3R)-3-methylmorpholin-4-yl]-N-(2,2,2-trifluoroethyl)-1,3,5-triazin-2-amine;

4-[6-amino-4-(difluoromethyl)-3-pyridyl]-6-[(3R)-3-methylmorpholin-4-yl]-N-(2,2,2-trifluoroethyl)-1,3,5-triazin-2-amine;

4-[6-amino-4-(difluoromethyl)-3-pyridyl]-N-(cyclopropylmethyl)-6-[(3R)-3-methylmorpholin-4-yl]-1,3,5-triazin-2-amine;

4-(difluoromethyl)-5-[4-[(3R)-3-methylmorpholin-4-yl]-6-(2,2,2-trifluoroethoxy)-1,3,5-triazin-2-yl]pyridin-2-amine;

5-[4-(2,2-difluoroethoxy)-6-[(3R)-3-methylmorpholin-4-yl]-1,3,5-triazin-2-yl]-4-(difluoromethyl)pyridin-2-amine;

5-[4-[(3aR,6aS)-1,3,3a,4,6,6a-hexahydrofuro[3,4-c]pyrrol-5-yl]-6-[(3R)-3-methylmorpholin-4-yl]-1,3,5-triazin-2-yl]-4-(difluoromethyl)pyridin-2-amine;

5-[4-[(4aS,7aR)-2,3,4a,5,7,7a-hexahydro-[1,4]dioxino[2,3-c]pyrrol-6-yl]-6-[(3R)-3-methylmorpholin-4-yl]-1,3,5-triazin-2-yl]-4-(difluoromethyl)pyridin-2-amine;

4-(difluoromethyl)-5-[4-(4,4-difluoro-1-piperidyl)-6-[(3R)-3-methylmorpholin-4-yl]-1,3,5-triazin-2-yl]pyridin-2-amine;

4-(difluoromethyl)-5-[4-[(3R)-3-methylmorpholin-4-yl]-6-(2-oxa-7-azaspiro[3.5]nonan-7-yl)-1,3,5-triazin-2-yl]pyridin-2-amine;

4-(difluoromethyl)-5-[4-(3,3-dimethylmorpholin-4-yl)-6-[(3R,5S)-3,5-dimethylmorpholin-4-yl]-1,3,5-triazin-2-yl]pyridin-2-amine;

4-(difluoromethyl)-5-[4-(3,3-dimethylmorpholin-4-yl)-6-[(3R)-3-(methoxymethyl)morpholin-4-yl]-1,3,5-triazin-2-yl]pyridin-2-amine;

[(3R)-4-[4-[6-amino-4-(difluoromethyl)-3-pyridyl]-6-(3,3-dimethylmorpholin-4-yl)-1,3,5-triazin-2-yl]morpholin-3-yl]methanol;

4-(difluoromethyl)-5-[4-(3,3-dimethylmorpholin-4-yl)-6-(3,7-dioxa-9-azabicyclo[3.3.1]nonan-9-yl)-1,3,5-triazin-2-yl]pyridin-2-amine;

5-[4-(4-cyclopropylpiperazin-1-yl)-6-(3,3-dimethylmorpholin-4-yl)-1,3,5-triazin-2-yl]-4-(difluoromethyl)pyridin-2-amine;

4-(difluoromethyl)-5-[4-(3,3-dimethylmorpholin-4-yl)-6-[4-(2-methoxyethyl)piperazin-1-yl]-1,3,5-triazin-2-yl]pyridin-2-amine;

4-(difluoromethyl)-5-[4-(3,3-dimethylmorpholin-4-yl)-6-(oxetan-3-yloxy)-1,3,5-triazin-2-yl]pyridin-2-amine;

4-(difluoromethyl)-5-[4-(3,3-dimethylmorpholin-4-yl)-6-[(3S)-tetrahydrofuran-3-yl]oxy-1,3,5-triazin-2-yl]pyridin-2-amine;

4-(difluoromethyl)-5-[4-(3,3-dimethylmorpholin-4-yl)-6-[(3R)-tetrahydrofuran-3-yl]oxy-1,3,5-triazin-2-yl]pyridin-2-amine;

4-(difluoromethyl)-5-[4-(3,3-dimethyl morpholin-4-yl)-6-tetrahydropyran-4-yloxy-1,3,5-triazin-2-yl]pyridin-2-amine;

4-(difluoromethyl)-5-[4-(3,3-dimethylmorpholin-4-yl)-6-(1,1-dioxo-1,4-thiazinan-4-yl)-1,3,5-triazin-2-yl]pyridin-2-amine;

[(3R)-4-[4-[6-amino-4-(difluoromethyl)-3-pyridyl]-6-[(3R)-3-methylmorpholin-4-yl]-1,3,5-triazin-2-yl]morpholin-3-yl]methanol;

4-(difluoromethyl)-5-[4-[(3R,5R)-3,5-dimethylmorpholin-4-yl]-6-[(3R)-3-methylmorpholin-4-yl]-1,3,5-triazin-2-yl]pyridin-2-amine;

4-(difluoromethyl)-5-[4-[(3S,5S)-3,5-dimethylmorpholin-4-yl]-6-[(3R)-3-methylmorpholin-4-yl]-1,3,5-triazin-2-yl]pyridin-2-amine;

4-(difluoromethyl)-5-[4-morpholino-6-(3-oxa-9-azabicyclo[3.3.1]nonan-9-yl)-1,3,5-triazin-2-yl]pyridin-2-amine;

5-[4,6-bis(3-oxa-9-azabicyclo[3.3.1]nonan-9-yl)-1,3,5-triazin-2-yl]-4-(difluoromethyl)pyridin-2-amine;

5-[4-[6-amino-4-(difluoromethyl)-3-pyridyl]-6-(3,7-dioxa-9-azabicyclo[3.3.1]nonan-9-yl)-1,3,5-triazin-2-yl]-4-(difluoromethyl)pyridin-2-amine;

4-(difluoromethyl)-5-[4-[(3R)-3-methylmorpholin-4-yl]-6-(4-morpholino-1-piperidyl)-1,3,5-triazin-2-yl]pyridin-2-amine;

5-[4-(4-cyclopropylpiperazin-1-yl)-6-[(3R)-3-methylmorpholin-4-yl]-1,3,5-triazin-2-yl]-4-(difluoromethyl)pyridin-2-amine;

5-[4-(4-cyclopropylpiperazin-1-yl)-6-[(3S,5R)-3,5-dimethylmorpholin-4-yl]-1,3,5-triazin-2-yl]-4-(difluoromethyl)pyridin-2-amine;

4-(difluoromethyl)-5-[4-[4-(2-methoxyethyl)piperazin-1-yl]-6-[(3R)-3-methylmorpholin-4-yl]-1,3,5-triazin-2-yl]pyridin-2-amine;

4-(difluoromethyl)-5-[4-[(3S,5R)-3,5-dimethylmorpholin-4-yl]-6-[4-(2-methoxyethyl) piperazin-1-yl]-1,3,5-triazin-2-yl]pyridin-2-amine;

4-(difluoromethyl)-5-[4-[(3R,5S)-3,5-dimethylmorpholin-4-yl]-6-(4-morpholino-1-piperidyl)-1,3,5-triazin-2-yl]pyridin-2-amine;

4-(difluoromethyl)-5-[4-(1,1-dioxo-1,4-thiazinan-4-yl)-6-[(3R)-3-methylmorpholin-4-yl]-1,3,5-triazin-2-yl]pyridin-2-amine;

4-(difluoromethyl)-5-[4-[(3S,5R)-3,5-dimethylmorpholin-4-yl]-6-(1,1-dioxo-1,4-thiazinan-4-yl)-1,3,5-triazin-2-yl]pyridin-2-amine;

4-(difluoromethyl)-5-[4-[(3R)-3-methylmorpholin-4-yl]-6-tetrahydropyran-4-yloxy-1,3,5-triazin-2-yl]pyridin-2-amine;

4-(difluoromethyl)-5-[4-[(3S,5R)-3,5-dimethylmorpholin-4-yl]-6-tetrahydropyran-4-yloxy-1,3,5-triazin-2-yl]pyridin-2-amine;

4-(difluoromethyl)-5-[4-[(3R)-3-methylmorpholin-4-yl]-6-[(3S)-tetrahydrofuran-3-yl]oxy-1,3,5-triazin-2-yl]pyridin-2-amine;

4-(difluoromethyl)-5-[4-[(3R)-3-methylmorpholin-4-yl]-6-[(3R)-tetrahydrofuran-3-yl]oxy-1,3,5-triazin-2-yl]pyridin-2-amine;

4-(difluoromethyl)-5-[4-[(3S,5R)-3,5-dimethylmorpholin-4-yl]-6-[(3S)-tetrahydrofuran-3-yl]oxy-1,3,5-triazin-2-yl]pyridin-2-amine;

4-(difluoromethyl)-5-[4-[(3S,5R)-3,5-dimethylmorpholin-4-yl]-6-[(3R)-tetrahydrofuran-3-yl]oxy-1,3,5-triazin-2-yl]pyridin-2-amine;

4-(difluoromethyl)-5-[4-[(3R)-3-methylmorpholin-4-yl]-6-(oxetan-3-yloxy)-1,3,5-triazin-2-yl]pyridin-2-amine;

4-(difluoromethyl)-5-[4-[(3S,5R)-3,5-dimethyl morpholin-4-yl]-6-(oxetan-3-yloxy)-1,3,5-triazin-2-yl]pyridin-2-amine;

4-(difluoromethyl)-5-[4-[(3R,5S)-3,5-dimethylmorpholin-4-yl]-6-(3,7-dioxa-9-azabicyclo[3.3.1]nonan-9-yl)-1,3,5-triazin-2-yl]pyridin-2-amine;

3-[4-[6-amino-4-(difluoromethyl)-3-pyridyl]-6-[(3R,5S)-3,5-dimethylmorpholin-4-yl]-1,3,5-triazin-2-yl]oxazolidin-2-one;

5-(4-((1R,2R,4S,5S)-7-oxa-9-azatricyclo[3.3.1.0$^{2,4}$]nonan-9-yl)-6-((2R,4S)-7-oxa-9-azatricyclo[3.3.1.0$^{2,4}$]nonan-9-yl)-1,3,5-triazin-2-yl)-4-(difluoromethyl)pyridin-2-amine;

5-[4,6-bis(6,6-difluoro-3-oxa-8-azabicyclo[3.2.1]octan-8-yl)-1,3,5-triazin-2-yl]-4-(difluoromethyl)pyridin-2-amine;

5-[4,6-bis(6,7-difluoro-3-oxa-8-azabicyclo[3.2.1]octan-8-yl)-1,3,5-triazin-2-yl]-4-(difluoromethyl)pyridin-2-amine;

5-[4-(6-amino-3-pyridyl)-6-[(3R)-3-methylmorpholin-4-yl]-1,3,5-triazin-2-yl]-4-(difluoromethyl)pyridin-2-amine;

4-(difluoromethyl)-5-[4-[4-(difluoromethyl)-3-pyridyl]-6-[(3R)-3-methylmorpholin-4-yl]-1,3,5-triazin-2-yl]pyridin-2-amine;

4-(difluoromethyl)-5-[4-[(3R)-3-methylmorpholin-4-yl]-6-(3-pyridyl)-1,3,5-triazin-2-yl]pyridin-2-amine;

4-(difluoromethyl)-5-[4-[(3R)-3-methylmorpholin-4-yl]-6-pyrazin-2-yl-1,3,5-triazin-2-yl]pyridin-2-amine;

4-(difluoromethyl)-5-[4-[(3R)-3-methylmorpholin-4-yl]-6-(1H-pyrazol-3-yl)-1,3,5-triazin-2-yl]pyridin-2-amine;

4-(difluoromethyl)-5-[4-[(3R)-3-methylmorpholin-4-yl]-6-(1H-pyrazol-4-yl)-1,3,5-triazin-2-yl]pyridin-2-amine;

4-(difluoromethyl)-5-[4-[(3R)-3-methylmorpholin-4-yl]-6-(1,2,4-triazol-1-yl)-1,3,5-triazin-2-yl]pyridin-2-amine;

4-(difluoromethyl)-5-[4-[(3R)-3-methylmorpholin-4-yl]-6-(1H-1,2,4-triazol-3-yl)-1,3,5-triazin-2-yl]pyridin-2-amine;

4-(difluoromethyl)-5-[4-[(3R)-3-methylmorpholin-4-yl]-6-(2H-tetrazol-5-yl)-1,3,5-triazin-2-yl]pyridin-2-amine.

In another preferred embodiment, said compound of formula (I) is selected from the group consisting of
4-(difluoromethyl)-5-(4,6-dimorpholino-1,3,5-triazin-2-yl)pyrimidin-2-amine;

5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine;

5-(4-(3-oxa-8-azabicyclo[3.2.1]octan-8-yl)-6-morpholino-1,3,5-triazin-2-yl)-4-(difluoromethyl)pyridin-2-amine;

5-(4,6-bis((S)-3-methylmorpholino)-1,3,5-triazin-2-yl)-4-(difluoromethyl)pyrimidin-2-amine;

(S)-4-(difluoromethyl)-5-(4-(3-methylmorpholino)-6-morpholino-1,3,5-triazin-2-yl)pyridin-2-amine;

4-(difluoromethyl)-5-(4-morpholino-6-(piperazin-1-yl)-1,3,5-triazin-2-yl)pyrimidin-2-amine;

4-(difluoromethyl)-5-(4,6-dimorpholino-1,3,5-triazin-2-yl)pyridin-2-amine; and (S)-4-(difluoromethyl)-5-(4-(3-methylmorpholino)-6-morpholino-1,3,5-triazin-2-yl)pyrimidin-2-amine;
and tautomers, solvates and pharmaceutically acceptable salts thereof.

In another preferred embodiment, said compound of formula (I) is selected from
4-(difluoromethyl)-5-(4,6-dimorpholino-1,3,5-triazin-2-yl)pyrimidin-2-amine;

5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine;

(S)-4-(difluoromethyl)-5-(4-(3-methylmorpholino)-6-morpholino-1,3,5-triazin-2-yl)pyridin-2-amine;
and tautomers, solvates and pharmaceutically acceptable salts thereof.

In another very preferred embodiment, said compound of formula (I) is 4-(difluoromethyl)-5-(4,6-dimorpholino-1,3,5-triazin-2-yl)pyrimidin-2-amine.

In another very preferred embodiment, said compound of formula (I) is 4-(difluoromethyl)-5-(4,6-dimorpholino-1,3,5-triazin-2-yl)pyrimidin-2-amine; and tautomers, solvates and pharmaceutically acceptable salts thereof.

In another very preferred embodiment, said compound of formula (I) is 5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine.

In another very preferred embodiment, said compound of formula (I) is 5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine; and tautomers, solvates and pharmaceutically acceptable salts thereof.

In another very preferred embodiment, said compound of formula (I) is (S)-4-(difluoromethyl)-5-(4-(3-methylmorpholino)-6-morpholino-1,3,5-triazin-2-yl)pyridin-2-amine.

In another very preferred embodiment, said compound of formula (I) is (S)-4-(difluoromethyl)-5-(4-(3-methylmorpholino)-6-morpholino-1,3,5-triazin-2-yl)pyridin-2-amine; and tautomers, solvates and pharmaceutically acceptable salts thereof.

In another preferred embodiment, said compound of formula (I) is selected from
4-[4-[6-amino-4-(difluoromethyl)-3-pyridyl]-6-morpholino-1,3,5-triazin-2-yl]morpholin-3-one;

4-[4-[2-amino-4-(difluoromethyl)pyrimidin-5-yl]-6-morpholino-1,3,5-triazin-2-yl]morpholin-3-one;

5-[4,6-bis(3,7-dioxa-9-azabicyclo[3.3.1]nonan-9-yl)-1,3,5-triazin-2-yl]-4-(difluoromethyl)pyridin-2-amine;

4-(difluoromethyl)-5-[4-(3,7-dioxa-9-azabicyclo[3.3.1]nonan-9-yl)-6-(3-oxa-8-azabicyclo[3.2.1]octan-8-yl)-1,3,5-triazin-2-yl]pyridin-2-amine;

5-[4,6-bis(3,3-dimethylmorpholin-4-yl)-1,3,5-triazin-2-yl]-4-(difluoromethyl)pyridin-2-amine;

5-[4,6-bis[(3R,5S)-3,5-dimethylmorpholin-4-yl]-1,3,5-triazin-2-yl]-4-(difluoromethyl)pyridin-2-amine;

5-[4,6-bis[(3R)-3-methylmorpholin-4-yl]-1,3,5-triazin-2-yl]-4-(difluoromethyl)pyridin-2-amine;

4-(difluoromethyl)-5-[4-(3,3-dimethylmorpholin-4-yl)-6-morpholino-1,3,5-triazin-2-yl]pyridin-2-amine;

5-[4-[6-amino-4-(difluoromethyl)-3-pyridyl]-6-[(3R)-3-methylmorpholin-4-yl]-1,3,5-triazin-2-yl]-4-(difluoromethyl)pyridin-2-amine;

4-(difluoromethyl)-5-[4-[(3R,5S)-3,5-dimethylmorpholin-4-yl]-6-[(3R)-3-methylmorpholin-4-yl]-1,3,5-triazin-2-yl]pyridin-2-amine;

4-(difluoromethyl)-5-[4-(3,3-dimethylmorpholin-4-yl)-6-[(3R)-3-methylmorpholin-4-yl]-1,3,5-triazin-2-yl]pyridin-2-amine;

4-(difluoromethyl)-5-[4-[(3R)-3-(methoxymethyl)morpholin-4-yl]-6-[(3R)-3-methylmorpholin-4-yl]-1,3,5-triazin-2-yl]pyridin-2-amine;

4-(difluoromethyl)-5-[4-(3,7-dioxa-9-azabicyclo[3.3.1]nonan-9-yl)-6-[(3R)-3-methylmorpholin-4-yl]-1,3,5-triazin-2-yl]pyridin-2-amine;

(4S,5R)-3-[4-[2-amino-4-(difluoromethyl)pyrimidin-5-yl]-6-morpholino-1,3,5-triazin-2-yl]-4-(hydroxymethyl)-5-methyl-oxazolidin-2-one; and tautomers, solvates and pharmaceutically acceptable salts thereof.

In another preferred embodiment, said compound of formula (I) is (4S,5R)-3-[4-[2-amino-4-(difluoromethyl)pyrimidin-5-yl]-6-morpholino-1,3,5-triazin-2-yl]-4-(hydroxymethyl)-5-methyl-oxazolidin-2-one.

In another preferred embodiment, said compound of formula (I) is (4S,5R)-3-[4-[2-amino-4-(difluoromethyl)pyrimidin-5-yl]-6-morpholino-1,3,5-triazin-2-yl]-4-(hydroxymethyl)-5-methyl-oxazolidin-2-one; and tautomers, solvates and pharmaceutically acceptable salts thereof.

In another preferred embodiment, said $R^1$ and $R^2$ are independently of each other a morpholinyl of formula (II).

In one preferred embodiment, said $R^1$ is equal to $R^2$. In another preferred embodiment, said $R^1$ is not equal to $R^2$.

In another preferred embodiment, said $R^1$ and $R^2$ are independently of each other a morpholinyl of formula (II) and said 5- to 6-membered heteroaryl ring W.

In another preferred embodiment, said $R^1$ and $R^2$ are independently of each other a morpholinyl of formula (II) and said saturated 4- to 6-membered heterocyclic ring Z.

In another preferred embodiment, said $R^1$ and $R^2$ are independently of each other a morpholinyl of formula (II) and said $OR^{12}$.

In another preferred embodiment, said $R^1$ and $R^2$ are independently of each other a morpholinyl of formula (II) and said $NR^{15}R^{16}$.

In another preferred embodiment, within said morpholinyl of formula (II)

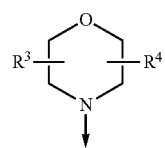

(II)

$R^3$ and $R^4$ are independently of each other H, $C_1$-$C_3$alkyl optionally substituted with one or two OH, $C_1$-$C_2$fluoroalkyl, $C_1$-$C_2$alkoxy, $C_1$-$C_2$alkoxyC$_1$-$C_3$alkyl, CN, or C(O)O—$C_1$-$C_2$alkyl; or $R^3$ and $R^4$ form together a bivalent residue —$R^5R^6$— selected from $C_1$-$C_3$alkylene optionally substituted with 1 to 4 F, —CH$_2$—O—CH$_2$—, —CH$_2$—NH—CH$_2$—, or any of the structures

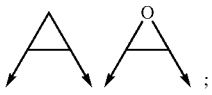

wherein the arrows denote the bonds in formula (II).

In the instance that R3 and R4 together form a bivalent residue and are bound to vicinal carbon atoms annulated morpholinyl substituents are formed. In the instance that R3 and R4 together form a bivalent residue and are spanning across the morpholine ring bridged morpholinyl substituents are formed. In the instance that R3 and R4 together form a bivalent residue and are bound to the same carbon atom of the morpholine, spiro morpholinyl substituents are formed.

In a preferred embodiment, $R^3$ and $R^4$ form together a bivalent residue —$R^5R^6$— selected from $C_1$-$C_3$alkylene optionally substituted with 1 to 4 F, —CH$_2$—O—CH$_2$—, —CH$_2$—NH—CH$_2$—, or any of the structures

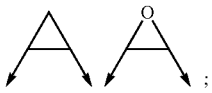

and forming a bridged morpholinyl substituent.

In another preferred embodiment, said $R^1$ and $R^2$ are independently of each other a morpholinyl of formula (II), wherein $R^3$ and $R^4$ form together a bivalent residue leading to a bridged morpholinyl, wherein $R^3$ and $R^4$ form together a bivalent residue —$R^5R^6$— selected from $C_1$-$C_3$alkylene, preferably $C_1$-$C_2$alkylene, —CH$_2$CF$_2$—, —CHFCHF—, —CH$_2$CF$_2$CH$_2$—, —CH$_2$—O—CH$_2$—, —CH$_2$—NH—CH$_2$—, or any of the structures

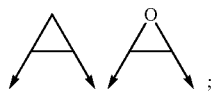

wherein the arrows denote the bonds in formula (II).

In a further preferred embodiment, said morpholinyl of formula (II)

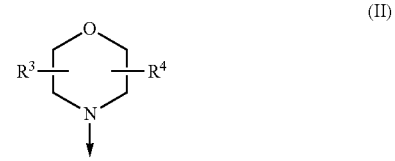

(II)

is independently of each other a morpholinyl of said formula (II), wherein $R^3$ and $R^4$ are independently of each other H, $C_1$-$C_3$alkyl, CH$_2$OH, CH$_2$CH$_2$OH, CH$_2$F, CHF$_2$, CF$_3$, CH$_2$CF$_3$, $C_1$-$C_2$alkoxy, $C_1$-$C_2$alkoxyC$_1$-$C_3$alkyl, CN, or C(O)O—$C_1$-$C_2$alkyl; or $R^3$ and $R^4$ form together a bivalent residue —$R^5R^6$— selected from $C_1$-$C_3$alkylene, preferably $C_1$-$C_2$alkylene, —CH$_2$CF$_2$—, —CHFCHF—, —CH$_2$CF$_2$CH$_2$—, —CH$_2$—O—CH$_2$—, —CH$_2$—NH—CH$_2$—, or any of the structures

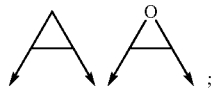

wherein the arrows denote the bonds in formula (II).

In a further preferred embodiment, said morpholinyl of formula (II) is independently of each other a morpholinyl of said formula (II), wherein $R^3$ and $R^4$ are independently of each other H or CH$_3$.

In a further preferred embodiment, said morpholinyl of formula (II) is independently of each other a morpholinyl of said formula (II), wherein $R^3$ and $R^4$ are independently of each other $C_2$-$C_3$alkyl, CH$_2$OH, CH$_2$CH$_2$OH, CH$_2$F, CHF$_2$, CF$_3$, CH$_2$CF$_3$, $C_1$-$C_2$alkoxy, $C_1$-$C_2$alkoxyC$_1$-$C_3$alkyl, CN, or C(O)O—$C_1$-$C_2$alkyl; or $R^3$ and $R^4$ form together a bivalent residue —$R^5R^6$— selected from —CH$_2$— or $C_3$alkylene, preferably —CH$_2$—, —CH$_2$CF$_2$—, —CHFCHF—, —CH$_2$CF$_2$CH$_2$—, —CH$_2$—O—CH$_2$—, —CH$_2$—NH—CH$_2$—, or any of the structures

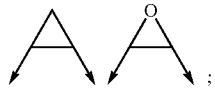

wherein the arrows denote the bonds in formula (II).

In a further preferred embodiment, said morpholinyl of formula (II) is independently of each other selected from

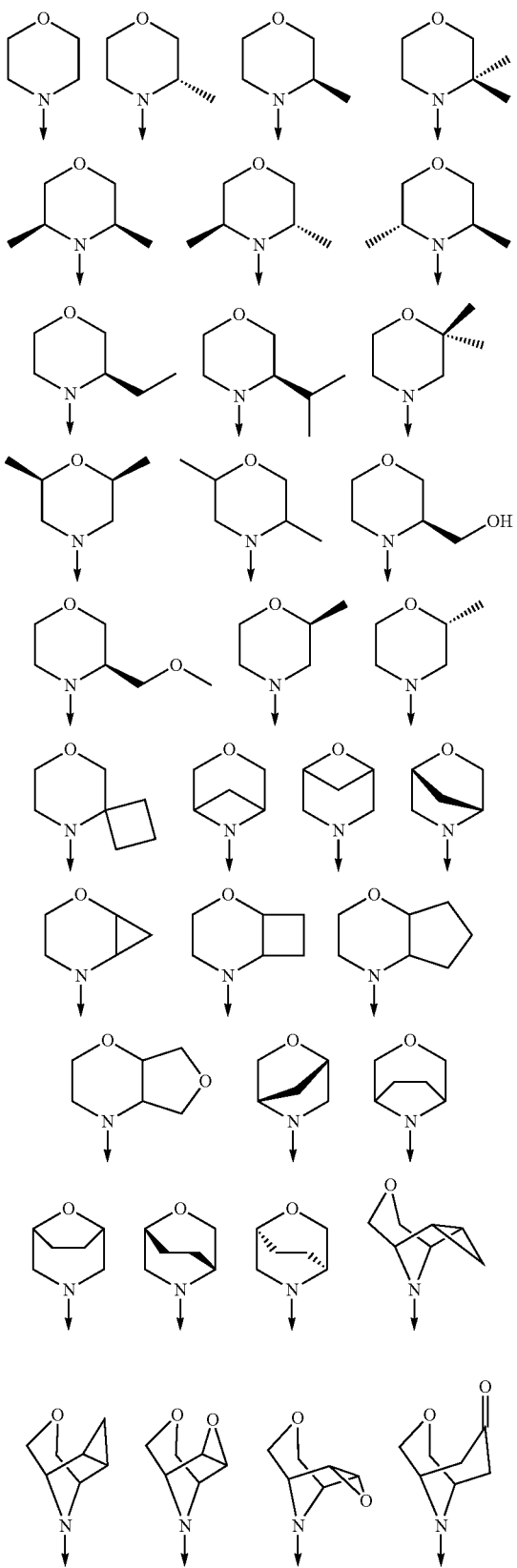

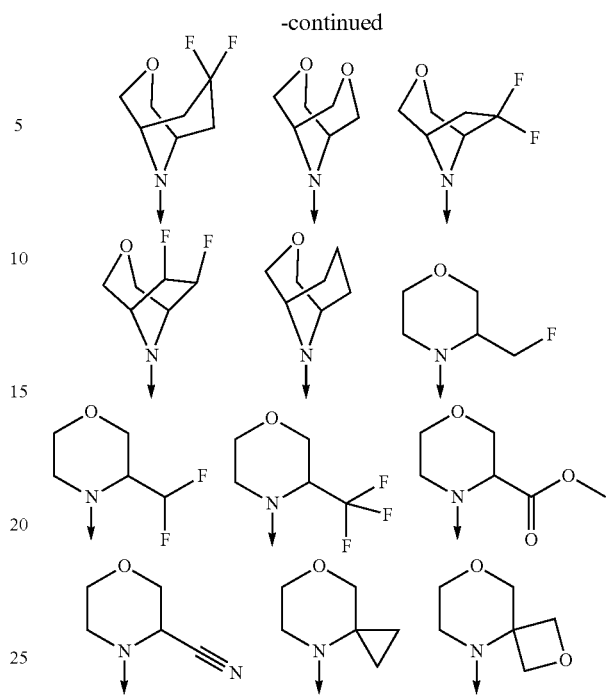

In a further preferred embodiment, said morpholinyl of formula (II) is independently of each other selected from

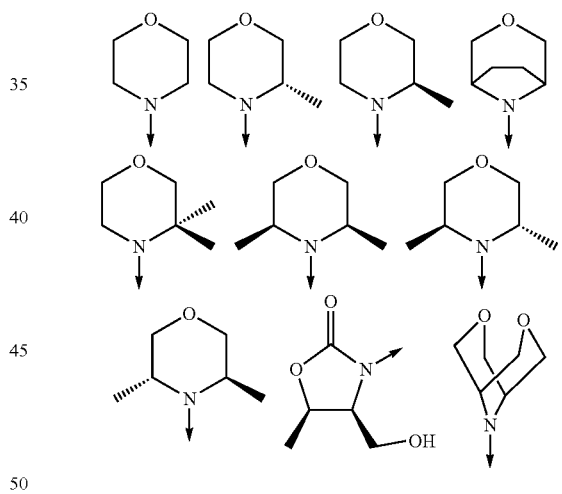

In a further preferred embodiment, $R^1$ or $R^2$ is said 5- to 6-membered heteroaryl ring W.

In a further preferred embodiment, said one to four heteroatoms of said 5- to 6-membered heteroaryl ring W are solely N, and wherein said 6-membered heteroaryl ring W is optionally substituted by 1 to 3 $R^8$, wherein $R^8$ is independently at each occurrence halogen, —OH, $C_1$-$C_3$alkyl optionally substituted with one or two OH, $C_1$-$C_2$fluoroalkyl, $C_1$-$C_2$alkoxy, $C_1$-$C_2$alkoxy$C_1$-$C_3$alkyl, $C_3$-$C_6$cycloalkyl, —$NH_2$, $NHCH_3$ or $N(CH_3)_2$; and tautomers, solvates and pharmaceutically acceptable salts thereof. Preferably, said 5- to 6-membered heteroaryl ring W containing one to four N is optionally substituted by 1 to 3 $R^8$, wherein $R^8$ is independently at each occurrence halogen, —OH, $C_1$-$C_3$alkyl, $CH_2OH$, $CH_2CH_2OH$, $CH_2F$, $CHF_2$, $CF_3$, $CH_2CF_3$, $C_1$-$C_2$alkoxy, $C_1$-$C_2$alkoxy$C_1$-$C_3$alkyl, $C_3$-$C_6$cycloalkyl, —$NH_2$, $NHCH_3$ or $N(CH_3)_2$; and tautomers, solvates and pharmaceutically acceptable salts thereof.

In a further preferred embodiment, said heteroaryl ring W is a 6-membered heteroaryl ring containing one to four heteroatoms, wherein said heteroatoms are solely N, and wherein said 6-membered heteroaryl ring W is optionally substituted by 1 to 3 $R^8$, wherein $R^8$ is independently at each occurrence halogen, preferably fluorine, —OH, $C_1$-$C_3$alkyl, $CH_2OH$, $CH_2CH_2OH$, $CH_2F$, $CHF_2$, $CF_3$, $CH_2CF_3$, $C_1$-$C_2$alkoxy, $C_1$-$C_2$alkoxy$C_1$-$C_3$alkyl, $C_3$-$C_6$cycloalkyl, —$NH_2$, $NHCH_3$ or $N(CH_3)_2$; and tautomers, solvates and pharmaceutically acceptable salts thereof.

In a further preferred embodiment, said 5- to 6-membered heteroaryl ring W is selected from

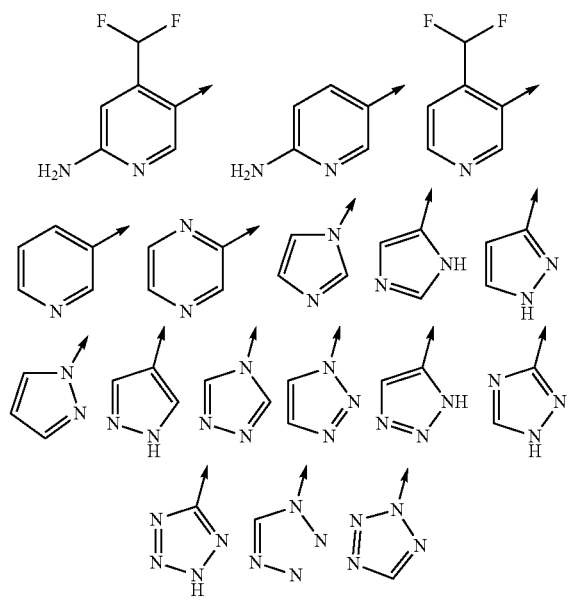

In a further very preferred embodiment, said heteroaryl ring W is a 6-membered heteroaryl ring selected from

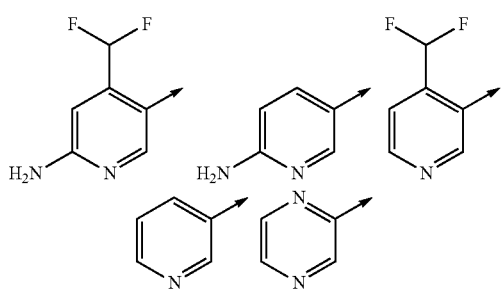

In a further preferred embodiment, $R^1$ or $R^2$ is said 4- to 6-membered heterocyclic ring Z.

In a further preferred embodiment, said heterocyclic ring Z is a saturated 5- to 6-membered heterocyclic ring Z containing 1 to 2 heteroatoms independently selected from N, O and S, optionally substituted by 1 to 3 $R^9$; wherein $R^9$ is independently at each occurrence halogen, —OH, $C_1$-$C_3$alkyl, $CH_2OH$, $CH_2CH_2OH$, $CH_2F$, $CHF_2$, $CF_3$, $CH_2CF_3$, $C_1$-$C_2$alkoxy, $C_1$-$C_2$alkoxy$C_1$-$C_3$alkyl, $C_3$-$C_6$cycloalkyl, =O, —$NH_2$, $NHCH_3$ or $N(CH_3)_2$; or two $R^9$ substituents form together a bivalent residue —$R^{10}R^{11}$— selected from $C_1$-$C_3$alkylene optionally substituted with 1 to 4 F, —$CH_2$—O—$CH_2$— or —O—$CH_2CH_2$—O—;

In a further preferred embodiment, said heterocyclic ring Z is a saturated 5- to 6-membered heterocyclic ring Z selected from

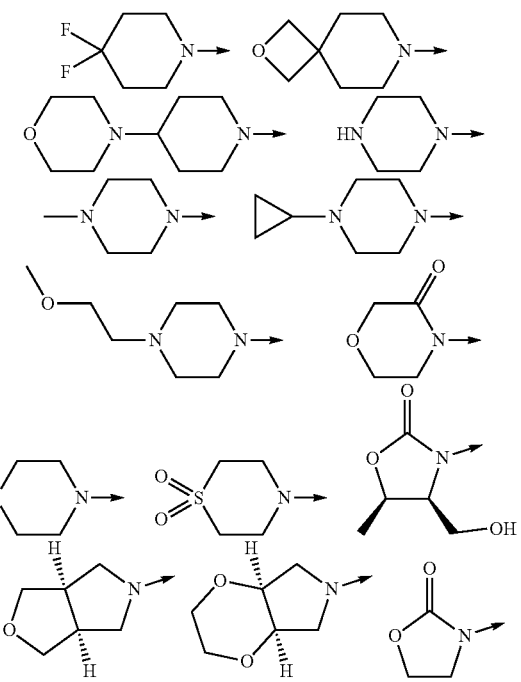

In an again further preferred embodiment, said heterocyclic ring Z is a saturated 5- to 6-membered heterocyclic ring Z selected from

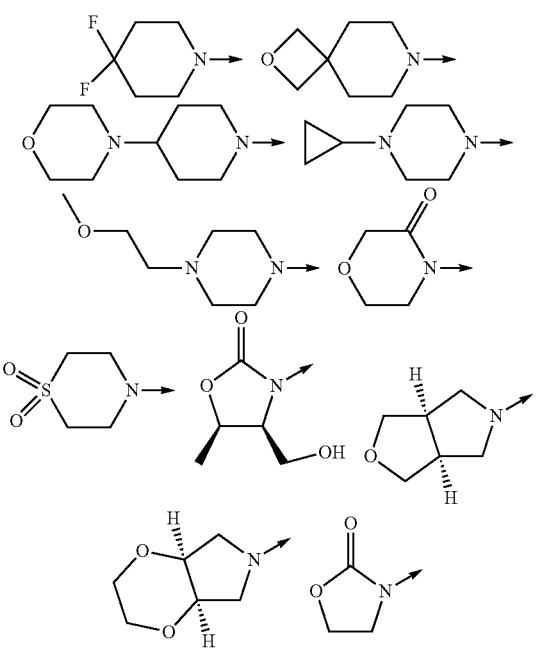

In a preferred embodiment, said heterocyclic ring Z is an oxazolidinyl optionally substituted with halogen, —OH, $C_1$-$C_3$alkyl, $CH_2OH$, $CH_2CH_2OH$, $CH_2F$, $CHF_2$, $CF_3$, $CH_2CF_3$, $C_1$-$C_2$alkoxy, $C_1$-$C_2$alkoxy$C_1$-$C_3$alkyl, =O, —$NH_2$, $NHCH_3$ or $N(CH_3)_2$.

In a further preferred embodiment, said heterocyclic ring Z is

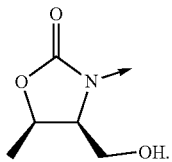

In a further preferred embodiment, $R^1$ or $R^2$ is said $OR^{12}$.

In a further preferred embodiment, said $R^{12}$ is $C_1$-$C_3$alkyl, $CH_2F$, $CHF_2$, $CF_3$, $CH_2CH_2F$, $CH_2CHF_2$, $CH_2CF_3$, $C_1$-$C_3$alkoxy, $C_3$-$C_6$cycloalkyl, $C_1$-$C_2$alkylene$C_3$-$C_6$cycloalkyl; Cycle-P or $C_1$-$C_2$alkyleneCycle-P, wherein Cycle-P represents a saturated 4- to 6-membered heterocyclic ring containing 1 to 2 heteroatoms independently selected from N, O and S, optionally substituted by 1 to 2 $R^{13}$, wherein $R^{13}$ is independently at each occurrence halogen, —OH, $C_1$-$C_3$alkyl, $CH_2OH$, $CH_2CH_2OH$, $C_1$-$C_2$fluoroalkyl, $C_1$-$C_2$alkoxy, $C_1$-$C_2$alkoxy$C_1$-$C_3$alkyl, —$NH_2$, $NHCH_3$ or $N(CH_3)$; Cycle-Q or $C_1$-$C_2$alkyleneCycle-Q, wherein Cycle-Q represents 5- to 6-membered heteroaryl ring containing 1 to 2 heteroatoms independently selected from N, O and S, optionally substituted by 1 to 3 $R^{14}$, wherein $R^{14}$ is independently at each occurrence halogen, —OH, $C_1$-$C_3$alkyl, $CH_2OH$, $CH_2CH_2OH$, $C_1$-$C_2$fluoroalkyl, $C_1$-$C_2$alkoxy, $C_1$-$C_2$alkoxy$C_1$-$C_3$alkyl, —$NH_2$, $NHCH_3$ or $N(CH_3)$.

In a further preferred embodiment, said $R^{12}$ is $C_1$-$C_3$alkyl, $CH_2F$, $CHF_2$, $CF_3$, $CH_2CH_2F$, $CH_2CHF_2$, $CH_2CF_3$, $C_1$-$C_3$alkoxy, $C_3$-$C_6$cycloalkyl, $C_1$-$C_2$alkylene$C_3$-$C_6$cycloalkyl; Cycle-P or $C_1$-$C_2$alkyleneCycle-P, wherein Cycle-P represents a saturated 4- to 6-membered heterocyclic ring containing 1 to 2 heteroatoms independently selected from O and S, preferably from O, optionally substituted by 1 to 2 $R^{13}$, wherein $R^{13}$ is independently at each occurrence halogen, —OH, $C_1$-$C_3$alkyl, $CH_2OH$, $CH_2CH_2OH$, $C_1$-$C_2$fluoroalkyl, $C_1$-$C_2$alkoxy, $C_1$-$C_2$alkoxy$C_1$-$C_3$alkyl, —$NH_2$, $NHCH_3$ or $N(CH_3)$; Cycle-Q or $C_1$-$C_2$alkyleneCycle-Q, wherein Cycle-Q represents 5- to 6-membered heteroaryl ring containing 1 to 2 heteroatoms, wherein said heteroatoms are N, and wherein said heteroaryl ring is optionally substituted by 1 to 3 $R^{14}$, wherein $R^{14}$ is independently at each occurrence halogen, —OH, $C_1$-$C_3$alkyl, $CH_2OH$, $CH_2CH_2OH$, $C_1$-$C_2$fluoroalkyl, $C_1$-$C_2$alkoxy, $C_1$-$C_2$alkoxy$C_1$-$C_3$alkyl, —$NH_2$, $NHCH_3$ or $N(CH_3)$.

In an again further preferred embodiment, said $OR^{12}$ is selected from

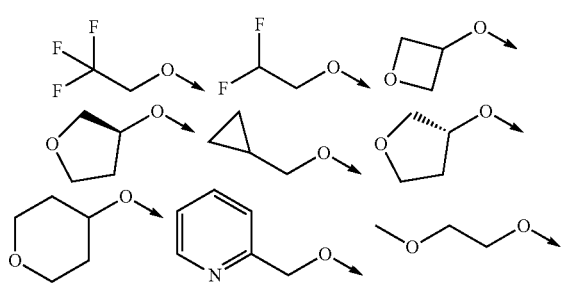

In a further preferred embodiment, $R^1$ or $R^2$ is said $NR^{15}R^{16}$.

In a further preferred embodiment, said $R^{15}$ and $R^{16}$ are independently of each other H, $C_1$-$C_3$alkyl, $CH_2OH$, $CH_2CH_2OH$, $C_1$-$C_2$fluoroalkyl, $C_1$-$C_2$alkoxy, $C_1$-$C_2$alkoxy$C_1$-$C_3$alkyl; Cycle-P or $C_1$-$C_2$alkyleneCycle-P, wherein Cycle-P represents a saturated 4- to 6-membered heterocyclic ring containing 1 to 2 heteroatoms independently selected from O and S, preferably from O, optionally substituted by 1 to 2 $R^{13}$, wherein $R^{13}$ is independently at each occurrence halogen, —OH, $C_1$-$C_3$alkyl, $CH_2OH$, $CH_2CH_2OH$, $C_1$-$C_2$fluoroalkyl, $C_1$-$C_2$alkoxy, $C_1$-$C_2$alkoxy$C_1$-$C_3$alkyl, —$NH_2$, $NHCH_3$ or $N(CH_3)$; Cycle-Q or $C_1$-$C_2$alkyleneCycle-Q, wherein Cycle-Q represents 5- to 6-membered heteroaryl ring containing 1 to 2 heteroatoms, wherein said heteroatoms are N, and wherein said heteroaryl ring is optionally substituted by 1 to 3 $R^{14}$, wherein $R^{14}$ is independently at each occurrence halogen, —OH, $C_1$-$C_3$alkyl, $CH_2OH$, $CH_2CH_2OH$, $C_1$-$C_2$fluoroalkyl, $C_1$-$C_2$alkoxy, $C_1$-$C_2$alkoxy$C_1$-$C_3$alkyl, —$NH_2$, $NHCH_3$ or $N(CH_3)$.

In a further preferred embodiment, said $R^{15}$ and $R^{16}$ are independently of each other H, $C_1$-$C_3$alkyl, $CH_2OH$, $CH_2CH_2OH$, $C_1$-$C_2$fluoroalkyl, $C_1$-$C_2$alkoxy, $C_1$-$C_2$alkoxy$C_1$-$C_3$alkyl; Cycle-P or $C_1$-$C_2$alkyleneCycle-P, wherein Cycle-P represents a saturated 4- to 6-membered heterocyclic ring containing 1 to 2 heteroatoms independently selected from O and S, preferably from O, optionally substituted by 1 to 2 $R^{13}$, wherein $R^{13}$ is independently at each occurrence halogen, —OH, $C_1$-$C_3$alkyl, $CH_2OH$, $CH_2CH_2OH$, $C_1$-$C_2$fluoroalkyl, $C_1$-$C_2$alkoxy, $C_1$-$C_2$alkoxy$C_1$-$C_3$alkyl, —$NH_2$, $NHCH_3$ or $N(CH_3)$; Cycle-Q or $C_1$-$C_2$alkyleneCycle-Q, wherein Cycle-Q represents 5- to 6-membered heteroaryl ring containing 1 to 2 heteroatoms, wherein said heteroatoms are N, and wherein said heteroaryl ring is optionally substituted by 1 to 3 $R^{14}$, wherein $R^{14}$ is independently at each occurrence halogen, —OH, $C_1$-$C_3$alkyl, $CH_2OH$, $CH_2CH_2OH$, $C_1$-$C_2$fluoroalkyl, $C_1$-$C_2$alkoxy, $C_1$-$C_2$alkoxy$C_1$-$C_3$alkyl, —$NH_2$, $NHCH_3$ or $N(CH_3)$.

In an again further preferred embodiment, said $NR^{15}R^{16}$ is selected from

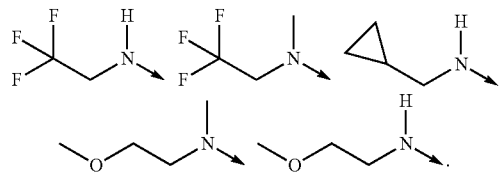

In another preferred embodiment of the present invention, said $R^1$ and said $R^2$ are independently of each other a morpholinyl of formula (II)

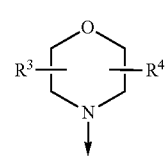

(II)

wherein the arrow denotes the bond in formula (I); and
wherein R³ and R⁴ are independently of each other H, C₁-C₃alkyl optionally substituted with one or two OH, C₁-C₂fluoroalkyl, C₁-C₂alkoxy, C₁-C₂alkoxyC₁-C₃alkyl, CN, or C(O)O—C₁-C₂alkyl; or R³ and R⁴ form together a bivalent residue —R⁵R⁶— selected from C₁-C₃alkylene optionally substituted with 1 to 4 F, —CH₂—O—CH₂—, —CH₂—NH—CH₂—, or any of the structures

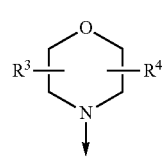

wherein the arrows denote the bonds in formula (II).

In another preferred embodiment of the present invention, said R¹ and said R² are independently of each other a morpholinyl of formula (II)

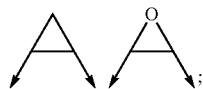

(II)

wherein the arrow denotes the bond in formula (I); and
wherein R³ and R⁴ are independently of each other H, C₁-C₃alkyl optionally substituted with one or two OH, C₁-C₂fluoroalkyl, C₁-C₂alkoxy, C₁-C₂alkoxyC₁-C₃alkyl, CN, or C(O)O—C₁-C₂alkyl; or R³ and R⁴ form together a bivalent residue —R⁵R⁶— selected from C₁-C₃alkylene optionally substituted with 1 to 4 F, —CH₂—O—CH₂—, —CH₂—NH—CH₂—, or any of the structures

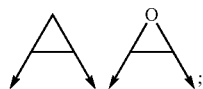

wherein the arrows denote the bonds in formula (II); with the provisos that
(a) when R¹ is 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl; then R² is not 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl;
(b) when R² is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl; then R¹ is not 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl.

In a further preferred embodiment, said R¹ is equal to said R², and said R¹ and said R² are independently of each other a morpholinyl of formula (II)

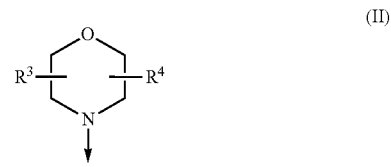

wherein the arrow denotes the bond in formula (I); and
wherein R³ and R⁴ are independently of each other H, C₁-C₃alkyl optionally substituted with one or two OH, C₁-C₂fluoroalkyl, C₁-C₂alkoxy, C₁-C₂alkoxyC₁-C₃alkyl, CN, or C(O)O—C₁-C₂alkyl; or R³ and R⁴ form together a bivalent residue —R⁵R⁶— selected from C₁-C₃alkylene optionally substituted with 1 to 4 F, —CH₂—O—CH₂—, —CH₂—NH—CH₂—, or any of the structures

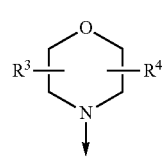

wherein the arrows denote the bonds in formula (II).

In a further preferred embodiment, said R¹ is equal to said R², and said R¹ and said R² are independently of each other a morpholinyl of formula (II)

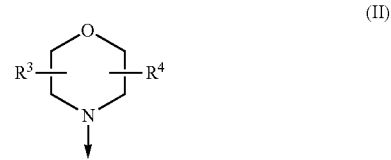

wherein the arrow denotes the bond in formula (I); and
wherein R³ and R⁴ are independently of each other H, C₁-C₃alkyl optionally substituted with one or two OH, C₁-C₂fluoroalkyl, C₁-C₂alkoxy, C₁-C₂alkoxyC₁-C₃alkyl, CN, or C(O)O—C₁-C₂alkyl; or R³ and R⁴ form together a bivalent residue —R⁵R⁶— selected from C₁-C₃alkylene optionally substituted with 1 to 4 F, —CH₂—O—CH₂—, —CH₂—NH—CH₂—, or any of the structures

wherein the arrows denote the bonds in formula (II); with the provisos that
(a) when R¹ is 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl; then R² is not 4-morpholinyl, 2-methyl-4-morpholinyl, 3-methyl-4-morpholinyl, octadeuterio-4-morpholinyl, 8-aza-3-oxabicyclo[3.2.1]

oct-8-yl, 3-aza-8-oxabicyclo[3.2.1]oct-3-yl, 4-piperazin-1-yl, 4-methylpiperazin-1-yl, or 4-thiomorpholinyl;

(b) when $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl; then $R^1$ is not 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl.

In a further preferred embodiment of the present invention, said $R^1$ and said $R^2$ are independently of each other a morpholinyl of formula (II)

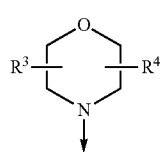

(II)

wherein the arrow denotes the bond in formula (I); and wherein $R^3$ and $R^4$ are independently of each other H, $C_1$-$C_3$alkyl, $CH_2OH$, $CH_2CH_2OH$, $CH_2F$, $CHF_2$, $CF_3$, $CH_2CF_3$, $C_1$-$C_2$alkoxy, $C_1$-$C_2$alkoxy$C_1$-$C_3$alkyl, CN, or $C(O)O$—$C_1$-$C_2$alkyl; or $R^3$ and $R^4$ form together a bivalent residue —$R^5R^6$— selected from $C_1$-$C_3$alkylene, preferably $C_1$-$C_2$alkylene, —$CH_2CF_2$—, —CHFCHF—, —$CH_2CF_2CH_2$—, —$CH_2$—O—$CH_2$—, —$CH_2$—NH—$CH_2$—, or any of the structures

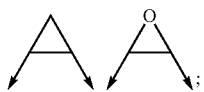

wherein the arrows denote the bonds in formula (II).

In a further preferred embodiment of the present invention, said $R^1$ and said $R^2$ are independently of each other a morpholinyl of formula (II)

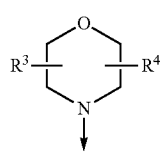

(II)

wherein the arrow denotes the bond in formula (I); and wherein $R^3$ and $R^4$ are independently of each other H, $C_1$-$C_3$alkyl, $CH_2OH$, $CH_2CH_2OH$, $CH_2F$, $CHF_2$, $CF_3$, $CH_2CF_3$, $C_1$-$C_2$alkoxy, $C_1$-$C_2$alkoxy$C_1$-$C_3$alkyl, CN, or $C(O)O$—$C_1$-$C_2$alkyl; or $R^3$ and $R^4$ form together a bivalent residue —$R^5R^6$— selected from $C_1$-$C_3$alkylene, preferably $C_1$-$C_2$alkylene, —$CH_2CF_2$—, —CHFCHF—, —$CH_2CF_2CH_2$—, —$CH_2$—O—$CH_2$—, —$CH_2$—NH—$CH_2$—, or any of the structures

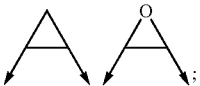

wherein the arrows denote the bonds in formula (II); with the provisos that (a) when $R^1$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl; then $R^2$ is not 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl;

(b) when $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl; then $R^1$ is not 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl.

In a further preferred embodiment of the present invention, $R^1$ is equal to $R^2$, and said $R^1$ and said $R^2$ are a morpholinyl of formula (II)

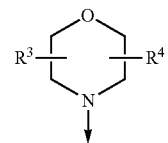

(II)

wherein the arrow denotes the bond in formula (I); and wherein $R^3$ and $R^4$ are independently of each other H, $C_1$-$C_3$alkyl, $CH_2OH$, $CH_2CH_2OH$, $CH_2F$, $CHF_2$, $CF_3$, $CH_2CF_3$, $C_1$-$C_2$alkoxy, $C_1$-$C_2$alkoxy$C_1$-$C_3$alkyl, CN, or $C(O)O$—$C_1$-$C_2$alkyl; or $R^3$ and $R^4$ form together a bivalent residue —$R^5R^6$— selected from $C_1$-$C_3$alkylene, preferably $C_1$-$C_2$alkylene, —$CH_2CF_2$—, —CHFCHF—, —$CH_2CF_2CH_2$—, —$CH_2$—O—$CH_2$—, —$CH_2$—NH—$CH_2$—, or any of the structures

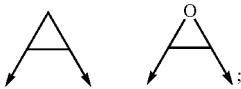

wherein the arrows denote the bonds in formula (II).

In a further preferred embodiment of the present invention, $R^1$ is equal to $R^2$, and said $R^1$ and said $R^2$ are a morpholinyl of formula (II)

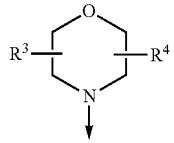

(II)

wherein the arrow denotes the bond in formula (I); and
wherein $R^3$ and $R^4$ are independently of each other H, $C_1$-$C_3$alkyl, $CH_2OH$, $CH_2CH_2OH$, $CH_2F$, $CHF_2$, $CF_3$, $CH_2CF_3$, $C_1$-$C_2$alkoxy, $C_1$-$C_2$alkoxy$C_1$-$C_3$alkyl, CN, or $C(O)O$—$C_1$-$C_2$alkyl; or $R^3$ and $R^4$ form together a bivalent residue —$R^5R^6$— selected from $C_1$-$C_3$alkylene, preferably $C_1$-$C_2$alkylene, —$CH_2CF_2$—, —CHFCHF—, —$CH_2CF_2CH_2$—, —$CH_2$—O—$CH_2$—, —$CH_2$—NH—$CH_2$—, or any of the structures

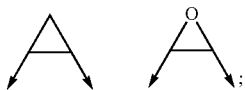

wherein the arrows denote the bonds in formula (II); with the provisos that (a) when $R^1$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl; then $R^2$ is not 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl;

(b) when $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl; then $R^1$ is not 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl.

In another aspect and preferred embodiment, the present invention provides for a compound of (I)

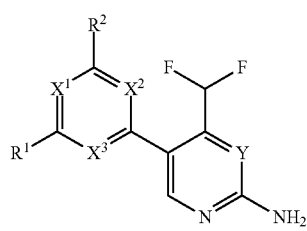

(I)

wherein
$X^1$, $X^2$ and $X^3$ are, independently of each other, N or CH; with the proviso that at least two of $X^1$, $X^2$ and $X^3$ are N; Y is N or CH; and wherein
$R^1$ and $R^2$ are independently of each other a morpholinyl of formula (II)

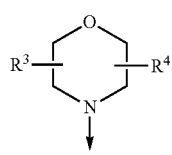

(II)

wherein the arrow denotes the bond in formula (I); and $R^1$ is not equal to $R^2$, and at least one of said $R^1$ and said $R^2$ are a morpholinyl of formula (II),

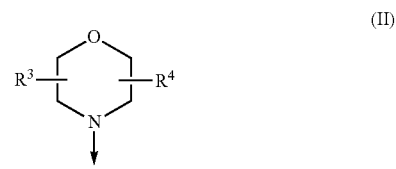

(II)

wherein $R^3$ and $R^4$ are independently of each other $C_2$-$C_3$alkyl, $CH_2OH$, $CH_2CH_2OH$, $CH_2F$, $CHF_2$, $CF_3$, $CH_2CF_3$, $C_1$-$C_2$alkoxy, $C_1$-$C_2$alkoxy$C_1$-$C_3$alkyl, CN, or $C(O)O$—$C_1$-$C_2$alkyl; or $R^3$ and $R^4$ form together a bivalent residue —$R^5R^6$— selected from —$CH_2$— or $C_3$alkylene, preferably —$CH_2$—, —$CH_2CF_2$—, —CHFCHF—, —$CH_2CF_2CH_2$—, —$CH_2$—O—$CH_2$—, —$CH_2$—NH—$CH_2$—, or any of the structures

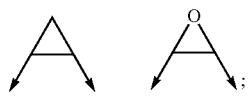

wherein the arrows denote the bonds in formula (II). Preferably, said $R^3$ and $R^4$ form together a bivalent residue —$R^5R^6$— selected from —$CH_2$— or $C_3$alkylene, preferably —$CH_2$—, —$CH_2CF_2$—, —CHFCHF—, —$CH_2CF_2CH_2$—, —$CH_2$—O—$CH_2$—, —$CH_2$—NH—$CH_2$—, or any of the structures

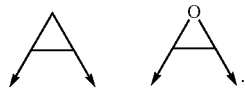

In a further aspect and preferred embodiment, the present invention provides for a compound of formula (I), wherein $R^1$ and $R^2$ are independently of each other said morpholinyl of formula (II) and said 5- to 6-membered heteroaryl ring W, and tautomers, solvates and pharmaceutically acceptable salts thereof.

In a further aspect and preferred embodiment, the present invention provides for a compound of (I)

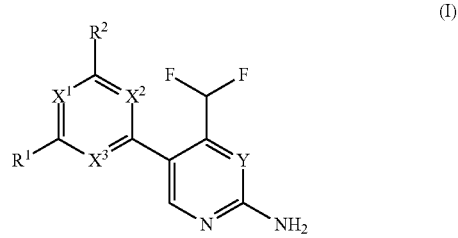

(I)

wherein
$X^1$, $X^2$ and $X^3$ are, independently of each other, N or CH; with the proviso that at least two of $X^1$, $X^2$ and $X^3$ are N; Y is N or CH; and

49

$R^1$ and $R^2$ are independently of each other
(i) a morpholinyl of formula (II)

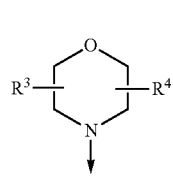
(II)

wherein the arrow denotes the bond in formula (I); and
wherein $R^3$ and $R^4$ are independently of each other H, $C_1$-$C_3$alkyl optionally substituted with one or two OH, $C_1$-$C_2$fluoroalkyl, $C_1$-$C_2$alkoxy, $C_1$-$C_2$alkoxyC$_1$-C$_3$alkyl, CN, or C(O)O—$C_1$-$C_2$alkyl; or $R^3$ and $R^4$ form together a bivalent residue —$R^5R^6$— selected from $C_1$-$C_3$alkylene optionally substituted with 1 to 4 F, —CH$_2$—O—CH$_2$—, —CH$_2$—NH—CH$_2$—, or any of the structures

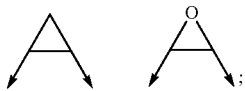;

wherein the arrows denote the bonds in formula (II); and
(ii) a 5- to 6-membered heteroaryl ring W containing one to four heteroatoms independently selected from N, O and S, optionally substituted by 1 to 3 $R^8$, wherein $R^8$ is independently at each occurrence halogen, —OH, $C_1$-$C_3$alkyl optionally substituted with one or two OH, $C_1$-$C_2$fluoroalkyl, $C_1$-$C_2$alkoxy, $C_1$-$C_2$alkoxyC$_1$-C$_3$alkyl, $C_3$-$C_6$cycloalkyl, —NH$_2$, NHCH$_3$ or N(CH$_3$)$_2$;

and prodrugs, metabolites, tautomers, solvates and pharmaceutically acceptable salts thereof, preferably and tautomers, solvates and pharmaceutically acceptable salts thereof.

In a preferred embodiment, the present invention provides for a compound of (I)

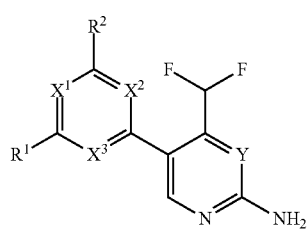
(I)

wherein
$X^1$, $X^2$ and $X^3$ are, independently of each other, N or CH; with the proviso that at least two of $X^1$, $X^2$ and $X^3$ are N; Y is N or CH; and

50

$R^1$ and $R^2$ are independently of each other
(i) a morpholinyl of formula (II)

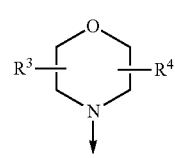
(II)

wherein the arrow denotes the bond in formula (I); and
wherein $R^3$ and $R^4$ are independently of each other H, $C_1$-$C_3$alkyl optionally substituted with one or two OH, $C_1$-$C_2$fluoroalkyl, $C_1$-$C_2$alkoxy, $C_1$-$C_2$alkoxyC$_1$-C$_3$alkyl, CN, or C(O)O—$C_1$-$C_2$alkyl; or $R^3$ and $R^4$ form together a bivalent residue —$R^5R^6$— selected from $C_1$-$C_3$alkylene optionally substituted with 1 to 4 F, —CH$_2$—O—CH$_2$—, —CH$_2$—NH—CH$_2$—, or any of the structures

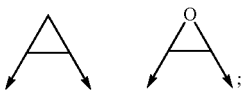;

wherein the arrows denote the bonds in formula (II); and
(ii) a 5- to 6-membered heteroaryl ring W containing one to four heteroatoms, wherein said heteroatoms are solely N, and wherein said 6-membered heteroaryl ring W is optionally substituted by 1 to 3 $R^8$, wherein $R^8$ is independently at each occurrence halogen, —OH, $C_1$-$C_3$alkyl optionally substituted with one or two OH, $C_1$-$C_2$fluoroalkyl, $C_1$-$C_2$alkoxy, $C_1$-$C_2$alkoxyC$_1$-C$_3$alkyl, $C_3$-$C_6$cycloalkyl, —NH$_2$, NHCH$_3$ or N(CH$_3$)$_2$; and tautomers, solvates and pharmaceutically acceptable salts thereof. Preferably, said 5- to 6-membered heteroaryl ring W containing one to four N is optionally substituted by 1 to 3 $R^8$, wherein $R^8$ is independently at each occurrence halogen, —OH, $C_1$-$C_3$alkyl, CH$_2$OH, CH$_2$CH$_2$OH, CH$_2$F, CHF$_2$, CF$_3$, CH$_2$CF$_3$, $C_1$-$C_2$alkoxy, $C_1$-$C_2$alkoxyC$_1$-C$_3$alkyl, $C_3$-$C_6$cycloalkyl, —NH$_2$, NHCH$_3$ or N(CH$_3$)$_2$;

and tautomers, solvates and pharmaceutically acceptable salts thereof.

In a further preferred embodiment, the present invention provides for a compound of (I)

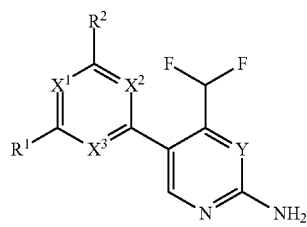
(I)

wherein
$X^1$, $X^2$ and $X^3$ are, independently of each other, N or CH; with the proviso that at least two of $X^1$, $X^2$ and $X^3$ are N; Y is N or CH; and $R^1$ and $R^2$ are independently of each other (i) a morpholinyl of formula (II)

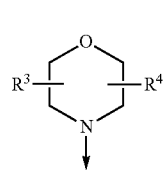

(II)

wherein the arrow denotes the bond in formula (I); and wherein $R^3$ and $R^4$ are independently of each other H, $C_1$-$C_3$alkyl, $CH_2OH$, $CH_2CH_2OH$, $CH_2F$, $CHF_2$, $CF_3$, $CH_2CF_3$, $C_1$-$C_2$alkoxy, $C_1$-$C_2$alkoxy$C_1$-$C_3$alkyl, CN, or C(O)O—$C_1$-$C_2$alkyl; or $R^3$ and $R^4$ form together a bivalent residue —$R^5R^6$— selected from $C_1$-$C_3$alkylene, preferably $C_1$-$C_2$alkylene, —$CH_2CF_2$—, —CHFCHF—, —$CH_2CF_2CH_2$—, —$CH_2$—O—$CH_2$—, —$CH_2$—NH—$CH_2$—, or any of the structures

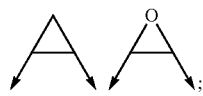

wherein the arrows denote the bonds in formula (II); and (ii) a 5- to 6-membered heteroaryl ring W containing one to four heteroatoms, wherein said heteroatoms are solely N, and wherein said 5- to 6-membered heteroaryl ring W is optionally substituted by 1 to 3 $R^8$, wherein $R^8$ is independently at each occurrence halogen, —OH, $C_1$-$C_3$alkyl, $CH_2OH$, $CH_2CH_2OH$, $CH_2F$, $CHF_2$, $CF_3$, $CH_2CF_3$, $C_1$-$C_2$alkoxy, $C_1$-$C_2$alkoxy$C_1$-$C_3$alkyl, $C_3$-$C_6$cycloalkyl, —$NH_2$, $NHCH_3$ or $N(CH_3)_2$;

and tautomers, solvates and pharmaceutically acceptable salts thereof.

In a further preferred embodiment, the present invention provides for a compound of (I)

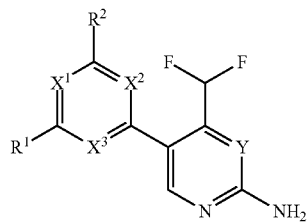

(I)

wherein $X^1$, $X^2$ and $X^3$ are, independently of each other, N or CH; with the proviso that at least two of $X^1$, $X^2$ and $X^3$ are N; Y is N or CH; and $R^1$ and $R^2$ are independently of each other (i) a morpholinyl of formula (II)

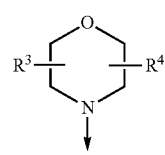

(II)

wherein the arrow denotes the bond in formula (I); and wherein $R^3$ and $R^4$ are independently of each other H, $C_1$-$C_3$alkyl, $CH_2OH$, $CH_2CH_2OH$, $CH_2F$, $CHF_2$, $CF_3$, $CH_2CF_3$, $C_1$-$C_2$alkoxy, $C_1$-$C_2$alkoxy$C_1$-$C_3$alkyl, CN, or C(O)O—$C_1$-$C_2$alkyl; or $R^3$ and $R^4$ form together a bivalent residue —$R^5R^6$— selected from $C_1$-$C_3$alkylene, preferably $C_1$-$C_2$alkylene, —$CH_2CF_2$—, —CHFCHF—, —$CH_2CF_2CH_2$—, —$CH_2$—O—$CH_2$—, —$CH_2$—NH—$CH_2$—, or any of the structures

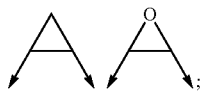

wherein the arrows denote the bonds in formula (II); and (ii) a 5- to 6-membered heteroaryl ring W containing one to four heteroatoms, wherein said heteroatoms are solely N, and wherein said 5- to 6-membered heteroaryl ring W is optionally substituted by 1 to 3 $R^8$, wherein $R^8$ is independently at each occurrence halogen, —OH, $C_1$-$C_3$alkyl, $CH_2OH$, $CH_2CH_2OH$, $CH_2F$, $CHF_2$, $CF_3$, $CH_2CF_3$, $C_1$-$C_2$alkoxy, $C_1$-$C_2$alkoxy$C_1$-$C_3$alkyl, $C_3$-$C_6$cycloalkyl, —$NH_2$, $NHCH_3$ or $N(CH_3)_2$;

and tautomers, solvates and pharmaceutically acceptable salts thereof.

In a further preferred embodiment, the present invention provides for a compound of (I)

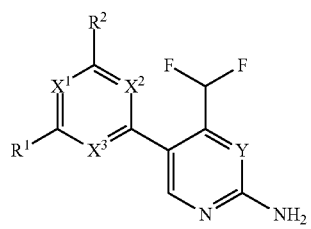

(I)

wherein $X^1$, $X^2$ and $X^3$ are, independently of each other, N or CH; with the proviso that at least two of $X^1$, $X^2$ and $X^3$ are N; Y is N or CH; and wherein $R^1$ and $R^2$ are independently of each other said morpholinyl of formula (II) and said 5- to 6-membered heteroaryl ring W, wherein said $R^1$ and said $R^2$ are independently of each other selected from

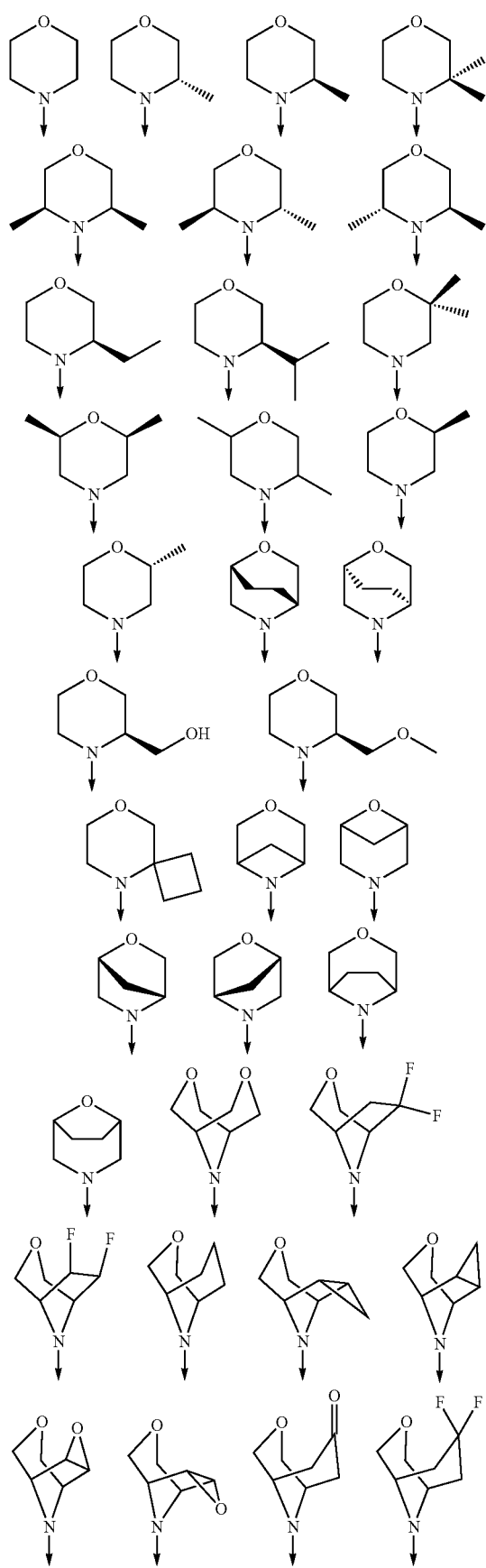
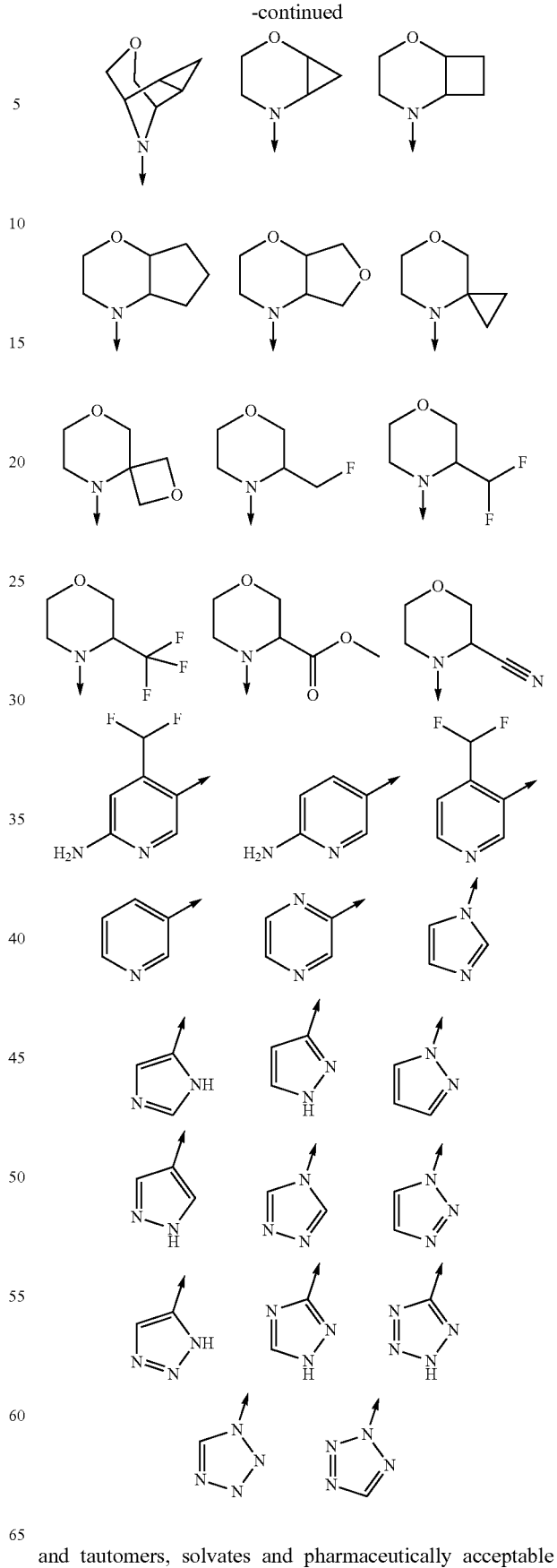
-continued
and tautomers, solvates and pharmaceutically acceptable salts thereof.

In a further preferred embodiment, the present invention provides for a compound of (I)

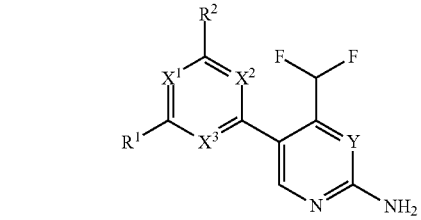
(I)

wherein $X^1$, $X^2$ and $X^3$ are, independently of each other, N or CH; with the proviso that at least two of $X^1$, $X^2$ and $X^3$ are N; Y is N or CH; and wherein $R^1$ and $R^2$ are independently of each other said morpholinyl of formula (II) and said 5- to 6-membered heteroaryl ring W, wherein said $R^1$ and said $R^2$ are independently of each other selected from

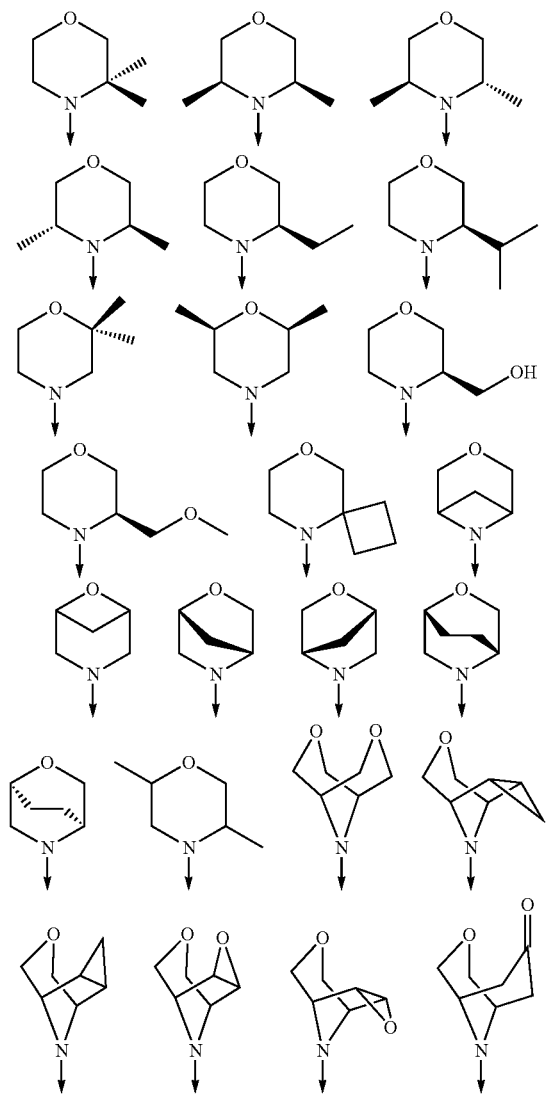

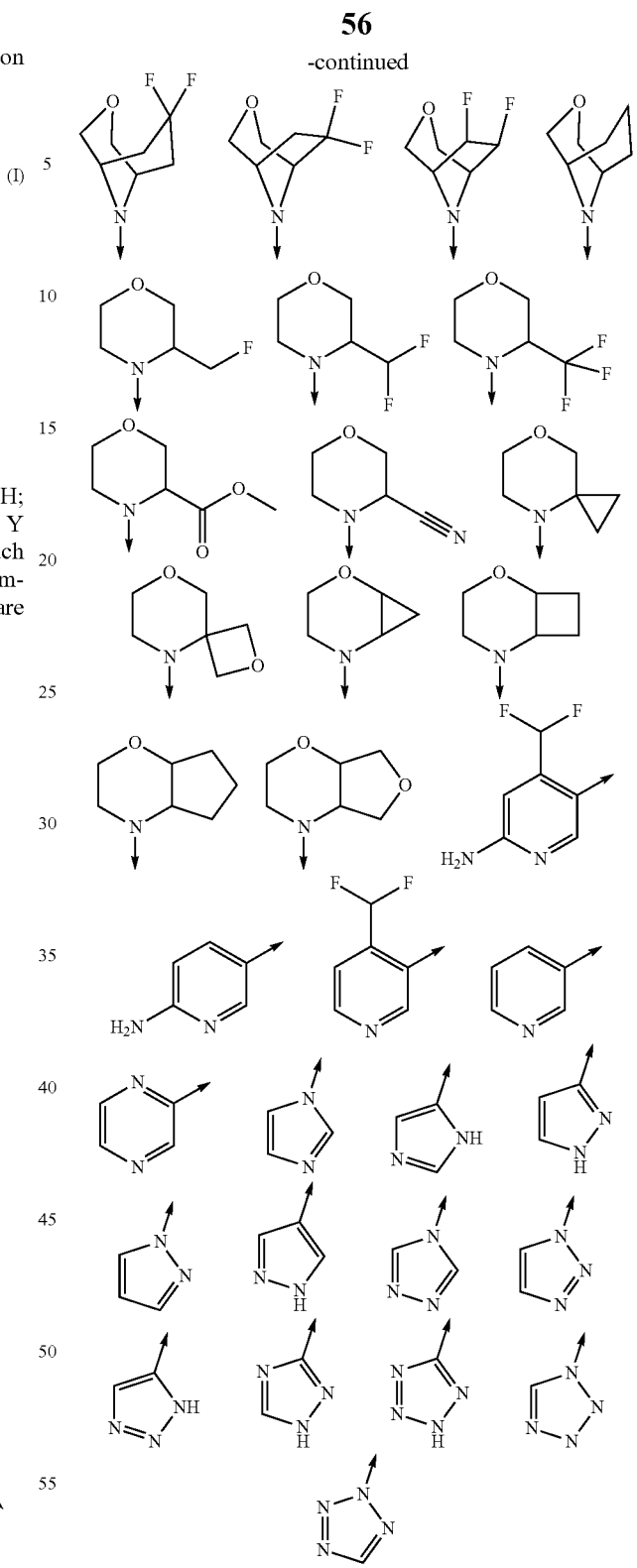

and tautomers, solvates and pharmaceutically acceptable salts thereof.

In a further aspect and preferred embodiment, the present invention provides for a compound of formula (I), wherein $R^1$ and $R^2$ are independently of each other said morpholinyl of formula (II) and said saturated 4- to 6-membered heterocyclic ring Z, and tautomers, solvates and pharmaceutically acceptable salts thereof.

In a further aspect and preferred embodiment, the present invention provides for a compound of (I)

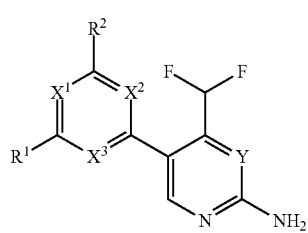

wherein
$X^1$, $X^2$ and $X^3$ are, independently of each other, N or CH; with the proviso that at least two of $X^1$, $X^2$ and $X^3$ are N; Y is N or CH; and $R^1$ and $R^2$ are independently of each other (i) a morpholinyl of formula (II)

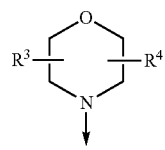

wherein the arrow denotes the bond in formula (I); and
wherein $R^3$ and $R^4$ are independently of each other H, $C_1$-$C_3$alkyl optionally substituted with one or two OH, $C_1$-$C_2$fluoroalkyl, $C_1$-$C_2$alkoxy, $C_1$-$C_2$alkoxyC$_1$-C$_3$alkyl, CN, or C(O)O—$C_1$-$C_2$alkyl; or $R^3$ and $R^4$ form together a bivalent residue —$R^5R^6$— selected from $C_1$-$C_3$alkylene optionally substituted with 1 to 4 F, —CH$_2$—O—CH$_2$—, —CH$_2$—NH—CH$_2$—, or any of the structures

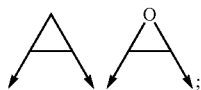

wherein the arrows denote the bonds in formula (II); and
(ii) a saturated 4- to 6-membered heterocyclic ring Z containing 1 to 3 heteroatoms independently selected from N, O and S, optionally substituted by 1 to 3 $R^9$; wherein $R^9$ is independently at each occurrence halogen, —OH, $C_1$-$C_3$alkyl optionally substituted with one or two OH, $C_1$-$C_2$fluoroalkyl, $C_1$-$C_2$alkoxy, $C_1$-$C_2$alkoxyC$_1$-$C_3$alkyl, $C_3$-$C_6$cycloalkyl, =O, —NH$_2$, NHCH$_3$ or N(CH$_3$)$_2$; or two $R^9$ substituents form together a bivalent residue —$R^{10}R^{11}$— selected from $C_1$-$C_3$alkylene optionally substituted with 1 to 4 F, —CH$_2$—O—CH$_2$— or —O—CH$_2$CH$_2$—O—; and prodrugs, metabolites, tautomers, solvates and pharmaceutically acceptable salts thereof, preferably and tautomers, solvates and pharmaceutically acceptable salts thereof.

In a further aspect and preferred embodiment, the present invention provides for a compound of (I)

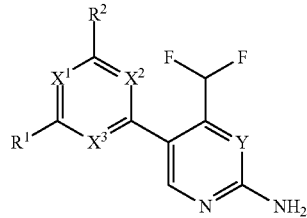

wherein
$X^1$, $X^2$ and $X^3$ are, independently of each other, N or CH; with the proviso that at least two of $X^1$, $X^2$ and $X^3$ are N; Y is N or CH; and
$R^1$ and $R^2$ are independently of each other
(i) a morpholinyl of formula (II)

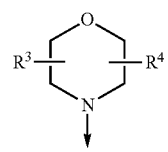

wherein the arrow denotes the bond in formula (I); and
wherein $R^3$ and $R^4$ are independently of each other H, $C_1$-$C_3$alkyl optionally substituted with one or two OH, $C_1$-$C_2$fluoroalkyl, $C_1$-$C_2$alkoxy, $C_1$-$C_2$alkoxyC$_1$-$C_3$alkyl, CN, or C(O)O—$C_1$-$C_2$alkyl; or $R^3$ and $R^4$ form together a bivalent residue —$R^5R^6$— selected from $C_1$-$C_3$alkylene optionally substituted with 1 to 4 F, —CH$_2$—O—CH$_2$—, —CH$_2$—NH—CH$_2$—, or any of the structures

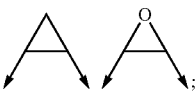

wherein the arrows denote the bonds in formula (II); and
(ii) a saturated 4- to 6-membered heterocyclic ring Z containing 1 to 3 heteroatoms independently selected from N, O and S, optionally substituted by 1 to 3 $R^9$; wherein $R^9$ is independently at each occurrence halogen, —OH, $C_1$-$C_3$alkyl optionally substituted with one or two OH, $C_1$-$C_2$fluoroalkyl, $C_1$-$C_2$alkoxy, $C_1$-$C_2$alkoxyC$_1$-$C_3$alkyl, $C_3$-$C_6$cycloalkyl, =O, —NH$_2$, NHCH$_3$ or N(CH$_3$)$_2$; or two $R^9$ substituents form together a bivalent residue —$R^{10}R^{11}$— selected from $C_1$-$C_3$alkylene optionally substituted with 1 to 4 F, —CH$_2$—O—CH$_2$— or —O—CH$_2$CH$_2$—O—;
and prodrugs, metabolites, tautomers, solvates and pharmaceutically acceptable salts thereof, preferably and tautomers, solvates and pharmaceutically acceptable salts thereof; with the provisos that
(a) when $R^1$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl; then $R^2$ is not 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl;

(b) when $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl; then $R^1$ is not 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl.

In a preferred embodiment, the present invention provides for a compound of (I)

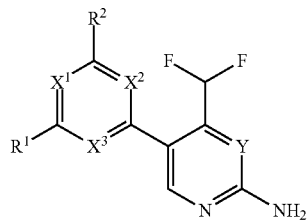

(I)

wherein $X^1$, $X^2$ and $X^3$ are, independently of each other, N or CH; with the proviso that at least two of $X^1$, $X^2$ and $X^3$ are N; Y is N or CH; and $R^1$ and $R^2$ are independently of each other (i) a morpholinyl of formula (II)

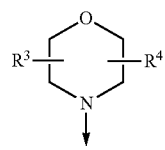

(II)

wherein the arrow denotes the bond in formula (I); and wherein $R^3$ and $R^4$ are independently of each other H, $C_1$-$C_3$alkyl optionally substituted with one or two OH, $C_1$-$C_2$fluoroalkyl, $C_1$-$C_2$alkoxy, $C_1$-$C_2$alkoxyC$_1$-C$_3$alkyl, CN, or C(O)O—$C_1$-$C_2$alkyl; or $R^3$ and $R^4$ form together a bivalent residue —$R^5R^6$— selected from $C_1$-$C_3$alkylene optionally substituted with 1 to 4 F, —CH$_2$—O—CH$_2$—, —CH$_2$—NH—CH$_2$—, or any of the structures

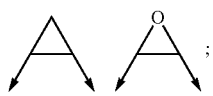;

wherein the arrows denote the bonds in formula (II); and (ii) a saturated 5- to 6-membered heterocyclic ring Z containing 1 to 2 heteroatoms independently selected from N, O and S, optionally substituted by 1 to 3 $R^9$; wherein $R^9$ is independently at each occurrence halogen, —OH, $C_1$-$C_3$alkyl, CH$_2$OH, CH$_2$CH$_2$OH, CH$_2$F, CHF$_2$, CF$_3$, CH$_2$CF$_3$, $C_1$-$C_2$alkoxy, $C_1$-$C_2$alkoxyC$_1$-$C_3$alkyl, $C_3$-$C_6$cycloalkyl, =O, —NH$_2$, NHCH$_3$ or N(CH$_3$)$_2$; or two $R^9$ substituents form together a bivalent residue —$R^{10}R^{11}$— selected from $C_1$-$C_3$alkylene optionally substituted with 1 to 4 F, —CH$_2$—O—CH$_2$— or —O—CH$_2$CH$_2$—O—;

and tautomers, solvates and pharmaceutically acceptable salts thereof.

In a preferred embodiment, the present invention provides for a compound of (I)

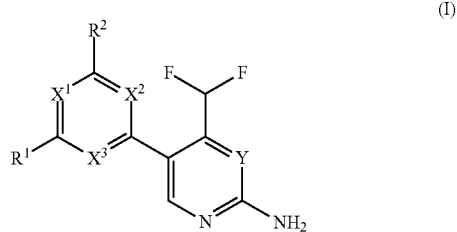

(I)

wherein $X^1$, $X^2$ and $X^3$ are, independently of each other, N or CH; with the proviso that at least two of $X^1$, $X^2$ and $X^3$ are N; Y is N or CH; and $R^1$ and $R^2$ are independently of each other (i) a morpholinyl of formula (II)

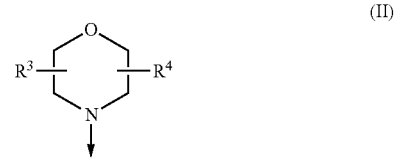

(II)

wherein the arrow denotes the bond in formula (I); and wherein $R^3$ and $R^4$ are independently of each other H, $C_1$-$C_3$alkyl optionally substituted with one or two OH, $C_1$-$C_2$fluoroalkyl, $C_1$-$C_2$alkoxy, $C_1$-$C_2$alkoxyC$_1$-$C_3$alkyl, CN, or C(O)O—$C_1$-$C_2$alkyl; or $R^3$ and $R^4$ form together a bivalent residue —$R^5R^6$— selected from $C_1$-$C_3$alkylene optionally substituted with 1 to 4 F, —CH$_2$—O—CH$_2$—, —CH$_2$—NH—CH$_2$—, or any of the structures

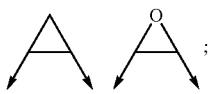;

wherein the arrows denote the bonds in formula (II); and (ii) a saturated 5- to 6-membered heterocyclic ring Z containing 1 to 2 heteroatoms independently selected from N, O and S, optionally substituted by 1 to 3 $R^9$; wherein $R^9$ is independently at each occurrence halogen, —OH, $C_1$-$C_3$alkyl, CH$_2$OH, CH$_2$CH$_2$OH, CH$_2$F, CHF$_2$, CF$_3$, CH$_2$CF$_3$, $C_1$-$C_2$alkoxy, $C_1$-$C_2$alkoxyC$_1$-$C_3$alkyl, $C_3$-$C_6$cycloalkyl, =O, —NH$_2$, NHCH$_3$ or N(CH$_3$)$_2$; or two $R^9$ substituents form together a bivalent residue —$R^{10}R^{11}$— selected from $C_1$-$C_3$alkylene optionally substituted with 1 to 4 F, —CH$_2$—O—CH$_2$— or —O—CH$_2$CH$_2$—O—;

and tautomers, solvates and pharmaceutically acceptable salts thereof; with the provisos that (a) when $R^1$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl; then $R^2$ is not 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl;

(b) when $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl; then $R^1$ is not 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl.

In a further preferred embodiment, the present invention provides for a compound of (I)

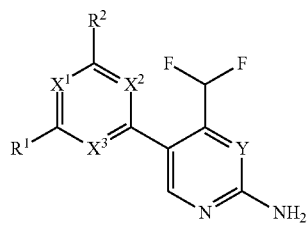
(I)

wherein
$X^1$, $X^2$ and $X^3$ are, independently of each other, N or CH; with the proviso that at least two of $X^1$, $X^2$ and $X^3$ are N; Y is N or CH; and
$R^1$ and $R^2$ are independently of each other
(i) a morpholinyl of formula (II)

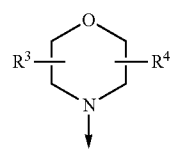
(II)

wherein the arrow denotes the bond in formula (I); and
wherein $R^3$ and $R^4$ are independently of each other H, $C_1$-$C_3$alkyl, $CH_2OH$, $CH_2CH_2OH$, $CH_2F$, $CHF_2$, $CF_3$, $CH_2CF_3$, $C_1$-$C_2$alkoxy, $C_1$-$C_2$alkoxyC_1$-$C_3$alkyl, CN, or $C(O)O$—$C_1$-$C_2$alkyl; or $R^3$ and $R^4$ form together a bivalent residue —$R^5R^6$— selected from $C_1$-$C_3$alkylene, preferably $C_1$-$C_2$alkylene, —$CH_2CF_2$—, —CHFCHF—, —$CH_2CF_2CH_2$—, —$CH_2$—O—$CH_2$—, —$CH_2$—NH—$CH_2$—, or any of the structures

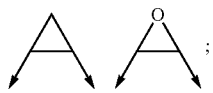;

wherein the arrows denote the bonds in formula (II); and (ii) a saturated 5- to 6-membered heterocyclic ring Z containing 1 to 2 heteroatoms independently selected from N, O and S, optionally substituted by 1 to 3 $R^9$; wherein $R^9$ is independently at each occurrence halogen, —OH, $C_1$-$C_3$alkyl, $CH_2OH$, $CH_2CH_2OH$, $CH_2F$, $CHF_2$, $CF_3$, $CH_2CF_3$, $C_1$-$C_2$alkoxy, $C_1$-$C_2$alkoxyC_1$-$C_3$alkyl, $C_3$-$C_8$cycloalkyl, =O, —$NH_2$, $NHCH_3$ or $N(CH_3)_2$; or two $R^9$ substituents form together a bivalent residue —$R^{10}R^{11}$— selected from $C_1$-$C_3$alkylene optionally substituted with 1 to 4 F, —$CH_2$—O—$CH_2$— or —O—$CH_2CH_2$—O—.

and tautomers, solvates and pharmaceutically acceptable salts thereof.

In a further preferred embodiment, the present invention provides for a compound of (I)

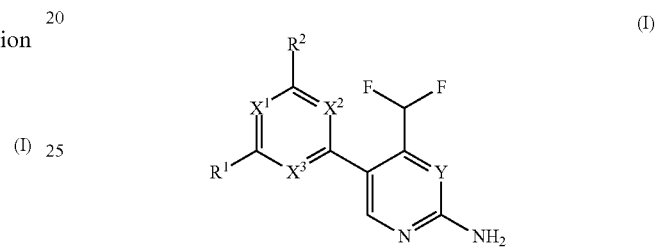
(I)

wherein
$X^1$, $X^2$ and $X^3$ are, independently of each other, N or CH; with the proviso that at least two of $X^1$, $X^2$ and $X^3$ are N; Y is N or CH; and
$R^1$ and $R^2$ are independently of each other
(i) a morpholinyl of formula (II)

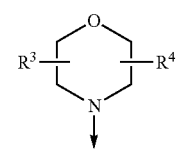
(II)

wherein the arrow denotes the bond in formula (I); and
wherein $R^3$ and $R^4$ are independently of each other H, $C_1$-$C_3$alkyl, $CH_2OH$, $CH_2CH_2OH$, $CH_2F$, $CHF_2$, $CF_3$, $CH_2CF_3$, $C_1$-$C_2$alkoxy, $C_1$-$C_2$alkoxyC_1$-$C_3$alkyl, CN, or $C(O)O$—$C_1$-$C_2$alkyl; or $R^3$ and $R^4$ form together a bivalent residue —$R^5R^6$— selected from $C_1$-$C_3$alkylene, preferably $C_1$-$C_2$alkylene, —$CH_2CF_2$—, —CHFCHF—, —$CH_2CF_2CH_2$—, —$CH_2$—O—$CH_2$—, —$CH_2$—NH—$CH_2$—, or any of the structures

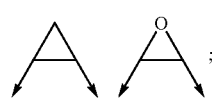;

wherein the arrows denote the bonds in formula (II); and
(ii) a saturated 5- to 6-membered heterocyclic ring Z containing 1 to 2 heteroatoms independently selected from N, O and S, optionally substituted by 1 to 3 $R^9$;

wherein $R^9$ is independently at each occurrence halogen, —OH, $C_1$-$C_3$alkyl, $CH_2OH$, $CH_2CH_2OH$, $CH_2F$, $CHF_2$, $CF_3$, $CH_2CF_3$, $C_1$-$C_2$alkoxy, $C_1$-$C_2$alkoxy$C_1$-$C_3$alkyl, $C_3$-$C_6$cycloalkyl, =O, —$NH_2$, $NHCH_3$ or $N(CH_3)_2$; or two $R^9$ substituents form together a bivalent residue —$R^{10}R^{11}$— selected from $C_1$-$C_3$alkylene optionally substituted with 1 to 4 F, —$CH_2$—O—$CH_2$— or —O—$CH_2CH_2$—O—.

and tautomers, solvates and pharmaceutically acceptable salts thereof;

with the provisos that (a) when $R^1$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl; then $R^2$ is not 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl;

(b) when $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl; then $R^1$ is not 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl.

In a further preferred embodiment, the present invention provides for a compound of (I)

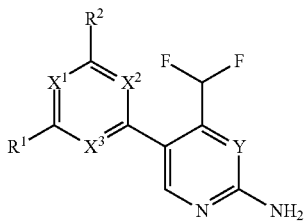

(I)

wherein $X^1$, $X^2$ and $X^3$ are, independently of each other, N or CH; with the proviso that at least two of $X^1$, $X^2$ and $X^3$ are N; Y is N or CH; and wherein $R^1$ and $R^2$ are independently of each other said morpholinyl of formula (II) and said saturated 4- to 6-membered heterocyclic ring Z, wherein said $R^1$ and said $R^2$ are independently of each other selected from

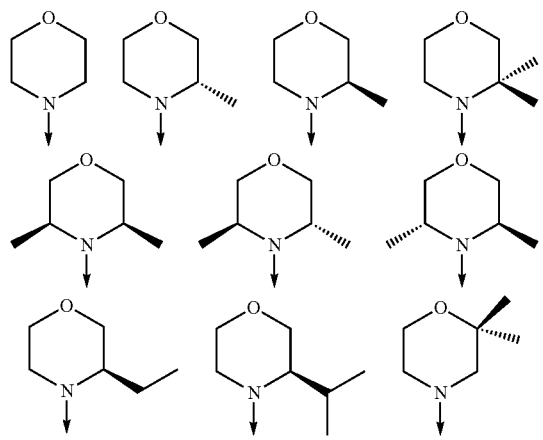

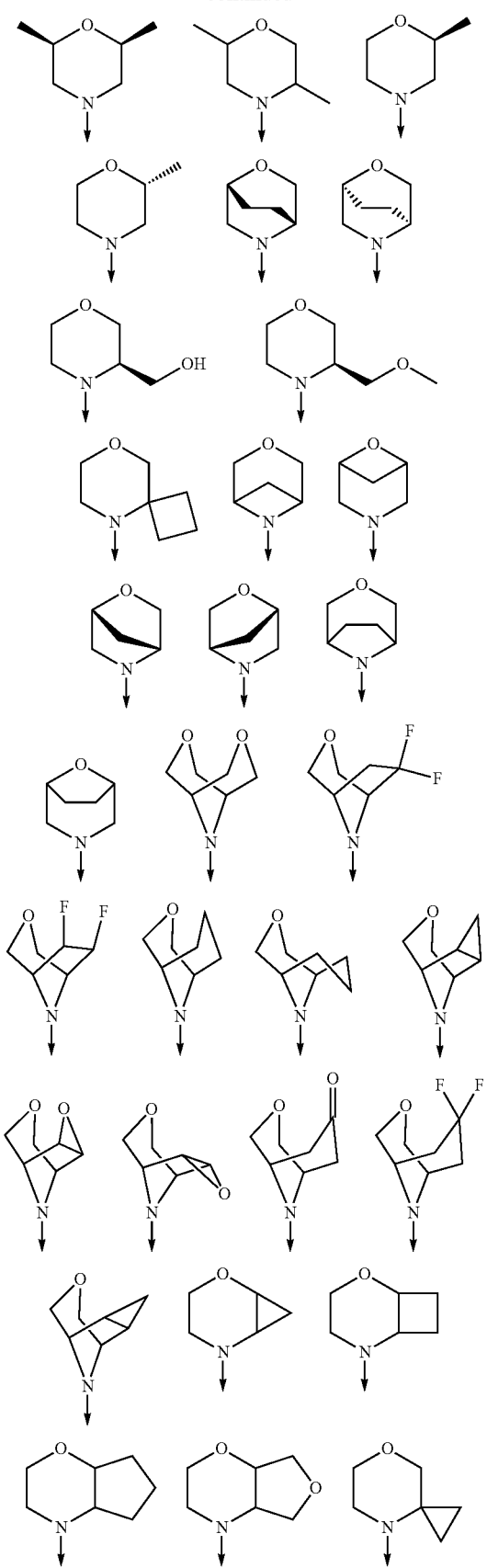

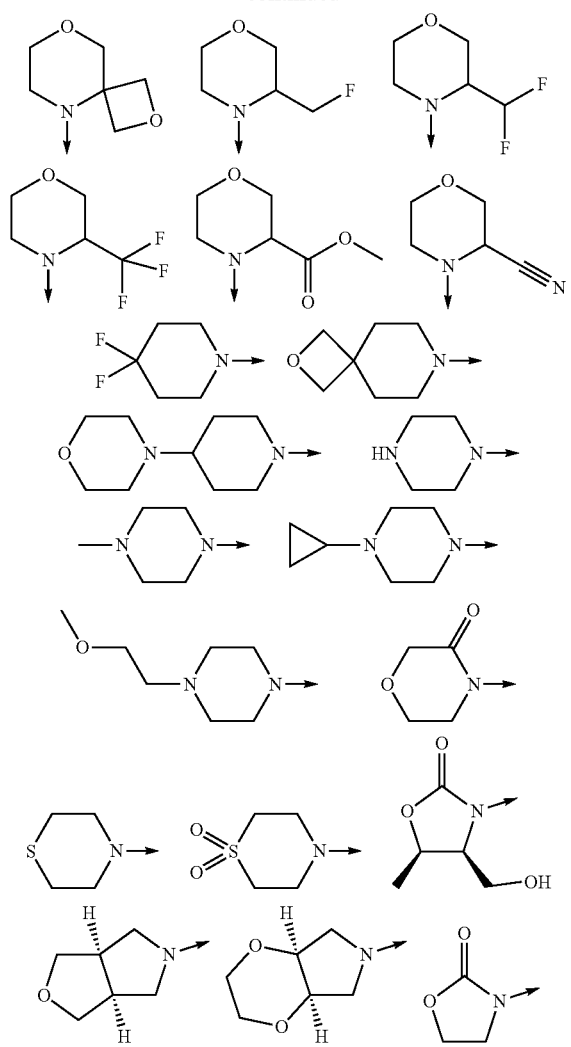

In a further preferred embodiment, the present invention provides for a compound of (I)

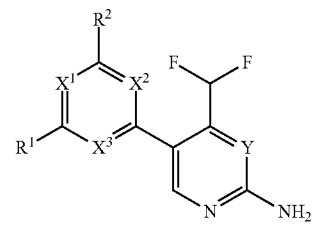

(I)

wherein $X^1$, $X^2$ and $X^3$ are, independently of each other, N or CH; with the proviso that at least two of $X^1$, $X^2$ and $X^3$ are N; Y is N or CH; and wherein $R^1$ and $R^2$ are independently of each other said morpholinyl of formula (II) and said saturated 4- to 6-membered heterocyclic ring Z, wherein said $R^1$ and said $R^2$ are independently of each other selected from

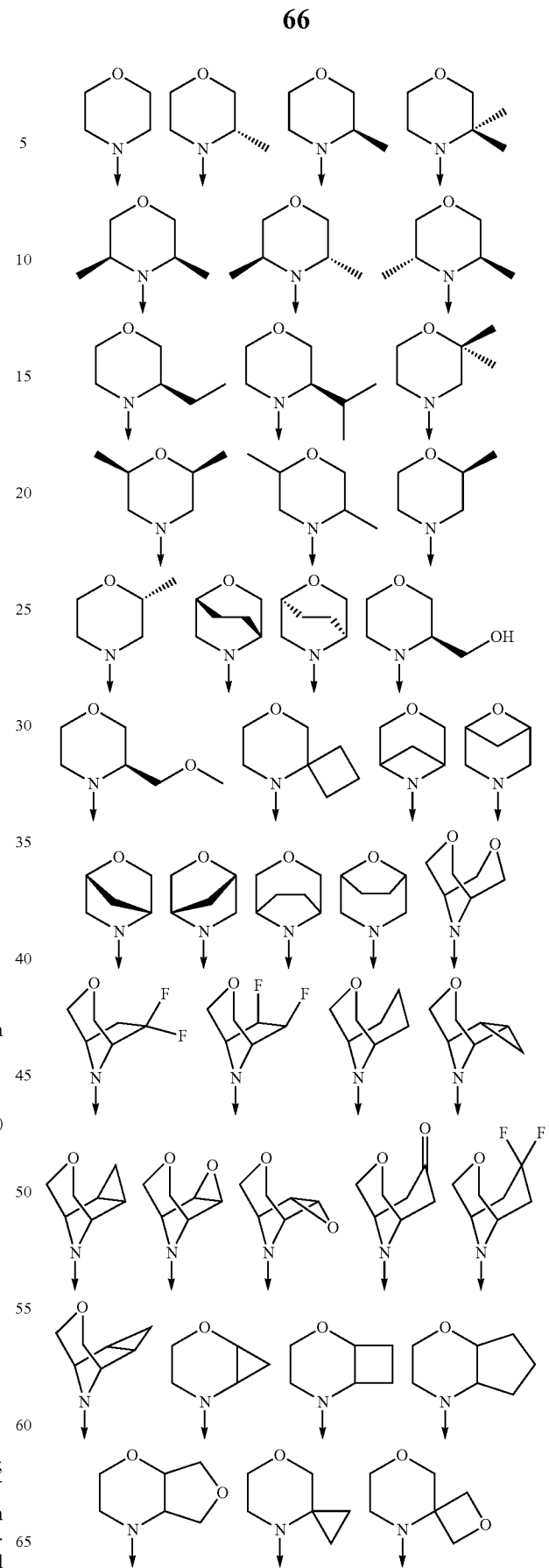

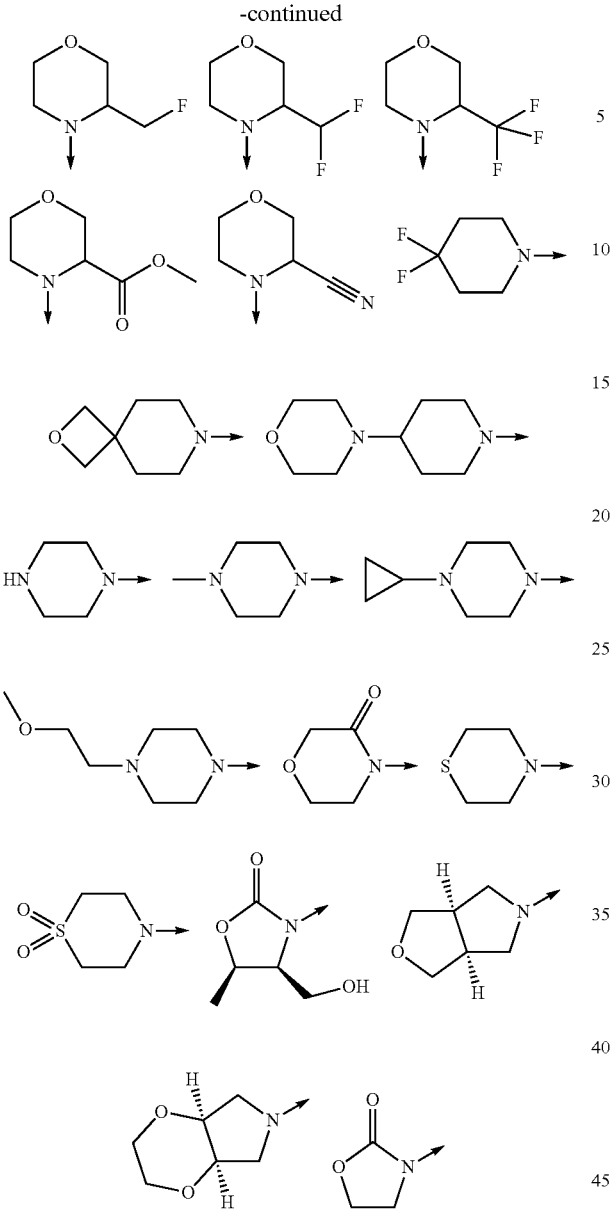

with the provisos that
(a) when $R^1$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl; then $R^2$ is not 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl;
(b) when $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl; then $R^1$ is not 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl.

In a further preferred embodiment, the present invention provides for a compound of (I)

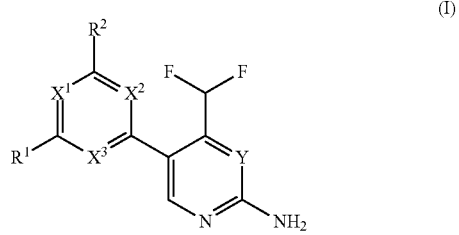

(I)

wherein $X^1$, $X^2$ and $X^3$ are, independently of each other, N or CH; with the proviso that at least two of $X^1$, $X^2$ and $X^3$ are N; Y is N or CH; and wherein $R^1$ and $R^2$ are independently of each other said morpholinyl of formula (II) and said saturated 4- to 6-membered heterocyclic ring Z, wherein said $R^1$ and said $R^2$ are independently of each other selected from

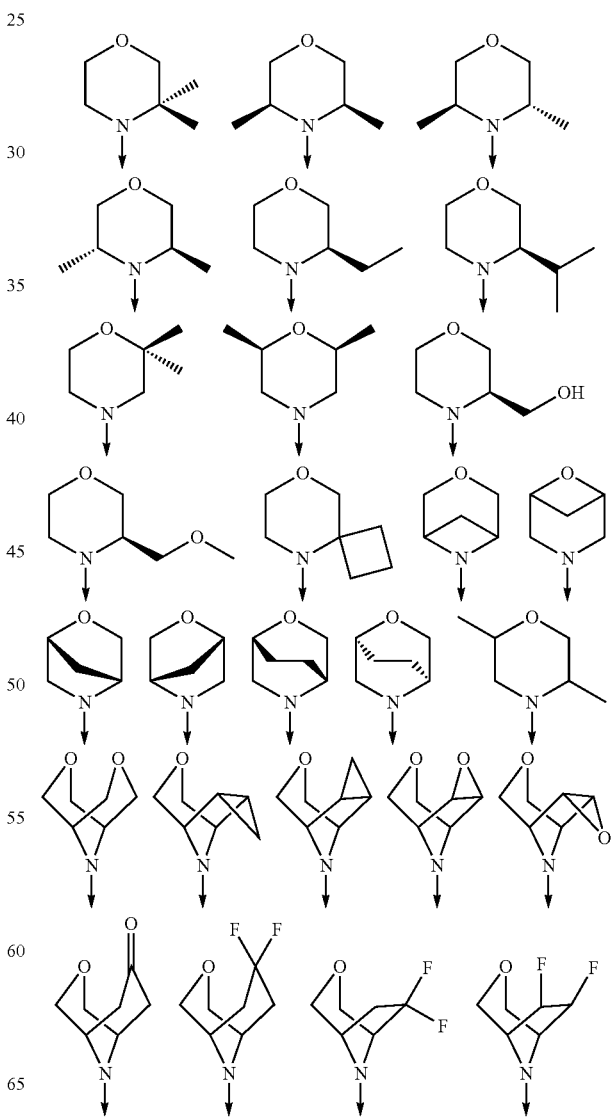

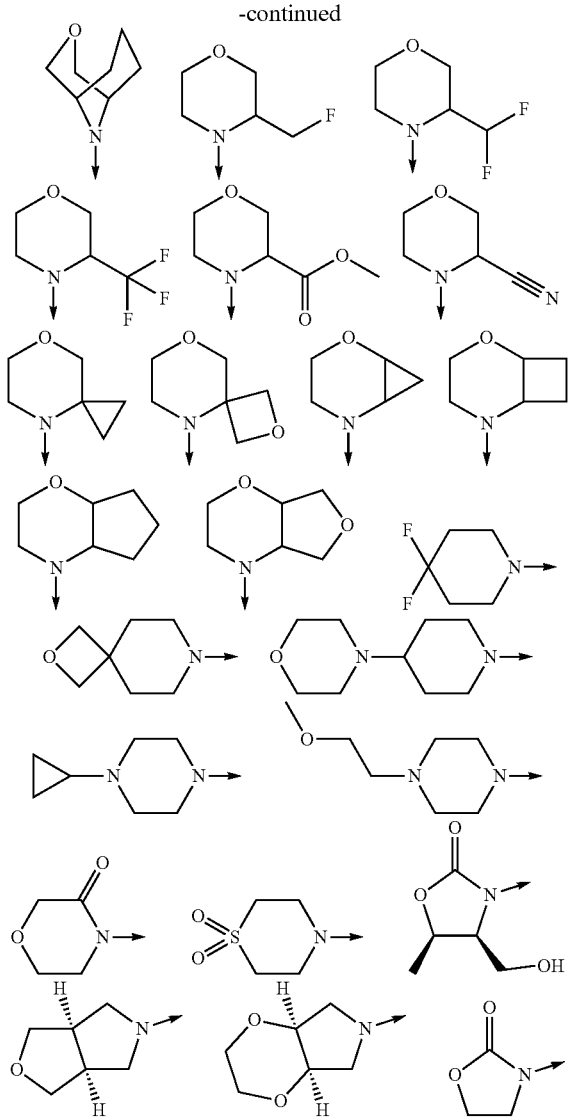

In a further aspect and preferred embodiment, the present invention provides for a compound of formula (I), wherein $R^1$ and $R^2$ are independently of each other said morpholinyl of formula (II) and said $OR^{12}$.

In a further aspect and preferred embodiment, the present invention provides for a compound of formula (I), wherein $R^1$ and $R^2$ are independently of each other said morpholinyl of formula (II) and said $NR^{15}R^{16}$.

In another preferred embodiment, $R^1$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl; and $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl.

In another preferred embodiment, $R^1$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl; and $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl, and $X^1$, $X^2$ and $X^3$ are N; and tautomers, solvates and pharmaceutically acceptable salts thereof. Preferably Y is N or CH; $R^1$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl; and $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl; and tautomers, solvates and pharmaceutically acceptable salts thereof.

In a further preferred embodiment, $R^1$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl; and $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl, and $X^1$ and $X^3$ are N, and $X^2$ is CH; and tautomers, solvates and pharmaceutically acceptable salts thereof. Preferably Y is N or CH; $R^1$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl; and $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl; and tautomers, solvates and pharmaceutically acceptable salts thereof.

In a preferred embodiment, $R^1$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl; and $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl, and $X^1$ and $X^2$ are N, and $X^3$ is CH; and tautomers, solvates and pharmaceutically acceptable salts thereof. Preferably, Y is N or CH; $R^1$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl; and $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl; and tautomers, solvates and pharmaceutically acceptable salts thereof.

In a preferred embodiment, $R^1$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl; and $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl, and $X^2$ and $X^3$ are N, and $X^1$ is CH; and tautomers, solvates and pharmaceutically acceptable salts thereof. Preferably, Y is N or CH; $R^1$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl or 3-aza-8-oxabicyclo[3.2.1]oct-3-yl; and $R^2$ is 4-morpholinyl, 2-methyl-4-morpholinyl, 3-methyl-4-morpholinyl, octadeuterio-4-morpholinyl, 8-aza-3-oxabicyclo[3.2.1]oct-8-yl, 3-aza-8-oxabicyclo[3.2.1]oct-3-yl, 4-piperazin-1-yl, 4-methylpiperazin-1-yl, or 4-thiomorpholinyl; and tautomers, solvates and pharmaceutically acceptable salts thereof.

In a preferred embodiment, the compound of formula (I) is selected from the group consisting of
4-(difluoromethyl)-5-(4,6-dimorpholino-1,3,5-triazin-2-yl)pyridin-2-amine;
4-(difluoromethyl)-5-(4,6-dimorpholino-1,3,5-triazin-2-yl)pyrimidin-2-amine;
5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine;
5-(4-(3-oxa-8-azabicyclo[3.2.1]octan-8-yl)-6-morpholino-1,3,5-triazin-2-yl)-4-(difluoromethyl)pyridin-2-amine;
5-(4-(3-oxa-8-azabicyclo[3.2.1]octan-8-yl)-6-morpholino-1,3,5-triazin-2-yl)-4-(difluoromethyl)pyrimidin-2-amine;
5-(4,6-bis((S)-3-methylmorpholino)-1,3,5-triazin-2-yl)-4-(difluoromethyl)pyridin-2-amine;
5-(4,6-bis((S)-3-methylmorpholino)-1,3,5-triazin-2-yl)-4-(difluoromethyl)pyrimidin-2-amine;
(S)-4-(difluoromethyl)-5-(4-(3-methylmorpholino)-6-morpholino-1,3,5-triazin-2-yl)pyridin-2-amine;
(S)-4-(difluoromethyl)-5-(4-(3-methylmorpholino)-6-morpholino-1,3,5-triazin-2-yl)pyrimidin-2-amine;
5-(4-(3-oxa-8-azabicyclo[3.2.1]octan-8-yl)-6-((S)-3-methylmorpholino)-1,3,5-triazin-2-yl)-4-(difluoromethyl)pyridin-2-amine;
5-(4-(3-oxa-8-azabicyclo[3.2.1]octan-8-yl)-6-((S)-3-methylmorpholino)-1,3,5-triazin-2-yl)-4-(difluoromethyl)pyrimidin-2-amine;
4-(difluoromethyl)-5-(4-morpholino-6-(piperazin-1-yl)-1,3,5-triazin-2-yl)pyridin-2-amine;
4-(difluoromethyl)-5-(4-morpholino-6-(piperazin-1-yl)-1,3,5-triazin-2-yl)pyrimidin-2-amine;
(S)-4-(difluoromethyl)-5-(4-(3-methylmorpholino)-6-(piperazin-1-yl)-1,3,5-triazin-2-yl)pyridin-2-amine; and
(S)-4-(difluoromethyl)-5-(4-(3-methylmorpholino)-6-(piperazin-1-yl)-1,3,5-triazin-2-yl)pyrimidin-2-amine;
and tautomers, solvates and pharmaceutically acceptable salts thereof.

In a preferred embodiment, the compound of formula (I) is selected from the group consisting of
4-(difluoromethyl)-5-(2,6-dimorpholinopyrimidin-4-yl)pyridin-2-amine;
4'-(difluoromethyl)-2,6-dimorpholino-[4,5'-bipyrimidin]-2'-amine;
5-(6-(3-oxa-8-azabicyclo[3.2.1]octan-8-yl)-2-(3-oxa-8-azabicyclo[3.2.1]octan-8-yl)pyrimidin-4-yl)-4-(difluoromethyl)pyridin-2-amine;
5-(6-(3-oxa-8-azabicyclo[3.2.1]octan-8-yl)-2-morpholinopyrimidin-4-yl)-4-(difluoromethyl)pyridin-2-amine;
6-(3-oxa-8-azabicyclo[3.2.1]octan-8-yl)-4'-(difluoromethyl)-2-morpholino-[4,5'-bipyrimidin]-2'-amine;
5-(2,6-bis((S)-3-methylmorpholino)pyrimidin-4-yl)-4-(difluoromethyl)pyridin-2-amine;
4'-(difluoromethyl)-2,6-bis((S)-3-methylmorpholino)-[4,5'-bipyrimidin]-2'-amine;
(S)-4-(difluoromethyl)-5-(6-(3-methylmorpholino)-2-morpholinopyrimidin-4-yl)pyridin-2-amine;
(S)-4'-(difluoromethyl)-6-(3-methylmorpholino)-2-morpholino-[4,5'-bipyrimidin]-2'-amine;
5-(2-(3-oxa-8-azabicyclo[3.2.1]octan-8-yl)-6-morpholinopyrimidin-4-yl)-4-(difluoromethyl)pyridin-2-amine;
2-(3-oxa-8-azabicyclo[3.2.1]octan-8-yl)-4'-(difluoromethyl)-6-morpholino-[4,5'-bipyrimidin]-2'-amine;
(S)-4-(difluoromethyl)-5-(2-(3-methylmorpholino)-6-morpholinopyrimidin-4-yl)pyridin-2-amine; and
(S)-4'-(difluoromethyl)-2-(3-methylmorpholino)-6-morpholino-[4,5'-bipyrimidin]-2'-amine;
and tautomers, solvates and pharmaceutically acceptable salts thereof.

In a preferred embodiment, the compound of formula (I) is selected from the group consisting of 4-(difluoromethyl)-5-(6-morpholino-2-(piperazin-1-yl)pyrimidin-4-yl)pyridin-2-amine and 4'-(difluoromethyl)-6-morpholino-2-(piperazin-1-yl)-[4,5'-bipyrimidin]-2'-amine; and tautomers, solvates and pharmaceutically acceptable salts thereof.

In a preferred embodiment, the compound of formula (I) is selected from the group consisting of 4-(difluoromethyl)-5-(4,6-dimorpholinopyrimidin-2-yl)pyridin-2-amine and 4'-(difluoromethyl)-4,6-dimorpholino-[2,5'-bipyrimidin]-2'-amine; and tautomers, solvates and pharmaceutically acceptable salts thereof.

In a preferred embodiment, the compound of formula (I) is selected from the group consisting of
4-(difluoromethyl)-5-(4,6-dimorpholino-1,3,5-triazin-2-yl)pyrimidin-2-amine;
5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine;
5-(4-(3-oxa-8-azabicyclo[3.2.1]octan-8-yl)-6-morpholino-1,3,5-triazin-2-yl)-4-(difluoromethyl)pyridin-2-amine;
5-(4,6-bis((S)-3-methylmorpholino)-1,3,5-triazin-2-yl)-4-(difluoromethyl)pyrimidin-2-amine;
(S)-4-(difluoromethyl)-5-(4-(3-methylmorpholino)-6-morpholino-1,3,5-triazin-2-yl)pyridin-2-amine;
4-(difluoromethyl)-5-(4-morpholino-6-(piperazin-1-yl)-1,3,5-triazin-2-yl)pyrimidin-2-amine;
4-(difluoromethyl)-5-(4,6-dimorpholino-1,3,5-triazin-2-yl)pyridin-2-amine; and
(S)-4-(difluoromethyl)-5-(4-(3-methylmorpholino)-6-morpholino-1,3,5-triazin-2-yl)pyrimidin-2-amine;
and tautomers, solvates and pharmaceutically acceptable salts thereof.

Preferred are compounds wherein $R^1$ and $R^2$ are 4-morpholinyl.

Likewise preferred are compounds wherein $R^1$ and $R^2$ are 3-aza-8-oxabicyclo[3.2.1]oct-3-yl.

Likewise preferred are compounds wherein $R^1$ and $R^2$ are (S)-3-methyl-4-morpholinyl.

Likewise preferred are compounds wherein $R^1$ is 4-morpholinyl and $R^2$ is (S)-3-methyl-4-morpholinyl.

Likewise preferred are compounds wherein $R^1$ is 4-morpholinyl and $R^2$ is 3-aza-8-oxabicyclo[3.2.1]oct-3-yl.

Likewise preferred are compounds wherein $R^1$ is 4-morpholinyl and $R^2$ is 4-piperazin-1-yl.

Likewise preferred are compounds wherein $R^1$ is 4-morpholinyl and $R^2$ is 4-thiomorpholinyl.

More preferred are compounds of formula (I) wherein $R^1$ and $R^2$ are 4-morpholinyl, and Y is CH.

Equally preferred are compounds of formula (I) wherein $R^1$ and $R^2$ are 4-morpholinyl, and Y is N.

More preferred are compounds of formula (I) wherein $R^1$ and $R^2$ are 3-aza-8-oxabicyclo[3.2.1]oct-3-yl, and Y is CH.

More preferred are compounds of formula (I) wherein $R^1$ and $R^2$ are (S)-3-methyl-4-morpholinyl, and Y is N.

More preferred are compounds of formula (I) wherein $R^1$ is 4-morpholinyl and $R^2$ is 4-piperazin-1-yl, and Y is N.

More preferred are compounds of formula (I) wherein $R^1$ is 4-morpholinyl and $R^2$ is (S)-3-methyl-4-morpholinyl, and Y is CH.

More preferred are compounds of formula (I) wherein $R^1$ is 4-morpholinyl and $R^2$ is 3-aza-8-oxabicyclo[3.2.1]oct-3-yl, and Y is N.

More preferred are compounds of formula (I) wherein $R^1$ is (S)-3-methyl-4-morpholinyl and $R^2$ is 3-aza-8-oxabicyclo[3.2.1]oct-3-yl, and Y is CH.

More preferred are compounds of formula (I) wherein $R^1$ is (S)-3-methyl-4-morpholinyl and $R^2$ is 4-piperazin-1-yl, and Y is CH.

Likewise preferred are compounds of formula (I) wherein $R^1$ is (S)-3-methyl-4-morpholinyl and $R^2$ is 4-piperazin-1-yl, and Y is N.

More preferred are compounds of formula (I) wherein $R^1$ is 4-morpholinyl and $R^2$ is 4-thiomorpholinyl, and Y is CH.

Likewise preferred are compounds of formula (I) wherein $R^1$ is 4-morpholinyl and $R^2$ is 4-thiomorpholinyl, and Y is N.

Even more preferred are compounds of formula (I), wherein $X^1$, $X^2$ and $X^3$ are N.

Likewise preferred are compounds of formula (I), wherein $X^1$ and $X^3$ are N, and $X^2$ is CH.

Most preferred are the following compounds shown by formula:

(The names of the corresponding structures were produced using ChemDraw Ultra, version 13.0.1 as well as lower and upper software versions thereof, CambridgeSoft Corp., Cambridge Mass.).

Compound 1

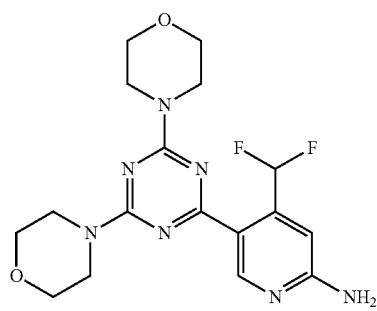

4-(difluoromethyl)-5-(4,6-dimorpholino-1,3,5-triazin-2-yl)pyridin-2-amine

Compound 2

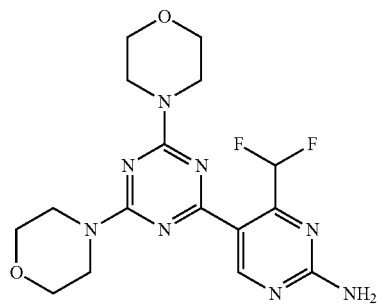

4-(difluoromethyl)-5-(4,6-dimorpholino-1,3,5-triazin-2-yl)pyrimidin-2-amine

Compound 3

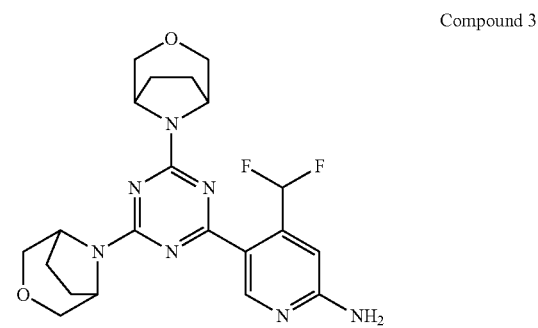 [SMILES: Nc1cc(C(F)F)c(-c2nc(N3C4CCC3COC4)nc(N3C4CCC3COC4)n2)cn1]

5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine Compound 4

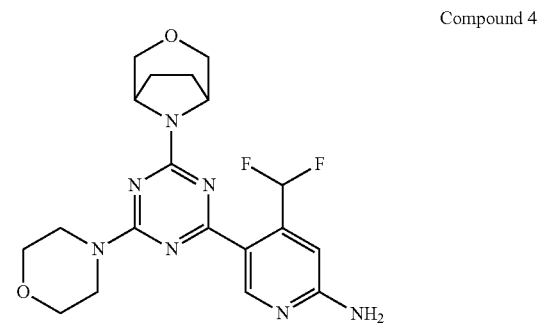 [SMILES: Nc1cc(C(F)F)c(-c2nc(N3CCOCC3)nc(N3C4CCC3COC4)n2)cn1]

5-(4-(3-oxa-8-azabicyclo[3.2.1]octan-8-yl)-6-morpholino-1,3,5-triazin-2-yl)-4-(difluoromethyl)pyridin-2-amine Compound 5

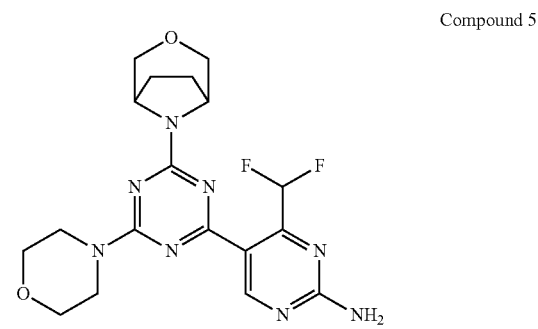 [SMILES: Nc1ncc(-c2nc(N3CCOCC3)nc(N3C4CCC3COC4)n2)c(C(F)F)n1]

75

5-(4-(3-oxa-8-azabicyclo[3.2.1]octan-8-yl)-6-morpholino-1,3,5-triazin-2-yl)-4-(difluoromethyl)pyrimidin-2-amine Compound 6

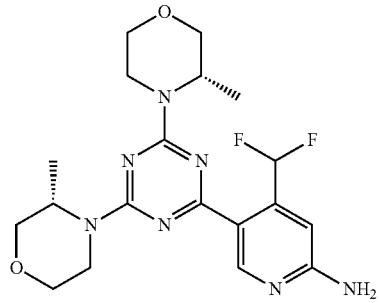

5-(4,6-bis((S)-3-methylmorpholino)-1,3,5-triazin-2-yl)-4-(difluoromethyl)pyridin-2-amine Compound 7

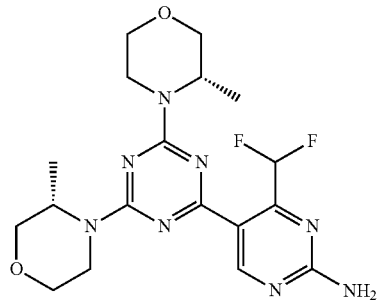

5-(4,6-bis((S)-3-methylmorpholino)-1,3,5-triazin-2-yl)-4-(difluoromethyl)pyrimidin-2-amine Compound 8

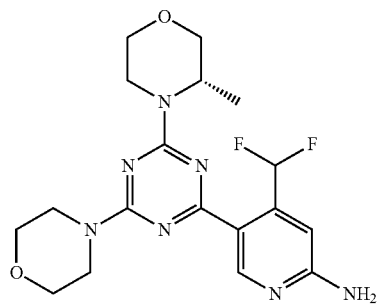

76

(S)-4-(difluoromethyl)-5-(4-(3-methylmorpholino)-6-morpholino-1,3,5-triazin-2-yl)pyridin-2-amine Compound 9

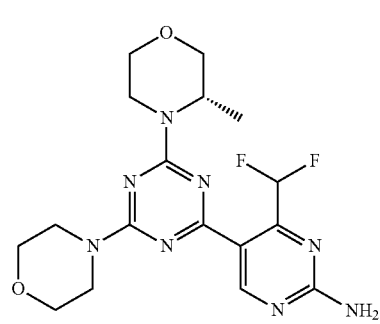

(S)-4-(difluoromethyl)-5-(4-(3-methylmorpholino)-6-morpholino-1,3,5-triazin-2-yl)pyrimidin-2-amine Compound 10

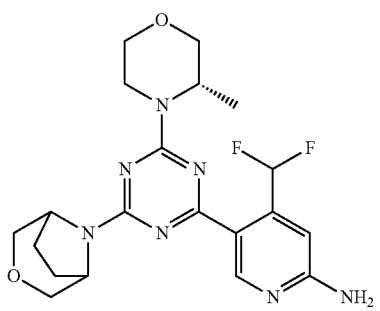

5-(4-(3-oxa-8-azabicyclo[3.2.1]octan-8-yl)-6-((S)-3-methylmorpholino)-1,3,5-triazin-2-yl)-4-(difluoromethyl)pyridin-2-amine Compound 11

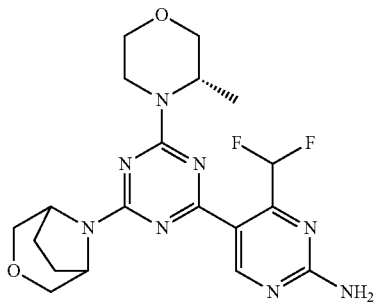

77

5-(4-(3-oxa-8-azabicyclo[3.2.1]octan-8-yl)-6-((S)-3-methylmorpholino)-1,3,5-triazin-2-yl)-4-(difluoromethyl)pyrimidin-2-amine

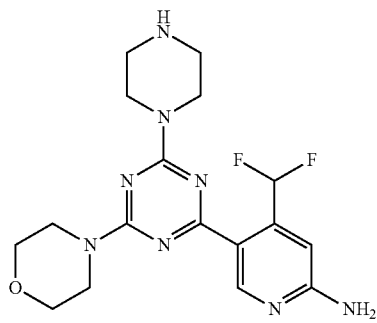

Compound 12

4-(difluoromethyl)-5-(4-morpholino-6-(piperazin-1-yl)-1,3,5-triazin-2-yl)pyridin-2-amine

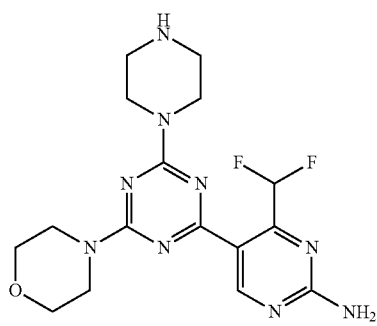

Compound 13

4-(difluoromethyl)-5-(4-morpholino-6-(piperazin-1-yl)-1,3,5-triazin-2-yl)pyrimidin-2-amine

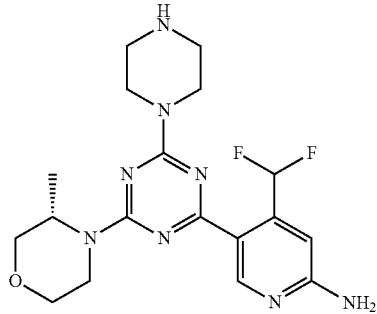

Compound 14

78

(S)-4-(difluoromethyl)-5-(4-(3-methylmorpholino)-6-(piperazin-1-yl)-1,3,5-triazin-2-yl)pyridin-2-amine

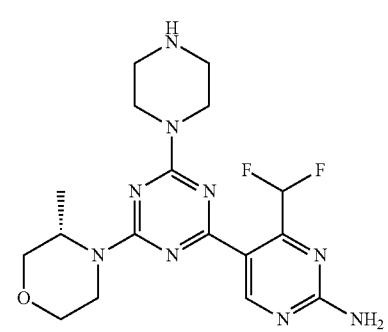

Compound 15

(S)-4-(difluoromethyl)-5-(4-(3-methylmorpholino)-6-(piperazin-1-yl)-1,3,5-triazin-2-yl)pyrimidin-2-amine

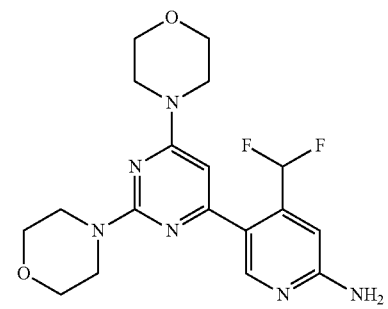

Compound 16

4-(difluoromethyl)-5-(2,6-dimorpholinopyrimidin-4-yl)pyridin-2-amine

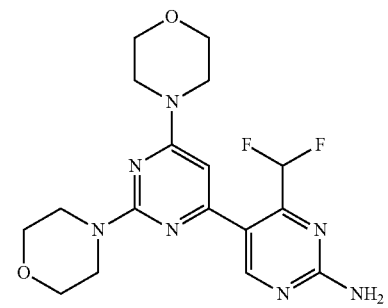

Compound 17

79

4'-(difluoromethyl)-2,6-dimorpholino-[4,5'-bipyrimidin]-2'-amine

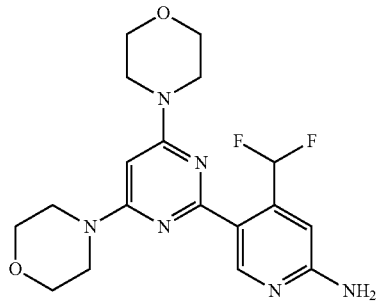

Compound 18

4-(difluoromethyl)-5-(4,6-dimorpholinopyrimidin-2-yl)pyridin-2-amine

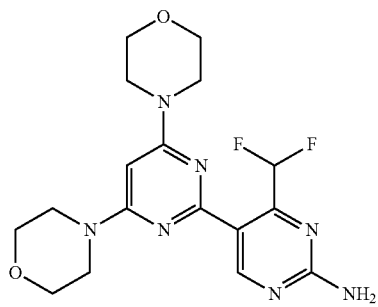

Compound 19

4'-(difluoromethyl)-4,6-dimorpholino-[2,5'-bipyrimidin]-2'-amine

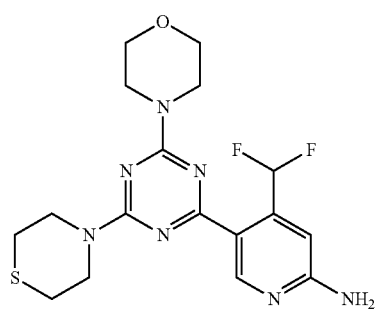

Compound 20

80

4-(difluoromethyl)-5-(4-morpholino-6-thiomorpholino-1,3,5-triazin-2-yl)pyridin-2-amine

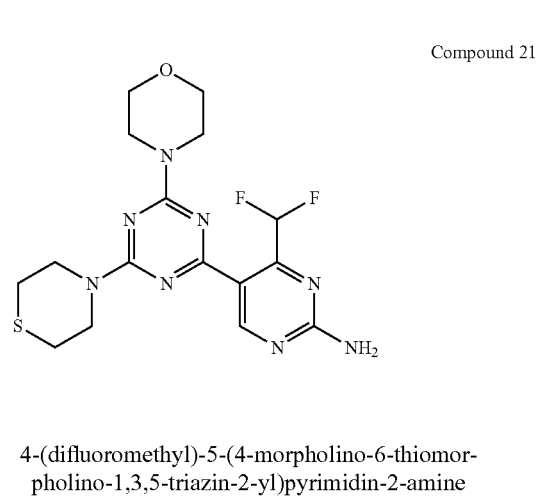

Compound 21

4-(difluoromethyl)-5-(4-morpholino-6-thiomorpholino-1,3,5-triazin-2-yl)pyrimidin-2-amine Further preferred are the following compounds Compound 22

5-(6-(3-oxa-8-azabicyclo[3.2.1]octan-8-yl)-2-(3-oxa-8-azabicyclo[3.2.1]octan-8-yl)pyrimidin-4-yl)-4-(difluoromethyl)pyridin-2-amine

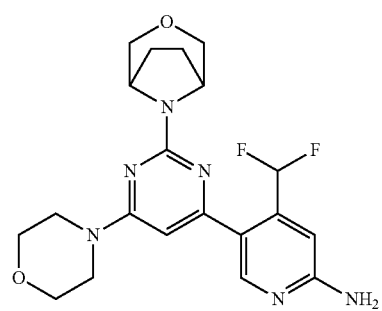

Compound 23

81

5-(2-(3-oxa-8-azabicyclo[3.2.1]octan-8-yl)-6-morpholinoprimidin-4-yl)-4-(difluoromethyl)pyridin-2-amine Compound 24

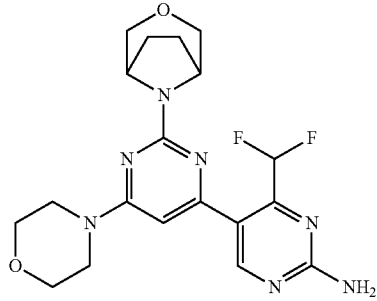

2-(3-oxa-8-azabicyclo[3.2.1]octan-8-yl)-4'-(difluoromethyl)-6-morpholino-[4,5'-bipyrimidin]-2'-amine Compound 25

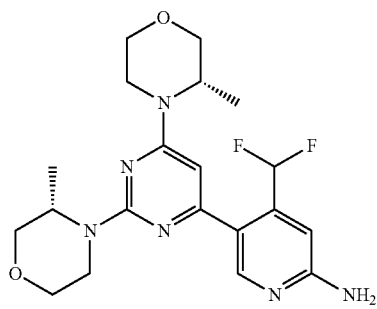

5-(2,6-bis((S)-3-methylmorpholino)pyrimidin-4-yl)-4-(difluoromethyl)pyridin-2-amine Compound 26

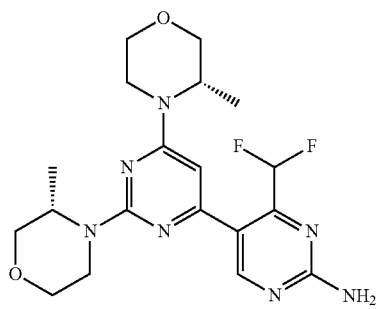

82

4'-(difluoromethyl)-2,6-bis((S)-3-methylmorpholino)-[4,5'-bipyrimidin]-2'-amine

Compound 27

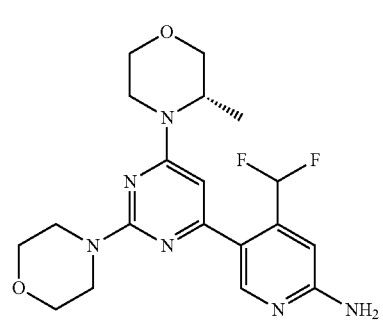

(S)-4-(difluoromethyl)-5-(6-(3-methylmorpholino)-2-morpholinopyrimidin-4-yl)pyridin-2-amine Compound 28

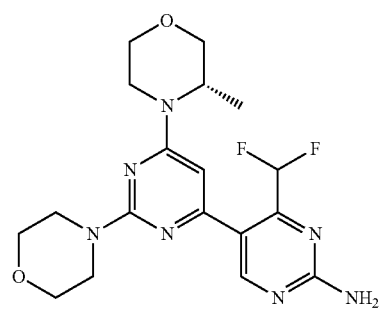

(S)-4'-(difluoromethyl)-6-(3-methylmorpholino)-2-morpholino-[4,5'-bipyrimidin]-2'-amine Compound 29

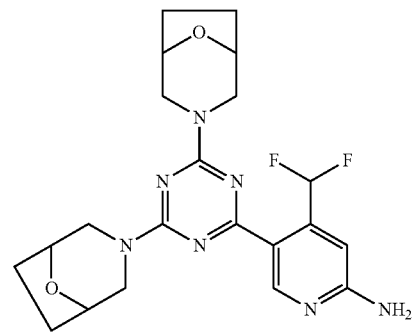

83 84

5-(4-(8-Oxa-3-azabicyclo[3.2.1]octan-3-yl)-6-(8-oxa-3-azabicyclo[3.2.1]octan-3-yl)-1,3,5-triazin-2-yl)-4-(difluoromethyl)pyridin-2-amine (S)-4'-(difluoromethyl)-2-(3-methylmorpholino)-6-morpholino-[4,5'-bipyrimidin]-2'-amine Compound 30

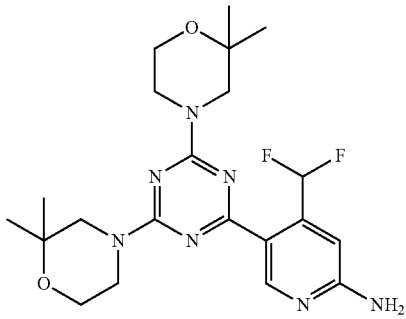

5-[4,6-bis(2,2-dimethylmorpholin-4-yl)-1,3,5-triazin-2-yl]-4-(difluoromethyl)pyridin-2-amine Compound 33

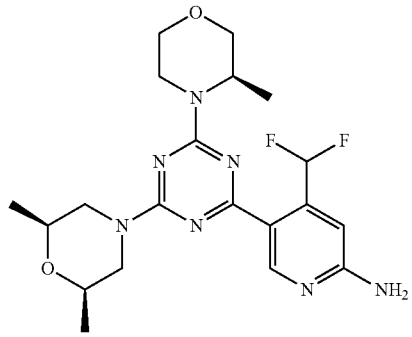

4-(difluoromethyl)-5-[4-[(2S,6R)-2,6-dimethylmorpholin-4-yl]-6-[(3R)-3-methylmorpholin-4-yl]-1,3,5-triazin-2-yl]pyridin-2-amine Compound 31

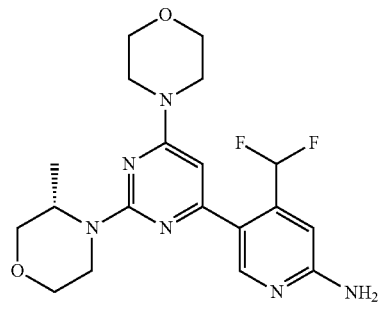

(S)-4-(difluoromethyl)-5-(2-(3-methylmorpholino)-6-morpholinopyrimidin-4-yl)pyridin-2-amine Compound 34

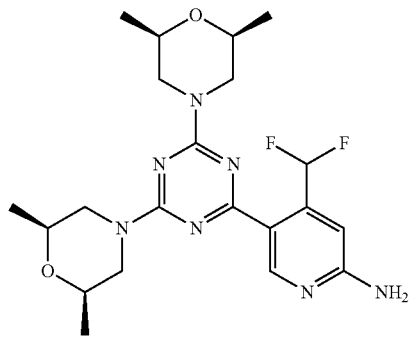

5-[4,6-bis[(2R,6S)-2,6-dimethylmorpholin-4-yl]-1,3,5-triazin-2-yl]-4-(difluoromethyl)pyridin-2-amine Compound 32

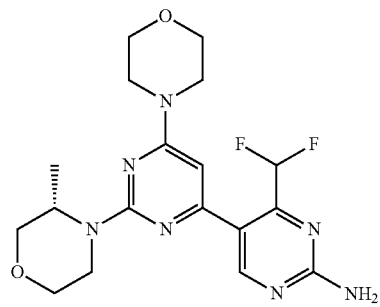

Compound 35

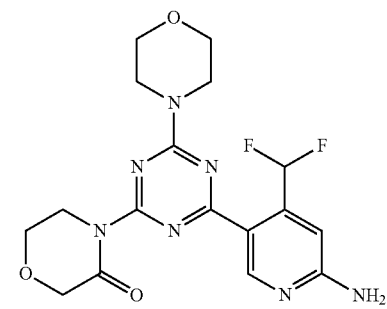

85

4-[4-[6-amino-4-(difluoromethyl)-3-pyridyl]-6-morpholino-1,3,5-triazin-2-yl]morpholin-3-one Compound 36

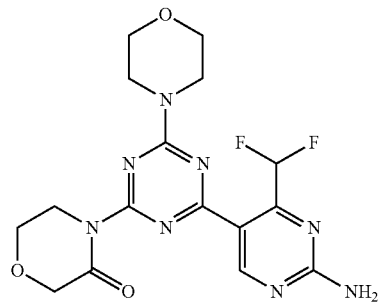

4-[4-[2-amino-4-(difluoromethyl)pyrimidin-5-yl]-6-morpholino-1,3,5-triazin-2-yl]morpholin-3-one Compound 37

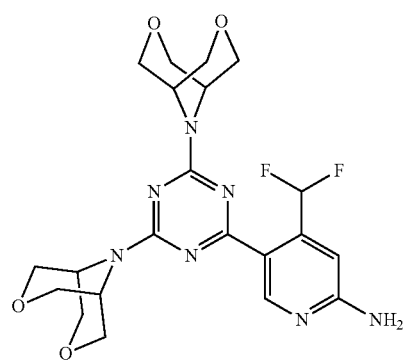

5-[4,6-bis(3,7-dioxa-9-azabicyclo[3.3.1]nonan-9-yl)-1,3,5-triazin-2-yl]-4-(difluoromethyl)pyridin-2-amine Compound 38

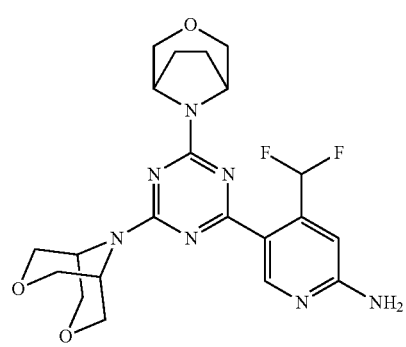

86

4-(difluoromethyl)-5-[4-(3,7-dioxa-9-azabicyclo[3.3.1]nonan-9-yl)-6-(3-oxa-8-azabicyclo[3.2.1]octan-8-yl)-1,3,5-triazin-2-yl]pyridin-2-amine Compound 39

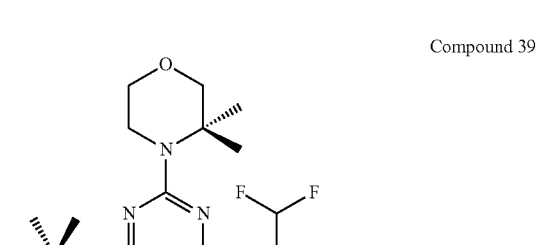

5-[4,6-bis(3,3-dimethylmorpholin-4-yl)-1,3,5-triazin-2-yl]-4-(difluoromethyl)pyridin-2-amine Compound 40

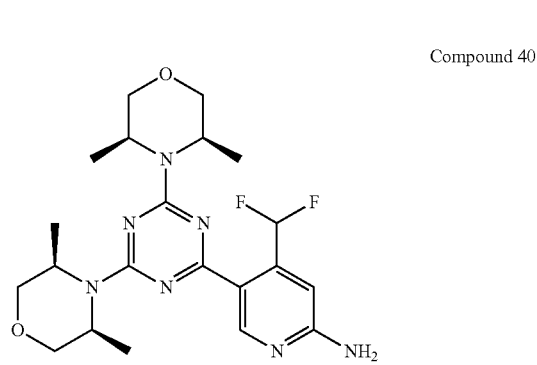 [SMILES: C[C@@H]1COC[C@H](C)N1c1nc(-c2cnc(N)cc2C(F)F)nc(N2[C@H](C)COC[C@@H]2C)n1]

5-[4,6-bis[(3R,5S)-3,5-dimethylmorpholin-4-yl]-1,3,5-triazin-2-yl]-4-(difluoromethyl)pyridin-2-amine Compound 41

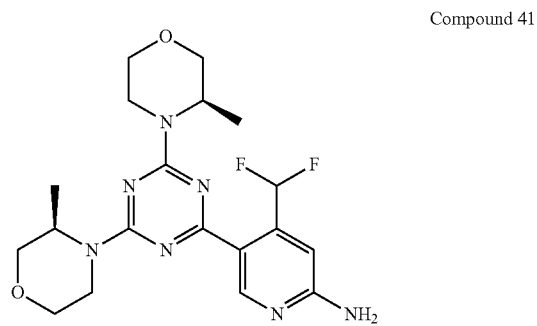 [SMILES: C[C@@H]1COCCN1c1nc(-c2cnc(N)cc2C(F)F)nc(N2CCOC[C@H]2C)n1]

87

5-[4,6-bis[(3R)-3-methylmorpholin-4-yl]-1,3,5-tri-
azin-2-yl]-4-(difluoromethyl)pyridin-2-amine

88

4-(difluoromethyl)-5-[4-[(3R,5S)-3,5-dimethylmor-
pholin-4-yl]-6-[(3R)-3-methylmorpholin-4-yl]-1,3,5-
triazin-2-yl]pyridin-2-amine Compound 42

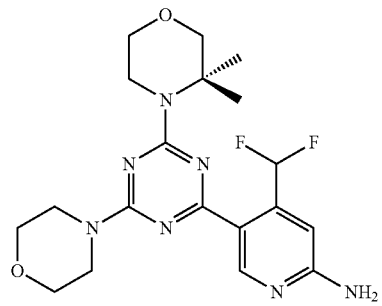

Compound 45

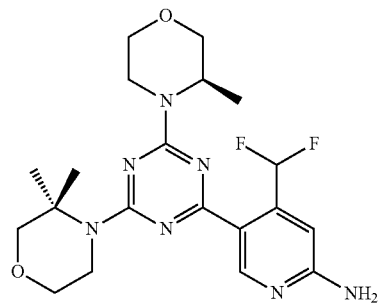

4-(difluoromethyl)-5-[4-(3,3-dimethylmorpholin-4-
yl)-6-morpholino-1,3,5-triazin-2-yl]pyridin-2-amine 4-(difluoromethyl)-5-[4-(3,3-dimethylmorpholin-4-
yl)-6-[(3R)-3-methylmorpholin-4-yl]-1,3,5-triazin-2-
yl]pyridin-2-amine Compound 43

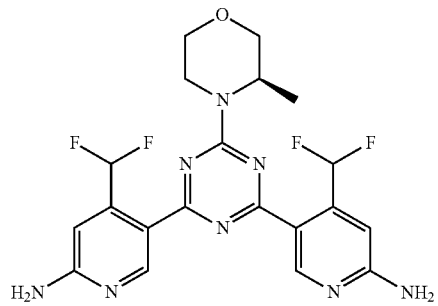

Compound 46

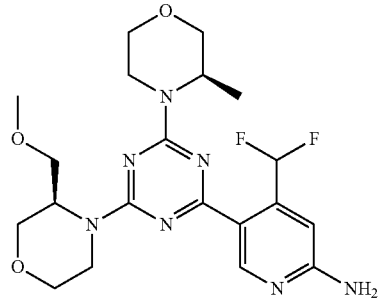

5-[4-[6-amino-4-(difluoromethyl)-3-pyridyl]-6-
[(3R)-3-methylmorpholin-4-yl]-1,3,5-triazin-2-yl]-4-
(difluoromethyl)pyridin-2-amine 4-(difluoromethyl)-5-[4-[(3R)-3-(methoxymethyl)
morpholin-4-yl]-6-[(3R)-3-methylmorpholin-4-yl]-1,
3,5-triazin-2-yl]pyridin-2-amine Compound 44

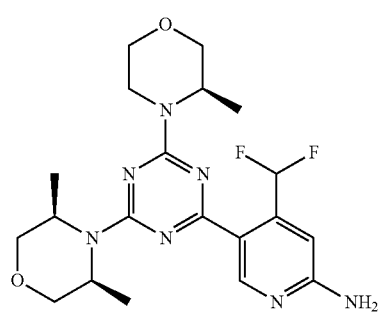

Compound 47

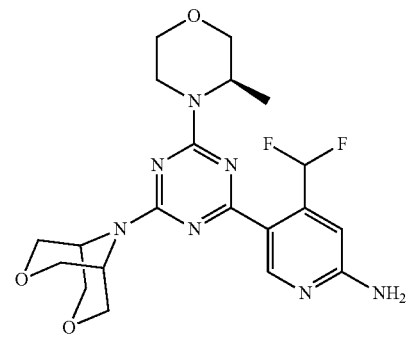

| 89 | 90 |
|---|---|
| 4-(difluoromethyl)-5-[4-(3,7-dioxa-9-azabicyclo[3.3.1]nonan-9-yl)-6-[(3R)-3-methylmorpholin-4-yl]-1,3,5-triazin-2-yl]pyridin-2-amine | 4-(difluoromethyl)-5-[4-[(3R)-3-methylmorpholin-4-yl]-6-(3-oxa-6-azabicyclo[3.1.1]heptan-6-yl)-1,3,5-triazin-2-yl]pyridin-2-amine |

Compound 48

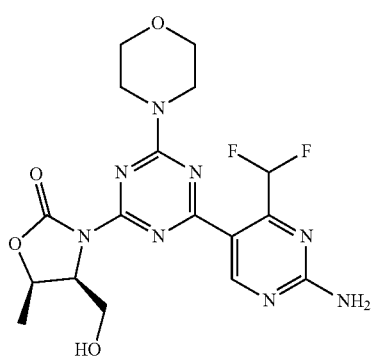

(4S,5R)-3-[4-[2-amino-4-(difluoromethyl)pyrimidin-5-yl]-6-morpholino-1,3,5-triazin-2-yl]-4-(hydroxymethyl)-5-methyl-oxazolidin-2-one Compound 49

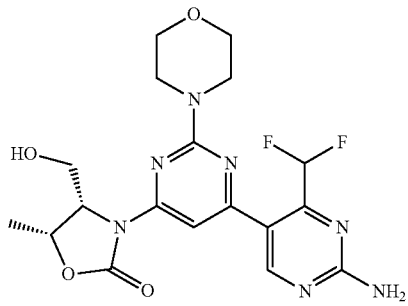

(4S,5R)-3-[6-[2-amino-4-(difluoromethyl)pyrimidin-5-yl]-2-morpholino-pyrimidin-4-yl]-4-(hydroxymethyl)-5-methyl-oxazolidin-2-one Compound 50

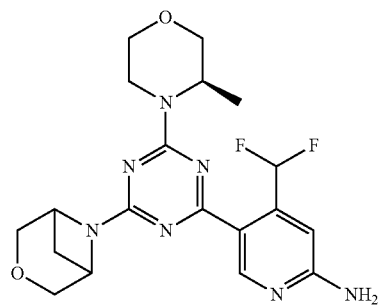

Compound 51

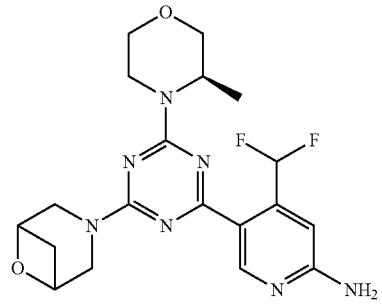

4-(difluoromethyl)-5-[4-[(3R)-3-methylmorpholin-4-yl]-6-(6-oxa-3-azabicyclo[3.1.1]heptan-3-yl)-1,3,5-triazin-2-yl]pyridin-2-amine Compound 52

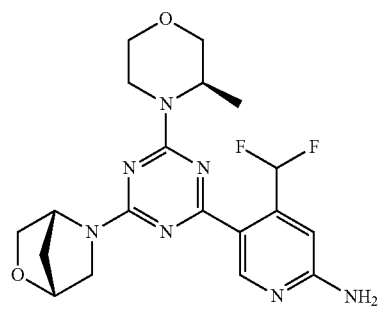

4-(difluoromethyl)-5-[4-[(3R)-3-methylmorpholin-4-yl]-6-[(1R,4R)-2-oxa-5-azabicyclo[2.2.1]heptan-5-yl]-1,3,5-triazin-2-yl]pyridin-2-amine Compound 53

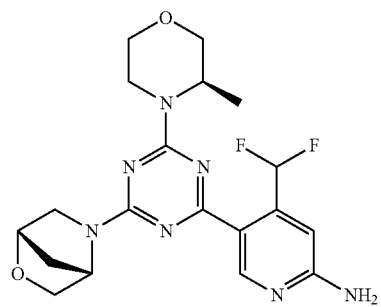

91

4-(difluoromethyl)-5-[4-[(3R)-3-methylmorpholin-4-yl]-6-[(1S,4S)-2-oxa-5-azabicyclo[2.2.1]heptan-5-yl]-1,3,5-triazin-2-yl]pyridin-2-amine

92

5-[4,6-bis[(3R)-3-isopropylmorpholin-4-yl]-1,3,5-triazin-2-yl]-4-(difluoromethyl)pyridin-2-amine Compound 54

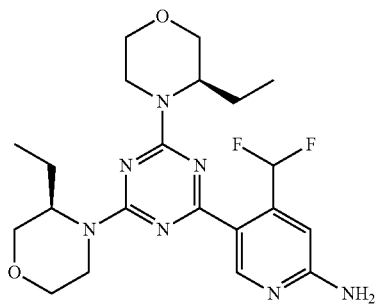

5-[4,6-bis[(3R)-3-ethylmorpholin-4-yl]-1,3,5-triazin-2-yl]-4-(difluoromethyl)pyridin-2-amine Compound 55

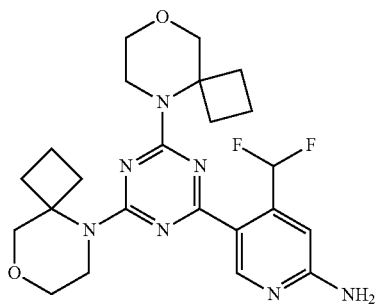

5-[4,6-bis(8-oxa-5-azaspiro[3.5]nonan-5-yl)-1,3,5-triazin-2-yl]-4-(difluoromethyl)pyridin-2-amine Compound 56

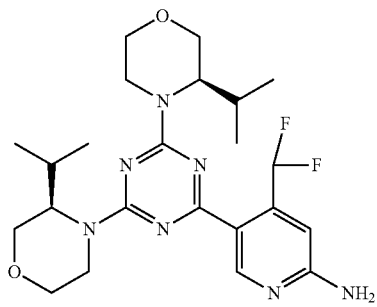

Compound 57

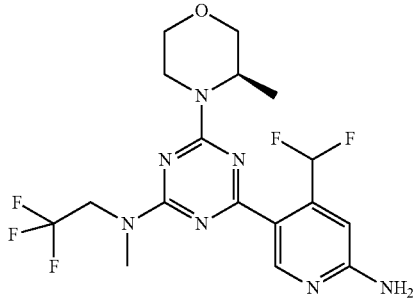

4-[6-amino-4-(difluoromethyl)-3-pyridyl]-N-methyl-6-[(3R)-3-methylmorpholin-4-yl]-N-(2,2,2-trifluoroethyl)-1,3,5-triazin-2-amine Compound 58

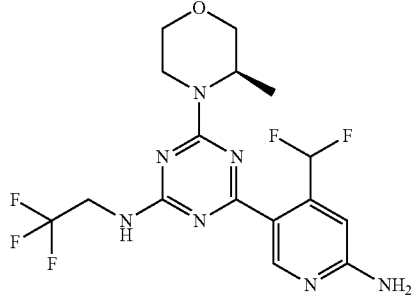

4-[6-amino-4-(difluoromethyl)-3-pyridyl]-6-[(3R)-3-methylmorpholin-4-yl]-N-(2,2,2-trifluoroethyl)-1,3,5-triazin-2-amine Compound 59

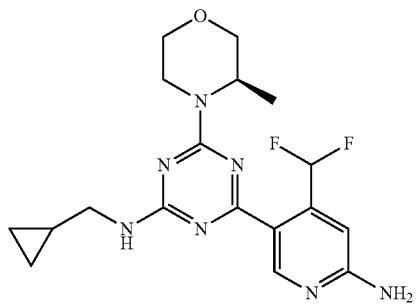

93

4-[6-amino-4-(difluoromethyl)-3-pyridyl]-N-(cyclo-
propylmethyl)-6-[(3R)-3-methylmorpholin-4-yl]-1,3,
5-triazin-2-amine

94

5-[4-[(3aR,6aS)-1,3,3a,4,6,6a-hexahydrofuro[3,4-c]
pyrrol-5-yl]-6-[(3R)-3-methylmorpholin 4-yl]-1,3,5-
triazin-2-yl]-4-(difluoromethyl)pyridin-2-amine Compound 60

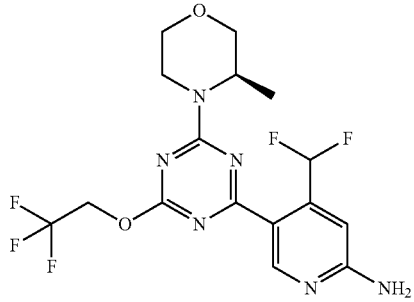

4-(difluoromethyl)-5-[4-[(3R)-3-methylmorpholin-4-
yl]-6-(2,2,2-trifluoroethoxy)-1,3,5-triazin-2-yl]pyri-
din-2-amine Compound 63

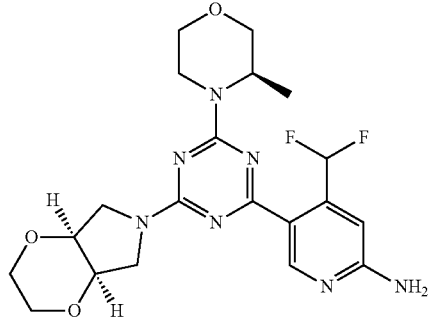

5-[4-[(4aS,7aR)-2,3,4a,5,7,7a-hexahydro-[1,4]di-
oxino[2,3-c]pyrrol-6-yl]-6-[(3R)-3-methylmorpho-
lin-4-yl]-1,3,5-triazin-2-yl]-4-(difluoromethyl)pyri-
din-2-amine Compound 61

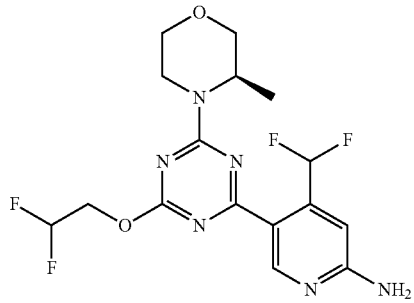

5-[4-(2,2-difluoroethoxy)-6-[(3R)-3-methylmorpho-
lin-4-yl]-1,3,5-triazin-2-yl]-4-(difluoromethyl)pyri-
din-2-amine Compound 64

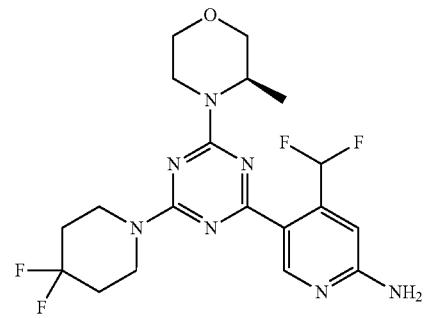

4-(difluoromethyl)-5-[4-(4,4-difluoro-1-piperidyl)-6-
[(3R)-3-methylmorpholin-4-yl]-1,3,5-triazin-2-yl]
pyridin-2-amine Compound 62

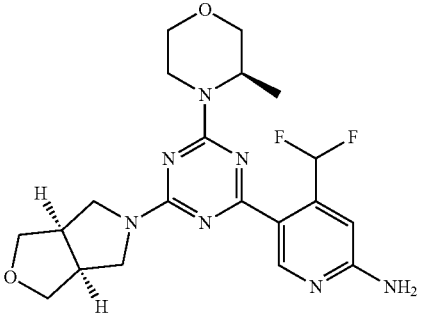

Compound 65

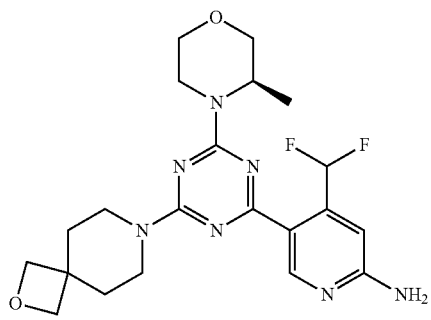

95

4-(difluoromethyl)-5-[4-[(3R)-3-methylmorpholin-4-yl]-6-(2-oxa-7-azaspiro[3.5]nonan-7-yl)-1,3,5-triazin-2-yl]pyridin-2-amine

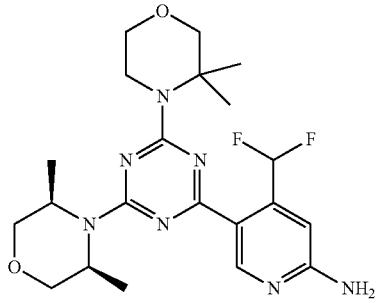

Compound 66

4-(difluoromethyl)-5-[4-(3,3-dimethylmorpholin-4-yl)-6-[(3R,5S)-3,5-dimethylmorpholin-4-yl]-1,3,5-triazin-2-yl]pyridin-2-amine

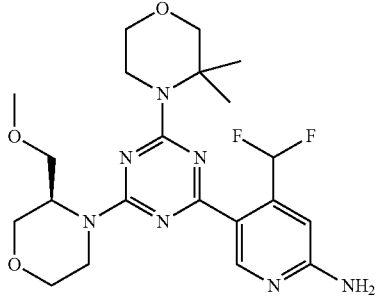

Compound 67

4-(difluoromethyl)-5-[4-(3,3-dimethylmorpholin-4-yl)-6-[(3R)-3-(methoxymethyl)morpholin-4-yl]-1,3,5-triazin-2-yl]pyridin-2-amine

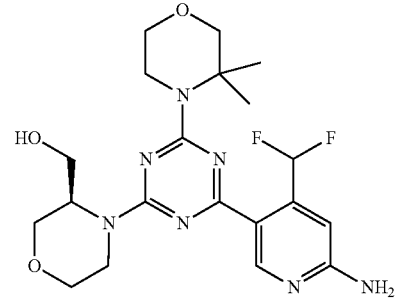

Compound 68

96

[(3R)-4-[4-[6-amino-4-(difluoromethyl)-3-pyridyl]-6-(3,3-dimethylmorpholin-4-yl)-1,3,5-triazin-2-yl]morpholin-3-yl]methanol

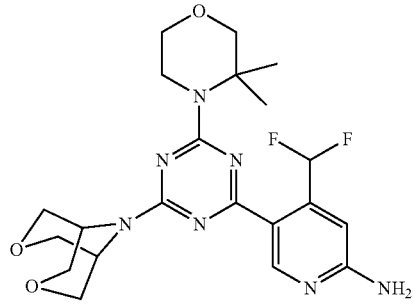

Compound 69

4-(difluoromethyl)-5-[4-(3,3-dimethylmorpholin-4-yl)-6-(3,7-dioxa-9-azabicyclo[3.3.1]nonan-9-yl)-1,3,5-triazin-2-yl]pyridin-2-amine

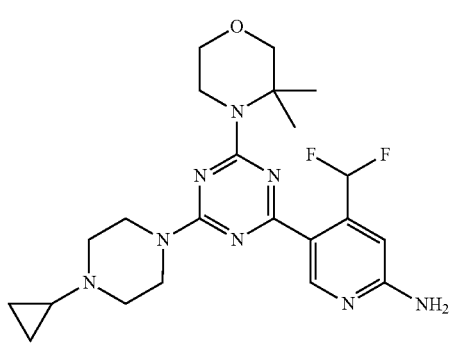

Compound 70

5-[4-(4-cyclopropylpiperazin-1-yl)-6-(3,3-dimethylmorpholin-4-yl)-1,3,5-triazin-2-yl]-4-(difluoromethyl)pyridin-2-amine

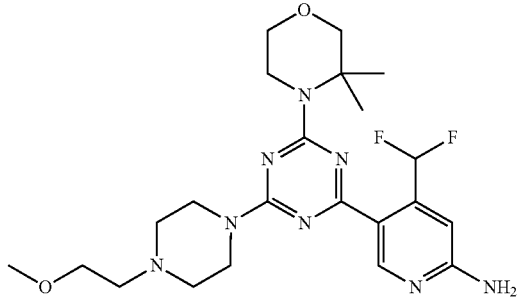

Compound 71

| 97 | 98 |
|---|---|
| 4-(difluoromethyl)-5-[4-(3,3-dimethylmorpholin-4-yl)-6-[4-(2-methoxyethyl)piperazin-1-yl]-1,3,5-triazin-2-yl]pyridin-2-amine | 4-(difluoromethyl)-5-[4-(3,3-dimethylmorpholin-4-yl)-6-[(3R)-tetrahydrofuran-3-yl]oxy-1,3,5-triazin-2-yl]pyridin-2-amine |

Compound 72

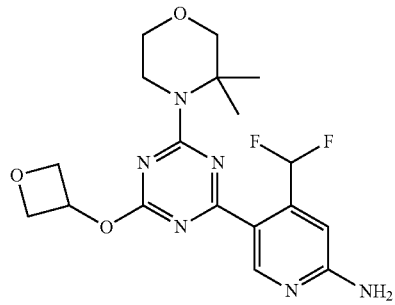

4-(difluoromethyl)-5-[4-(3,3-dimethylmorpholin-4-yl)-6-(oxetan-3-yloxy)-1,3,5-triazin-2-yl]pyridin-2-amine Compound 75

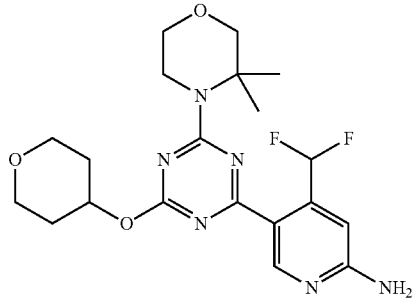

4-(difluoromethyl)-5-[4-(3,3-dimethylmorpholin-4-yl)-6-tetrahydropyran-4-yloxy-1,3,5-triazin-2-yl]pyridin-2-amine Compound 73

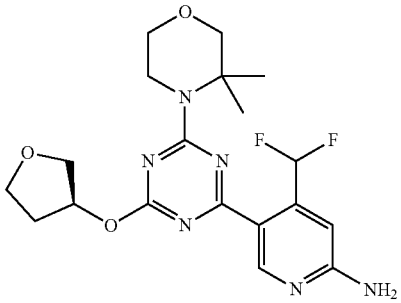

4-(difluoromethyl)-5-[4-(3,3-dimethylmorpholin-4-yl)-6-[(3S)-tetrahydrofuran-3-yl]oxy-1,3,5-triazin-2-yl]pyridin-2-amine Compound 76

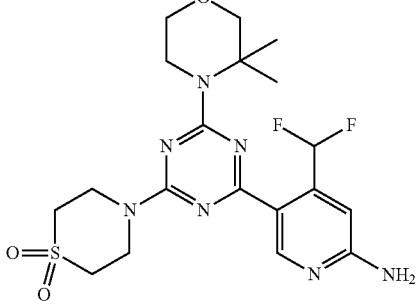

4-(difluoromethyl)-5-[4-(3,3-dimethylmorpholin-4-yl)-6-(1,1-dioxo-1,4-thiazinan-4-yl)-1,3,5-triazin-2-yl]pyridin-2-amine Compound 74

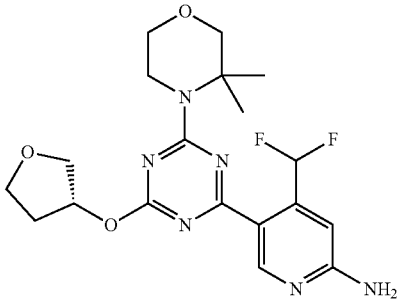

Compound 77

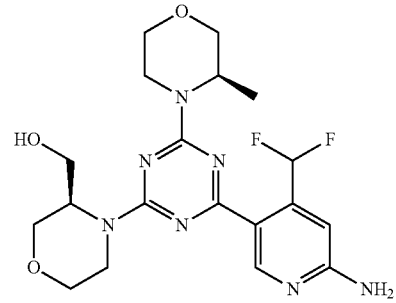

99

[(3R)-4-[4-[6-amino-4-(difluoromethyl)-3-pyridyl]-6-[(3R)-3-methylmorpholin-4-yl]-1,3,5-triazin-2-yl]morpholin-3-yl]methanol Further preferred compounds are

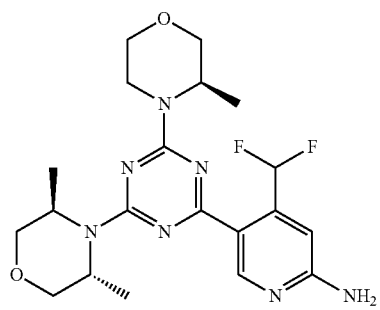

4-(difluoromethyl)-5-[4-[(3R,5R)-3,5-dimethylmorpholin-4-yl]-6-[(3R)-3-methylmorpholin-4-yl]-1,3,5-triazin-2-yl]pyridin-2-amine Compound

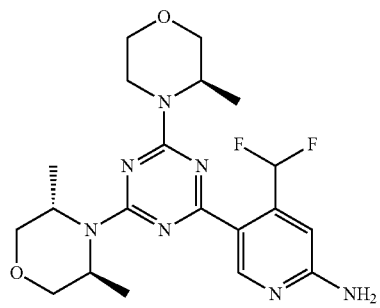

4-(difluoromethyl)-5-[4-[(3S,5S)-3,5-dimethylmorpholin-4-yl]-6-[(3R)-3-methylmorpholin-4-yl]-1,3,5-triazin-2-yl]pyridin-2-amine Compound

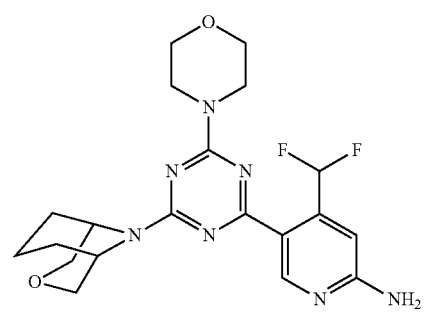

100

4-(difluoromethyl)-5-[4-morpholino-6-(3-oxa-9-azabicyclo[3.3.1]nonan-9-yl)-1,3,5-triazin-2-yl]pyridin-2-amine Compound

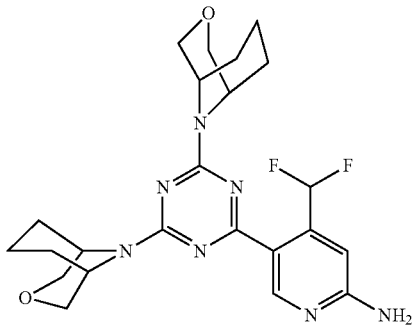

5-[4,6-bis(3-oxa-9-azabicyclo[3.3.1]nonan-9-yl)-1,3,5-triazin-2-yl]-4-(difluoromethyl)pyridin-2-amine Compound

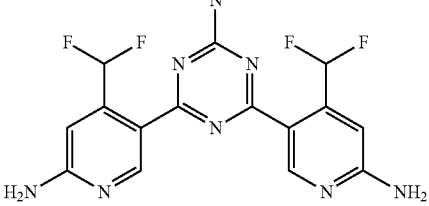

5-[4-[6-amino-4-(difluoromethyl)-3-pyridyl]-6-(3,7-dioxa-9-azabicyclo[3.3.1]nonan-9-yl)-1,3,5-triazin-2-yl]-4-(difluoromethyl)pyridin-2-amine Compound

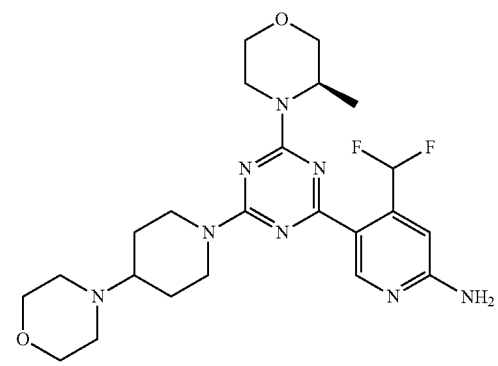

101

4-(difluoromethyl)-5-[4-[(3R)-3-methylmorpholin-4-yl]-6-(4-morpholino-1-piperidyl)-1,3,5-triazin-2-yl]pyridin-2-amine

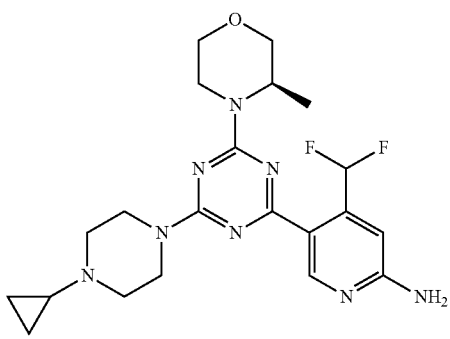

5-[4-(4-cyclopropylpiperazin-1-yl)-6-[(3R)-3-methylmorpholin-4-yl]-1,3,5-triazin-2-yl]-4-(difluoromethyl)pyridin-2-amine

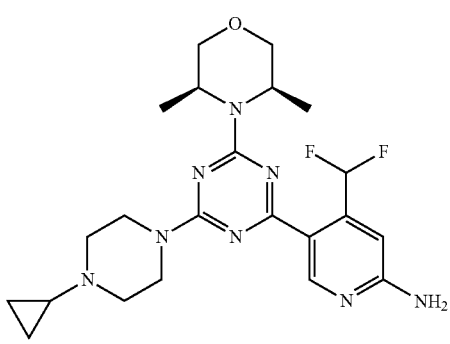

5-[4-(4-cyclopropylpiperazin-1-yl)-6-[(3S,5R)-3,5-dimethylmorpholin-4-yl]-1,3,5-triazin-2-yl]-4-(difluoromethyl)pyridin-2-amine Compound

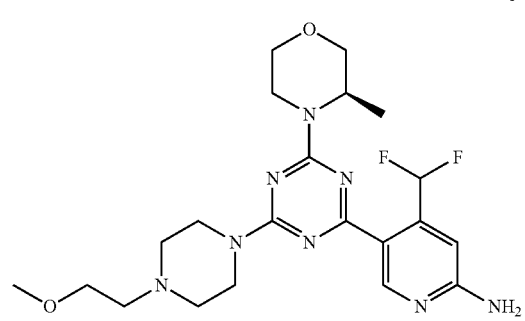

102

4-(difluoromethyl)-5-[4-[4-(2-methoxyethyl)piperazin-1-yl]-6-[(3R)-3-methylmorpholin-4-yl]-1,3,5-triazin-2-yl]pyridin-2-amine Compound

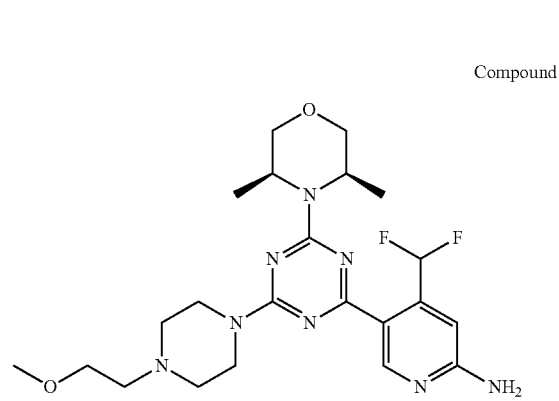 [SMILES: COCCN1CCN(c2nc(-c3cnc(N)cc3C(F)F)nc(N3[C@H](C)COC[C@@H]3C)n2)CC1]

4-(difluoromethyl)-5-[4-[(3S,5R)-3,5-dimethylmorpholin-4-yl]-6-[4-(2-methoxyethyl) piperazin-1-yl]-1,3,5-triazin-2-yl]pyridin-2-amine Compound

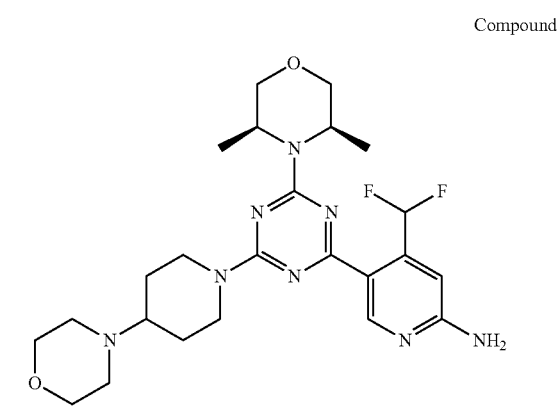 [SMILES: C[C@@H]1COC[C@H](C)N1c1nc(-c2cnc(N)cc2C(F)F)nc(N2CCC(N3CCOCC3)CC2)n1]

4-(difluoromethyl)-5-[4-[(3R,5S)-3,5-dimethylmorpholin-4-yl]-6-(4-morpholino-1-piperidyl)-1,3,5-triazin-2-yl]pyridin-2-amine Compound

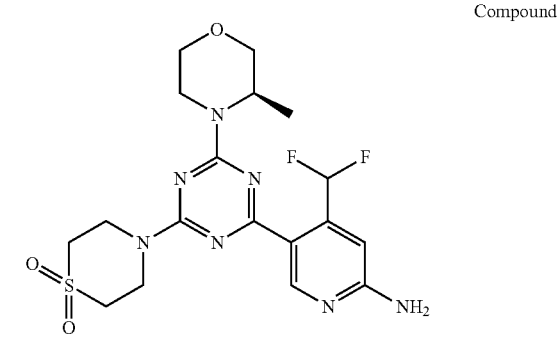 [SMILES: C[C@@H]1COCCN1c1nc(-c2cnc(N)cc2C(F)F)nc(N2CCS(=O)(=O)CC2)n1]

103

4-(difluoromethyl)-5-[4-(1,1-dioxo-1,4-thiazinan-4-yl)-6-[(3R)-3-methylmorpholin-4-yl]-1,3,5-triazin-2-yl]pyridin-2-amine

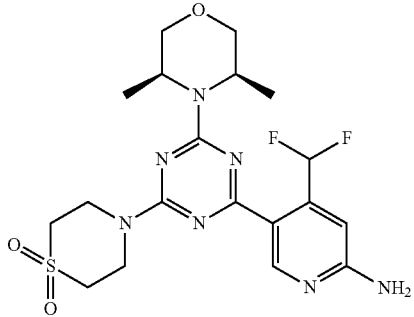

Compound 4-(difluoromethyl)-5-[4-[(3S,5R)-3,5-dimethylmorpholin-4-yl]-6-(1,1-dioxo-1,4-thiazinan-4-yl)-1,3,5-triazin-2-yl]pyridin-2-amine

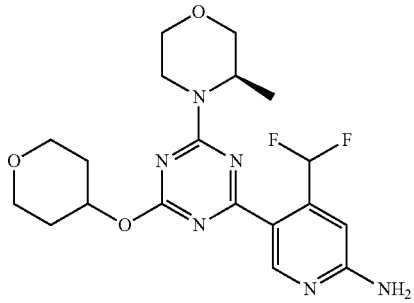

Compound 4-(difluoromethyl)-5-[4-[(3R)-3-methylmorpholin-4-yl]-6-tetrahydropyran-4-yloxy-1,3,5-triazin-2-yl]pyridin-2-amine

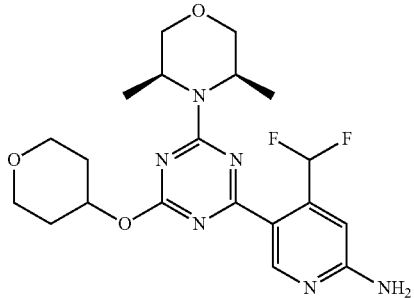

Compound

104

4-(difluoromethyl)-5-[4-[(3S,5R)-3,5-dimethylmorpholin-4-yl]-6-tetrahydropyran-4-yloxy-1,3,5-triazin-2-yl]pyridin-2-amine

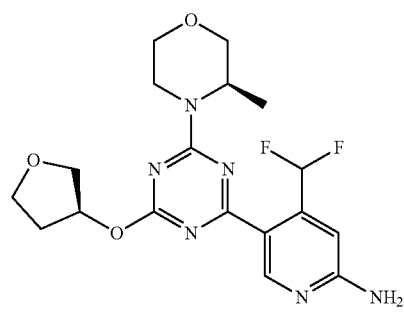

Compound 4-(difluoromethyl)-5-[4-[(3R)-3-methylmorpholin-4-yl]-6-[(3S)-tetrahydrofuran-3-yl]oxy-1,3,5-triazin-2-yl]pyridin-2-amine

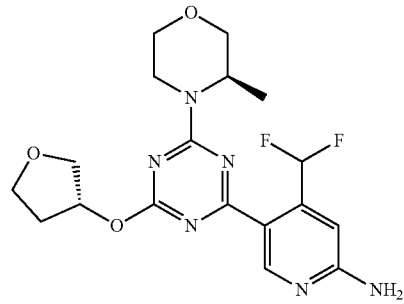

Compound 4-(difluoromethyl)-5-[4-[(3R)-3-methylmorpholin-4-yl]-6-[(3R)-tetrahydrofuran-3-yl]oxy-1,3,5-triazin-2-yl]pyridin-2-amine

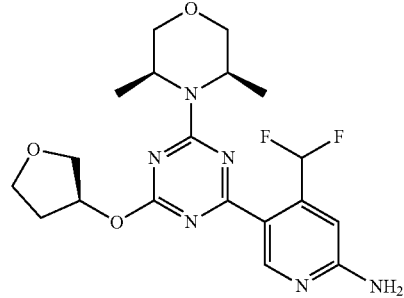

Compound

105

4-(difluoromethyl)-5-[4-[(3S,5R)-3,5-dimethylmorpholin-4-yl]-6-[(3S)-tetrahydrofuran-3-yl]oxy-1,3,5-triazin-2-yl]pyridin-2-amine

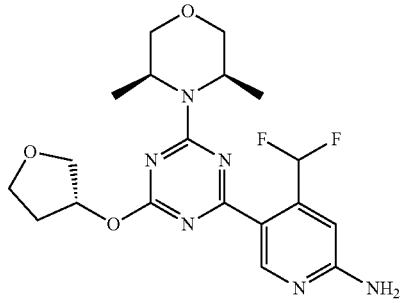

4-(difluoromethyl)-5-[4-[(3S,5R)-3,5-dimethylmorpholin-4-yl]-6-[(3R)-tetrahydrofuran-3-yl]oxy-1,3,5-triazin-2-yl]pyridin-2-amine

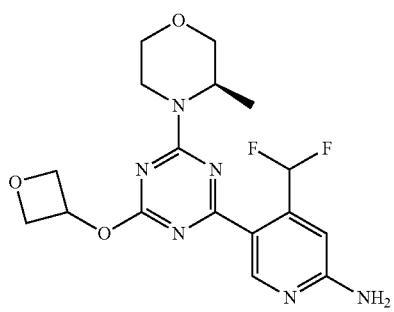 [SMILES: C[C@@H]1COCCN1c1nc(OC2COC2)nc(-c2cnc(N)cc2C(F)F)n1]

4-(difluoromethyl)-5-[4-[(3R)-3-methylmorpholin-4-yl]-6-(oxetan-3-yloxy)-1,3,5-triazin-2-yl]pyridin-2-amine Compound

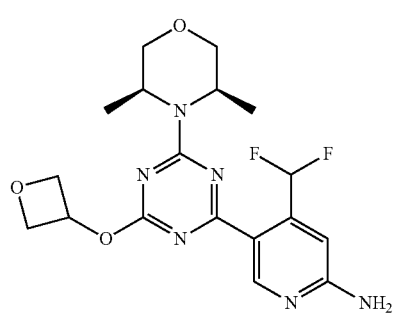

106

4-(difluoromethyl)-5-[4-[(3S,5R)-3,5-dimethylmorpholin-4-yl]-6-(oxetan-3-yloxy)-1,3,5-triazin-2-yl]pyridin-2-amine Compound

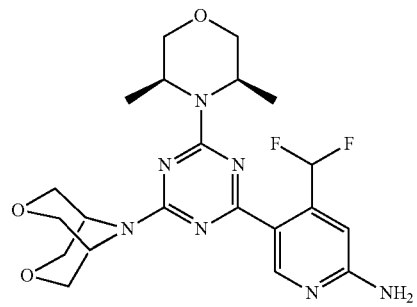

4-(difluoromethyl)-5-[4-[(3R,5S)-3,5-dimethylmorpholin-4-yl]-6-(3,7-dioxa-9-azabicyclo[3.3.1]nonan-9-yl)-1,3,5-triazin-2-yl]pyridin-2-amine Compound 3-[4-[6-amino-4-(difluoromethyl)-3-pyridyl]-6-[(3R,5S)-3,5-dimethylmorpholin-4-yl]-1,3,5-triazin-2-yl]oxazolidin-2-one Compound

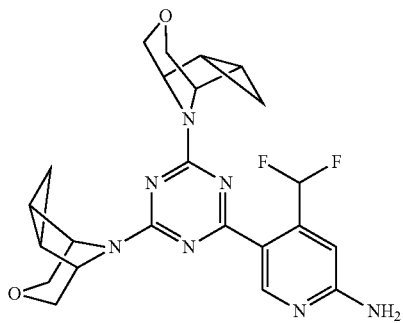

107

5-(4-((1R,2R,4S,5S)-7-oxa-9-azatricyclo[3.3.1.0²,⁴]
nonan-9-yl)-6-((2R,4S)-7-oxa-9-azatricyclo[3.3.
1.0²,⁴]nonan-9-yl)-1,3,5-triazin-2-yl)-4-(difluorom-
ethyl)pyridin-2-amine

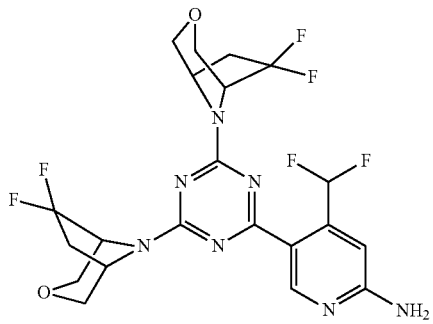

5-[4,6-bis(6,6-difluoro-3-oxa-8-azabicyclo[3.2.1]
octan-8-yl)-1,3,5-triazin-2-yl]-4-(difluoromethyl)
pyridin-2-amine Compound

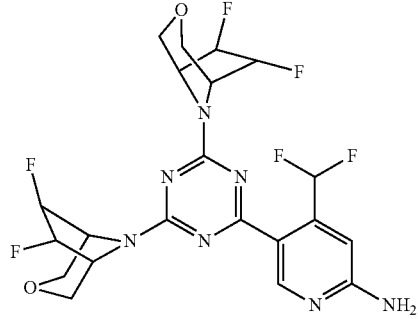

5-[4,6-bis(6,7-difluoro-3-oxa-8-azabicyclo[3.2.1]
octan-8-yl)-1,3,5-triazin-2-yl]-4-(difluoromethyl)
pyridin-2-amine Compound

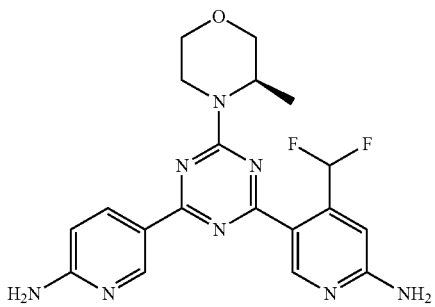

108

5-[4-(6-amino-3-pyridyl)-6-[(3R)-3-methylmorpho-
lin-4-yl]-1,3,5-triazin-2-yl]-4-(difluoromethyl)pyri-
din-2-amine Compound

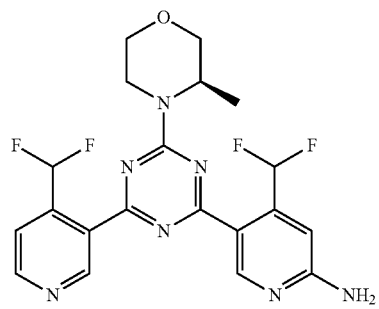

4-(difluoromethyl)-5-[4-[4-(difluoromethyl)-3-
pyridyl]-6-[(3R)-3-methylmorpholin-4-yl]-1,3,5-
triazin-2-yl]pyridin-2-amine Compound 4-(difluoromethyl)-5-[4-[(3R)-3-methylmorpholin-4-
yl]-6-(3-pyridyl)-1,3,5-triazin-2-yl]pyridin-2-amine Compound

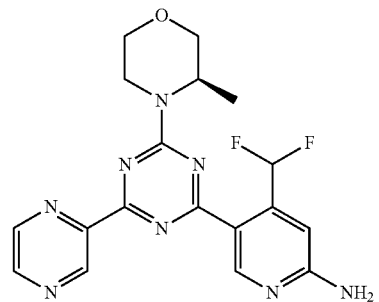

4-(difluoromethyl)-5-[4-[(3R)-3-methylmorpholin-4-yl]-6-pyrazin-2-yl-1,3,5-triazin-2-yl]pyridin-2-amine

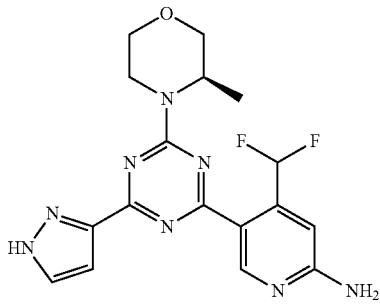

Compound 109

4-(difluoromethyl)-5-[4-[(3R)-3-methylmorpholin-4-yl]-6-(1H-pyrazol-3-yl)-1,3,5-triazin-2-yl]pyridin-2-amine

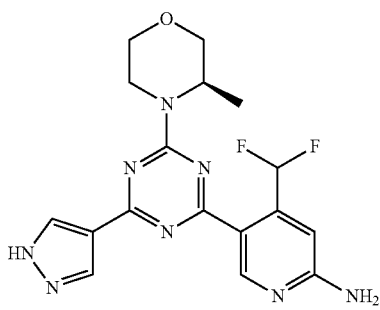

Compound 4-(difluoromethyl)-5-[4-[(3R)-3-methylmorpholin-4-yl]-6-(1H-pyrazol-4-yl)-1,3,5-triazin-2-yl]pyridin-2-amine

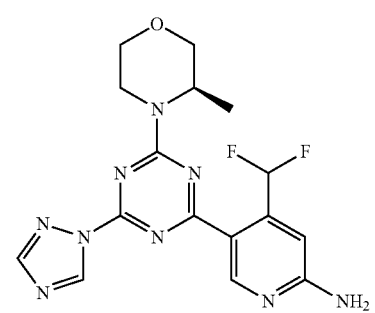

Compound 4-(difluoromethyl)-5-[4-[(3R)-3-methylmorpholin-4-yl]-6-(1,2,4-triazol-1-yl)-1,3,5-triazin-2-yl]pyridin-2-amine

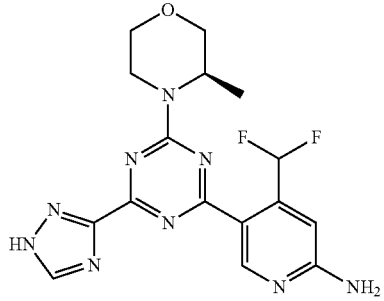

Compound 110

4-(difluoromethyl)-5-[4-[(3R)-3-methylmorpholin-4-yl]-6-(1H-1,2,4-triazol-3-yl)-1,3,5-triazin-2-yl]pyridin-2-amine

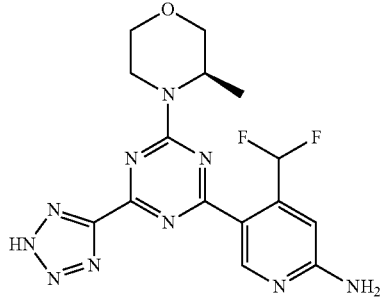

Compound 4-(difluoromethyl)-5-[4-[(3R)-3-methylmorpholin-4-yl]-6-(2H-tetrazol-5-yl)-1,3,5-triazin-2-yl]pyridin-2-amine Preparation of Compounds of the Invention The compounds of the invention may be synthesized by synthetic routes that include processes analogous to those well known in the chemical arts, particularly in light of the description contained herein. The starting materials are generally available from commercial sources or are readily prepared using methods well known to those skilled in the art.

In preparing compounds of the invention, protection of remote functionality (e.g., primary or secondary amine) of intermediates may be necessary. The need for such protection will vary depending on the nature of the remote functionality and the conditions of the preparation methods. Suitable amino-protecting groups include tert-butyloxycarbonyl (BOC), bis-tert-butyloxycarbonyl or dimethylaminomethylenyl. The need for such protection is readily determined by one skilled in the art. For a general description of protecting groups and their use, see T. W. Greene, Protective Groups in Organic Synthesis, John Wiley & Sons, New York, 1991.

Methods of Separation

In the methods of preparing the compounds of this invention, it may be advantageous to separate reaction products from one another and/or from starting materials. The desired products of each step or series of steps are separated and/or purified to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; high, medium and low pressure liquid chromatography methods and apparatus; small scale analytical; and preparative thin or thick layer chromatography, as well as techniques of small scale thin layer and flash chromatography.

Selection of appropriate methods of separation depends on the nature of the materials involved, for example, presence or absence of polar functional groups in chromatography, stability of materials in acidic and basic media in multiphase extraction, and the like. One skilled in the art will apply techniques most likely to achieve the desired separation.

Examples

The Examples are intended to illustrate the present invention without restricting it.

The chemical reactions described in the Examples may be readily adapted to prepare a number of other lipid kinase inhibitors of the invention, and alternative methods for preparing the compounds of this invention are deemed to be within the scope of this invention. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds of the invention.

As a rule, $^1$H NMR and mass spectra have been obtained for the compounds prepared. In the Examples described below, unless otherwise indicated, all temperatures are set forth in degrees Celsius (° C.). Reagents were purchased from commercial suppliers such as Sigma Aldrich, Fluorochem, Acros, Lancaster, TCI or Maybridge, and were used without further purification unless otherwise indicated. The reactions set forth below were done generally under a positive pressure of nitrogen or with a drying tube (unless otherwise stated) in anhydrous solvents, and the reaction flasks were typically fitted with rubber septa for the introduction of substrates and reagents via syringe. Glassware was oven dried. Column chromatography was performed using Merck silica gel. $^1$H NMR spectra were recorded on a Bruker instrument operating at 400 MHz. $^1$H NMR spectra were obtained for solutions in various deuterated solvents such as CDCl$_3$, (CD$_3$)$_2$SO, CD$_3$OD or (CD$_3$)$_2$CO. The chemical shift δ values were reported in ppm and corrected to the signal of the deuterated solvents (7.26 ppm for CDCl$_3$) or TMS (0 ppm). $^{19}$F NMR spectra were calibrated relative to CFCl$_3$ (δ=0 ppm) as external standard. $^{19}$F NMR spectra were recorded $^1$H-decoupled. When peak multiplicities are reported, the following abbreviations are used: s (singlet), d (doublet), t (triplet), m (multiplet), quint (quintet), br (broadened). Coupling constants, when given, are reported in Hertz (Hz). MALDI-ToF Mass spectra (MS) have been obtained on a Voyager-De™ Pro measured in m/z.

The following abbreviations are used hereinafter: BSA (bovine serum albumin), DMSO (dimethyl sulfoxide), ESI (electrospray ionization), HCl (hydrochloric acid), M (molar), MALDI (Matrix-assisted Laser Desorption/Ionization), MS (mass spectrometry), PBS (phosphate buffered saline), TLC (thin layer chromatography).

Preparation of Intermediate Compounds

The following methods were used to prepare the intermediates compounds used to produce compounds of formula (I).

Method 1: 8-(4-(3-oxa-8-azabicyclo[3.2.1]octan-8-yl)-6-chloro-1,3,5-triazin-2-yl)-3-oxa-8-azabicyclo[3.2.1]octane (i1)

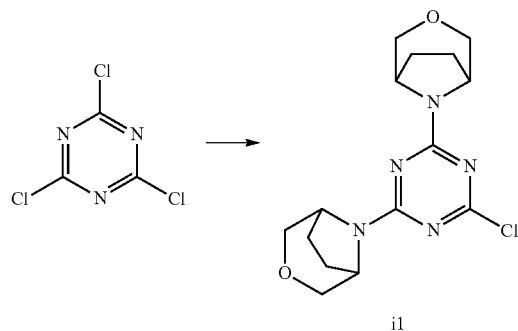 [SMILES: Clc1nc(Cl)nc(Cl)n1 ; Clc1nc(N2C3CCC2COC3)nc(N2C3CCC2COC3)n1]

i1

3-Oxa-8-azabicyclo[3.2.1]octane.HCl (Advanced ChemBlocks Inc, product number A-861, 2.00 g, 13.4 mmol, 2.0 eq.) and N,N-diisopropylethylamine (4.80 mL, 27.6 mmol, 4.1 eq.) are charged into a flask and dissolved in dichloromethane (20 mL). The flask is placed in an ice bath and the solution subsequently cooled down to 0° C. This solution is then added dropwise to a solution of cyanuric chloride in dichloromethane (20 mL) at 0° C. The resulting reaction mixture is stirred overnight, while it is allowed to warm up to room temperature. Additional dichloromethane (100 mL) is added and the organic layer is washed with a saturated aqueous solution of sodium bisulfate. The organic layer is then dried over anhydrous sodium sulfate, filtered and the solvent is evaporated under reduced pressure. Purification by flash chromatography (cyclohexane/ethyl acetate 4:1) gives the desired intermediate ii as a colorless solid (79% yield). $^1$H NMR (400 MHz, CDCl$_3$): δ 4.70-4.54 (m, 4H), 3.80-3.58 (m, 8H), 2.14-1.89 (m, 8H); MS (MALDI): m/z=338.4 ([M+H]$^+$).

Method 1 is also used for the preparation of the following intermediate compounds i2 to i10, and intermediates i79 to i81.

| Reagent | Structure | NMR | MS |
|---|---|---|---|
| i2 | (morpholine) | ¹H NMR (400 MHz, CDCl₃): δ 3.78 (m, 8 H), 3.70 (m, 8 H). | MS (MALDI): m/z = 287.6 ([M + H]⁺). |
| i3 | ((S)-3-methylmorpholine) | ¹H NMR (400 MHz, CDCl₃): δ 4.75-4.56 (m, 2 H), 4.34-4.30 (m, 2 H), 3.94 (dd, $^2J_{H,H}$ = 12.0 Hz, $^3J_{H,H}$ = 4.0 Hz, 2 H), 3.74 (d, $^2J_{H,H}$ = 12.0 Hz, 2 H), 3.63 (dd, $^2J_{H,H}$ = 12.0 Hz, $^3J_{H,H}$ = 4.0 Hz, 2 H), 3.49 (dt, $^2J_{H,H}$ = 12.0 Hz, $^3J_{H,H}$ = 4.0 Hz, 2 H), 3.25 (dt, $^2J_{H,H}$ = 12.0 Hz, $^3J_{H,H}$ = 4.0 Hz, 2 H), 1.31 (d, $^3J_{H,H}$ = 8.0 Hz, 6 H). | MS (MALDI): m/z = 314.4 ([M + H]⁺). |
| i4 | (3,3-dimethylmorpholine) | ¹H NMR (400 MHz, CDCl₃): δ 3.81-3.72 (m, 8 H), 3.43 (s, 4 H), 1.43 (br s, 12 H). | MS (MALDI): m/z = 342.5 ([M + H]⁺). |
| i5 | ((R)-3-methylmorpholine) | ¹H NMR (400 MHz, CDCl₃): δ 4.75-4.56 (m, 2 H), 4.34-4.30 (m, 2 H), 3.94 (dd, $^2J_{H,H}$ = 12.0 Hz, $^3J_{H,H}$ = 4.0 Hz, 2 H), 3.74 (d, $^2J_{H,H}$ = 12.0 Hz, 2 H), 3.63 (dd, $^2J_{H,H}$ = 12.0 Hz, $^3J_{H,H}$ = 4.0 Hz, 2 H), 3.49 (dt, $^2J_{H,H}$ = 12.0 Hz, $^3J_{H,H}$ = 4.0 Hz, 2 H), 3.25 (dt, $^2J_{H,H}$ = 12.0 Hz, $^3J_{H,H}$ = 4.0 Hz, 2 H), 1.31 (d, $^3J_{H,H}$ = 8.0 Hz, 6 H). | MS (MALDI): m/z = 314.3 ([M + H]⁺). |
| i6 | ((3R,5S)-3,5-dimethylmorpholine) | ¹H NMR (400 MHz, CDCl₃): δ 4.40-4.37 (m, 4 H), 3.74 (d, $^3J_{H,H}$ = 11.6 Hz, 4 H), 3.53 (dd, $^3J_{H,H}$ = 11.6 Hz, $^2J_{H,H}$ = 4.0 Hz, 4 H), 1.26 (d, $^3J_{H,H}$ = 6.9 Hz, 12 H). | MS (MALDI): m/z = 342.8 ([M + H]⁺). |

| Reagent | Structure | NMR | MS |
|---|---|---|---|
| i7 | 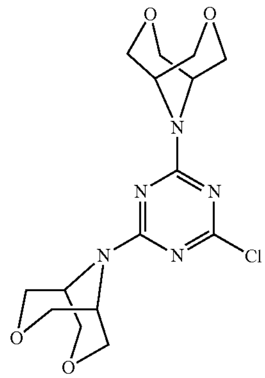 [SMILES: Clc1nc(N2C3COCC2COC3)nc(N2C3COCC2COC3)n1] | ¹H NMR (400 MHz, CDCl₃): δ 4.53 (br s, 2 H), 4.36 (br s, 2 H), 4.12-4.06 (m, 8 H), 3.92-3.83 (m, 8 H). | MS (MALDI): m/z = 370.3 ([M]⁺). |
| i8 | 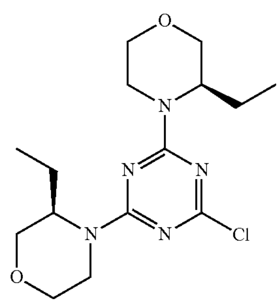 [SMILES: CC[C@@H]1COCCN1c1nc(Cl)nc(N2CCOC[C@H]2CC)n1] | ¹H NMR (400 MHz, (CD₃)₂SO): δ 4.36-4.21 (m, 4 H), 3.85-3.75 (m, 4 H), 3.48-3.45 (m, 2 H), 3.40-3.34 (m, 2 H), 3.14-3.09 (m, 2 H), 1.72 (m, 4 H), 0.82 (m, 6 H). | MS (MALDI): m/z = 342.3 ([M]⁺). |
| i9 | 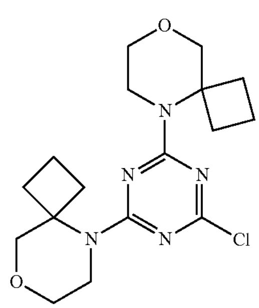 [SMILES: Clc1nc(N2CCOCC23CCC3)nc(N2CCOCC23CCC3)n1] | ¹H NMR (400 MHz, (CD₃)₂SO): δ 3.64 (m, 8 H), 3.351-3.48 (m, 4 H), 2.46-2.38 (m, 4 H), 2.20-2.16 (m, 4 H), 1.73-1.66 (m, 4 H). | MS (MALDI): m/z = 366.7 ([M]⁺). |
| i10 | 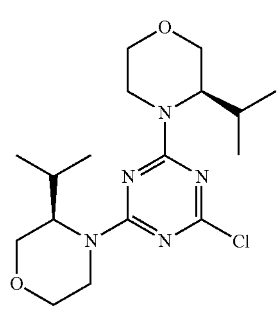 [SMILES: CC(C)[C@@H]1COCCN1c1nc(Cl)nc(N2CCOC[C@H]2C(C)C)n1] | ¹H NMR (400 MHz, (CD₃)₂SO): δ 4.40-4.25 (m, 2 H), 4.20-4.05 (m, 2 H), 4.08 (m, 2 H), 3.95 (m, 2 H), 3.83 (m, 4 H), 3.08 (m, 2 H), 2.30 (m, 2 H), 0.98 (m, 6 H), 0.48 (m, 6 H). | MS (MALDI): m/z = 370.4 ([M]⁺). |

| Reagent | Structure | NMR | MS |
|---|---|---|---|
| i79 | (2,6-dimethylmorpholine, NH) | bis(2,6-dimethylmorpholinyl)-chlorotriazine | ¹H NMR (400 MHz, CDCl₃): δ 4.59-4.31 (m, 4 H), 3.66-3.46 (m, 4 H), 2.70 (m, 4 H), 1.14 (m, 12 H). | MS (MALDI): m/z = 342.4 ([M + H]⁺). |
| i80 | (2,2-dimethylmorpholine, NH) | bis(2,2-dimethylmorpholinyl)-chlorotriazine | ¹H NMR (400 MHz, CDCl₃): δ 3.73-3.64 (m, 8 H), 3.57 (s, 2 H), 3.51 (s, 2 H), 1.14 (s, 12 H). | MS (MALDI): m/z = 342.3 ([M + H]⁺). |
| i81 | (8-oxa-3-azabicyclo[3.2.1]octane) | bis(8-oxa-3-azabicyclo[3.2.1]oct-3-yl)-chlorotriazine | ¹H NMR (400 MHz, CDCl₃): δ 4.41 (br s, 4 H), 4.32-4.16 (m, 4 H), 3.24-3.10 (m, 4 H), 1.99-1.84 (m, 4 H), 1.84-1.67 (m, 4 H). | MS (MALDI): m/z = 338.4 ([M + H]⁺) |

Method 2: 2,4-dichloro-6-morpholino-1,3,5-triazine (i11)

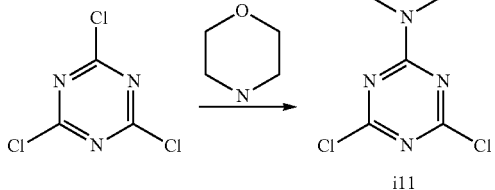

To a solution of cyanuric chloride (18.1 g, 0.100 mol, 1.0 eq.) in dichloromethane (200 mL) is dropwise added a cold solution of morpholine (17.4 g, 0.200 mol, 2.0 eq.) at −78° C. over 2 hours. The resulting mixture is allowed to warm to 0° C. with stirring and mixed with an ice cold saturated solution of sodium bisulfate in water. The phases are separated and the organic phase is washed with half concentrated brine dried over sodium sulfate and evaporated to yield the title compound i11 as a colorless solid. $^1$H NMR (400 MHz, CDCl$_3$): δ 3.90-3.86 (m, 4H), 3.77-3.72 (m, 4H).

Method 3: 8-(4-chloro-6-morpholino-1,3,5-triazin-2-yl)-3-oxa-8-azabicyclo[3.2.1]octane (i12)

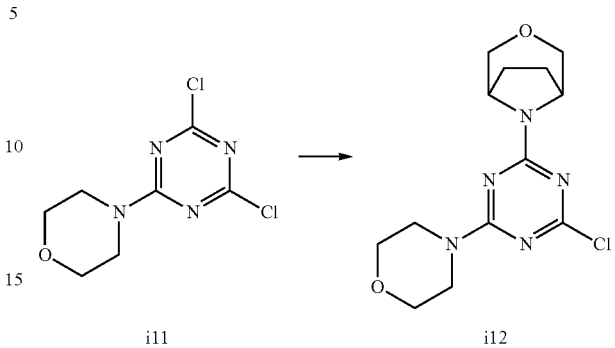

3-Oxa-8-azabicyclo[3.2.1]octane.HCl (Advanced ChemBlocks Inc, product number A-861, 200 mg, 1.34 mmol, 1.1 eq.) and N,N-diisopropylethylamine (470 μL, 2.69 mmol, 2.1 eq.) are charged in a flask and dissolved in ethanol (3 mL). The flask is placed in an ice bath. A solution of compound i11 (300 mg, 1.28 mmol, 1.0 eq.) in ethanol (2 mL) is added to the above solution at 0° C. The resulting mixture is stirred overnight, while allowing it to warm up to room temperature. Deionized water (20 mL) is added and the aqueous layer is extracted with ethyl acetate (3×30 mL). The combined organic layer is dried over anhydrous sodium sulfate, filtered and the solvent is evaporated under reduced pressure. Purification by flash chromatography (cyclohexane/ethyl acetate 9:1→8:2) gives the desired intermediate i12 as a colorless solid (78% yield). $^1$H NMR (400 MHz, CDCl$_3$): δ 4.69-4.56 (m, 2H), 3.86-3.59 (m, 12H), 2.12-1.91 (m, 4H); MS (MALDI): m/z=312.7 ([M+H]$^+$).

Method 3 is also used for the preparation of the following intermediate compounds i13 to i16.

| | Reagent | Structure | NMR |
|---|---|---|---|
| i13 | ![morpholine with methyl stereocenter] | ![triazine with chiral morpholine] | $^1$H NMR (400 MHz, CDCl$_3$): δ 4.71-4.61 (m, 1 H), 4.34-4.31 (m, 1 H), 3.96-3.92 (m, 1 H), 3.79-3.70 (m, 9 H), 3.65-3.61 (m, 1 H), 3.51-3.45 (m, 1 H), 3.29-3.21 (m, 1 H), 1.36-1.30 (d, $^3J_{H,H}$ = 6.9 Hz, 3 H). |
| i14 | ![Boc-piperazine] | ![Boc-piperazinyl triazine] | $^1$H NMR (400 MHz, CDCl$_3$): δ 3.79-3.71 (m, 12 H), 3.46 (m, 4 H), 1.48 (s, 9 H). |

| Reagent | Structure | NMR |
|---|---|---|
| i15 | thiomorpholine | $^1$H NMR (400 MHz, CDCl$_3$): δ 4.12-3.98 (m, 4 H), 3.84-3.70 (m, 4 H), 3.70-3.62 (m, 4 H), 2.66-2.56 (m, 4 H). |
| i16 | (S)-3-methylmorpholine derivative | $^1$H NMR (400 MHz, CDCl$_3$): δ 3.77 (m, 4 H), 3.68-3.63 (m, 8 H), 3.44 (s, 2 H), 1.44 (s, 6 H). |

Method 4: (S)-4-(4,6-dichloro-1,3,5-triazin-2-yl)-3-methylmorpholine (i17)

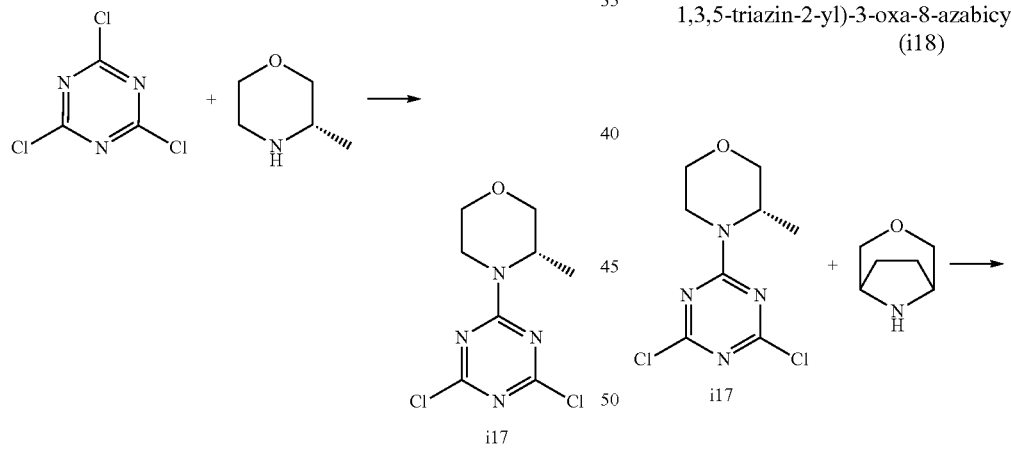

To a solution of cyanuric chloride (450 mg, 2.44 mol, 1.0 eq.) in dichloromethane (4 mL) is slowly added a solution of (S)-3-methylmorpholine (Activate Scientific, product number AS3424, 0.28 mL, 2.44 mol, 1.0 eq.) and triethylamine (0.35 mL, 2.51 mol, 1.02 eq.) in dichloromethane (2 mL) at −50° C. The resulting mixture is stirred for 2 hours at −50° C., then allowed to warm to 0° C. with stirring and mixed with an ice cold saturated solution of sodium bisulfate in water. The phases are separated and the organic phase is washed with brine dried over sodium sulfate and evaporated to yield the title compound i17 as a colorless solid (95% yield). $^1$H NMR (400 MHz, CDCl$_3$): δ 4.78-4.69 (m, 1H), 4.43-4.39 (m, 1H), 3.98-3.96 (m, 1H), 3.78-3.76 (m, 1H), 3.67-3.65 (m, 1H), 3.51-3.47 (m, 1H), 3.40-3.37 (m, 1H), 1.36 (m, 3H).

Method 5: 8-(4-chloro-6-((S)-3-methylmorpholino)-1,3,5-triazin-2-yl)-3-oxa-8-azabicyclo[3.2.1]octane (i18)

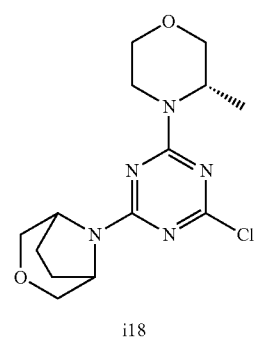

3-Oxa-8-azabicyclo[3.2.1]octane.HCl (Advanced ChemBlocks Inc, product number A-861, 383 mg, 2.55 mmol, 1.1 eq.) and N,N-diisopropylethylamine (1.0 mL, 5.60 mmol, 2.4 eq.) are charged in a flask and dissolved in ethanol (4 mL). The flask is placed in an ice bath. A solution of compound i17 (580 mg, 2.33 mmol, 1.0 eq.) in ethanol (2 mL) is added to the above solution at 0° C. The resulting mixture is stirred for 4 hours, while allowing it to warm up to room temperature. Deionized water (20 mL) is added and the aqueous layer is extracted with ethyl acetate (3×30 mL). The combined organic layer is dried over anhydrous sodium sulfate, filtered and the solvent is evaporated under reduced pressure. Purification by flash chromatography (cyclohexane/ethyl acetate 9:1→8:2) gives the desired intermediate i18 as a colorless solid (88% yield). $^1$H NMR (400 MHz, CDCl$_3$): δ 4.75-4.52 (m, 3H), 4.37-4.24 (m, 1H), 3.95-3.92 (m, 1H), 3.73-3.70 (m, 3H), 3.64-3.61 (m, 3H), 3.52-3.42 (m, 1H), 3.29-3.17 (m, 1H), 2.11-1.89 (m, 4H), 1.31 (m, 3H).

Method 6: tert-butyl 4-(4,6-dichloro-1,3,5-triazin-2-yl)piperazine-1-carboxylate (i19)

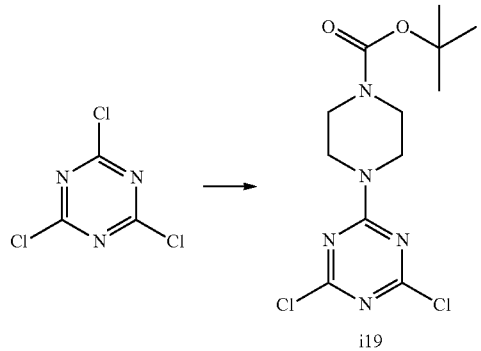 [SMILES: Clc1nc(Cl)nc(Cl)n1 ; CC(C)(C)OC(=O)N1CCN(c2nc(Cl)nc(Cl)n2)CC1]

To a cooled (−50° C.) solution of cyanuric chloride (1.0 g, 5.42 mmol, 1.0 eq.) in dichloromethane (4 mL) is added dropwise a solution of tert-butyl piperazine-1-carboxylate (Sigma, product number 343536, 1.02 g, 5.48 mmol, 1.01 eq.) and triethylamine (0.767 mL, 5.53 mmol, 1.02 eq.) in dichloromethane (2 mL). The resulting reaction mixture is stirred at −50° C. for 4 hours. A saturated aqueous solution of sodium bisulfate (10 mL) and dichloromethane (20 mL) are added. The mixture is transferred to a separating funnel. The organic layer is separated, washed with a saturated aqueous solution of sodium bisulfate (20 mL), dried over anhydrous sodium sulfate, filtered and then the solvent is evaporated under reduced pressure to give pure intermediate i19 (80% yield). $^1$H NMR (400 MHz, CDCl$_3$): δ 3.88-3.85 (m, 4H), 3.53-3.51 (m, 4H), 1.49 (m, 9H).

Method 7: tert-butyl 4-(4-(3-oxa-8-azabicyclo[3.2.1]octan-8-yl)-6-chloro-1,3,5-triazin-2-yl)piperazine-1-carboxylate (i20)

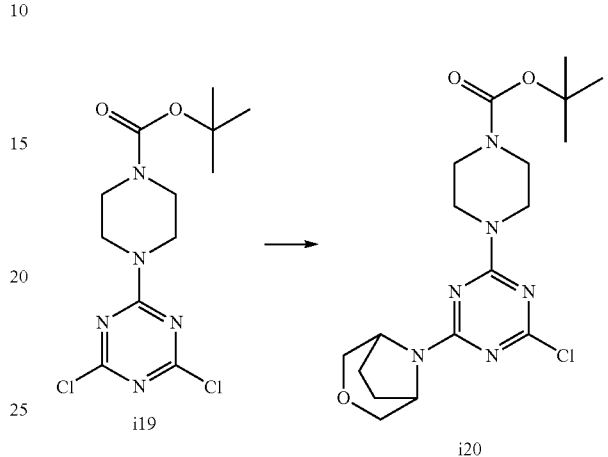

3-Oxa-8-azabicyclo[3.2.1]octane-HCl (Advanced ChemBlocks Inc, product number A-861, 235 mg, 1.57 mmol, 1.0 eq.) and N,N-diisopropylethylamine (592 µL, 3.14 mmol, 2.1 eq.) are charged in a flask and dissolved in ethanol (6 mL). The flask is placed in an ice bath. A solution of compound i19 (500 mg, 1.5 mmol, 1.0 eq.) in ethanol (2 mL) is added to the above solution at 0° C. The resulting mixture is stirred overnight, while allowed to warm up to room temperature. Deionized water (10 mL) is added and the aqueous layer is extracted with ethyl acetate (3×30 mL). The combined organic layer is dried over anhydrous sodium sulfate, filtered and the solvent is evaporated under reduced pressure. Purification by flash chromatography (cyclohexane/ethyl acetate 8:2) gave the desired intermediate i20 as a colorless solid (77% yield). $^1$H NMR (400 MHz, CDCl$_3$): δ 4.68-4.60 (m, 2H), 3.76-3.70 (m, 6H), 3.64-3.62 (m, 2H), 3.47-3.45 (m, 4H), 2.08-1.95 (m, 4H), 1.48 (br s, 9H); MS (MALDI): m/z=411.8 ([M+H]$^+$).

Method 7 is also used for the preparation of the following intermediate compound i21.

| | Reagent | Structure | NMR | MS |
|---|---|---|---|---|
| i21 | 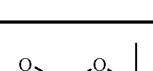 | 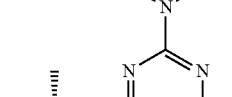 | $^1$H NMR (400 MHz, CDCl$_3$): δ 4.76-4.61 (m, 1 H), 4.35-4.30 (m, 1 H), 3.94 (dd, $^2J_{H,H}$ = 12 Hz, $^3J_{H,H}$ = 4.0 Hz, 1 H), 3.76-3.72 (m, 5 H), 3.65 (dd, $^2J_{H,H}$ = 12 Hz, $^3J_{H,H}$ = 4.0 Hz, 1 H), 3.51-3.44 (m, 5 H), 3.25 (dt, $^2J_{H,H}$ = 12 Hz, $^3J_{H,H}$ = 4.0 Hz, 1 H), 1.48 (s, 9 H), 1.30 (d, $^3J_{H,H}$ = 8.0 Hz, 3 H). | MS (MALDI): m/z = 399.1 ([M + H]$^+$). |

Method 8: 4,4'-(6-chloropyrimidine-2,4-diyl)dimorpholine (i22) and 4,4'-(2-chloropyrimidine-4,6-diyl) dimorpholine (i23)

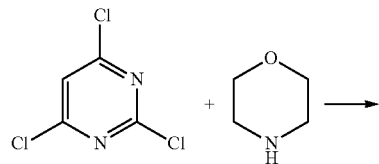

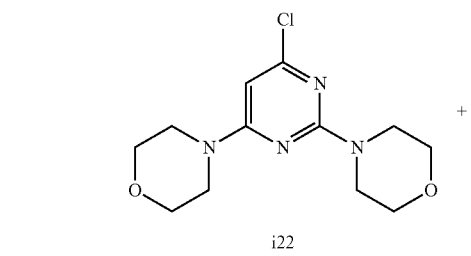

i22 i23

2,4,6-Trichloropyrimidine (Manchester Organics, product number Y17832, 11.2 g, 61 mmol, 1.0 eq.), N,N-diisopropylethylamine (23.3 mL, 134.2 mmol, 2.2 eq.) and morpholine (11.7 mL, 134.2 mmol, 2.2 eq.) are charged in a flask and dissolved in ethanol (120 mL). The flask is equipped with a refluxed condenser and placed in an oil bath preheated at 100° C. The reaction mixture is stirred at this temperature for 18 hours. After this time, the reaction mixture is cooled down to room temperature and volatiles are removed under reduced pressure. The resulting mixture is dissolved in dichloromethane (100 mL) and washed twice with an aqueous solution of sodium bisulfate (2×80 mL). The organic layer is dried over anhydrous sodium sulfate, filtered and concentrated under reduced pressure using a rotary evaporator. Products i22 and i23 are isolated by flash chromatography on silica gel (cyclohexane/ethyl acetate 3:1→1:1). The product fractions are pooled and evaporated to yield i22 as a colorless powder (13.8 g, 80%) and i23 as a colorless powder (2.2 g, 13% yield).

4,4'-(6-chloropyrimidine-2,4-diyl)dimorpholine (i22): $^1$H NMR (400 MHz, CDCl$_3$): δ 5.85 (s, 1H), 3.71-3.75 (m, 12H), 3.52-3.55 (m, 4H); MS (MALDI): m/z: 285.4 ([M+H]$^+$).

4,4'-(2-chloropyrimidine-4,6-diyl)dimorpholine (i23): $^1$H NMR (400 MHz, CDCl$_3$): δ 5.38 (s, 1H), 3.73-3.76 (m, 8H), 3.52-3.54 (m, 8H); MS (MALDI): m/z: 285.2 ([M+H]$^+$).

Method 9: 8-(4-(3-oxa-8-azabicyclo[3.2.1]octan-8-yl)-6-chloropyrimidin-2-yl)-3-oxa-8-azabicyclo[3.2.1]octane (i24)

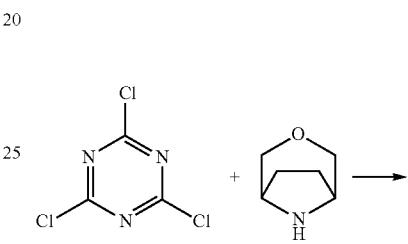

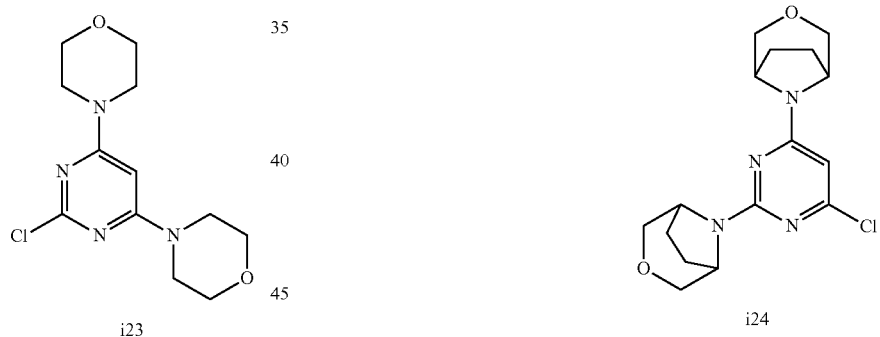

i24

A solution of 2,4,6-trichloropyrimidine (0.676 mL, 5.88 mmol, 1.0 eq.), 3-oxa-8-azabicyclo[3.2.1]octane hydrochloride (1.76 g, 11.8 mmol, 2.0 eq.), and N,N-diisopropylethylamine (4.10 mL, 23.5 mmol, 4.0 eq.) in ethyl acetate (18 volumes) is heated for 16 hours (100° C.). Then, the solvent is removed under reduced pressure and the residue is dissolved in dichloromethane (60 volumes) and washed with a saturated aqueous sodium bisulfate (3×60 volumes). The organic layer is dried over anhydrous sodium sulfate, filtered and concentrated under reduced pressure. Purification by column chromatography on silica gel (cyclohexane/ethyl acetate 3:1→1:1) affords the desired intermediate i24 as a colorless solid (1.23 g, 62%). $^1$H NMR (400 MHz, CDCl$_3$): δ 5.80 (s, 1H), 4.59 (s, 2H), 4.35 (m, 2H), 3.76 (t, $^2J_{H,H}$=10.8 Hz, 4H), 3.59 (d, $^2J_{H,H}$=10.8 Hz, 4H), 2.03 (m, 8H); MS (MALDI): m/z=337.7 ([M+H]$^+$).

Method 9 is also used for the preparation of the following intermediate compound i25.

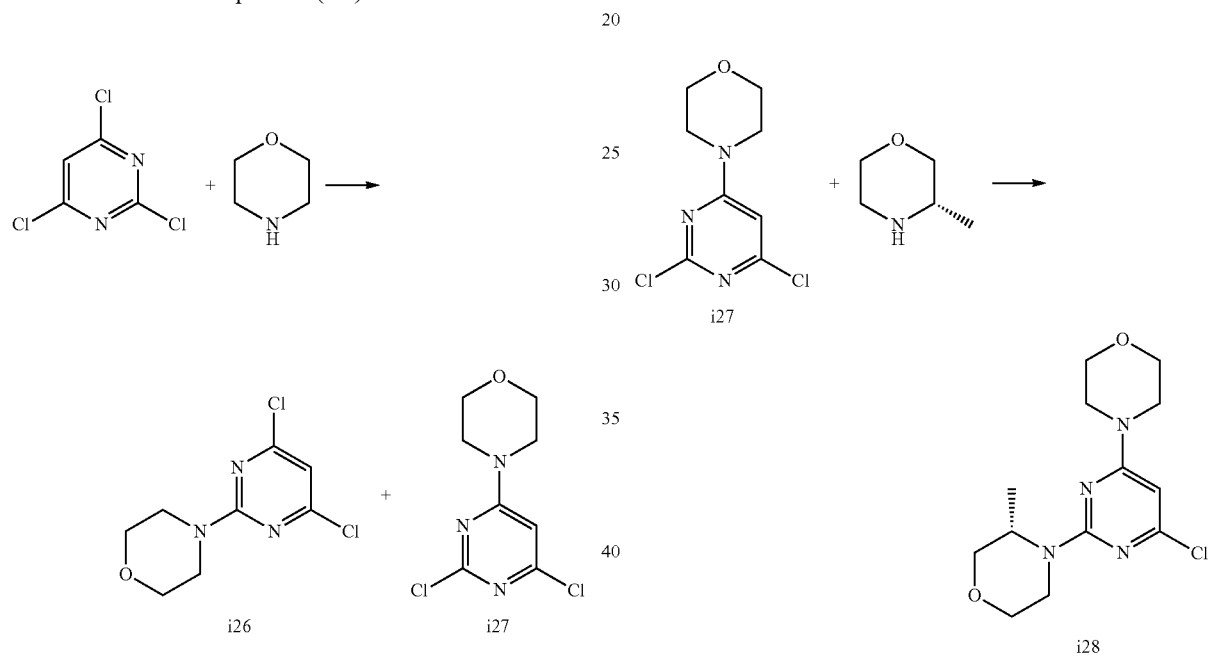

| Reagent | Structure | NMR | MS |
| --- | --- | --- | --- |
| i25 | 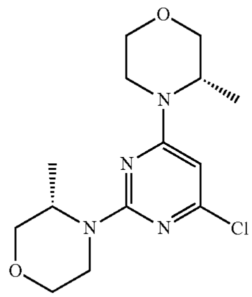 [SMILES: C[C@H]1COCCN1c1cc(Cl)nc(N2CCOC[C@@H]2C)n1] | $^1$H NMR (400 MHz, CDCl$_3$): δ 5.83 (s, 1 H), 4.64-4.57 (m, 1 H), 4.27 (dd, $^3J_{H,H}$ = 2.4 Hz, $^2J_{H,H}$ = 13.5 Hz, 1 H), 4.20-4.11 (m, 1 H), 3.97-3.87 (m, 3 H), 3.77-3.63 (m, 4 H), 3.56-3.46 (m, 2 H), 3.26-3.15 (m, 2 H), 1.28 (d, $^3J_{H,H}$ = 3.2 Hz, 3 H), 1.27 (d, $^3J_{H,H}$ = 3.2 Hz, 3 H). | MS (MALDI): m/z = 313.6 ([M + H]$^+$). |

Method 10: 4-(4,6-dichloropyrimidin-2-yl)morpholine (i26) and 4-(2,6-dichloropyrimidin-4-yl)morpholine (i27)

Method 11: (S)-4-(2-chloro-6-morpholinopyrimidin-4-yl)-3-methylmorpholine (i28)

To a solution of 2,4,6-trichloropyrimidine (14.0 mL, 122 mmol, 1.0 eq.) in EtOH (150 mL) is added a solution of morpholine (11.2 mL, 256 mmol, 2.1 eq.) and N,N-diisopropylethylamine (44.6 mL, 256 mmol, 2.1 eq.) in EtOH (150 mL) dropwise at 0° C. The reaction mixture is stirred overnight at room temperature and the solvent is removed under reduced pressure. The crude product is extracted with dichloromethane (3×100 mL) and the organic phase is successively washed with saturated aqueous sodium bisulfate (3×400 mL). The combined organic layers are dried over anhydrous sodium sulfate, filtered and evaporated under reduced pressure. The crude mixture is purified by flash column chromatography (SiO$_2$, cyclohexane/ethyl acetate 9:1→3:1) to yield i26 (5.02 g, 18%) and i27 (16.7 g, 59%), both as colorless solids.

4-(4,6-dichloropyrimidin-2-yl)morpholine (i26): $^1$H NMR (400 MHz, CDCl$_3$): δ 6.56 (s, 1H), 3.78 (m, 4H) 3.74 (m, 4H).

4-(2,6-dichloropyrimidin-4-yl)morpholine (i27): $^1$H NMR (400 MHz, CDCl$_3$): δ 6.41 (s, 1H), 3.78 (m, 4H), 3.65 (m, 4H).

A solution of i27 (694 mg, 2.97 mmol, 1.0 eq.), (S)-3-methylmorpholine (0.500 mL, 4.46 mmol, 1.5 eq.) and N,N-diisopropylethylamine (1.29 mL, 7.43 mmol, 2.5 eq.) in EtOH (5.0 mL) is heated to reflux for 3 days. Then, the solvent is removed under reduced pressure. The residue is dissolved in dichloromethane (60 volumes) and washed with saturated aqueous sodium bisulfate (3×60 volumes). The organic layer is dried over anhydrous sodium sulfate, filtered and concentrated under reduced pressure. The crude mixture is purified by flash chromatography (SiO$_2$, cyclohexane/ethyl acetate 3:1→1:1) to afford the title compound (S)-4-(2-chloro-6-morpholinopyrimidin-4-yl)-3-methylmorpholine (i28) as a colorless solid (425 mg, 48%). $^1$H NMR (400 MHz, CDCl$_3$): δ 5.85 (s, 1H), 4.62 (dd, $^2J_{H,H}$=13.6 Hz, $^3J_{H,H}$=2.9 Hz, 1H), 4.25 (dd, $^2J_{H,H}$=13.6 Hz, $^3J_{H,H}$=2.9 Hz, 1H), 3.93 (dd, $^2J_{H,H}$=11.4 Hz, $^3J_{H,H}$=3.8 Hz, 1H), 3.75, (t, $^3J_{H,H}$=5.0 Hz, 4H), 3.71 (s, 1H), 3.66 (dd, $^2J_{H,H}$=11.3 Hz, $^3J_{H,H}$=3.2 Hz, 1H), 3.53 (m, 5H), 3.23 (m, 1H), 1.26 (d, $^2J_{H,H}$=11.3 Hz, 3H); MS (MALDI): m/z=299.4 ([M+H]$^+$).

Method 11 is also used for the preparation of the following intermediate compound i29.

| Reagent | Structure | NMR | MS |
|---|---|---|---|
| i29 | 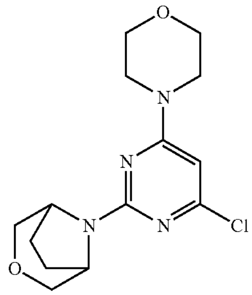 [SMILES: Clc1cc(N2CCOCC2)nc(N2C3CCC2COC3)n1] | $^1$H NMR (400 MHz, CDCl$_3$): δ 5.86 (s, 1 H), 4.60 (br s, 2 H), 3.80-3.72 (m, 6 H), 3.62-3.56 (m, 2 H), 3.56-3.50 (m, 4 H), 2.08-1.90 (m, 4 H). | MS (MALDI): m/z = 309.6 ([M + H]$^+$). |

Method 12: (S)-4-(6-chloro-2-morpholinopyrimidin-4-yl)-3-methylmorpholine (i30)

Method 13: 4-(4-chloro-6-morpholino-1,3,5-triazin-2-yl)morpholin-3-one (i31)

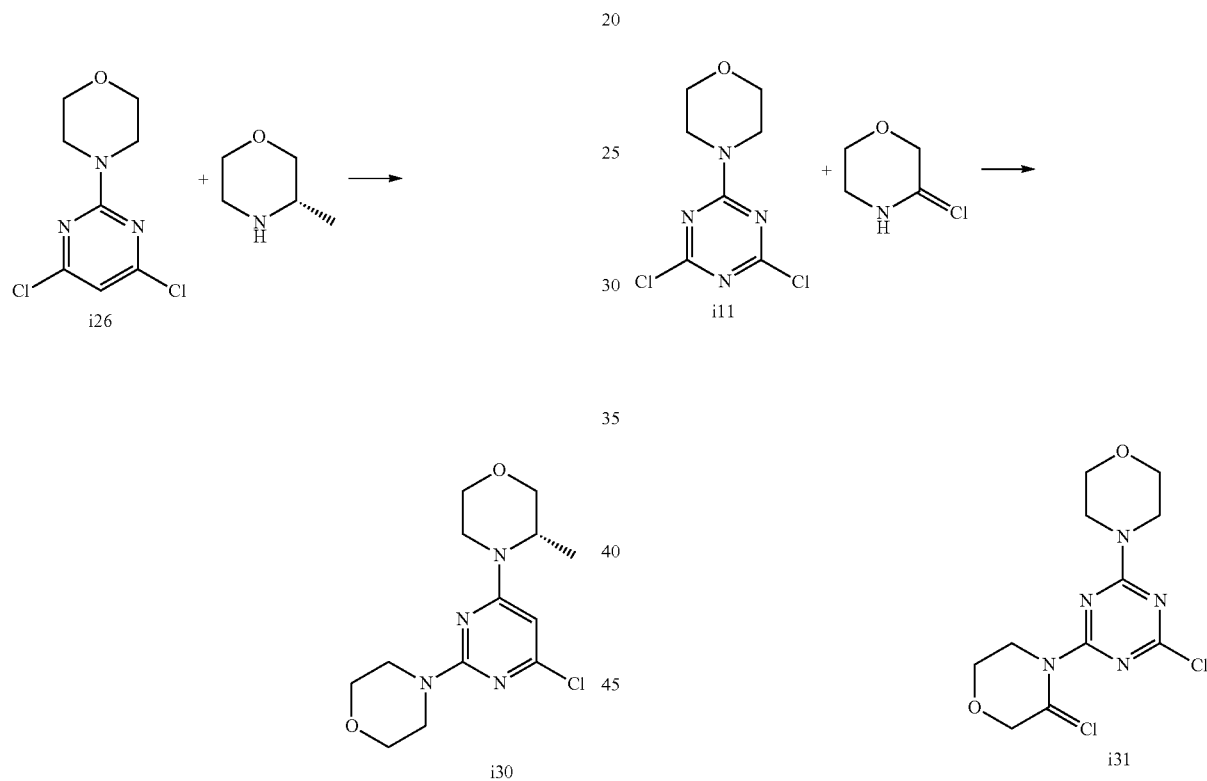

A solution of (S)-3-methylmorpholine (194 mg, 1.32 mmol, 1.5 eq.), i26 (300 mg, 1.28 mmol, 1.0 eq.) and N,N-diisopropylethylamine (3.0 eq.) in DMF (17 volumes) is heated for 16 hours (130° C.). Then, the solvent is removed under reduced pressure. The residue is dissolved in dichloromethane (100 volumes) and washed with saturated aqueous sodium bisulfate (3×100 volumes). The organic layer is dried over anhydrous sodium sulfate, filtered and concentrated under reduced pressure. The crude mixture is purified by flash chromatography (SiO$_2$, cyclohexane/ethyl acetate 5:1) to afford the title compound i30 as a colorless solid (257 mg, 67%). $^1$H NMR (400 MHz, CDCl$_3$): δ 5.84 (s, 1H), 4.18 (m, 1H), 3.94 (m, 2H), 3.71 (m, 10H), 3.53, (dt, $^2J_{H,H}$=12.0 Hz, $^3J_{H,H}$=3.1 Hz, 1H), 3.20 (dt, $^2J_{H,H}$=12.8 Hz, $^3J_{H,H}$=3.8 Hz, 1H), 1.27 (d, $^3J_{H,H}$=6.8 Hz, 3H); MS (MALDI): m/z=298.4 ([M]$^+$).

A round bottom flask was charged with compound i11 (5.37 g, 22.9 mmol, 1.5 eq), morpholine-3-one (1.54 g, 15.3 mmol, 1.0 eq), 4,5-bis(diphenylphosphino)-9,9-dimethylxanthene (530 mg, 0.915 mmol, 0.06 eq.), cesium carbonate (9.95 g, 30.5 mmol, 2.0 eq) and palladium(II) acetate (383 mg, 0.170 mmol, 0.04 eq.). The reaction mixture was flushed with nitrogen and 1,4-dioxane (100 mL) was added. The reaction mixture was stirred at reflux (100° C.) for 4 hours. The reaction mixture was cooled to room temperature and filtered. The filter cake was washed with dichloromethane (2×30 mL). Solvents were removed under reduced pressure and the crude product was purified using silica gel chromatography (cyclohexane/ethyl acetate 1:0→1:3) to yield the title compound i31 as a colorless solid (390 mg, 31%). $^1$H NMR (400 MHz, CDCl$_3$): δ 4.32 (s, 2H), 4.03-3.97 (m, 4H), 3.93-3.86 (m, 4H), 3.75-3.73 (m, 4H); MS (MALDI): m/z=299.6 ([M+H]$^+$).

Method 14: 8-(4,6-dichloro-1,3,5-triazin-2-yl)-3-oxa-8-azabicyclo[3.2.1]octane (i32)

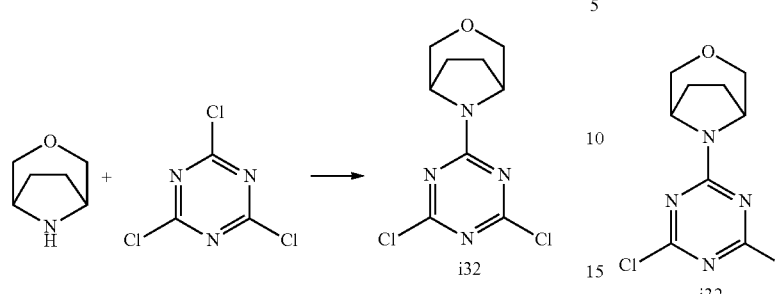

A solution of cyanuric chloride (1.97 g, 10.7 mmol, 1.0 eq.) in dichloromethane (10 mL) is cooled to −50° C. A solution of 3-oxa-8-azabicyclo[3.2.1]octane hydrochloride (1.60 g, 10.7 mmol, 1.0 eq.) and N,N-diisopropylethylamine (3.73 mL, 21.4 mmol, 2.0 eq.) in dichloromethane (40 mL) is slowly added over a period of 5 hours. The mixture is stirred for another 5 hours at this temperature. Then, dichloromethane (20 mL) and saturated aqueous sodium bisulfate (50 mL) are added and the mixture is allowed to warm to room temperature. The layers are separated and the organic layer is washed with saturated aqueous sodium bisulfate (2×50 mL). The organic layer is dried over anhydrous sodium sulfate and the solvent is removed under reduced pressure. The crude mixture is recrystallized from n-heptane/dichloromethane (20 mL/13 mL) to afford the title compound 8-(4,6-dichloro-1,3,5-triazin-2-yl)-3-oxa-8-azabicyclo[3.2.1]octane (i32) as a colorless solid (2.47 g, 47%). $^1$H NMR (400 MHz, CDCl$_3$): δ 4.74 (m, 2H), 3.72 (d, $^3J_{H,H}$=1.5 Hz, 4H), 2.08 (m, 4H).

Method 14 is also used for the preparation of the following intermediate compounds i33 and i34.

Method 15: 9-(4-(3-oxa-8-azabicyclo[3.2.1]octan-8-yl)-6-chloro-1,3,5-triazin-2-yl)-3,7-dioxa-9-azabicyclo[3.3.1]nonane (i35)

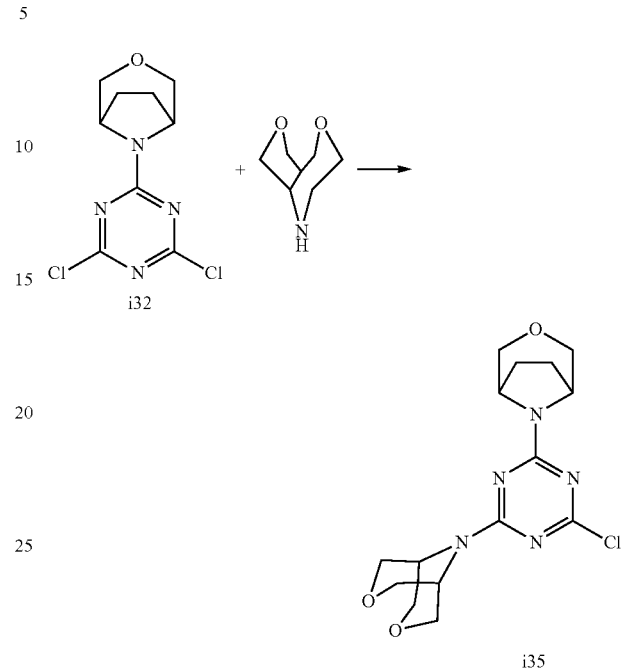

To a solution of 3,7-dioxa-9-azabicyclo[3.3.1]nonane (184 mg, 0.700 mmol, 1.0 eq.) and N,N-diisopropylethylamine (0.170 mL, 0.970 mmol, 1.4 eq.) in 1,4-dioxane (1.0 mL) a solution of i32 (100 mg, 0.770 mmol, 1.1 eq.) in 1,4-dioxane (2.0 mL) is added. The resulting mixture is heated for 1 hour at 70° C. Then, dichloromethane (50 mL) and water (50 mL) are added. The aqueous layer is extracted

| | Reagent | Structure | NMR |
|---|---|---|---|
| i33 | ![structure] | ![structure] | $^1$H NMR (400 MHz, CDCl$_3$): δ 4.54-4.60 (m, 1 H), 4.20 (dd, $^3J_{H,H}$ = 2.9 Hz, $^2J_{H,H}$ = 14 Hz, 1 H), 3.92 (dd, $^3J_{H,H}$ = 3.4 Hz, $^2J_{H,H}$ = 12 Hz, 1 H), 3.71 (d, $^2J_{H,H}$ = 12 Hz, 1 H), 3.57 (dd, $^3J_{H,H}$ = 3.2 Hz, $^2J_{H,H}$ = 12 Hz, 1 H), 3.42 (m, 1 H), 3.32 (m, 1 H), 1.27 (d, $^3J_{H,H}$ = 6.9 Hz, 3 H). |
| i34 | ![structure] | ![structure] | $^1$H NMR (400 MHz, (CD$_3$)$_2$SO): δ 3.88-3.81 (m, 4 H), 3.51 (s, 2 H), 1.46 (s, 6 H). | with dichloromethane (3×50 mL), the combined organic layers are dried over anhydrous sodium sulfate and the solvent is evaporated. The crude mixture is purified by automated flash chromatography on silica gel (cyclohexane/ethyl acetate 2:1→0:1) to afford the title compound 9-(4-(3-oxa-8-azabicyclo[3.2.1]octan-8-yl)-6-chloro-1,3,5-triazin-2-yl)-3,7-dioxa-9-azabicyclo[3.3.1]nonane (i35) as a colorless solid (192 mg, 77%). $^1$H NMR (400 MHz, (CD$_3$)$_2$SO): δ 4.70 (m, 1H), 4.55 (m, 2H), 4.44 (m, 1H), 4.12 (m, 4H), 3.90 (m, 4H), 3.72 (m, 2H), 3.64 (m, 2H), 2.08 (m, 2H), 1.97 (m, 2H); MS (MALDI): m/z=354.3 ([M]$^+$).

Method 16: 9-(4-chloro-6-((R)-3-methylmorpholino)-1,3,5-triazin-2-yl)-3,7-dioxa-9-azabicyclo[3.3.1]nonane (i36)

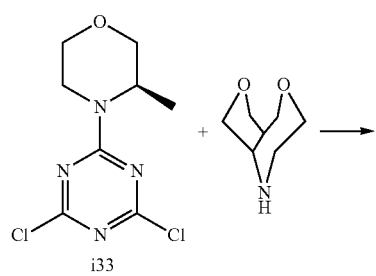

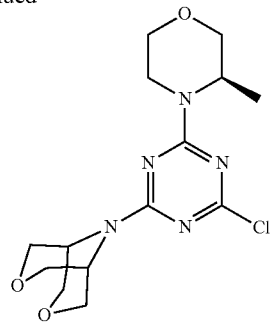

To a solution of 3,7-dioxa-9-azabicyclo[3.3.1]nonane (173 mg, 1.27 mmol, 1.05 eq.) and N,N-diisopropylethylamine (0.50 mL, 2.52 mmol, 2.1 eq.) in tetrahydrofuran (5 mL) a solution of i33 (300 mg, 2.52 mmol, 2.1 eq.) in 1,4-dioxane (2.0 mL) is added. The resulting mixture is heated for 2 hours (70° C.). Then, ethyl acetate (20 mL) and saturated aqueous sodium bisulfate (20 mL) are added. The phases are separated and the organic layer is washed with saturated aqueous sodium bisulfate (2×20 mL). The organic layer is dried over anhydrous sodium sulfate and the solvent is removed under reduced pressure. The crude mixture is purified by automated flash chromatography (SiO$_2$, cyclohexane/ethyl acetate 2:1→0:1) to afford the title compound i36 as a colorless solid (316 mg, 76%). $^1$H NMR (400 MHz, (CD$_3$)$_2$SO): δ 4.55-4.53 (m, 1H), 4.42 (m, 1H), 4.32 (m, 1H), 4.25-4.16 (m, 1H), 4.01-3.97 (m, 4H), 3.87 (dd, $^3J_{H,H}$=3.8 Hz, $^2J_{H,H}$=11.2 Hz, 1H), 3.73-3.65 (m, 5H), 3.53 (dd, $^3J_{H,H}$=3.0 Hz, $^2J_{H,H}$=11.6 Hz, 1H), 3.38 (m, 1H), 3.15 (m, 1H), 1.20 (d, $3J_{H,H}$=6.9 Hz, 3H).

Method 16 is also used for the preparation of the following intermediate compounds i37 to i53, and intermediate i82.

| | Reagent | Structure | NMR | MS |
|---|---|---|---|---|
| i37 | ![structure] | ![structure] | $^1$H NMR (400 MHz, (CD$_3$)$_2$SO): δ 4.58-4.50 (m, 1 H), 4.44-4.35 (m, 2 H), 4.25-4.12 (m, 1 H), 3.90-3.86 (m, 1 H), 3.75-3.65 (m, 3 H), 3.56-3.49 (m, 3 H), 3.38 (m, 1 H), 3.16 (m, 1 H), 1.25 (d, $^3J_{H,H}$ = 6.9 Hz, 6 H), 1.19 (d, $^3J_{H,H}$ = 6.9 Hz, 3 H). | MS (MALDI): m/z = 328.2 ([M + H]$^+$). |
| i38 | ![structure] | ![structure] | $^1$H NMR (400 MHz, (CD$_3$)$_2$SO): δ 4.54-4.46 (m, 1 H), 4.18-4.13 (m, 1 H), 3.88 (m, 1 H), 3.80-3.65 (m, 5 H), 3.54 (m, 1 H), 3.44-3.36 (m, 3 H), 3.18 (m, 1 H), 1.44 (s, 6 H), 1.21 (d, $^3J_{H,H}$ = 6.9 Hz, 3 H). | |

| Reagent | Structure | NMR | MS |
|---|---|---|---|
| i39 | [morpholine with CH2OMe substituent] | ¹H NMR (400 MHz, (CD₃)₂SO): δ 4.65-4.51 (m, 2 H), 4.31-4.20 (m, 2 H), 3.66 (m, 3 H), 3.69-3.56 (m, 2 H), 3.54-3.48 (m, 3 H), 3.42-3.35 (m, 2 H), 3.31 (s, 3 H), 3.21-3.13 (m, 2 H), 1.21 (d, ³J$_{H,H}$ = 6.9 Hz, 3 H). | MS (MALDI): m/z = 344.2 ([M + H]⁺). |
| i40 | [bicyclic amine with O] | ¹H NMR (400 MHz, (CD₃)₂SO): δ 4.55-4.51 (m, 1 H), 4.42-4.35 (m, 2 H), 4.12-4.25 (m, 2 H), 4.04-4.07 (m, 1 H), 3.86-3.88 (m, 1 H), 3.78-3.75 (m, 2 H), 3.69-3.65 (m, 1 H), 3.55-3.51 (m, 1 H), 3.38 (m, 1 H), 3.20-3.13 (m, 1 H), 2.68 (m, 1 H), 1.81 (m, 1 H), 1.20 (d, ³J$_{H,H}$ = 6.9 Hz, 3 H). | |
| i41 | [bicyclic amine with O] | ¹H NMR (400 MHz, (CD₃)₂SO): δ 4.69-4.53 (m, 3 H), 4.31-4.15 (m, 1 H), 3.93-3.78 (m, 3 H), 3.71-3.53 (m, 4 H), 3.42-3.35 (m, 1 H), 3.22-3.16 (m, 1 H), 3.12-3.08 (m, 1 H), 1.81 (m, 1 H), 1.21 (d, ³J$_{H,H}$ = 6.9 Hz, 3 H). | |
| i42 | [bicyclic amine with O] | ¹H NMR (400 MHz, (CD₃)₂SO): δ 4.95-4.88 (m, 1 H), 4.64 (m, 1 H), 4.54 (m, 1 H), 4.31-4.09 (m, 1 H), 3.89-3.85 (m, 1 H), 3.75-3.73 (m, 2 H), 3.66-3.63 (m, 2 H), 3.52 (m, 1 H), 3.45-3.32 (m, 3 H), 3.18-3.12 (m, 1 H), 1.90-1.83 (m, 2 H), 1.21 (d, ³J$_{H,H}$ = 6.9 Hz, 3 H). | MS (MALDI): m/z = 312.2 ([M + H]⁺). |
| i43 | [bicyclic amine with O] | ¹H NMR (400 MHz, (CD₃)₂SO): δ 4.94-4.88 (m, 1 H), 4.64 (m, 1 H), 4.54 (m, 1 H), 4.29-4.12 (m, 1 H), 3.89-3.85 (m, 1 H), 3.75-3.73 (m, 2 H), 3.66-3.63 (m, 2 H), 3.52 (m, 1 H), 3.45-3.32 (m, 2 H), 3.18-3.12 (m, 1 H), 1.90-1.83 (m, 2 H), 1.21 (d, ³J$_{H,H}$ = 6.9 Hz, 3 H). | MS (MALDI): m/z = 312.2 ([M + H]⁺). |

| Reagent | Structure | NMR | MS |
|---|---|---|---|
| i44 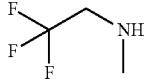 | 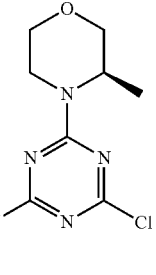 | ¹H NMR (400 MHz, (CD₃)₂SO): δ 4.62-4.17 (m, 4 H), 3.88 (m, 1 H), 3.68 (m, 1 H), 3.54-3.51 (m, 1 H), 3.41 (m, 1 H), 3.25-3.15 (m, 4 H), 1.21 (m, 3 H). | MS (MALDI): m/z = 326.8 ([M + H]⁺). |
| i45 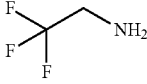 | 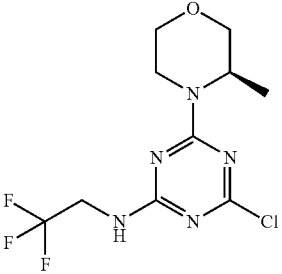 [SMILES: C[C@@H]1COCCN1c1nc(Cl)nc(NCC(F)(F)F)n1] | ¹H NMR (400 MHz, (CD₃)₂SO): δ 8.55-40 (m, 1 H), 4.65-4.77 (m, 1 H), 4.36-4.01 (m, 3 H), 3.83 (m, 1 H), 3.62 (m, 1 H), 3.52 (m, 1 H), 3.35 (m, 1 H), 3.10 (m, 1 H), 1.18 (d, ³J$_{H,H}$ = 6.9 Hz, 3 H). | MS (MALDI): m/z = 312.1 ([M + H]⁺). |
| i46 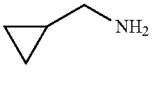 | 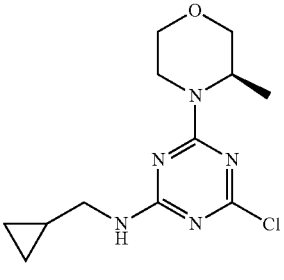 [SMILES: C[C@@H]1COCCN1c1nc(Cl)nc(NCC2CC2)n1] | ¹H NMR (400 MHz, (CD₃)₂SO): δ 8.12-7.89 (m, 1 H), 4.52 (m, 1 H), 4.16 (m, 1 H), 3.88 (m, 1 H), 3.68 (m, 1 H), 3.52 (m, 1 H), 3.35 (m, 2 H), 3.10 (m, 2 H), 1.18 (d, ³J$_{H,H}$ = 6.9 Hz, 3 H), 1.04 (m, 1 H), 0.42 (m, 2 H), 0.20 (m, 2 H). | MS (MALDI): m/z = 284.9 ([M + H]⁺). |
| i47 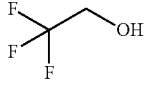 | 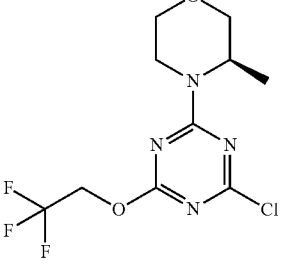 | ¹H NMR (400 MHz, (CD₃)₂SO): δ 5.10-4.97 (m, 2 H), 4.70-4.54 (m, 1 H), 4.25 (m, 1 H), 3.91 (m, 1 H), 3.71 (m, 1 H), 3.57 (m, 1 H), 3.41 (m, 1 H), 3.29 (m, 1 H), 1.25 (d, ³J$_{H,H}$ = 6.9 Hz, 3 H). | MS (MALDI): m/z = 313.6 ([M + H]⁺). |
| i48 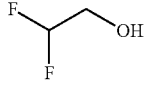 | 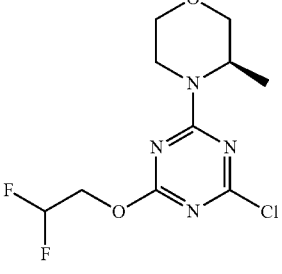 | ¹H NMR (400 MHz, (CD₃)₂SO): δ 6.37 (m, 1 H), 4.68-4.53 (m, 3 H), 4.25 (m, 1 H), 3.90 (m, 1 H), 3.70 (m, 1 H), 3.55 (m, 1 H), 3.41 (m, 1 H), 3.25 (m, 1 H), 1.24 (d, ³J$_{H,H}$ = 6.9 Hz, 3 H). | MS (MALDI): m/z = 295.7 ([M + H]⁺). |

| Reagent | Structure | NMR | MS |
|---|---|---|---|
| i49 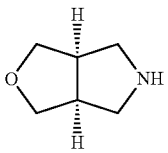 | 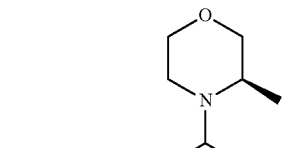 | $^1$H NMR (400 MHz, (CD$_3$)$_2$SO): δ 4.55 (m, 1 H), 4.21 (m, 1 H), 3.89 (m, 1 H), 3.79-3.66 (m, 5 H), 3.54-3.51 (m, 3 H), 3.45-3.32 (m, 3 H), 3.11 (m, 1 H), 2.97 (m, 2 H), 1.20 (d, $^3J_{H,H}$ = 6.9 Hz, 3 H). | MS (MALDI): m/z = 326.2 ([M + H]$^+$). |
| i50 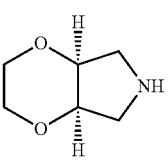 | 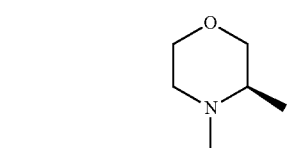 | $^1$H NMR (400 MHz, (CD$_3$)$_2$SO): δ 4.56 (m, 1 H), 4.24 (m, 3 H), 3.88 (m, 1 H), 3.77 (m, 2 H), 3.67-3.51 (m, 8 H), 3.40-3.37 (m, 1 H), 3.16 (m, 1 H), 1.21 (d, $^3J_{H,H}$ = 6.9 Hz, 3 H). | MS (MALDI): m/z = 342.8 ([M + H]$^+$). |
| i51 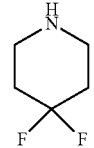 | 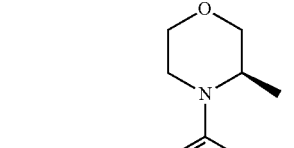 | $^1$H NMR (400 MHz, (CD$_3$)$_2$SO): δ 4.56 (m, 1 H), 4.24 (m, 1 H), 3.87 (m, 5 H), 3.68 (m, 1 H), 3.53 (m, 1 H), 3.35 (m, 1 H), 3.18 (m, 1 H), 2.01 (m, 4 H), 1.21 (d, $^3J_{H,H}$ = 6.9 Hz, 3 H). | |
| i52 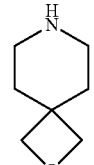 | 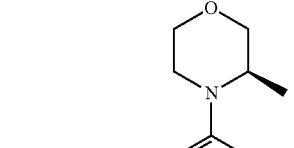 | $^1$H NMR (400 MHz, (CD$_3$)$_2$SO): δ 4.53 (m, 1 H), 4.35 (m, 5 H), 4.20 (m, 1 H), 3.87 (m, 1 H), 3.65 (m, 4 H), 3.52 (m, 1 H), 3.37 (m, 1 H), 3.16 (m, 1 H), 1.79 (m, 4 H), 1.20 (d, $^3J_{H,H}$ = 6.9 Hz, 3 H). | MS (MALDI): m/z = 340.2 ([M + H]$^+$). |
| i53 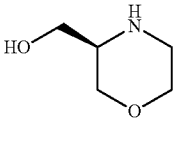 | 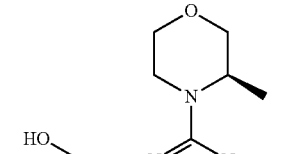 | $^1$H NMR (400 MHz, (CD$_3$)$_2$SO): δ 4.65 (m, 4.55 (m, 1 H), 4.32 (m, 1 H), 4.22 (m, 2 H), 3.98 (m, 1 H), 3.86 (m, 2 H), 3.63 (m, 2 H), 3.55 (m, 1 H), 3.49-3.34 (m, 4 H), 3.17 (m, 1 H), 3.12 (m, 1 H), 1.21 (d, $^3J_{H,H}$ = 6.9 Hz, 3 H). | MS (MALDI): m/z = 330.1 ([M + H]$^+$). |

| Reagent | Structure | NMR | MS |
|---|---|---|---|
| i82 | 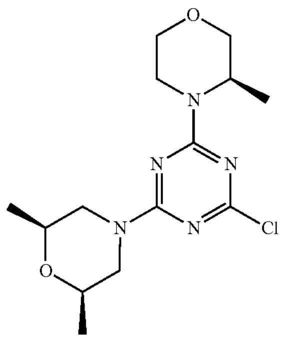 | ¹H NMR (400 MHz, (CD₃)₂SO): δ 4.67-4.53 (m, 1 H), 4.45-4.34 (m, 2 H), 4.31-4.09 (m, 1 H), 3.88 (m, 1 H), 3.68 (m, 1 H), 3.55 (m, 3 H), 3.38 (m, 1 H), 3.13 (m, 1 H), 2.55 (m, 2 H), 1.20 (d, ³J$_{H,H}$ = 6.9 Hz, 3 H), 1.19 (d, ³J$_{H,H}$ = 6.9 Hz, 6 H). | MS (MALDI): m/z = 328.3 ([M + H]⁺). |

Method 17: 9-(4-chloro-6-(3,3-dimethylmorpholino)-1,3,5-triazin-2-yl)-3,7-dioxa-9-azabicyclo[3.3.1]nonane (i54)

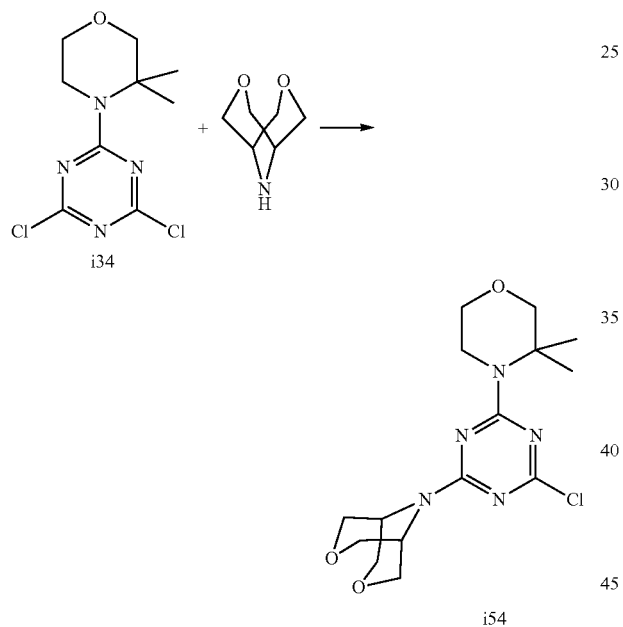

To a solution of 3,7-dioxa-9-azabicyclo[3.3.1]nonane (155 mg, 1.20 mmol, 1.05 eq.) and N,N-diisopropylethylamine (0.42 mL, 2.40 mmol, 2.1 eq.) in 1,4-dioxane (5 mL) a solution of i34 (300 mg, 1.14 mmol, 1 eq.) in 1,4-dioxane (1 mL) is added. The resulting mixture is heated for 2 hours (70° C.). Then, ethyl acetate (20 mL) and saturated aqueous sodium bisulfate (20 mL) are added. The phases are separated and the organic layer is washed with saturated aqueous sodium bisulfate (2×20 mL). The organic layer is dried over anhydrous sodium sulfate and the solvent is removed under reduced pressure. The crude mixture is purified by automated flash chromatography (SiO₂, cyclohexane/ethyl acetate 2:1→0:1) to afford the title compound i54 as a colorless solid (178 mg, 44%). ¹H NMR (400 MHz, (CD₃)₂SO): δ 4.32 (m, 2H), 4.05-3.98 (m, 4H), 3.77 (m, 4H), 3.71 (m, 4H), 3.44 (m, 2H), 1.41 (s, 6H). MS (MALDI): m/z=356.3 ([M+H]⁺).

Method 17 is also used for the preparation of the following intermediate compounds i55 to i64.

| Reagent | Structure | NMR | MS |
|---|---|---|---|
| i55 | 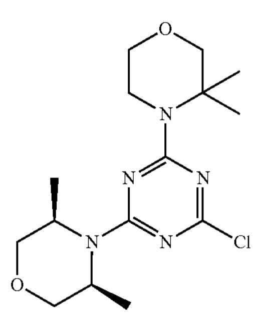 [SMILES: C[C@@H]1COC[C@H](C)N1c1nc(Cl)nc(N2CCOCC2(C)C)n1] | ¹H NMR (400 MHz, (CD₃)₂SO): δ 4.36 (m, 2 H), 3.77-3.74 (m, 6 H), 3.55 (m, 2 H), 3.44 (m, 2 H), 1.44 (s, 6 H), 1.26 (d, ³J$_{H,H}$ = 6.9 Hz, 6 H). | MS (MALDI): m/z = 343.0 ([M + H]⁺). |

-continued

| Reagent | Structure | NMR | MS |
|---|---|---|---|
| i56 | (morpholine with CH2OMe substituent) | ¹H NMR (400 MHz, (CD₃)₂SO): δ 4.52 (m, 1 H), 4.20 (m, 1 H), 3.90 (m, 2 H), 3.77 (m, 4 H), 3.65 (m, 1 H), 3.51-3.41 (m, 5 H), 3.28 (s, 3 H), 3.12 (m, 1 H), 1.44 (s, 3 H), 1.43 (s, 3 H). | |
| i57 | (3-(hydroxymethyl)morpholine) | ¹H NMR (400 MHz, (CD₃)₂SO): δ 4.98 (m, 1 H), 4.35 (m, 1 H), 4.18 (m, 1 H), 4.00 (m, 1 H), 3.87 (m, 1 H), 3.81-3.65 (m, 5 H), 3.51-3.35 (m, 5 H), 3.21-3.04 (m, 1 H), 1.44 (s, 3 H), 1.45 (s, 3 H). | MS (MALDI): m/z = 344.2 ([M + H]⁺). |
| i58 | (1-cyclopropylpiperazine) | ¹H NMR (400 MHz, (CD₃)₂SO): δ 3.77 (m, 4 H), 3.65 (m, 4 H), 3.44 (m, 2 H), 2.56 (m, 4 H), 1.64 (m, 1 H), 1.44 (s, 6 H), 0.44 (m, 2 H), 0.35 (m, 2 H). | MS (MALDI): m/z = 351.2 ([M + H]⁺). |
| i59 | (1-(2-methoxyethyl)piperazine) | ¹H NMR (400 MHz, (CD₃)₂SO): δ 3.76 (m, 4 H), 3.68 (m, 4 H), 3.47-3.44 (m, 4 H), 3.24 (m, 3 H), 2.52-2.45 (m, 6 H), 1.44 (s, 6 H). | MS (MALDI): m/z = 369.0 ([M + H]⁺). |
| i60 | (3-hydroxyoxetane) | ¹H NMR (400 MHz, (CD₃)₂SO): δ 5.56 (m, 1 H), 4.87 (m, 2 H), 4.60 (m, 2 H), 3.81 (m, 4 H), 3.48 (m, 2 H), 3.13 (s, 6 H). | MS (MALDI): m/z = 301.1 ([M + H]⁺). |

| Reagent | Structure | NMR | MS |
|---|---|---|---|
| i61 | 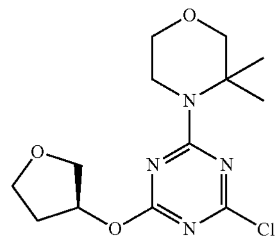 [SMILES: CC1(C)COCCN1c1nc(Cl)nc(O[C@H]2CCOC2)n1] | ¹H NMR (400 MHz, (CD₃)₂SO): δ 5.46 (m, 1 H), 3.84-3.73 (m, 8 H), 3.49 (m, 2 H), 2.21 (m, 1 H), 2.05 (m, 1 H), 1.46 (s, 3 H), 1.45 (s, 3 H). | MS (MALDI): m/z = 315.0 ([M + H]⁺). |
| i62 | 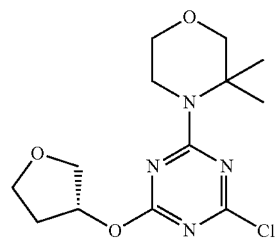 [SMILES: CC1(C)COCCN1c1nc(Cl)nc(O[C@@H]2CCOC2)n1] | ¹H NMR (400 MHz, (CD₃)₂SO): δ 5.46 (m, 1 H), 3.84-3.73 (m, 8 H), 3.49 (m, 2 H), 2.21 (m, 1 H), 2.05 (m, 1 H), 1.46 (s, 3 H), 1.45 (s, 3 H). | MS (MALDI): m/z = 315.0 ([M + H]⁺). |
| i63 | 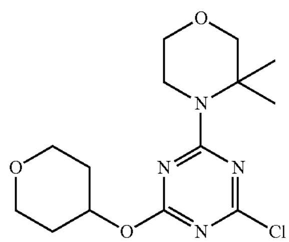 [SMILES: CC1(C)COCCN1c1nc(Cl)nc(OC2CCOCC2)n1] | ¹H NMR (400 MHz, (CD₃)₂SO): δ 5.11 (m, 1 H), 3.82 (m, 6 H), 3.47 (m, 4 H), 1.99 (m, 2 H), 1.65 (m, 2 H), 1.46 (s, 6 H). | MS (MALDI): m/z = 329.8 ([M + H]⁺). |
| i64 | 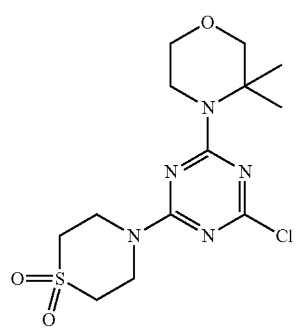 [SMILES: CC1(C)COCCN1c1nc(Cl)nc(N2CCS(=O)(=O)CC2)n1] | ¹H NMR (400 MHz, (CD₃)₂SO): δ 4.12 (m, 4 H), 3.79 (m, 4 H), 3.46 (m, 2 H), 3.22 (m, 4 H), 1.46 (s, 6 H). | MS (MALDI): m/z = 362.9 ([M + H]⁺). |

Method 18: 4-(difluoromethyl)pyridin-2-amine (i65)

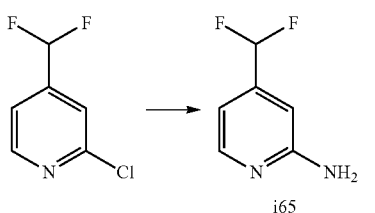 [SMILES: FC(F)c1ccnc(Cl)c1 ; Nc1cc(C(F)F)ccn1]

Palladium acetate (275 mg, 1.22 mmol, 0.05 eq.) and 2-dicyclohexylphosphino-2',4',6'-triisopropylbiphenyl (Sigma-Aldrich, product number 638064, 1.17 g, 2.45 mmol, 0.10 eq.) are dissolved in 1,4-dioxane (10 mL) under nitrogen atmosphere, and the resulting mixture is allowed to stir at room temperature for 45 minutes. This solution is then added to a mixture of tert-butylcarbamate (Sigma, product number 167398, 4.30 g, 36.7 mmol, 1.5 eq.), Cs₂CO₃ (15.9 g, 48.8 mmol, 2.0 eq.) and 2-chloro-4-difluoromethyl-pyridine (Manchester Organics, product number U15343, 4.00 g, 24.5 mmol, 1.0 eq.) in 1,4-dioxane (80 mL) under nitrogen atmosphere. The resulting reaction mixture is then heated at 90° C. for 3 hours, during which it turned brownish. After this time, the mixture is allowed to cool to room temperature. It is then diluted with ethyl acetate, washed with an aqueous saturated solution of ammonium chloride (2×30 mL) and deionized water. The organic layer is dried over anhydrous sodium sulfate, filtered and the solvent is evaporated under reduced pressure. The brownish residue is mixed with 4 M HCl in dioxane (50 mL, excess) and methanol (20 mL), and then heated at 80° C. for 45 minutes. Deionized water is added and the aqueous layer is washed with ethyl acetate (3×). The aqueous layer is then basified to pH=9, with solid sodium hydroxide. The aqueous layer is extracted with ethyl acetate (3×). The combined organic layer is dried over anhydrous sodium sulfate, filtered and concentrated to dryness under reduced pressure. The desired product i65 is obtained as a colorless solid, which is used in the next step without further purification (98% yield). $^1$H NMR (400 MHz, CDCl$_3$): δ 8.16 (d, $^2J_{H,H}$=5.2 Hz, 1H), 6.74 (d, $^2J_{H,H}$=4.8 Hz, 1H), 6.59 (s, 1H), 6.51 (t, $^2J_{H,F}$=56 Hz, 1H), 4.61 (br s, 2H); $^{19}$F NMR (376 MHz, CDCl$_3$): δ−116.0 (s, 2F).

Method 19:
5-bromo-4-(difluoromethyl)pyridin-2-amine (i66)

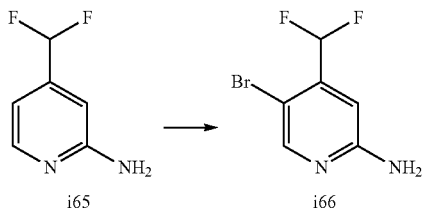 [SMILES: Nc1cc(C(F)F)ccn1 ; Nc1cc(C(F)F)c(Br)cn1]

To a solution of compound i65 (3.00 g, 20.8 mmol, 1.0 eq.) in tetrahydrofuran (60 mL) is added N-bromosuccinimide (3.89 g, 21.9 mmol, 1.05 eq.) at 0° C. in an ice bath. The resulting mixture is stirred overnight, while it is allowed to warm up to room temperature. Ethyl acetate is added and the organic layer is washed with aqueous sodium carbonate (8%). The organic layer is then separated and acidified with an aqueous 3 M HCl-solution. The aqueous layer is washed with ethyl acetate (3×50 mL) and then basified to pH=10, with solid sodium hydroxide. The aqueous layer is extracted with ethyl acetate (3×50 mL). The combined organic layer is dried over anhydrous sodium sulfate, filtered and concentrated to dryness under reduced pressure. The desired product i66 is obtained as a brownish solid, which is used in the next step without further purification (79% yield). $^1$H NMR (400 MHz, CDCl$_3$): δ 8.20 (s, 1H), 6.75 (s, 1H), 6.71 (t, $^2J_{H,F}$=54 Hz, 1H); 4.62 (br s, 2H); $^{19}$F NMR (376 MHz, CDCl$_3$): δ−118.9 (s, 2F).

Method 20: N'-(5-bromo-4-(difluoromethyl)pyridin-2-yl)-N,N-dimethylformimidamide (i67)

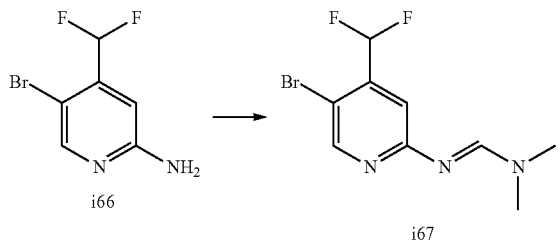

To a solution of compound i66 (3.68 g, 16.5 mmol, 1.0 eq.) in tetrahydrofuran (50 mL) is added N,N-dimethylformamide dimethyl acetal (Manchester Organics, product number 005030, 3.30 mL, 24.8 mmol, 1.5 eq.) and the resulting mixture is stirred at 60° C. for 3 hours. The mixture is allowed to cool to room temperature and the solvent is evaporated under reduced pressure. The crude product is purified by column chromatography on silica gel (cyclohexane/ethyl acetate 1:1) to afford the desired product i67 as a yellowish solid (82% yield). $^1$H NMR (400 MHz, CDCl$_3$): δ 8.43 (s, 1H), 8.34 (br s, 1H), 7.17 (s, 1H), 6.73 (t, $^2J_{H,F}$=54 Hz, 1H), 3.12 (s, 3H), 3.10 (s, 3H); $^{19}$F NMR (376 MHz, CDCl$_3$): δ−118.6 (s, 2F); MS (MALDI): m/z=278.5 ([M+H]$^+$).

Method 21: N'-(4-(difluoromethyl)-5-(4,4,5,5-tetramethyl-1,3,2-dioxaborolan-2-yl)pyridin-2-yl)-N,N-dimethylformimidamide (i68)

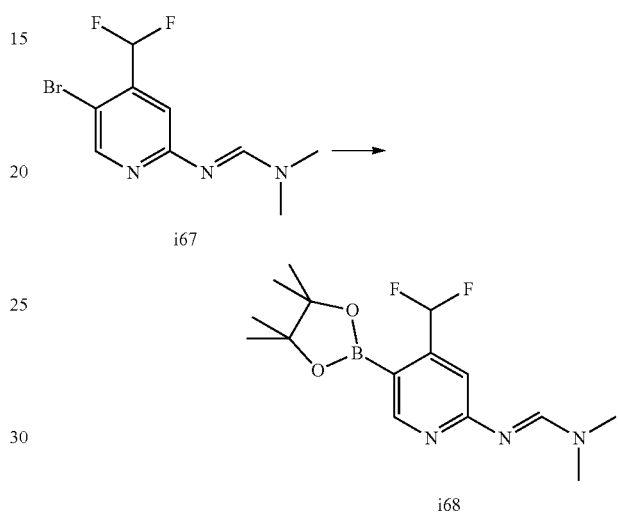

To a 2 M solution of isopropylmagnesium chloride (Sigma, product number 230111, 3.10 mL, 6.20 mmol, 1.15 eq.) in tetrahydrofuran (6 mL) is slowly added a solution of compound i67 (1.50 g, 5.39 mmol, 1.0 eq.) in tetrahydrofuran (5 mL) at 0° C. The resulting brownish mixture is stirred at 0° C. for 45 minutes and then at room temperature for 15 minutes. After this time, TLC monitoring (cyclohexane/ethyl acetate 1:1) showed complete consumption of starting material. 2-Isopropoxy-4,4,5,5-tetramethyl-1,3,2-dioxaborolane (Manchester Organics, product number W23343, 1.43 mL, 7.00 mmol, 1.3 eq.) is added and the mixture is heated at 60° C. for 3 hours. The mixture is then placed in an Erlenmeyer flask, cooled to 0° C. with an ice bath and quenched with a 15% aqueous solution of ammonium chloride. The layers are separated and the aqueous layer is extracted with ethyl acetate (3×40 mL). The combined organic layers are dried over anhydrous sodium sulfate, filtered and the solvent is evaporated under reduced pressure. Heptane is added and the organic layer is washed with a saturated aqueous solution of sodium bicarbonate, dried over anhydrous sodium sulfate, filtered and then concentrated to dryness under reduced pressure. The desired product i68 is obtained as a brownish oil, which is used in the next step without further purification (94% yield). $^1$H NMR (400 MHz, CDCl$_3$): δ 8.66 (s, 1H), 8.51 (s, 1H), 7.34-7.04 (m, 2H), 3.12 (s, 3H), 3.12 (s, 3H), 1.34 (s, 12H); $^{19}$F NMR (376 MHz, CDCl$_3$): δ−115.6 (s, 2F); MS (MALDI): m/z=326.0 ([M+H]$^+$).

Method 22: 4-(difluoromethyl)pyrimidin-2-amine (i69)

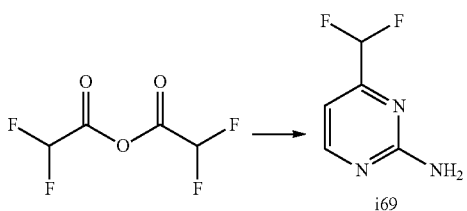 [SMILES: O=C(OC(=O)C(F)F)C(F)F ; Nc1nccc(C(F)F)n1]

To a solution of ethyl vinyl ether (4.00 mL, 41.8 mmol, 1.0 eq.) in a mixture of pyridine (4.10 mL, 50.7 mmol, 1.2 eq.) and dichloromethane (40 mL), is added dropwise a solution of 2,2-difluoroacetic anhydride (Manchester Organics, (product number L24754, 5.90 mL, 50.1 mmol, 1.2 eq.) in dichloromethane (5 mL) at −70° C. in a dry ice/isopropanol bath. The resulting solution is allowed to warm up to room temperature overnight. The mixture is then washed with deionized water, dried over anhydrous sodium sulfate, filtered and the solvent is evaporated under reduced pressure to afford an orange oil.

A solution of guanidine-HCl (Sigma, product number 50940, 4.80 g, 50.2 mmol, 1.2 eq.) in ethanol (20 mL) is stirred at room temperature for 1 hour. To this solution are added sodium hydroxide pellets (2.00 g, 50.0 mmol, 1.2 eq.) in one portion. The resulting suspension is stirred at room temperature overnight.

The resulting mixture is diluted with dichloromethane (20 mL) and added dropwise over 1 hour. The resulting suspension is stirred at room temperature for 2 hours. Dichloromethane is evaporated under reduced pressure. Deionized water (25 mL) is added to the residue. The resulting mixture is stirred vigorously for 2 hours and is then allowed to stand at room temperature overnight. The formed solid is filtered off, washed with deionized water (2×) and heptane (1×) and then dried in vacuo. The desired product i69 is obtained as a colorless solid (65% yield). $^1$H NMR (400 MHz, CDCl$_3$): δ 8.43 (d, $^2J_{H,H}$=4.8 Hz, 1H), 7.02 (br s, 2H), 6.76 (d, $^2J_{H,H}$=5.2 Hz, 1H), 6.67 (t, $^2J_{H,F}$=55 Hz, 1H); $^{19}$F NMR (376 MHz, CDCl$_3$): δ−120.5 (s, 2F).

Method 23: 5-bromo-4-(difluoromethyl)pyrimidin-2-amine (i70)

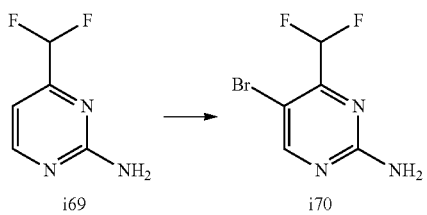 [SMILES: Nc1nccc(C(F)F)n1 ; Nc1ncc(Br)c(C(F)F)n1]

To a solution of compound i69 (3.00 g, 20.7 mmol, 1.0 eq.) in tetrahydrofuran (90 mL) is added N-bromosuccinimide (3.86 g, 21.7 mmol, 1.0 eq.) portionwise at 0° C. The reaction mixture is allowed to warm up to room temperature overnight. After this time, the solvent is evaporated under reduced pressure. The residue is taken up in ethyl acetate (200 mL), washed with an aqueous saturated solution of sodium carbonate (4×), dried over anhydrous sodium sulfate, filtered and then concentrated to dryness under reduced pressure. The desired product i70 is obtained as a yellowish solid, which is used in the next step without further purification (98% yield). $^1$H NMR (400 MHz, (CD$_3$)$_2$SO): δ 8.50 (s, 1H), 7.30 (br s, 2H), 6.87 (t, $^2J_{H,F}$=53 Hz, 1H); $^{19}$F NMR (376 MHz, (CD$_3$)$_2$SO): δ−121.4 (s, 2F).

Method 24: N-tert-butyl carboxylate-N-(5-bromo-4-(difluoromethyl)pyrimidin-2-yl)-carbamate (i71)

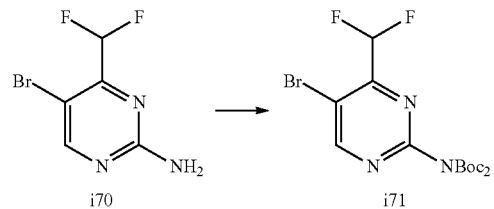

Compound i70 (4.35 g, 19.4 mmol, 1.0 eq.) and 4-(dimethylamino)pyridine (480 mg, 3.92 mmol, 0.20 eq.) are dissolved in tetrahydrofuran (50 mL). N,N-Diisopropylethylamine (7.50 mL, 42.1 mmol, 2.2 eq.) and di-tert-butyl dicarbonate (9.33 g, 42.7 mmol, 2.2 eq.) are then added at 0° C. and the resulting solution is allowed to warm up to room temperature overnight. The solvent is evaporated under reduced pressure. The crude product is purified by column chromatography on silica gel (cyclohexane/ethyl acetate 9:1→4:1) to afford the desired product i71 as a colorless solid (85% yield). $^1$H NMR (400 MHz, CDCl$_3$): δ 8.92 (s, 1H), 6.73 (t, $^2J_{H,F}$=53 Hz, 1H), 1.47 (s, 18H); $^{19}$F NMR (376 MHz, CDCl$_3$): δ−120.4 (s, 2F).

Method 25: methyl (4R,5R)-5-methyl-2-oxo-oxazolidine-4-carboxylate (i72)

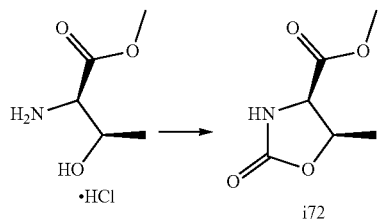

Under nitrogen atmosphere, an oven-dried flask equipped with a reflux condenser is charged with H-D-allo-threonine methyl ester.HCl (Bachem, product number 4044567, 2.00 g, 11.8 mmol, 1.0 eq.) and triphosgene (1.16 g, 3.91 mmol, 0.33 eq.). Tetrahydrofuran (20 mL) is added and the resulting mixture is heated to reflux for 1 hour. The mixture is then cooled down to room temperature, an aqueous NH$_4$Cl-solution (15%) is added and the aqueous layer is extracted with dichloromethane (3×). The combined organic layer is dried over anhydrous sodium sulfate, filtered and the solvent is evaporated under reduced pressure. Purification by column chromatography on silica gel (cyclohexane/ethyl acetate 1:1) gives the desired intermediate i72 as a colorless oil (66% yield). $^1$H NMR (400 MHz, (CD$_3$)$_2$SO): δ 7.98 (br s, 1H), 4.91-4.82 (m, 1H), 4.42 (d, $^3J_{H,H}$=8.4 Hz, 1H), 3.71 (s, 3H), 1.17 (d, $^3J_{H,H}$=6.5 Hz, 3H).

151

Method 26: (4S,5R)-4-[[tert-butyl(dimethyl)silyl]oxymethyl]-5-methyl-oxazolidin-2-one

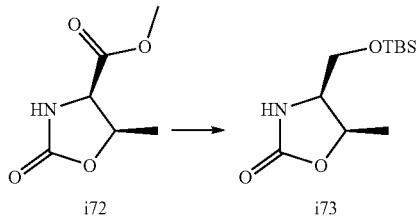 [SMILES: COC(=O)[C@@H]1NC(=O)O[C@@H]1C ; C[C@H]1OC(=O)N[C@H]1CO[Si](C)(C)C(C)(C)C]

To a solution of methyl (4R,5R)-5-methyl-2-oxo-oxazolidine-4-carboxylate (i72, 1.18 g, 7.41 mmol, 1.0 eq.) in tetrahydrofuran (15 mL) is added LiBH$_4$ (200 mg, 9.18 mmol, 1.2 eq.) portionwise at 0° C. under nitrogen atmosphere. The reaction mixture is allowed to stir at 0° C. for 10 minutes and then at room temperature for 1.5 hours. The reaction mixture is quenched by addition of an aqueous saturated NH$_4$Cl-solution, stirred for an additional hour at room temperature and then reduced to dryness under reduced pressure. The resulting residue is triturated with a mixture of ethyl acetate and dichloromethane (1:1), the solids are filtered off, washed with ethyl acetate/dichloromethane (1:1) and the filtrate is reduced to dryness under reduced pressure. The above residue is then dissolved in N,N-dimethylformamide (20 mL). Imidazole (581 mg, 8.53 mmol, 1.2 eq.) and tert-butyldimethylsilyl chloride (1.23 g, 8.16 mmol, 1.1 eq.) are added and the resulting reaction mixture is stirred at room temperature overnight. Brine is added and the aqueous layer is extracted with ethyl acetate (3×). The combined organic layer is dried over anhydrous sodium sulfate, filtered and the solvent is evaporated. Purification by column chromatography on silica gel (cyclohexane/ethyl acetate 3:1) gives the desired intermediate i73 as a colorless solid (64% yield). $^1$H NMR (400 MHz, (CD$_3$)$_2$SO): δ 7.41 (br s, 1H), 4.72-4.63 (m, 1H), 3.66-3.61 (m, 1H), 3.58 (br d, $^3J_{H,H}$=4.4 Hz, 2H), 1.32 (d, $^3J_{H,H}$=6.6 Hz, 3H), 0.86 (s, 9H), 0.05 (d, $^4J_{H,H}$=2.6 Hz, 6H).

General Procedure 1:

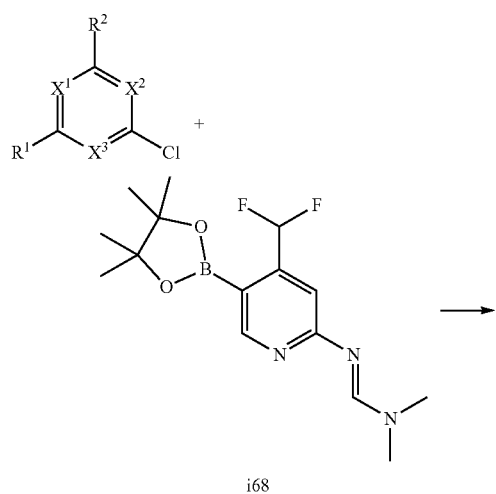

152

-continued

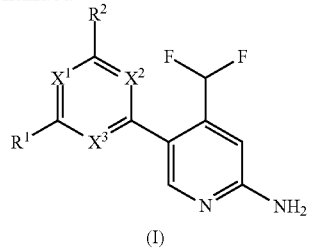

Substituted monochloro-triazine or substituted monochloro-pyrimidine (1.0 eq.), compound i68 (1.1 eq.), potassium phosphate tribasic (2.0 eq.) and chloro(2-dicyclohexylphosphino-2',4',6'-triisopropyl-1,1'-biphenyl) [2-(2'-amino-1,1'-biphenyl)]-palladium(II) (Sigma-Aldrich, product number 741825, 0.05 eq.) are charged in a flask. Under nitrogen atmosphere, 1,4-dioxane (30 volumes) and deionized water (1.5 volume) are added and the resulting mixture is then directly placed into an oil bath pre-heated at 95° C. The reaction mixture is stirred at this temperature for 2 hours. A 5 M aqueous HCl-solution (20 eq.) is added. The resulting mixture is heated to 60° C. overnight. The pH of the resulting mixture is adjusted to 8-9 by addition of a 2 M aqueous solution of sodium hydroxide, the mixture is then extracted with ethyl acetate (3×20 volumes). The combined organic layers are dried over anhydrous sodium sulfate, filtered and the solvent is evaporated under reduced pressure. Purification by flash chromatography affords the desired products of structure (I).

General Procedure 2:

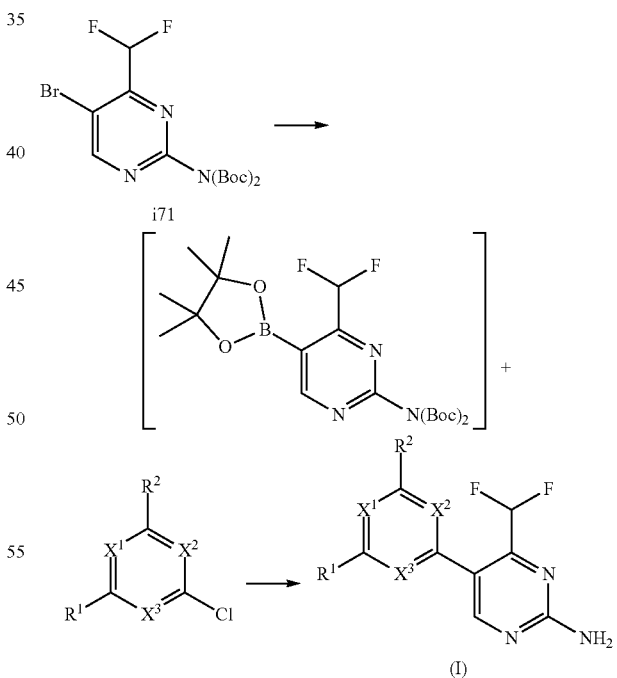

Compound i71 (1.0 eq.), 4,4,4',4',5,5,5',5'-octamethyl-2,2'-bi(1,3,2-dioxaborolane) (Manchester Organics, product number M23170, 1.5 eq.), potassium acetate (3.0 eq.) and [1,1'-bis(diphenylphosphino)-ferrocene]-dichloropalladium (II) (Sigma-Aldrich, product number 697230, 0.099 eq.) are dissolved in 1,4-dioxane (12.5 volumes) under nitrogen atmosphere. The resulting mixture is heated at 100° C. for 15 minutes (solution turned black). TLC monitoring (cyclohexane/ethyl acetate 3:1) is used to show complete consumption of starting material.

To the resulting mixture, substituted chloro-triazine or substituted chloropyrimidine (1.1 eq.), an aqueous solution of potassium carbonate (2 M, 3.0 eq.) and a previously mixed solution of triphenylphosphine (0.12 eq.) and palladium acetate (0.04 eq.) in tetrahydrofuran (100 volumes) are added. The resulting mixture is heated at 60° C. for 2 hours and subsequently allowed to cool to room temperature. A 5 M aqueous HCl-solution (20 eq.) is added. The resulting mixture is heated to 60° C. overnight. The pH of the resulting mixture is adjusted to 8-9 by addition of a 2 M aqueous solution of sodium hydroxide, the mixture is then extracted with ethyl acetate (3×20 volumes). The combined organic layers are dried over anhydrous sodium sulfate, filtered and the solvent is evaporated under reduced pressure. Purification by flash chromatography affords the desired products.

Method 27: tert-butyl N-tert-butoxycarbonyl-N-(5-(4-chloro-6-morpholino-1,3,5-triazin-2-yl)-4-(difluoromethyl)pyrimidin-2-yl)carbamate (i74)

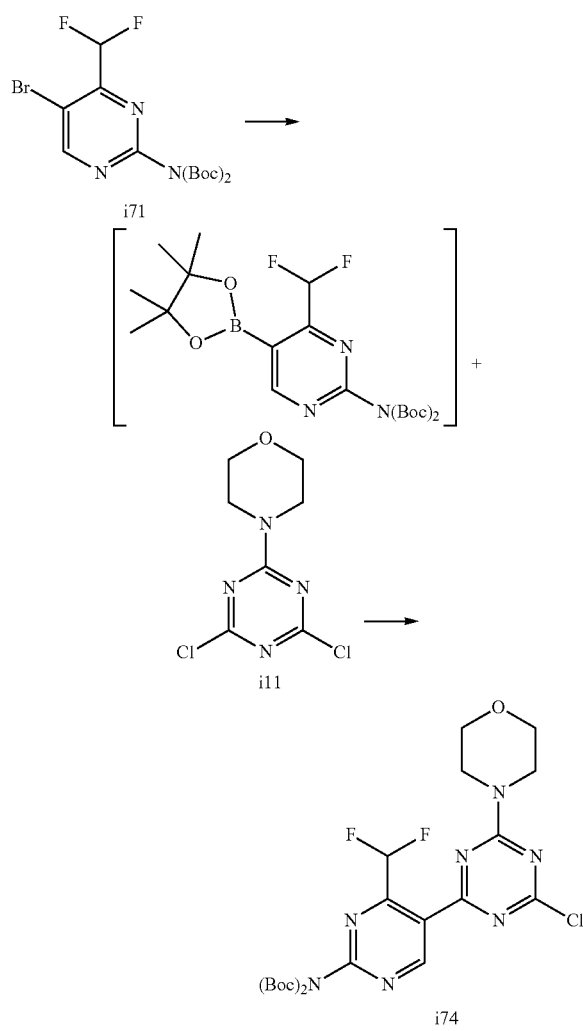

Intermediate i71 (2.00 g, 4.71 mmol, 1.0 eq.), bis(pinacolato)diboron (1.80 g, 7.09 mmol, 1.5 eq.), KOAc (1.60 g, 16.3 mmol, 3.4 eq.) and [1,1'-bis(diphenylphosphino)ferrocene]-dichloropalladium(II) (350 mg, 478 μmol, 0.10 eq.) are mixed in 1,4-dioxane under nitrogen atmosphere and heated at 95° C. for 45 minutes. A pre-catalyst solution of palladium(II) acetate (43.0 mg, 192 μmol, 0.04 eq.) and triphenylphosphine 148 mg, 564 μmol, 0.12 eq.) in tetrahydrofuran (2 mL) is also prepared and stirred at room temperature for 1 hour. This solution is then added to the cooled above solution at room temperature, followed by the addition of 4-(4,6-dichloro-1,3,5-triazin-2-yl)morpholine i11 (1.65 g, 7.05 mmol, 1.5 eq.) and aqueous $K_2CO_3$-solution (2.4 M, 5.90 mL, 14.2 mmol, 3.0 eq.). The resulting mixture is heated at 55° C. overnight. After this time, the mixture is poured onto an aqueous $NH_4Cl$-solution (15%) and extracted with ethyl acetate (3×). The combined organic layer is dried over anhydrous sodium sulfate, filtered and concentrated under reduced pressure. Purification by column chromatography on silica gel (cyclohexane/ethyl acetate 1:0→4:1) gives product i74 as a colorless solid (36% yield). $^1$H NMR (400 MHz, $CDCl_3$): δ 9.57 (s, 1H), 7.55 (t, $^2J_{H,F}$=54 Hz, 1H), 3.99-3.91 (m, 4H), 3.84-3.76 (m, 4H), 1.49 (s, 18H); $^{19}$F NMR (376 MHz, $CDCl_3$): δ−121.0 (s, 2F).

Method 28: (2R,3S)-3-amino-4-((tert-butyldiphenylsilyl)oxy)butan-2-ol (i75)

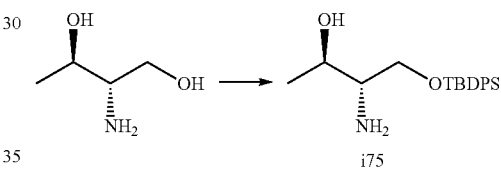

D-allo-Threoninol (307 mg, 2.92 mmol, 1.0 eq.) is dissolved in N,N-dimethylformamide (3 mL) and imidazole (597 mg, 8.77 mmol, 3.0 eq.) is added. After 5 minutes, TBDPSCl (760 μL, 2.92 mmol, 1.0 eq.) is added slowly and then the reaction mixture is stirred at room temperature overnight. After this time, the solvent is evaporated under reduced pressure. The resulting residue is taken up in ethyl acetate and washed with an aqueous saturated solution of sodium bicarbonate (1×) and brine (1×). The organic layer is dried over anhydrous sodium sulfate, filtered and concentrated under reduced pressure. Purification by column chromatography on silica gel (100% ethyl acetate) gives the desired intermediate i75 as a colorless semisolid (50% yield). $^1$H NMR (400 MHz, $CDCl_3$): δ 7.70-7.61 (m, 4H), 7.47-7.36 (m, 6H), 3.82-3.73 (m, 1H), 3.69 (d, $^3J_{H,H}$=5.8 Hz, 2H), 2.58 (q, $^3J_{H,H}$=5.8 Hz, 1H), 1.12 (d, $^3J_{H,H}$=6.5 Hz, 3H), 1.07 (s, 9H).

Method 29: (4S,5R)-4-(((tert-butyldiphenylsilyl)oxy)methyl)-5-methyloxazolidin-2-one (i76)

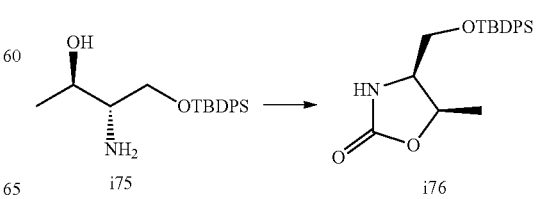

Under nitrogen atmosphere, in an oven-dried flask equipped with a reflux condenser, intermediate i75 (433 mg, 1.26 mmol, 1.0 eq.) and triethylamine (440 µL, 3.15 mmol, 2.5 eq.) are dissolved in dichloromethane (5 mL). At 0° C. in an ice-bath, triphosgene is then added (187 mg, 630 µmol, 0.5 eq.). The resulting mixture is stirred overnight, while it is allowed to warm up to room temperature. The reaction is then quenched by addition of an aqueous NH$_4$Cl-solution (15%) and the aqueous mixture is extracted with dichloromethane (3×). The combined organic layer is dried over anhydrous sodium sulfate, filtered and the solvent is evaporated under reduced pressure. Purification by column chromatography on silica gel (cyclohexane/ethyl acetate 1:0→3:2) gives the desired intermediate i76 as a colorless solid (73% yield). $^1$H NMR (400 MHz, CDCl$_3$): δ 7.66-7.61 (m, 4H), 7.47-7.38 (m, 6H), 4.99 (br s, 1H), 4.82-4.74 (m, 1H), 3.85-3.79 (m, 1H), 3.68-3.65 (m, 2H), 1.34 (d, $^3J_{H,H}$=6.7 Hz, 3H), 1.06 (s, 9H).

Method 30: (4S,5R)-4-(((tert-butyldiphenylsilyl)oxy)methyl)-3-(2,6-dibromopyrimidin-4-yl)-5-methyloxazolidin-2-one (i77)

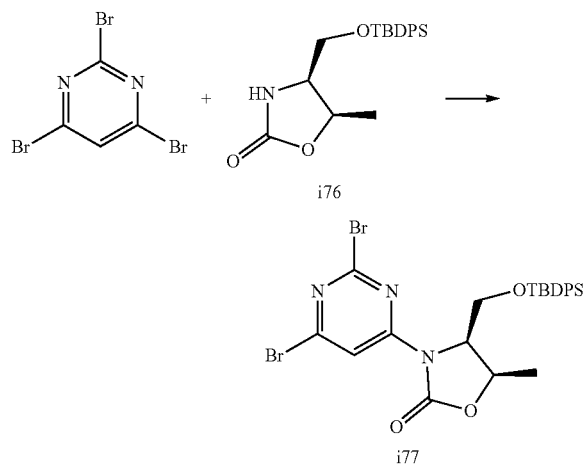

Under nitrogen atmosphere, (4S,5R)-4-(((tert-butyldiphenylsilyl)oxy)methyl)-5-methyloxazolidin-2-one (i76, 681 mg, 1.84 mmol, 1.0 eq.) is dissolved in N,N-dimethylformamide (10 mL) and NaH (60% dispersion in mineral oil, 155 mg, 3.88 mmol, 2.1 eq.) is added portionwise at 0° C., in an ice-bath. After 5 minutes, 2,4,6-tribromopyrimidine (583 mg, 1.84 mmol, 1.0 eq.) is added. The resulting mixture is stirred overnight, while it is allowed to warm up to room temperature. The reaction is then quenched by addition of an aqueous NH$_4$Cl-solution (15%) and the aqueous mixture is extracted with ethyl acetate (3×). The combined organic layer is dried over anhydrous sodium sulfate, filtered and the solvent is evaporated under reduced pressure. Purification by column chromatography on silica gel (cyclohexane/ethyl acetate 1:0→9:1) gives the desired product i77 as a colorless foam (55% yield). $^1$H NMR (400 MHz, CDCl$_3$): δ 8.25 (s, 1H), 7.54-7.50 (m, 2H), 7.45-7.33 (m, 6H), 7.26-7.21 (m, 2H), 4.85 (quint, $^3J_{H,H}$=6.9 Hz, 1H), 4.56-4.52 (m, 1H), 4.14 (dd, $^2J_{H,H}$=12 Hz, $^3J_{H,H}$=2.8 Hz, 1H), 3.98 (dd, $^2J_{H,H}$=12 Hz, $^3J_{H,H}$=1.4 Hz, 1H), 1.77 (d, $^3J_{H,H}$=6.5 Hz, 3H), 1.04 (s, 9H).

Method 31: (4S,5R)-3-(6-bromo-2-morpholinopyrimidin-4-yl)-4-(((tert-butyldiphenylsilyl)oxy)methyl)-5-methyloxazolidin-2-one (i78)

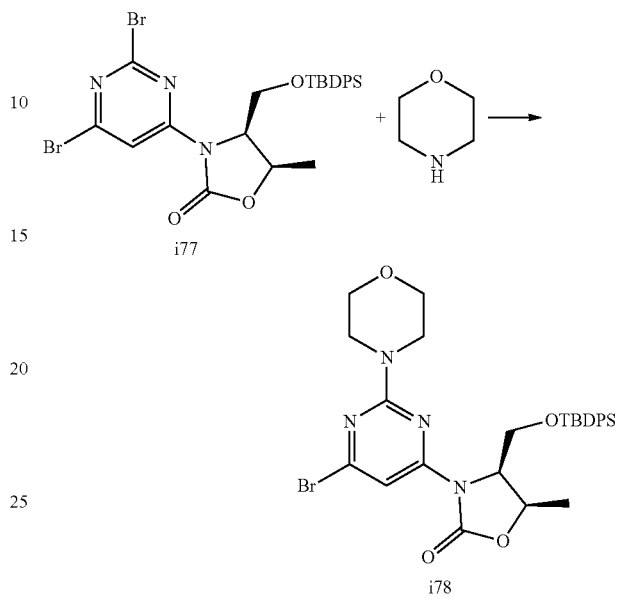

Intermediate i77 (530 mg, 876 µmol, 1.0 eq.), morpholine (80.0 µL, 915 µmol, 1.0 eq.) and N,N-diisopropylethylamine (200 µL, 1.15 mmol, 1.3 eq.) are mixed in acetonitrile (7 mL) and the resulting mixture is heated at 85° C. overnight. Then, the mixture is allowed to cool down to room temperature and the solvent is evaporated under reduced pressure. The desired product i78 is obtained as a colorless solid (12% yield) after purification by column chromatography on silica gel (cyclohexane/ethyl acetate 1:0→85:15).
$^1$H NMR (400 MHz, CDCl$_3$): δ 7.70 (s, 1H), 7.59-7.55 (m, 2H), 7.46-7.31 (m, 6H), 7.22-7.16 (m, 2H), 4.82 (quint, $^3J_{H,H}$=6.2 Hz, 1H), 4.50-4.44 (m, 1H), 4.09 (dd, $^2J_{H,H}$=11 Hz, $^3J_{H,H}$=3.1 Hz, 1H), 3.88 (dd, $^2J_{H,H}$=11 Hz, $^3J_{H,H}$=1.3 Hz, 1H), 3.69-3.33 (m, 8H), 1.74 (d, $^3J_{H,H}$=6.6 Hz, 3H), 1.01 (s, 9H).

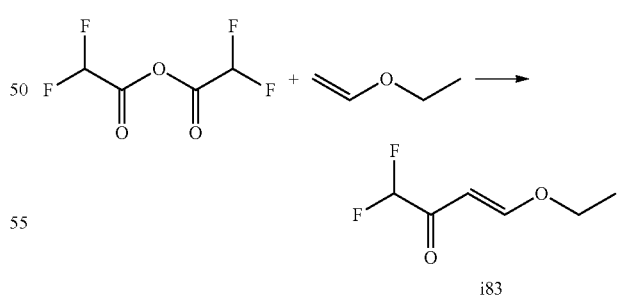

Method 32: (E)-4-ethoxy-1,1-difluoro-but-3-en-2-one (i83)

To a cooled (−70° C.) solution of pyridine (61.5 mL, 760.5 mmol, 1.2 eq) in dichloromethane (500 mL) is added ethyl vinyl ether (60 mL, 626.5 mmol, 1 eq), followed by a solution a difluoroacetic anhydride (88.5 mL, 760.5 mmol, 1.2 eq) in dichloromethane (75 mL). Then the mixture is slowly warmed to room temperature overnight. The mixture is transferred into a separating funnel and the organic layer is washed with water (6×800 mL) until the pH of the aqueous layer becomes neutral. The organic layer is dried over sodium sulfate and solvent is removed under reduced pressure to afford the desired product i83 as an orange oil (76.7 g, 81%). $^1$H NMR (400 MHz, DMSO-d$_6$): δ 7.92 (d, $^3J_{H,H}$=12.5 Hz, 1H), 6.34 (t, $^2J_{H,F}$=53.6 Hz, 1H), 5.87 (d, $^3J_{H,H}$=12.5 Hz, 1H), 4.14 (q, $^3J_{H,H}$=7.1 Hz, 2H), 1.28 (t, $^3J_{H,H}$=7.1 Hz, 3H); $^{19}$F {1H} NMR (400 MHz, DMSO-d$_6$): δ −127.39 (s, 2F).

Method 33: (E)-3-(difluoromethyl)-5-ethoxy-3-hydroxy-pent-4-enenitrile (i84)

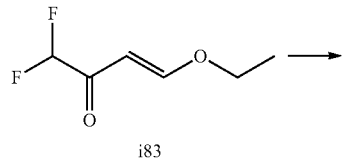

i83

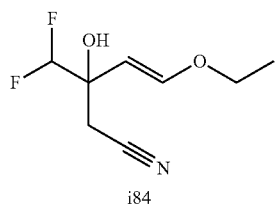

i84

To a cooled (−70° C.) solution of n-butyl lithium 2.5M (102.9 mL, 256.7 mmol, 1 eq) in tetrahydrofuran (435 mL) is added acetonitrile (13.4 mL, 256.7 mmol, 1 eq). A white suspension is formed and is stirred at −70° C. for 1 h30. A solution of (E)-4-ethoxy-1,1-difluoro-but-3-en-2-one (i83) (38.5 g, 256.7 mmol, 1 eq) in tetrahydrofuran (65 mL) is added to the white suspension (mixture becomes an orange solution). The mixture is stirred at −70° C. for 1 h and slowly warmed to room temperature. Water (400 mL) is added.

Then ethyl acetate (600 mL) is added. Layers are separated and aqueous layer is extracted with ethyl acetate (3×600 mL). Combined organic layers are dried over sodium sulfate and solvent is evaporated under reduced pressure. Filtration on a short pad of silica gel, using a mixture of cyclohexane/ethyl acetate (3:1) as eluent, gives the desired product i84 as a dark orange oil (43.4 g, 88%). $^1$H NMR (400 MHz, DMSO-d$_6$): δ 6.66 (d, $^3J_{H,H}$=12.8 Hz, 1H), 6.20 (s, 1H), 5.79 (t, $^2J_{H,F}$=55.8 Hz, 1H), 4.75 (d, $^3J_{H,H}$=12.8 Hz, 1H), 3.74 (q, $^3J_{H,H}$=7.0 Hz, 2H), 2.88 (d, $^3J_{H,H}$=16.8 Hz, 1H), 2.81 (d, $^3J_{H,H}$=16.8 Hz, 1H), 1.21 (t, $^3J_{H,H}$=7.0 Hz, 1H); $^{19}$F {1H} NMR (400 MHz, DMSO-d$_6$): δ −129.32 (d, $^2J_{F,F}$=311.2 Hz, 1F), −130.05 (d, $^2J_{F,F}$=311.2 Hz, 1F).

Method 34: 4-(difluoromethyl)pyridin-2-amine (i65)

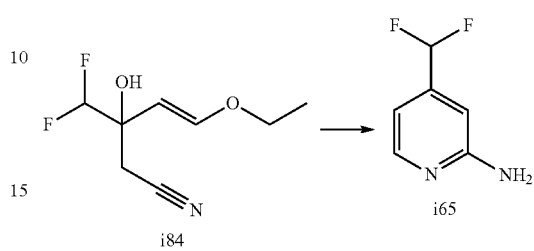

To a solution of (E)-3-(difluoromethyl)-5-ethoxy-3-hydroxy-pent-4-enenitrile (i84) (8.1 g, 42.4 mmol, 1 eq) in acetic acid (80 mL) is added O-methylhydroxylamine hydrochloride (Fluorochem, product number 078603) (10.6 g, 127.2 mmol, 3 eq). Mixture is stirred at 50° C. for 7 h. Then reaction mixture is cooled down to room temperature and hydrobromic acid in acetic acid (33%) (14.2 mL, 84.8 mmol, 2 eq) is added. Reaction mixture is stirred at 90° C. overnight. Reaction mixture is degassed and placed under nitrogen. Reaction mixture is maintained at room temperature with a water bath with ice while zinc powder (8.12 g, 127.2 mmol, 3 eq) is added portionwise. Reaction mixture is stirred 3 h at room temperature. Mixture is filtered over a short pad of celite and the cake is washed with ethyl acetate. Then the major part of the solvent is removed under reduced pressure. 60 mL of aqueous ammonium hydroxide (28%) is added. Aqueous layer is extracted with dichloromethane (3×150 mL). Combined organic layers are dried over sodium sulfate. Compound i65 is recrystallized from dichloromethane and heptane as anti-solvent (solvent switch at the rotavap). Compound i65 is collected, as a light yellow solid, by filtration (5.12 g, 84%).

Preparation of Compounds of the Invention

Example 1: 4-(difluoromethyl)-5-(4,6-dimorpholino-1,3,5-triazin-2-yl)pyridin-2-amine (1)

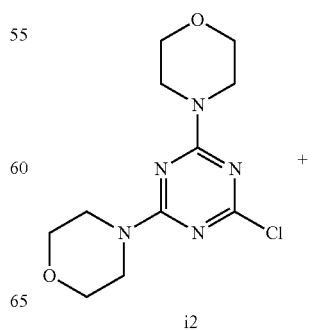

i2

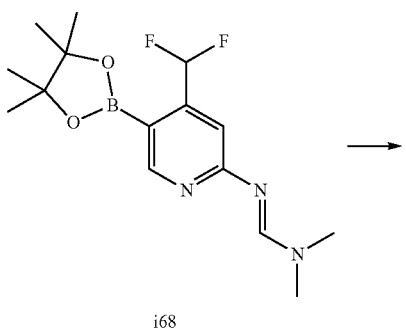

i68

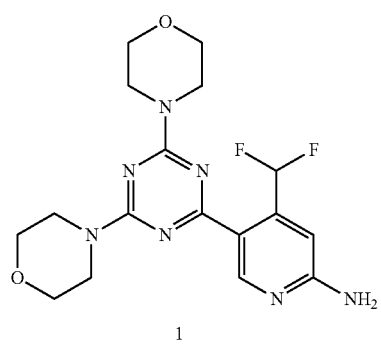

1

According to general procedure 1, compound 1 is obtained from starting materials i2 and i68 in 73% yield as a colorless solid. $^1$H NMR (400 MHz, CDCl$_3$): δ 9.02 (s, 1H), 7.65 (t, $^2J_{H,F}$=55 Hz, 1H), 6.83 (s, 1H), 4.85 (br s, 2H), 3.89-3.79 (m, 8H), 3.77-3.72 (m, 8H); $^{19}$F NMR (376 MHz, CDCl$_3$): δ−115.9 (s, 2F); MS (MALDI): m/z=393.9 ([M+H]$^+$).

Example 2: 4-(difluoromethyl)-5-(4,6-dimorpholino-1,3,5-triazin-2-yl)pyrimidin-2-amine (2)

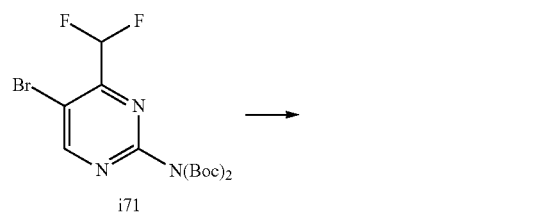

i71

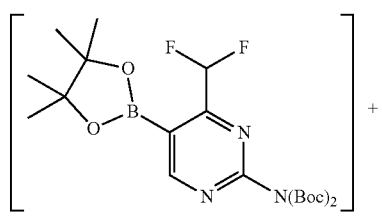

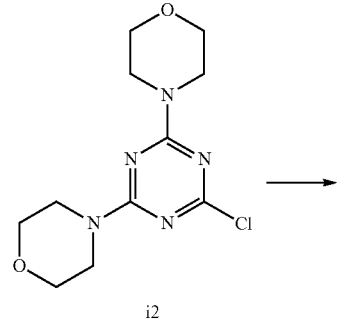

i2

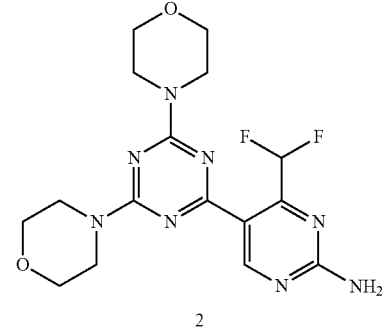

2

According to general procedure 2, compound 2 is obtained from starting materials i2 and i71 in 74% yield as a colorless solid. $^1$H NMR (400 MHz, CDCl$_3$): δ 9.20 (s, 1H), 7.62 (t, $^2J_{H,F}$=54 Hz, 1H), 5.97 (br s, 2H), 3.91-3.68 (m, 16H); $^{19}$F NMR (376 MHz, CDCl$_3$): δ−121.5 (s, 2F); MS (MALDI): m/z=395.2 ([M+H]$^+$).

Example 3: 5-(4-(3-oxa-8-azabicyclo[3.2.1]octan-8-yl)-6-(3-oxa-8-azabicyclo[3.2.1]octan-8-yl)-1,3,5-triazin-2-yl)-4-(difluoromethyl)pyridin-2-amine (3)

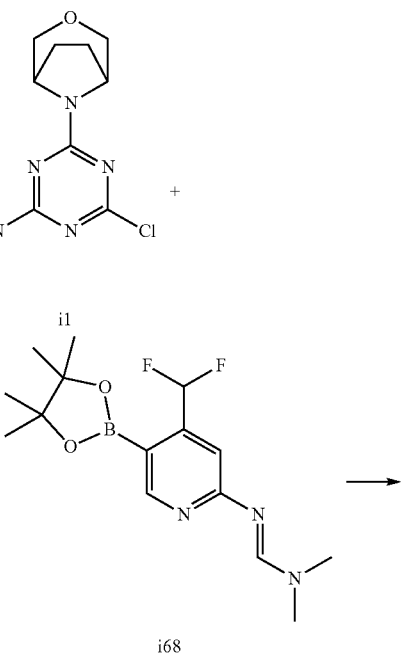

161
-continued

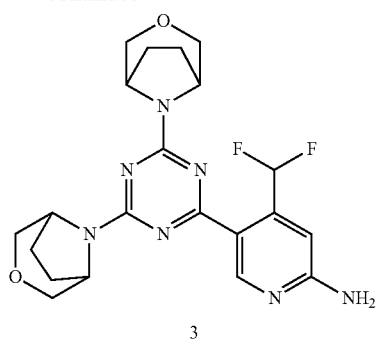

3

According to general procedure 1, compound 3 is obtained from starting materials ii and i68 in 75% yield as a colorless solid. $^1$H NMR (400 MHz, CDCl$_3$): δ 9.04 (s, 1H), 7.71 (t, $^2J_{H,F}$=55 Hz, 1H), 6.83 (s, 1H), 4.89 (br s, 2H), 4.71-4.64 (m, 4H), 3.79-3.76 (m, 4H), 3.67-3.62 (m, 4H), 2.09-1.98 (m, 8H); $^{19}$F NMR (376 MHz, CDCl$_3$): δ −115.4-(−117.3) (m, 2F); MS (MALDI): m/z=446.3 ([M+H]$^+$).

Example 4: 5-(4-(3-oxa-8-azabicyclo[3.2.1]octan-8-yl)-6-morpholino-1,3,5-triazin-2-yl)-4-(difluoromethyl)pyridin-2-amine (4)

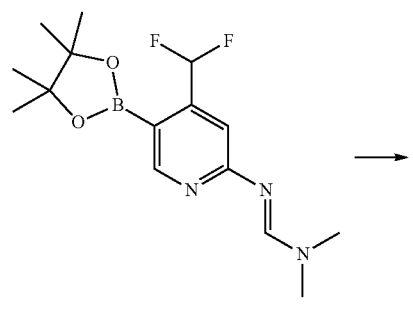

i68

162
-continued

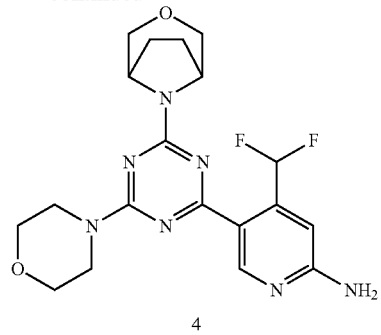

4

According to general procedure 1, compound 4 is obtained from starting materials i12 and i68 in 57% yield as a colorless solid. $^1$H NMR (400 MHz, CDCl$_3$): δ 9.03 (s, 1H), 7.68 (m, 1H), 6.83 (s, 1H), 4.94 (br s, 2H), 4.70-4.65 (m, 2H), 3.93-3.57 (m, 12H), 2.14-1.92 (m, 4H); $^{19}$F NMR (376 MHz, CDCl$_3$): δ−116.0-(−116.2) (m, 2F); MS (MALDI): m/z=420.6 ([M+H]$^+$).

Example 5: 5-(4-(3-oxa-8-azabicyclo[3.2.1]octan-8-yl)-6-morpholino-1,3,5-triazin-2-yl)-4-(difluoromethyl)pyrimidin-2-amine (5)

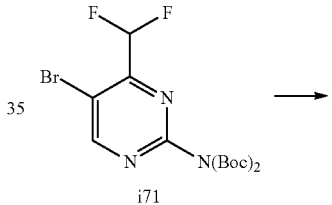

i71

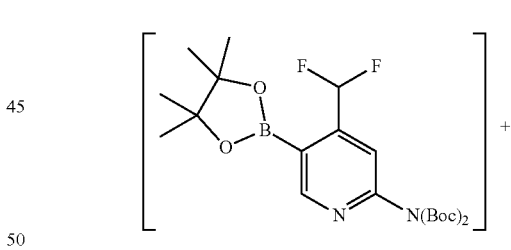

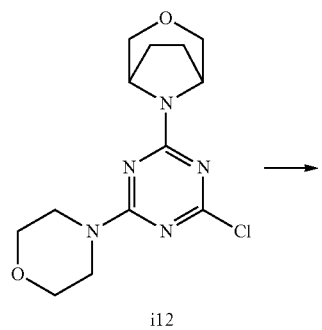

i12

-continued

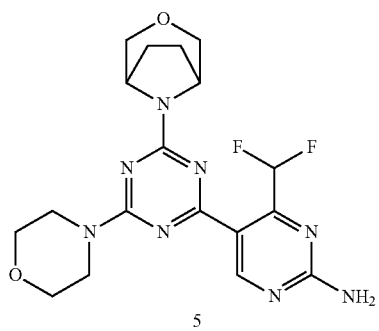

5

According to general procedure 2, compound 5 is obtained from starting materials i71 and i12 in 50% yield as a colorless solid. $^{1}$H NMR (400 MHz, CDCl$_3$): δ 9.23 (s, 1H), 7.65 (t, $^{2}J_{H,F}$=54 Hz, 1H), 5.66 (br s, 2H), 4.68 (m, 2H), 3.90-3.61 (m, 12H), 2.13-1.92 (4H); $^{19}$F NMR (376 MHz, CDCl$_3$): δ−120.4-(−121.5) (m, 2F); MS (MALDI): m/z=420.9 ([M+H]$^+$).

Example 6: 5-(4,6-bis((S)-3-methylmorpholino)-1,3,5-triazin-2-yl)-4-(difluoromethyl)pyridin-2-amine (6)

-continued

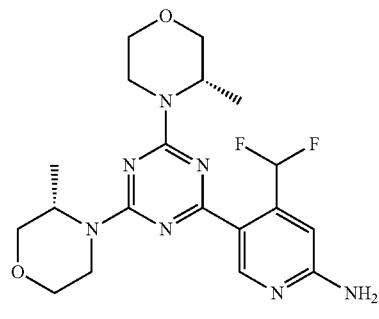

6

According to general procedure 1, compound 6 is obtained from starting materials i3 and i68 in 79% yield as a colorless solid. $^{1}$H NMR (400 MHz, CDCl$_3$): δ 8.87 (s, 1H), 7.70 (t, $^{2}J_{H,F}$=55 Hz, 1H), 6.86 (s, 1H), 5.48 (br s, 2H), 4.73-4.72 (m, 2H), 4.41-4.38 (m, 2H), 3.98 (dd, $J_{H,H}$=11.6, 3.8 Hz, 2H), 3.78 (d, $J_{H,H}$=12 Hz, 2H), 3.67 (dd, $J_{H,H}$=12, 3.2 Hz, 2H), 3.52 (td, $J_{H,H}$=12, 3.0 Hz, 2H), 3.27 (td, $J_{H,H}$=13, 3.8 Hz, 2H), 1.33 (d, $^{3}J_{H,H}$=6.8 Hz, 6H); $^{19}$F NMR (376 MHz, CDCl$_3$): δ−115.4-(−116.2) (m, 2F); MS (MALDI): m/z=421.9 ([M+H]$^+$).

Example 7: 5-(4,6-bis((S)-3-methylmorpholino)-1,3,5-triazin-2-yl)-4-(difluoromethyl)pyrimidin-2-amine (7)

-continued

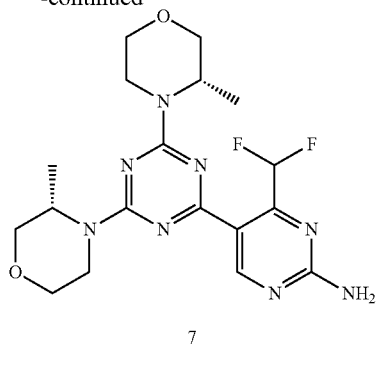

7

According to general procedure 2, compound 7 is obtained from starting materials i71 and i3 in 52% yield as a colorless solid. $^1$H NMR (400 MHz, CDCl$_3$): δ 9.24 (s, 1H), 7.66 (t, $^2J_{H,F}$=54 Hz, 1H), 5.77 (br s, 2H), 4.73 (br s, 2H), 4.45-4.32 (m, 2H), 3.98 (dd, $J_{H,H}$=12, 3.6 Hz, 2H), 3.78 (d, $J_{H,H}$=12 Hz, 2H), 3.67 (dd, $J_{H,H}$=11, 2.8 Hz, 2H), 3.52 (td, $J_{H,H}$=12, 2.8 Hz, 2H), 3.27 (td, $J_{H,H}$=13, 3.2 Hz, 2H), 1.33 (d, $^3J_{H,H}$=6.8 Hz, 6H); $^{19}$F NMR (376 MHz, CDCl$_3$): δ–120.5-(–122.7) (m, 2F); MS (MALDI): m/z=423.3 ([M+H]$^+$).

Example 8: (S)-4-(difluoromethyl)-5-(4-(3-methyl-morpholino)-6-morpholino-1,3,5-triazin-2-yl)pyridin-2-amine (8)

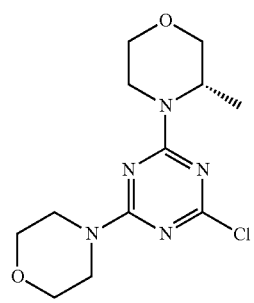

i13

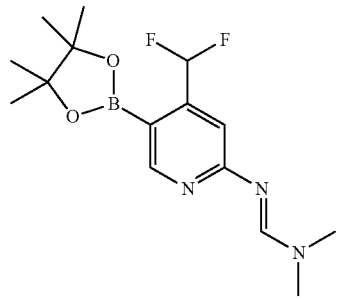

i68

-continued

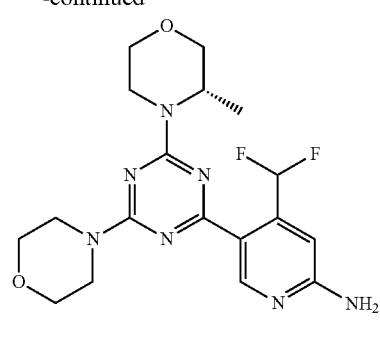

8

According to general procedure 1, compound 8 is obtained from starting materials i13 and i68 in 47% yield as a colorless solid. $^1$H NMR (400 MHz, CDCl$_3$): δ 9.03 (s, 1H), 7.70 (t, $^2J_{H,F}$=55 Hz, 1H), 6.84 (s, 1H), 4.78 (br s, 2H), 4.75 (m, 1H), 4.42-4.38 (m, 1H), 4.00-3.96 (m, 1H), 3.84-3.366 (m, 10H), 3.55-3.50 (m, 1H), 3.30-3.25 (m, 1H), 1.33 (d, $^3J_{H,H}$=6.8 Hz, 3H); $^{19}$F NMR (376 MHz, CDCl$_3$): δ–116.1-(–115.9) (m, 2F); MS (MALDI): m/z=408.9 ([M+H]$^+$).

Example 9: (S)-4-(difluoromethyl)-5-(4-(3-methyl-morpholino)-6-morpholino-1,3,5-triazin-2-yl)pyrimidin-2-amine (9)

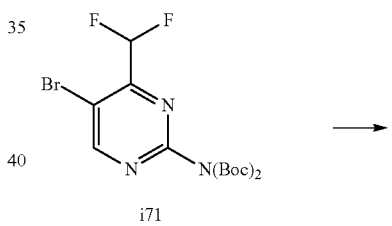

i71

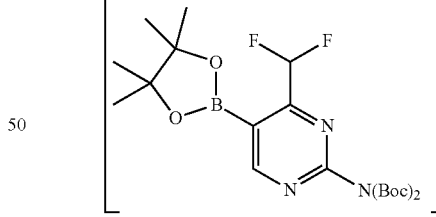

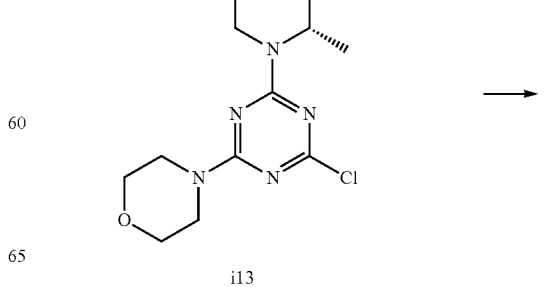

i13

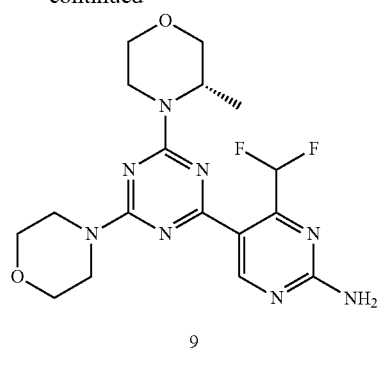

9

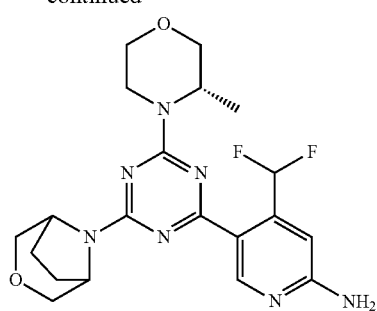

10

According to general procedure 2, compound 9 is obtained from starting materials i71 and i13 in 60% yield as a colorless solid. $^1$H NMR (400 MHz, CDCl$_3$): δ 9.24 (s, 1H), 7.66 (t, $^2J_{H,F}$=54 Hz, 1H), 5.67 (br s, 2H), 4.74 (m, 1H), 4.41-4.38 (m, 1H), 4.00-3.97 (m, 1H), 3.90-3.72 (m, 9H), 3.68-3.36 (m, 1H), 3.56-3.49 (m, 1H), 3.32-3.25 (m, 1H), 1.33 (d, $^3J_{H,H}$=6.9 Hz, 3H); $^{19}$F NMR (376 MHz, CDCl$_3$): δ−121.3-(−121.6) (m, 2F); MS (MALDI): m/z=409.4 ([M+H]$^+$).

According to general procedure 1, compound 10 is obtained from starting materials i18 and i68 in 42% yield as a colorless solid. $^1$H NMR (400 MHz, CDCl$_3$): δ 9.04 (s, 1H), 7.69 (t, $^2J_{H,F}$=55 Hz, 1H), 6.84 (s, 1H), 4.85 (br s, 2H), 4.71-4.65 (m, 3H), 4.42-4.39 (m, 1H), 3.98-3.95 (m, 1H), 3.79-3.76 (m, 3H), 3.70-3.65 (m, 3H), 3.56-3.53 (m, 1H), 3.30-3.27 (m, 1H), 2.10-1.99 (m, 4H), 1.33 (m, 3H); $^{19}$F NMR (376 MHz, CDCl$_3$): δ−115.9-(−116.2) (m, 2F); MS (MALDI): m/z=434.2 ([M+H]$^+$).

Example 10: 5-(4-(3-oxa-8-azabicyclo[3.2.1]octan-8-yl)-6-((S)-3-methylmorpholino)-1,3,5-triazin-2-yl)-4-(difluoromethyl)pyridin-2-amine (10)

Example 11: 5-(4-(3-oxa-8-azabicyclo[3.2.1]octan-8-yl)-6-((S)-3-methylmorpholino)-1,3,5-triazin-2-yl)-4-(difluoromethyl)pyrimidin-2-amine (11)

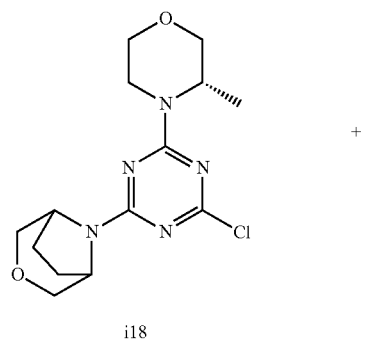

i18

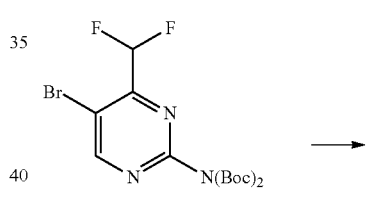

i71

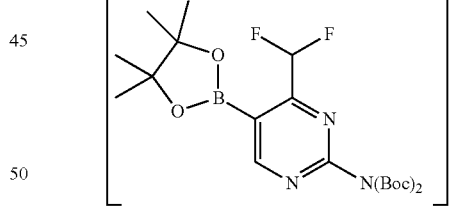

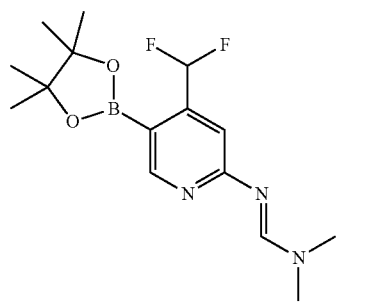

i68

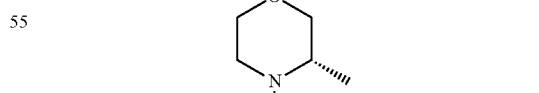

i18

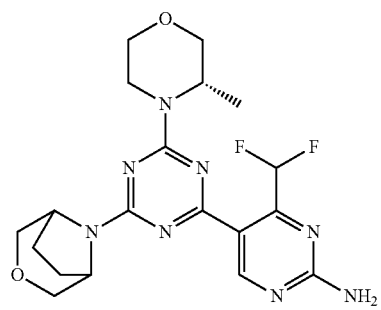

11

According to general procedure 2, compound 11 is obtained from starting materials i71 and i18 in 46% yield as a colorless solid. $^1$H NMR (400 MHz, CDCl$_3$): δ 9.25 (s, 1H), 7.68 (t, $^2J_{H,F}$=55 Hz, 1H), 5.81 (br s, 2H), 4.71-4.65 (m, 3H), 4.42-4.38 (m, 1H), 4.00-3.96 (m, 1H), 3.81-3.60 (m, 6H), 3.55-3.50 (m, 1H), 3.31-3.24 (m, 1H), 2.11-2.00 (m, 4H), 1.37-1.28 (m, 3H); $^{19}$F NMR (376 MHz, CDCl$_3$): δ−121.5-(−121.7) (m, 2F); MS (MALDI): m/z=434.6 ([M+H]$^+$).

Example 12: 4-(difluoromethyl)-5-(4-morpholino-6-(piperazin-1-yl)-1,3,5-triazin-2-yl)pyridin-2-amine (12)

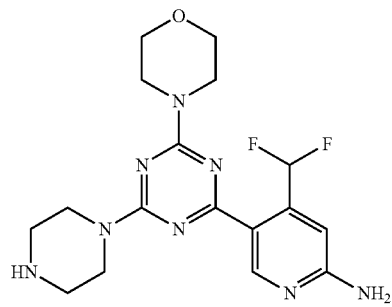

12

According to general procedure 1, compound 12 is obtained from starting materials i68 and i14 in 86% yield as a colorless solid. $^1$H NMR (400 MHz, (CD$_3$)$_2$SO): δ 8.85 (s, 1H), 7.74 (t, $^2J_{H,F}$=55 Hz, 1H), 6.84 (s, 2H), 6.75 (s, 1H), 3.82-3.70 (m, 8H), 3.69-3.60 (m, 4H), 2.88-2.80 (m, 4H): $^{19}$F NMR (376 MHz, (CD$_3$)$_2$SO): δ−115.4 (s, 2F); MS (MALDI): m/z=393.8 ([M+H]$^+$).

Example 13: 4-(difluoromethyl)-5-(4-morpholino-6-(piperazin-1-yl)-1,3,5-triazin-2-yl)pyrimidin-2-amine (13)

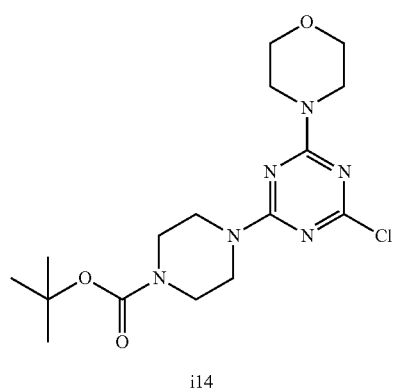

i14

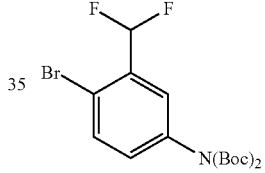

i71

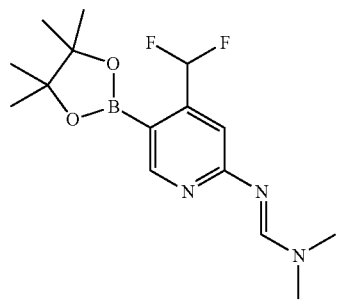

i68

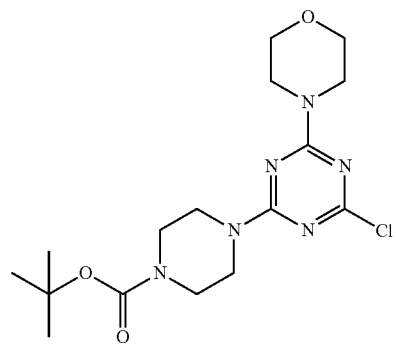

i14

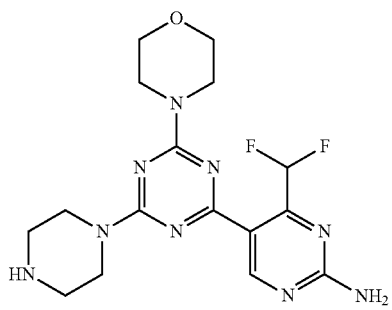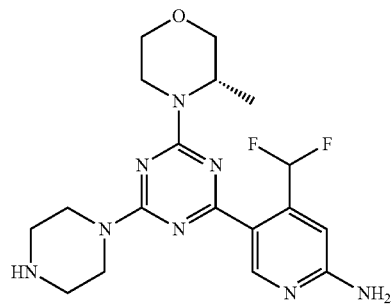

According to general procedure 2, compound 13 is obtained from starting materials i71 and i14 in 55% yield as a colorless solid. $^1$H NMR (400 MHz, CDCl$_3$): δ 9.23 (s, 1H), 7.64 (t, $^2J_{H,F}$=55 Hz, 1H), 5.60 (br s, 2H), 3.83-3.75 (m, 12H), 2.94-2.88 (m, 4H); $^{19}$F NMR (376 MHz, CDCl$_3$): δ−111.4 (s, 2F); MS (MALDI): m/z=395.1 ([M+H]$^+$).

Example 14: (S)-4-(difluoromethyl)-5-(4-(3-methyl-morpholino)-6-(piperazin-1-yl)-1,3,5-triazin-2-yl)pyridin-2-amine (14)

According to general procedure 1, compound 14 is obtained from starting materials i21 and i68 in 47% yield as a colorless solid. $^1$H NMR (400 MHz, CDCl$_3$): δ 9.02 (s, 1H), 7.67 (t, $^2J_{H,F}$=56 Hz, 1H), 6.84 (s, 1H), 4.90 (br s, 2H), 4.74 (s, 1H), 4.40 (d, $J_{H,H}$=16 Hz, 1H), 3.98 (dd, $J_{H,H}$=4.0 Hz, 12 Hz, 1H), 3.91 (m, 4H), 3.78 (d, $J_{H,H}$=12 Hz, 1H), 3.68 (dd, $J_{H,H}$=4.0, 12 Hz, 1H), 3.56 (t, $J_{H,H}$=4.0 Hz, 1H), 3.26 (dt, $J_{H,H}$=4.0, 12 Hz, 1H), 2.99 (t, $J_{H,H}$=4.0 Hz, 4H), 1.32 (d, $J_{H,H}$=8.0 Hz, 3H); $^{19}$F NMR (376 MHz, CDCl$_3$): δ−115.9 (s, 2F); MS (MALDI): m/z=407.2 ([M+H]$^+$).

Example 15: (S)-4-(difluoromethyl)-5-(4-(3-methyl-morpholino)-6-(piperazin-1-yl)-1,3,5-triazin-2-yl)pyrimidin-2-amine (15)

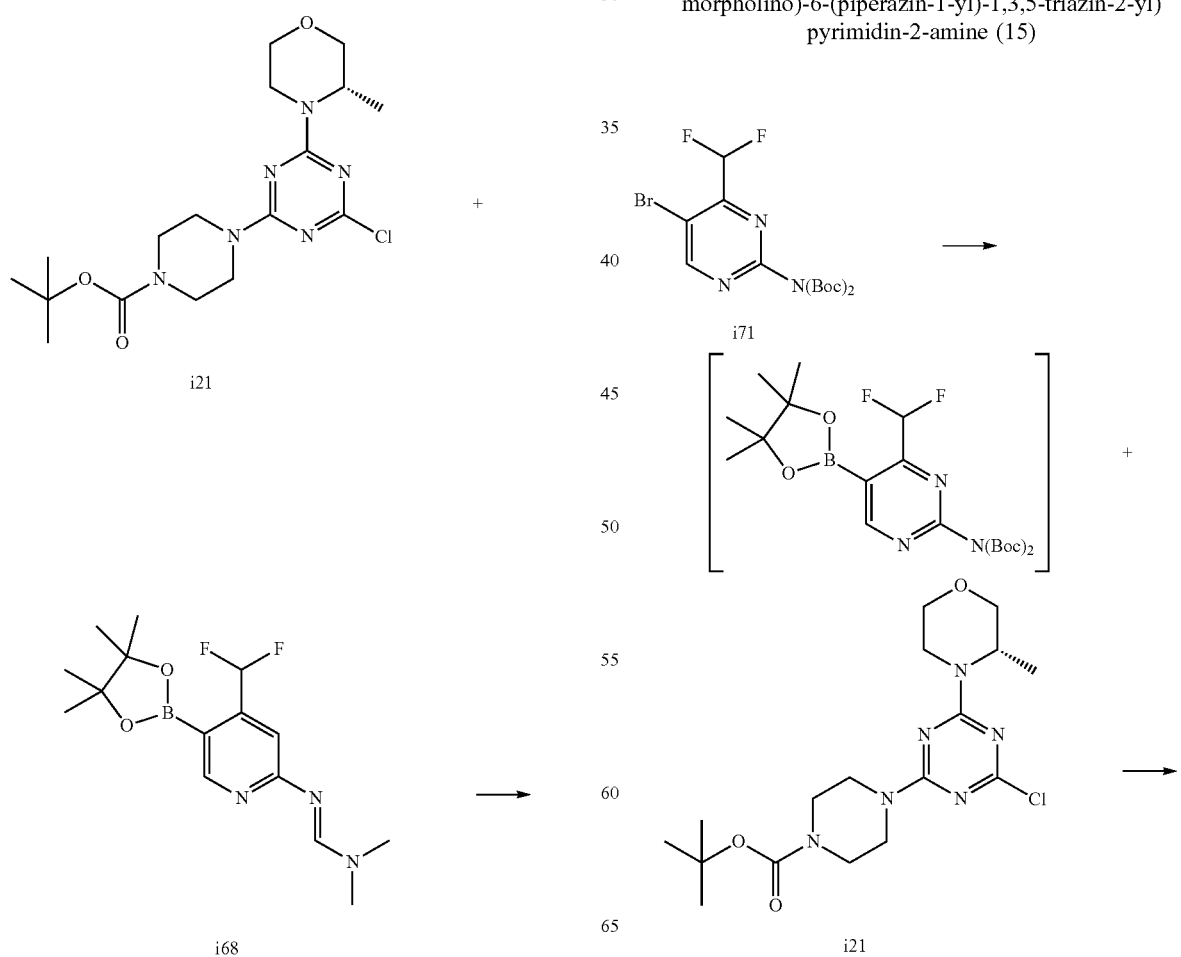

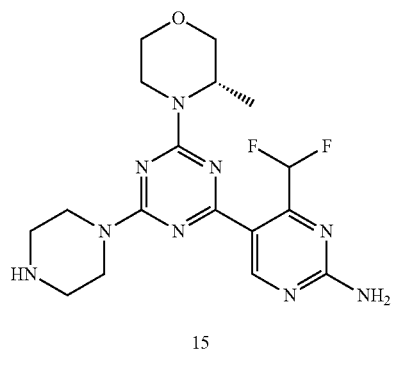

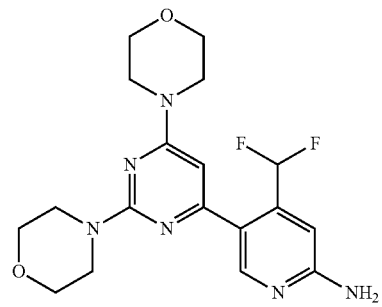

According to general procedure 2, compound 15 is obtained from starting materials i71 and i21 in 30% yield as a colorless solid. $^1$H NMR (400 MHz, CDCl$_3$): δ 9.24 (s, 1H), 7.66 (t, $^2J_{H,F}$=56 Hz, 1H), 5.69 (br s, 2H), 4.74 (s, 1H), 4.40 (d, $J_{H,H}$=16 Hz, 1H), 4.38 (dd, $J_{H,H}$=4.0, 12 Hz, 1H), 3.83 (m, 4H), 3.78 (d, $J_{H,H}$=12 Hz, 1H), 3.68 (dd, $J_{H,H}$=4.0, 12 Hz, 1H), 3.54 (dt, $J_{H,H}$=4.0, 12 Hz, 1H), 3.28 (dt, $J_{H,H}$=4.0, 12 Hz, 1H), 2.92 (t, $J_{H,H}$=8.0 Hz, 4H), 1.33 (t, $J_{H,H}$=8.0 Hz, 3H); $^{19}$F NMR (376 MHz, CDCl$_3$): δ−121.4 (s, 2F); MS (MALDI): m/z=408.7 ([M+H]$^+$).

According to general procedure 1, compound 16 is obtained from starting materials i22 and i68 in 73% yield as a colorless solid. $^1$H NMR (400 MHz, CDCl$_3$): δ 8.31 (s, 1H), 7.30 (t, $^2J_{H,F}$=55 Hz, 1H), 6.85 (s, 1H), 6.04 (s, 1H), 4.73 (br s, 2H), 3.81-3.72 (m, 12H), 3.65-3.59 (m, 4H); $^{19}$F NMR (376 MHz, CDCl$_3$): δ−115.1 (s, 2F); MS (MALDI): m/z=394.3 ([M+H]$^+$).

Example 16: 4-(difluoromethyl)-5-(2,6-dimorpholinopyrimidin-4-yl)pyridin-2-amine (16)

Example 17: 4'-(difluoromethyl)-2,6-dimorpholino-[4,5'-bipyrimidin]-2'-amine (17)

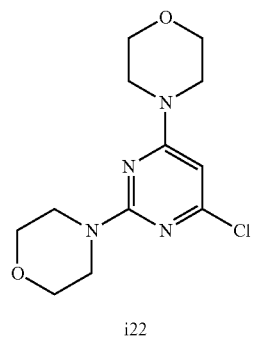

i22

+

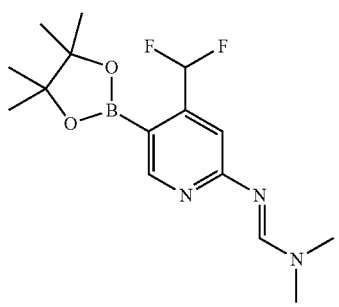

i68

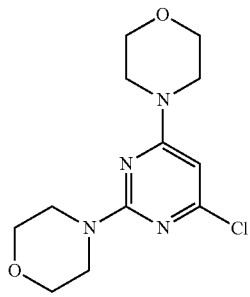

i22

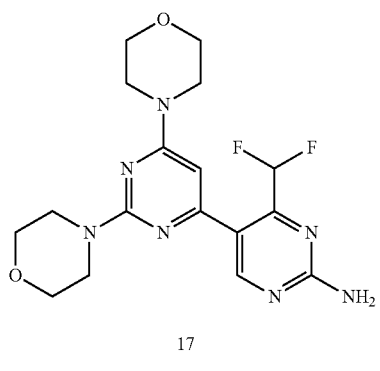

17

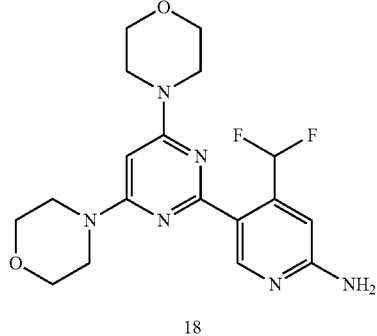

18

According to general procedure 2, compound 17 is obtained from starting materials i71 and i22 in 7% yield as a colorless solid. $^1$H NMR (400 MHz, CDCl$_3$): δ 8.60 (s, 1H), 7.11 (t, $^2J_{H,F}$=55 Hz, 1H), 6.02 (s, 1H), 5.46 (br s, 2H), 3.80-3.74 (m, 12H), 3.64-3.60 (m, 4H); $^{19}$F NMR (376 MHz, CDCl$_3$): δ−119.5 (s, 2F); MS (MALDI): m/z=394.3 ([M+H]$^+$).

Example 18: 4-(difluoromethyl)-5-(4,6-dimorpholinopyrimidin-2-yl)pyridin-2-amine (18)

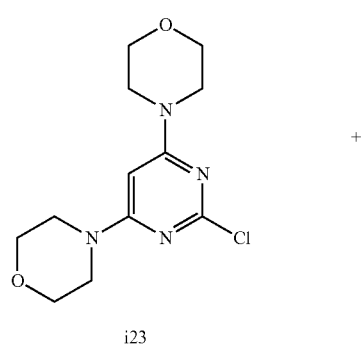

i23

According to general procedure 1, compound 18 is obtained from starting materials i23 and i68 in 89% yield as a colorless solid. $^1$H NMR (400 MHz, CDCl$_3$): δ 8.94 (s, 1H), 7.61 (t, $^2J_{H,F}$=55 Hz, 1H), 6.83 (s, 1H), 5.50 (s, 1H), 4.74 (br s, 2H), 3.82-3.78 (m, 8H), 3.61-3.57 (m, 8H); $^{19}$F NMR (376 MHz, CDCl$_3$): δ−115.4 (s, 2F); MS (MALDI): m/z=393.3 ([M+H]$^+$).

Example 19: 4'-(difluoromethyl)-4,6-dimorpholino-[2,5'-bipyrimidin]-2'-amine (19)

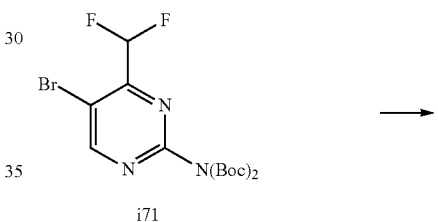

i71

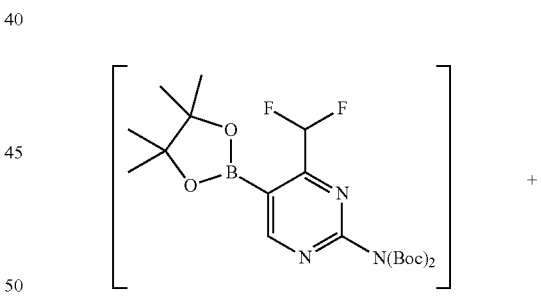

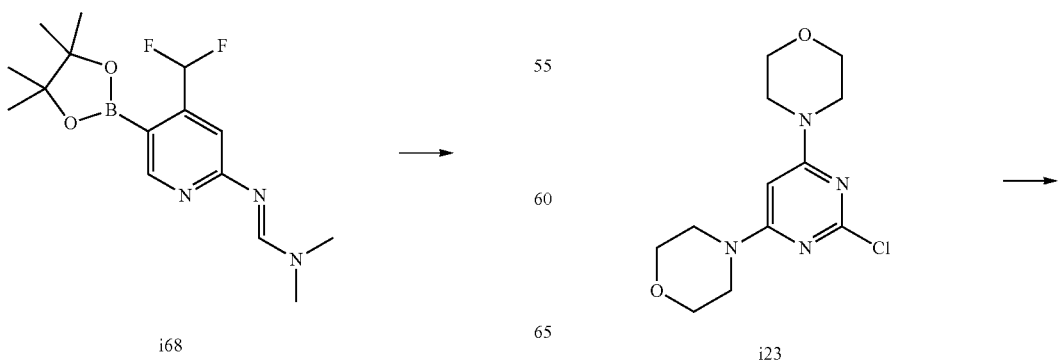

i68 i23

-continued

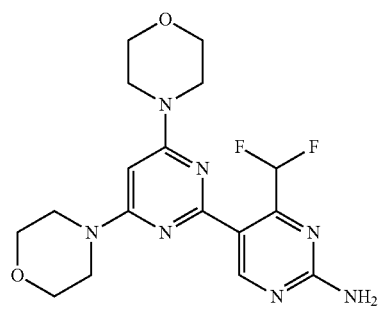

19

According to general procedure 2, compound 19 is obtained from starting materials i71 and i23 in 7% yield as a colorless solid. $^1$H NMR (400 MHz, CDCl$_3$): δ 9.16 (s, 1H), 7.58 (t, $^2J_{H,F}$=55 Hz, 1H), 5.75 (br s, 2H), 5.50 (s, 1H), 3.82-3.79 (m, 8H), 3.61-3.58 (m, 8H); $^{19}$F NMR (376 MHz, CDCl$_3$): δ−121.1 (s, 2F); MS (MALDI): m/z=395.3 ([M+H]$^+$).

Example 20: 4-(difluoromethyl)-5-(4-morpholino-6-thiomorpholino-1,3,5-triazin-2-yl)-pyridin-2-amine (20)

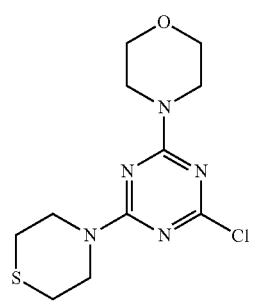

i15

+

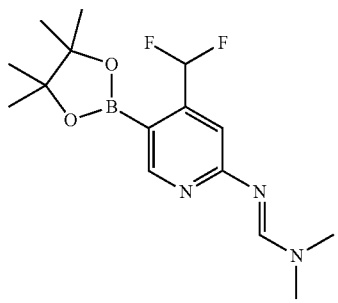

i68

-continued

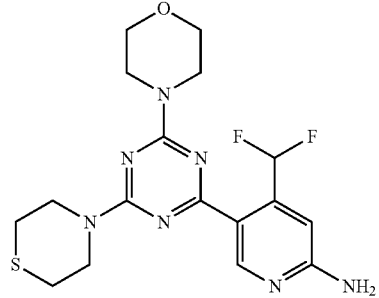

20

According to general procedure 1, compound 20 is obtained from starting materials i15 and i68 in 77% yield as a colorless solid. $^1$H NMR (400 MHz, CDCl$_3$): δ 9.02 (s, 1H), 7.65 (t, J=55 Hz, 1H), 6.84 (s, 1H), 4.83 (br s, 2H), 4.23-4.07 (m, 4H), 3.90-3.79 (m, 4H), 3.79-3.71 (m, 4H), 2.71-2.62 (m, 4H); $^{19}$F NMR (376 MHz, CDCl$_3$): δ−116.0 (s, 2F); MS (MALDI): m/z=410.3 ([M+H]$^+$).

Example 21: 4-(difluoromethyl)-5-(4-morpholino-6-thiomorpholino-1,3,5-triazin-2-yl)-pyrimidin-2-amine (21)

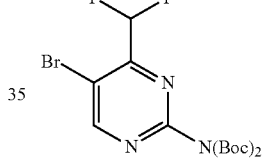

i71

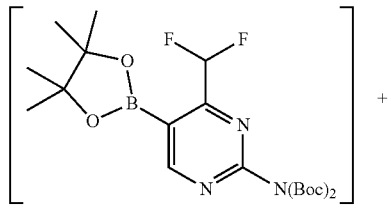

+

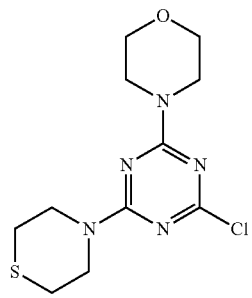

i15

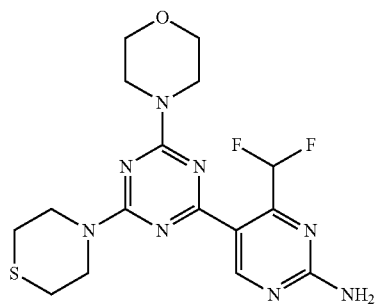

21

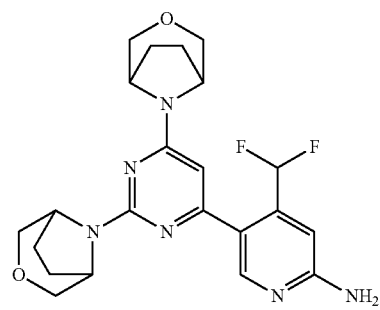

22

According to general procedure 2, compound 21 is obtained from starting materials i71 and i15 in 70% yield as a colorless solid. $^1$H NMR (400 MHz, CDCl$_3$): δ 9.21 (s, 1H), 7.60 (t, $^2$J$_{H,F}$=54 Hz, 1H), 5.90 (br s, 2H), 4.22-4.06 (m, 4H), 3.91-3.78 (m, 4H), 3.78-3.71 (m, 4H), 2.71-2.62 (m, 4H); $^{19}$F NMR (376 MHz, CDCl$_3$): δ−120.5-(−121.5) (m, 2F); MS (MALDI): m/z=411.2 ([M+H]$^+$).

Example 22: 5-(6-(3-oxa-8-azabicyclo[3.2.1]octan-8-yl)-2-(3-oxa-8-azabicyclo[3.2.1]octan-8-yl)pyrimidin-4-yl)-4-(difluoromethyl)pyridin-2-amine (22)

According to general procedure 1, compound 22 is obtained from starting materials i24 and i68 in 61% yield as a colorless solid. $^1$H NMR (400 MHz, (CD$_3$)$_2$SO): δ 8.34 (s, 1H), 7.55 (t, $^2$J$_{H,F}$=55 Hz, 1H), 6.76 (s, 1H), 6.60 (br s, 2H), 6.36 (s, 1H), 4.64-4.47 (m, 4H), 3.67-3.49 (m, 4H), 3.56-3.49 (m, 4H), 1.98-1.79 (m, 8H); $^{19}$F NMR (376 MHz, (CD$_3$)$_2$SO): δ−114.9-(−115.2) (m, 2F); MS (MALDI): m/z=445.3 ([M+H]$^+$).

Example 23: 5-(2-(3-oxa-8-azabicyclo[3.2.1]octan-8-yl)-6-morpholinopyrimidin-4-yl)-4-(difluoromethyl)pyridin-2-amine (23)

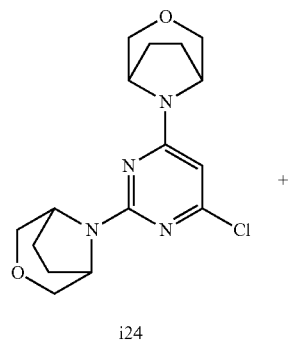

i24

+

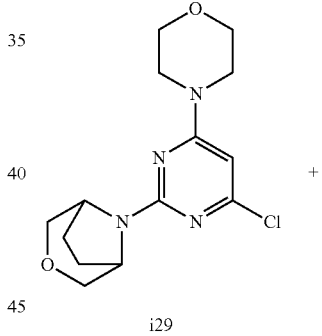

i29

+

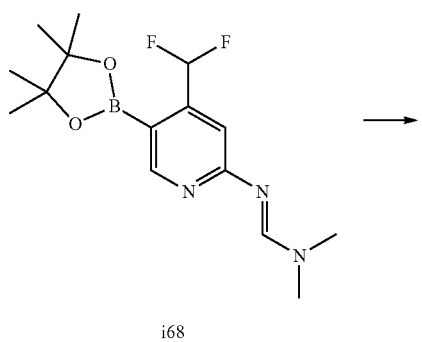

i68

→

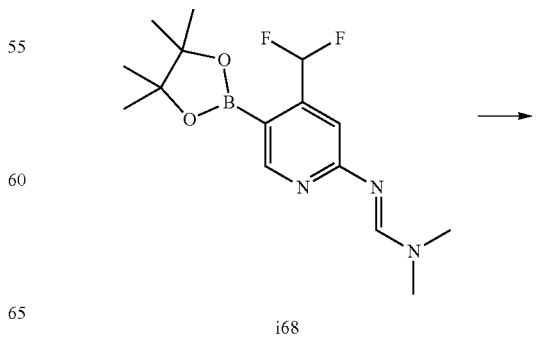

i68

→

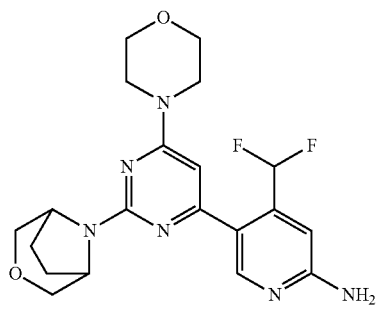

23

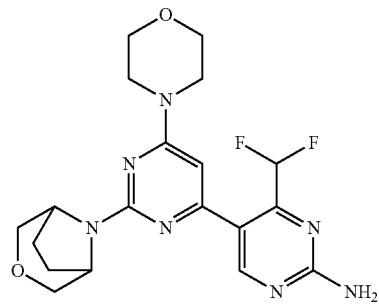

24

According to general procedure 1, compound 23 is obtained from starting materials i29 and i68 in 54% yield as a colorless solid. $^1$H NMR (400 MHz, CDCl$_3$): δ 8.30 (s, 1H), 7.30 (t, $^2J_{H,F}$=55 Hz, 1H), 6.84 (s, 1H), 6.04 (s, 1H), 4.85 (br s, 2H), 4.62 (br s, 2H), 3.82-3.74 (m, 6H), 3.65-3.56 (m, 6H), 2.09-2.00 (m, 2H), 2.00-1.91 (m, 2H); $^{19}$F NMR (376 MHz, CDCl$_3$): δ–115.2-(–116.2) (m, 2F); MS (MALDI): m/z=419.0 ([M+H]$^+$).

Example 24: 2-(3-oxa-8-azabicyclo[3.2.1]octan-8-yl)-4'-(difluoromethyl)-6-morpholino-[4,5'-bipyrimidin]-2'-amine (24)

According to general procedure 2, compound 24 is obtained from starting materials i29 and i71 in 72% yield as a colorless solid. $^1$H NMR (400 MHz, (CD$_3$)$_2$SO): δ 8.71 (s, 1H), 7.35 (s, 2H), 7.32 (t, $^2J_{H,F}$=54 Hz, 1H), 6.45 (s, 1H), 4.54 (br s, 2H), 3.71-3.50 (m, 12H), 1.95-1.78 (m, 4H); $^{19}$F NMR (376 MHz, (CD$_3$)$_2$SO): δ–119.2 (s, 2F); MS (MALDI): m/z=420.6 ([M+H]$^+$).

Example 25: 5-(2,6-bis((S)-3-methylmorpholino)pyrimidin-4-yl)-4-(difluoromethyl)pyridin-2-amine (25)

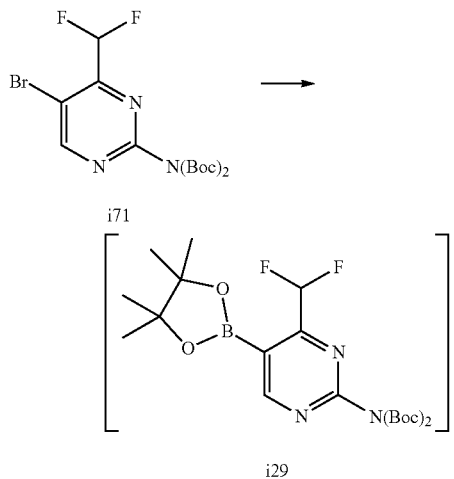

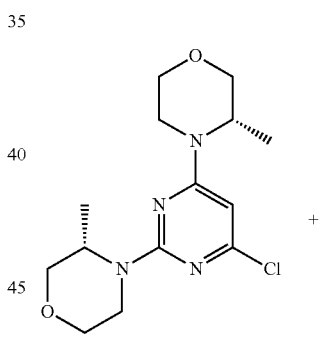

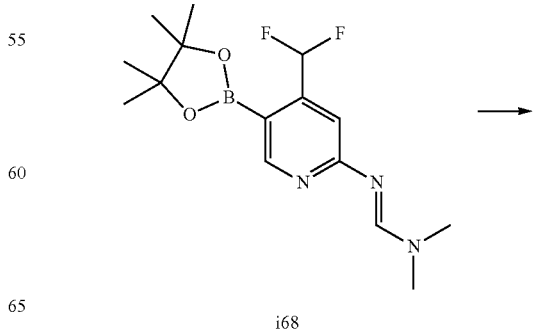

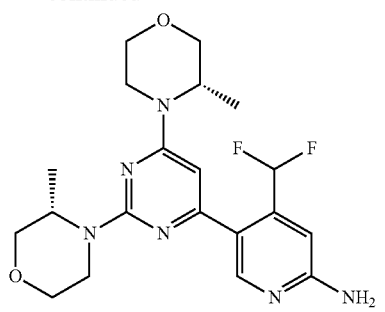

25

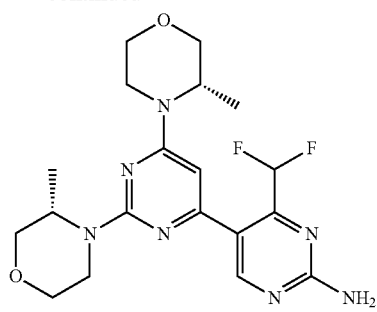

26

According to general procedure 1, compound 25 is obtained from starting materials i25 and i68 in 57% yield as a colorless solid. $^1$H NMR (400 MHz, (CD$_3$)$_2$SO): δ 8.31 (s, 1H), 7.52 (t, $^2J_{H,F}$=55 Hz, 1H), 6.76 (s, 1H), 6.59 (br s, 2H), 6.30 (s, 1H), 4.60-4.50 (m, 1H), 4.44-4.33 (m, 1H), 4.24-4.15 (m, 1H), 4.12-4.04 (m, 1H), 3.94-3.83 (m, 2H), 3.74-3.64 (m, 2H), 3.59-3.51 (m, 2H), 3.45-3.35 (m, 2H), 3.14-3.02 (m, 2H), 1.18 (t, $^3J_{H,H}$=7.2 Hz, 6H); $^{19}$F NMR (376 MHz, (CD$_3$)$_2$SO): δ−113.7-(−115.9) (m, 2F); MS (MALDI): m/z=421.1 ([M+H]$^+$).

Example 26: 4'-(difluoromethyl)-2,6-bis((S)-3-methylmorpholino)-[4,5'-bipyrimidin]-2'-amine (26)

According to general procedure 2, compound 26 is obtained from starting materials i25 and i71 in 56% yield as a colorless solid. $^1$H NMR (400 MHz, CDCl$_3$): δ 8.60 (s, 1H), 7.14 (t, $^2J_{H,F}$=54 Hz, 1H), 5.98 (s, 1H), 5.48 (br s, 2H), 4.71-4.62 (m, 1H), 4.34-4.23 (m, 2H), 4.08-3.92 (m, 3H), 3.83-3.65 (m, 4H), 3.61-3.49 (m, 2H), 3.25 (dt, $^2J_{H,H}$=13 Hz, $^3J_{H,H}$=3.6 Hz, 2H), 1.33-1.27 (m, 6H); $^{19}$F NMR (376 MHz, CDCl$_3$): δ−119.5 (s, 1F), 119.7 (m, 1F); MS (MALDI): m/z=423.0 ([M+H]$^+$).

Example 27: (S)-4-(difluoromethyl)-5-(6-(3-methylmorpholino)-2-morpholinopyrimidin-4-yl)pyridin-2-amine (27)

i71

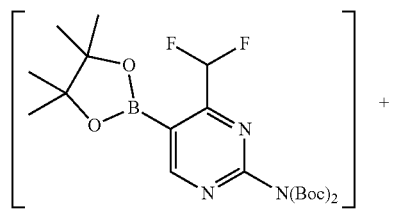

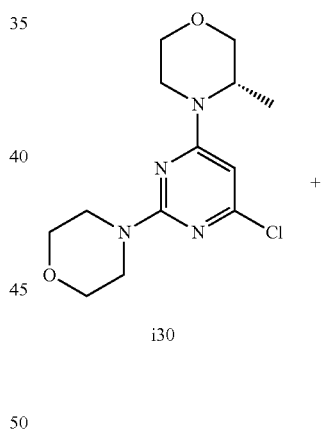

i30

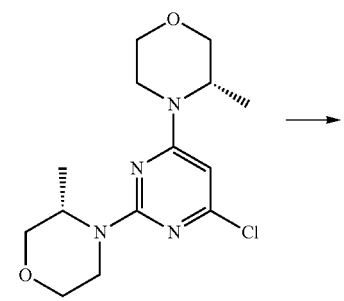

i25

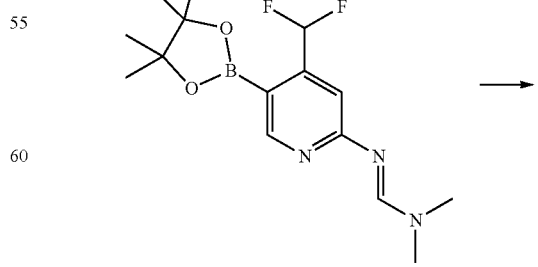

i68

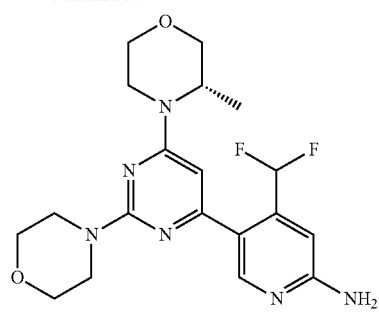

27

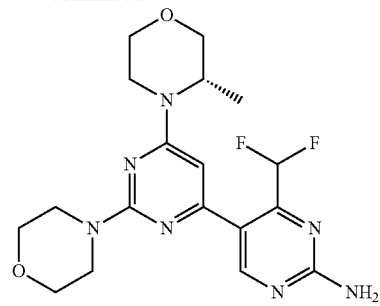

28

According to general procedure 1, compound 27 is obtained from starting materials i30 and i68 in 74% yield as a colorless solid. $^1$H NMR (400 MHz, CDCl$_3$): δ 8.31 (s, 1H), 7.30 (t, $^2J_{H,F}$=55 Hz, 1H), 6.85 (s, 1H), 6.02 (s, 1H), 4.75 (br s, 2H), 4.35-4.25 (m, 1H), 4.06-3.96 (m, 2H), 3.83-3.69 (m, 10H), 3.58 (dt, $^2J_{H,H}$=12 Hz, $^3J_{H,H}$=3.2 Hz, 1H), 3.25 (dt, $^2J_{H,H}$=13 Hz, $^3J_{H,H}$=3.8 Hz, 1H), 1.31 (d, $^3J_{H,H}$=6.8 Hz, 3H); $^{19}$F NMR (376 MHz, CDCl$_3$): δ −114.9- (−115.0) (m, 2F); MS (MALDI): m/z=407.1 ([M+H]$^+$).

Example 28: (S)-4'-(difluoromethyl)-6-(3-methyl-morpholino)-2-morpholino-[4,5'-bipyrimidin]-2'-amine (28)

According to general procedure 2, compound 28 is obtained from starting materials i30 and i71 in 53% yield as a colorless solid. $^1$H NMR (400 MHz, CDCl$_3$): δ 8.60 (s, 1H), 7.13 (t, $^2J_{H,F}$=54 Hz, 1H), 6.01 (s, 1H), 5.47 (br s, 2H), 4.71-4.63 (m, 1H), 4.31 (dd, $^2J_{H,H}$=14 Hz, $^3J_{H,H}$=2.4 Hz, 1H), 3.97 (dd, $^2J_{H,H}$=11 Hz, $^3J_{H,H}$=3.4 Hz, 1H), 3.79 (t, $^3J_{H,H}$=4.6 Hz, 4H), 3.72-3.66 (m, 2H), 3.65-3.58 (m, 3H), 3.58-3.50 (m, 2H), 3.30-3.21 (m, 1H), 1.30 (d, $^3J_{H,H}$=6.8 Hz, 3H); $^{19}$F NMR (376 MHz, CDCl$_3$): δ −119.7 (br s, 2F); MS (MALDI): m/z=408.9 ([M+H]$^+$).

Example 29: 5-(4-(8-Oxa-3-azabicyclo[3.2.1]octan-3-yl)-6-(8-oxa-3-azabicyclo[3.2.1]octan-3-yl)-1,3,5-triazin-2-yl)-4-(difluoromethyl)pyridin-2-amine 29

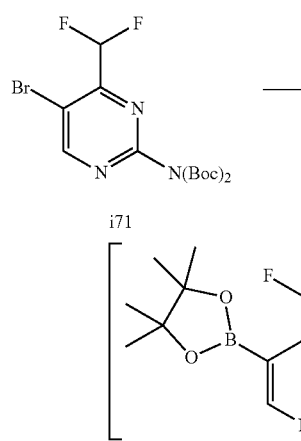

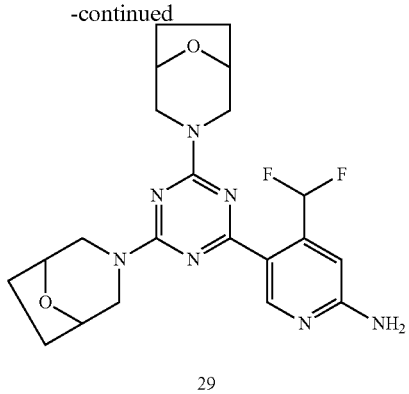

29

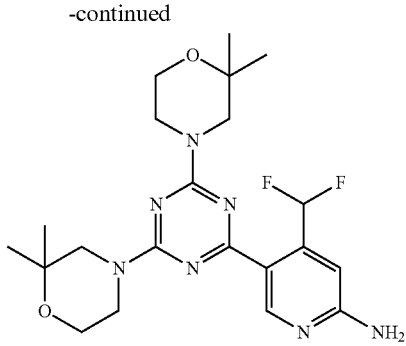

30

According to general procedure 1, compound 29 is obtained from starting materials i68 and i81 in 89% yield as a colorless solid. $^1$H NMR (400 MHz, CDCl$_3$): δ 9.03 (s, 1H), 7.69 (t, $^2J_{H,F}$=55 Hz, 1H), 6.83 (s, 1H), 4.85 (br s, 2H), 4.50-4.24 (m, 8H), 3.28-3.12 (m, 4H), 1.94 (br s, 4H), 1.86-1.71 (m, 4H); $^{19}$F NMR (376 MHz, CDCl$_3$): δ−115.1-(−117.2) (m, 2F); MS (MALDI): m/z=446.3 ([M+H]$^+$).

Example 30: 5-[4,6-bis(2,2-dimethylmorpholin-4-yl)-1,3,5-triazin-2-yl]-4-(difluoromethyl)pyridin-2-amine 30

According to general procedure 1, compound 30 is obtained from starting materials i68 and i80 in 63% yield as a colorless solid. $^1$H NMR (400 MHz, (CD$_3$)$_2$SO): δ 8.86 (s, 1H), 7.71 (t, $^2J_{H,F}$=55 Hz, 1H), 6.84 (br s, 2H), 6.76 (s, 1H), 3.81-3.56 (m, 12H), 1.14 (s, 12H); MS (MALDI): m/z=451.2 ([M+H]$^+$).

Example 31: (S)-4-(difluoromethyl)-5-(2-(3-methyl-morpholino)-6-morpholinopyrimidin-4-yl)pyridin-2-amine (31)

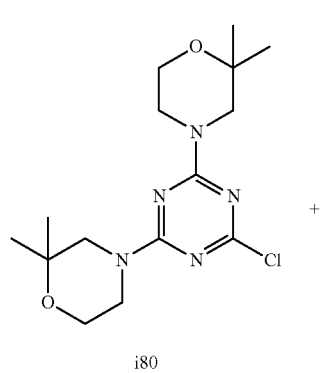

i80

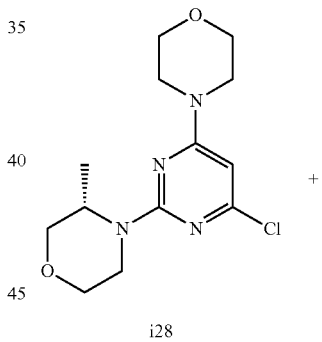

i28

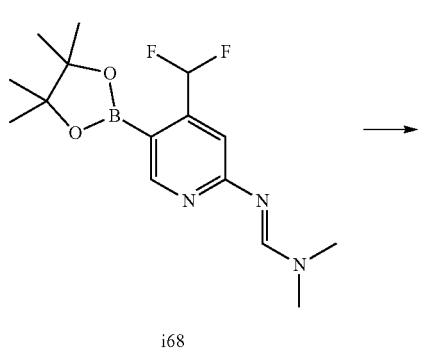

i68

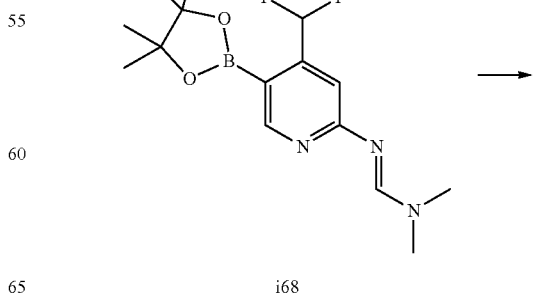

i68

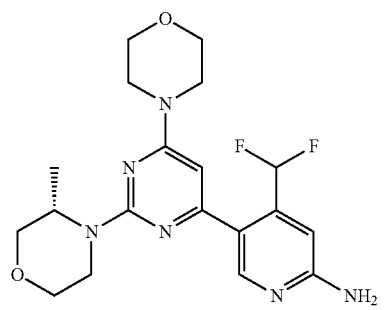

31

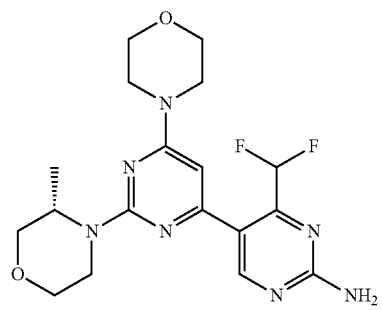

32

According to general procedure 1, compound 31 is obtained from starting materials i28 and i68 in 58% yield as a colorless solid. $^1$H NMR (400 MHz, (CD$_3$)$_2$SO): δ 8.31 (s, 1H), 7.52 (t, $^2J_{H,F}$=55 Hz, 1H), 6.74 (s, 1H), 6.59 (br s, 2H), 6.35 (s, 1H), 4.59-4.51 (m, 1H), 4.22-4.14 (m, 1H), 3.91-3.84 (m, 1H), 3.72-3.50 (m, 10H), 3.44-3.35 (m, 1H), 3.14-3.03 (m, 1H), 1.16 (d, 3J$_{H,H}$=6.7 Hz, 3H); $^{19}$F NMR (376 MHz, (CD$_3$)$_2$SO): δ−113.7-(−115.3) (m, 2F); MS (MALDI): m/z=407.1 ([M+H]$^+$).

Example 32: (S)-4'-(difluoromethyl)-2-(3-methyl-morpholino)-6-morpholino-[4,5'-bipyrimidin]-2'-amine (32)

According to general procedure 2, compound 32 is obtained from starting materials i28 and i71 in 63% yield as a colorless solid. $^1$H NMR (400 MHz, CDCl$_3$): δ 8.60 (s, 1H), 7.13 (t, $^2J_{H,F}$=54 Hz, 1H), 5.99 (s, 1H), 5.46 (br s, 2H), 4.34-4.25 (m, 1H), 4.06-3.97 (m, 2H), 3.82-3.68 (m, 10H), 3.58 (dt, $^2J_{H,H}$=12 Hz, $^3J_{H,H}$=3.2 Hz, 1H), 3.26 (dt, $^2J_{H,H}$=13 Hz, $^3J_{H,H}$=3.7 Hz, 1H), 1.31 (d, $^3J_{H,H}$=6.8 Hz, 3H); $^{19}$F NMR (376 MHz, (CD$_3$)$_2$SO): δ−119.5 (s, 2F); MS (MALDI): m/z=408.7 ([M+H]$^+$).

Example 33: 4-(difluoromethyl)-5-[4-[(2S,6R)-2,6-dimethylmorpholin-4-yl]-6-[(3R)-3-methylmorpholin-4-yl]-1,3,5-triazin-2-yl]pyridin-2-amine 33

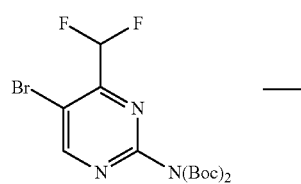

i71

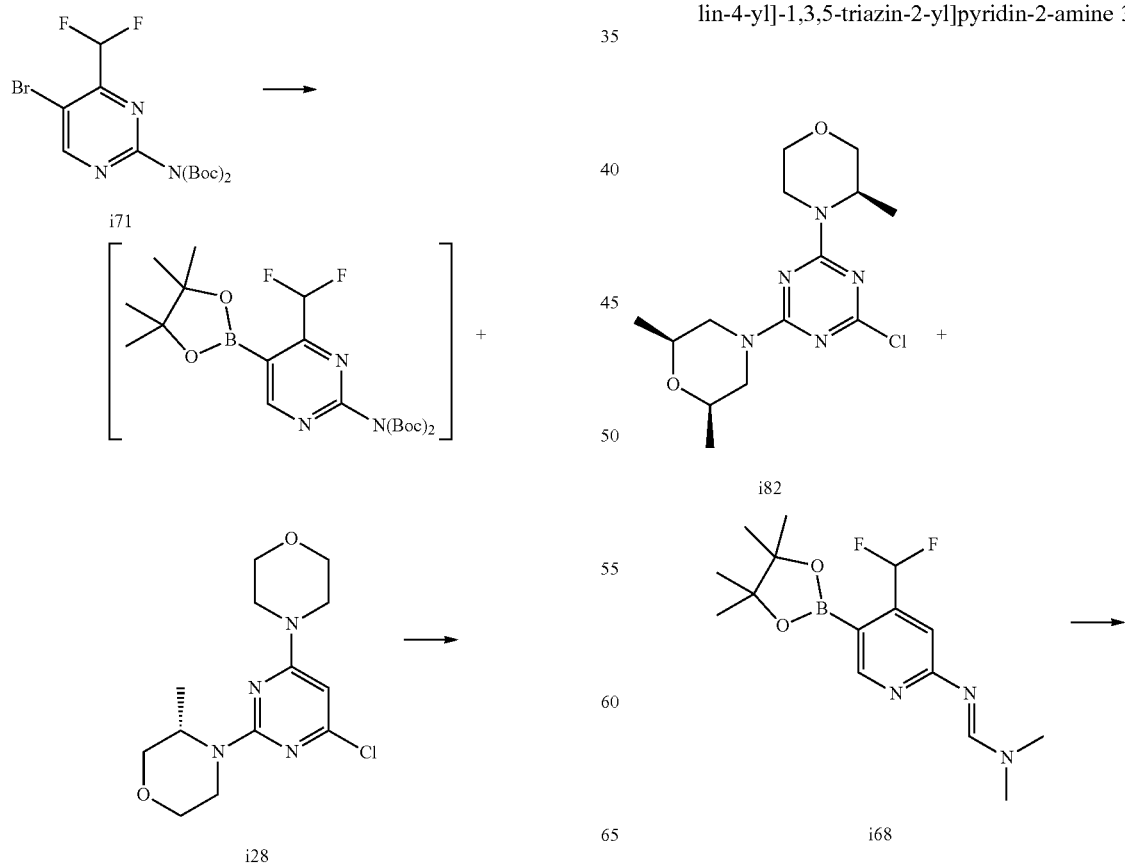

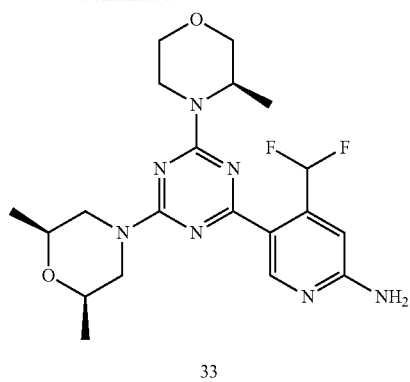

33

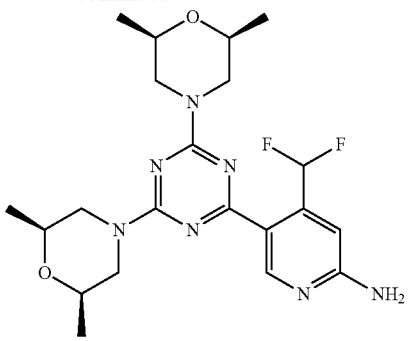

34

According to general procedure 1, compound 33 is obtained from starting materials i68 and i82 in 71% yield as a colorless solid. $^1$H NMR (400 MHz, (CD$_3$)$_2$SO): δ 8.87 (s, 1H), 7.74 (t, $^2J_{H,F}$=55 Hz, 1H), 6.83 (br s, 2H), 6.76 (s, 1H), 4.71-4.62 (m, 1H), 4.45-4.34 (m, 2H), 4.31-4.09 (m, 1H), 3.90 (m, 1H), 3.71 (m, 1H), 3.55 (m, 3H), 3.38 (m, 1H), 3.13 (m, 1H), 2.55 (m, 2H), 1.20 (d, $^3J_{H,H}$=6.9 Hz, 3H), 1.19 (d, $^3J_{H,H}$=6.9 Hz, 6H); MS (MALDI): m/z=436.1 ([M+H]$^+$).

Example 34: 5-[4,6-bis[(2R,6S)-2,6-dimethylmorpholin-4-yl]-1,3,5-triazin-2-yl]-4-(difluoromethyl)pyridin-2-amine 34

According to general procedure 1, compound 34 is obtained from starting materials i68 and i79 in 75% yield as a colorless solid. $^1$H NMR (400 MHz, (CD$_3$)$_2$SO): δ 8.86 (s, 1H), 7.71 (t, $^2J_{H,F}$=55 Hz, 1H), 6.83 (br s, 2H), 6.76 (s, 1H), 4.64-4.46 (m, 4H), 3.60-3.48 (m, 4H), 2.63 (m, 4H), 1.14 (m, 12H); MS (MALDI): m/z=450.0 ([M+H]$^+$).

Example 35: 4-[4-[6-amino-4-(difluoromethyl)-3-pyridyl]-6-morpholino-1,3,5-triazin-2-yl]morpholin-3-one (35)

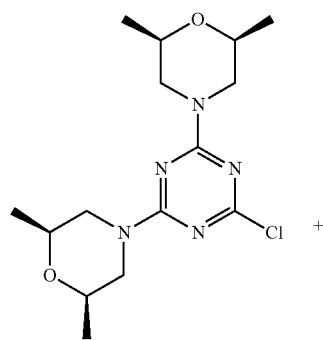

i79

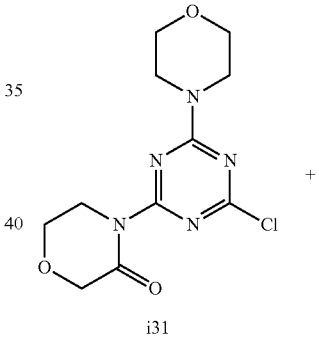

i31

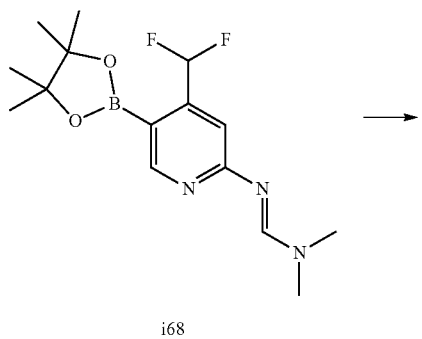

i68

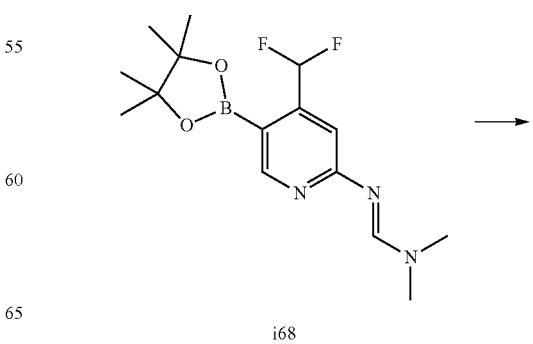

i68

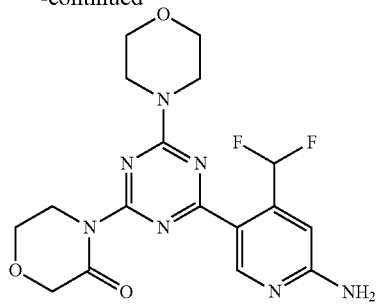

35

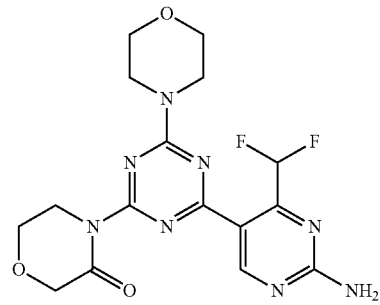

36

According to general procedure 1, compound 35 is obtained from starting materials i31 and i68 in 10% yield as a colorless solid. $^1$H NMR (400 MHz, CDCl$_3$): δ 9.08 (s, 1H), 7.96 (t, $^2J_{H,F}$=56 Hz, 1H), 6.86 (s, 1H), 4.98 (br s, 2H), 4.35 (s, 2H), 4.07-4.00 (m, 4H), 3.95 (br s, 2H), 3.90 (br s, 2H), 3.78 (br s, 4H); $^{19}$F NMR (376 MHz, CDCl$_3$): δ −117.4 (s, 2F).

According to general procedure 2, compound 36 is obtained from starting materials i31 and i71 in 6% yield as a colorless solid. $^1$H NMR (400 MHz, (CD$_3$)$_2$SO): δ 9.22 (s, 1H), 8.10 (t, $^2J_{H,F}$=56 Hz, 1H), 7.97 (br s, 2H), 4.28 (s, 2H), 3.98 (s, 4H), 3.90 (br s, 2H), 3.81 (br s, 2H), 3.70 (br s, 4H); $^{19}$F NMR (376 MHz, (CD$_3$)$_2$SO): δ −121.1 (s, 2F); MS (MALDI): m/z=408.7 ([M+H]$^+$).

Example 36: 4-[4-[2-amino-4-(difluoromethyl)pyrimidin-5-yl]-6-morpholino-1,3,5-triazin-2-yl]morpholin-3-one (36)

Example 37: 5-[4,6-bis(3,7-dioxa-9-azabicyclo[3.3.1]nonan-9-yl)-1,3,5-triazin-2-yl]-4-(difluoromethyl)pyridin-2-amine (37)

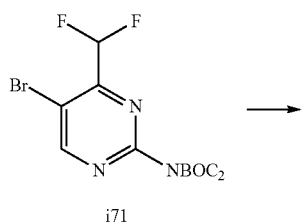

i71

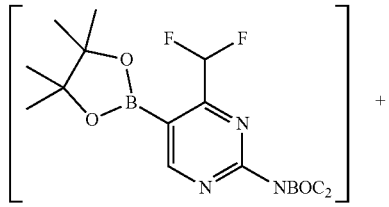

+

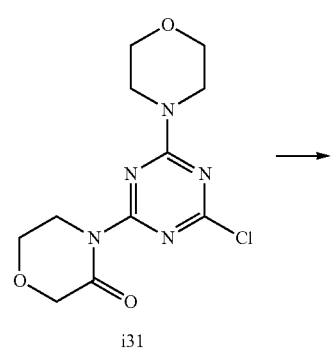

i31

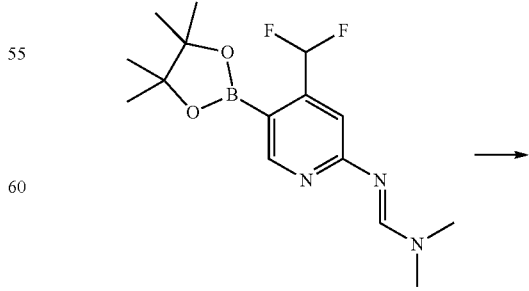

i68

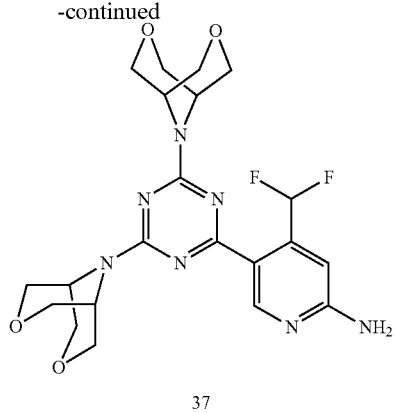

37

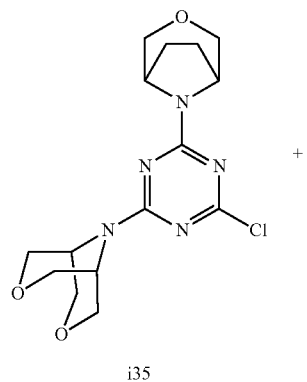

38

According to general procedure 1, compound 37 is obtained from starting materials i7 and i68 in 39% yield as a colorless solid. $^1$H NMR (400 MHz, (CD$_3$)$_2$SO): δ 8.85 (s, 1H), 7.68 (t, $^3J_{H,F}$=55 Hz, 1H), 6.87 (br s, 2H), 6.74 (s, 1H), 4.51 (br s, 2H), 4.45 (br s, 2H), 4.07-3.93 (m, 8H), 3.79-3.67 (m, 8H); $^{19}$F NMR (376 MHz, (CD$_3$)$_2$SO): δ−115.8 (s, 2F); MS (MALDI): m/z=478.1 ([M+H]$^+$).

Example 38: 4-(difluoromethyl)-5-[4-(3,7-dioxa-9-azabicyclo[3.3.1]nonan-9-yl)-6-(3-oxa-8-azabicyclo[3.2.1]octan-8-yl)-1,3,5-triazin-2-yl]pyridin-2-amine (38)

According to general procedure 1, compound 38 is obtained from starting materials i35 and i68 in 67% yield as a colorless solid. $^1$H NMR (400 MHz, (CD$_3$)$_2$SO): δ 8.87 (s, 1H), 7.73 (t, $^3J_{H,F}$=55 Hz, 1H), 6.87 (br s, 2H), 6.75 (s, 1H), 4.70-4.54 (m, 2H), 4.53-4.43 (m, 2H), 4.05-3.97 (m, 4H), 3.79-3.67 (m, 4H), 3.63-3.55 (m, 4H) 2.00-1.83 (m, 4H); $^{19}$F NMR (376 MHz, (CD$_3$)$_2$SO): δ−115.8 (s, 1F), −115.9 (s, 1F); MS (MALDI): m/z=462.1 ([M+H]$^+$).

Example 39: 5-[4,6-bis(3,3-dimethylmorpholin-4-yl)-1,3,5-triazin-2-yl]-4-(difluoromethyl)pyridin-2-amine (39)

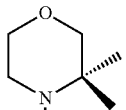

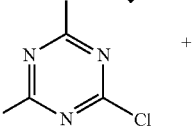

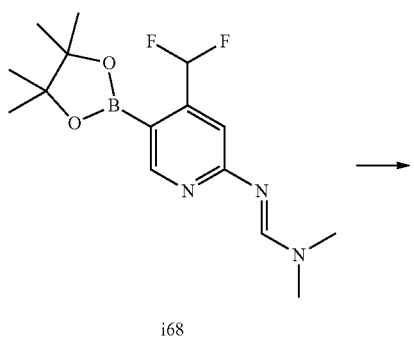

i68

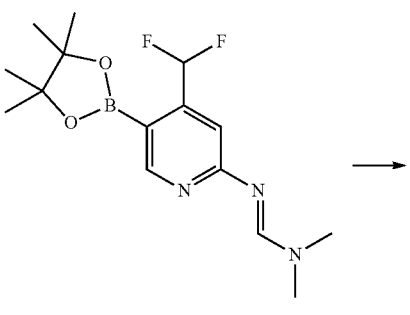

i68

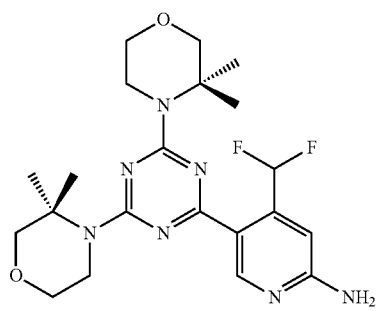

39

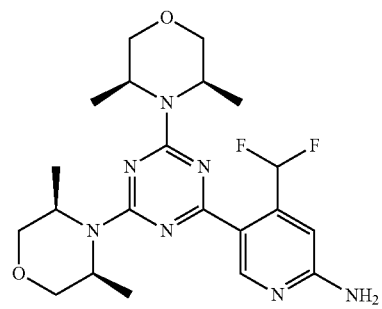

40

According to general procedure 1, compound 39 is obtained from starting materials i4 and i68 in 28% yield as a colorless solid. $^1$H NMR (400 MHz, (CD$_3$)$_2$SO): δ 8.78 (s, 1H), 7.70 (t, $^2J_{H,F}$=55 Hz, 1H), 6.82 (br s, 2H), 6.77 (s, 1H), 3.87-3.75 (m, 8H), 3.45 (br s, 4H), 1.49 (s, 12H); $^{19}$F NMR (376 MHz, (CD$_3$)$_2$SO): δ−114.9-(−115.1) (m, 2F); MS (MALDI): m/z=450.1 ([M+H]$^+$).

Example 40: 5-[4,6-bis[(3R,5S)-3,5-dimethylmorpholin-4-yl]-1,3,5-triazin-2-yl]-4-(difluoromethyl)pyridin-2-amine (40)

According to general procedure 1, compound 40 is obtained from starting materials i6 and i68 in 42% yield as a colorless solid. $^1$H NMR (400 MHz, (CD$_3$)$_2$SO): δ 8.90 (s, 1H), 7.82 (t, $^2J_{H,F}$=55 Hz, 1H), 6.84 (br s, 2H), 6.77 (s, 1H), 4.59-4.43 (m, 4H), 3.82-3.73 (m, 4H), 3.60-3.51 (m, 4H), 1.29 (d, $^2J_{H,H}$=6.9 Hz, 12H); $^{19}$F NMR (376 MHz, (CD$_3$)$_2$SO): δ−114.9-(−115.0) (m, 2F); MS (MALDI): m/z=450.2 ([M+H]$^+$).

Example 41: 5-[4,6-bis[(3R)-3-methylmorpholin-4-yl]-1,3,5-triazin-2-yl]-4-(difluoromethyl)pyridin-2-amine (41)

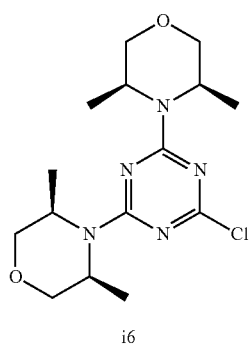

i6

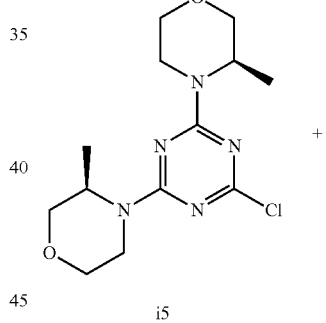

i5

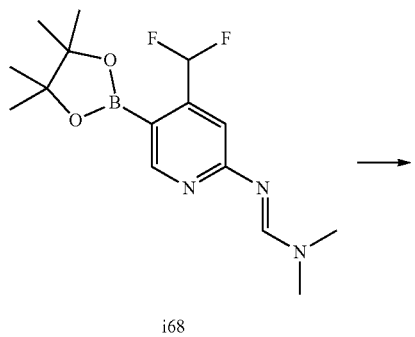

i68

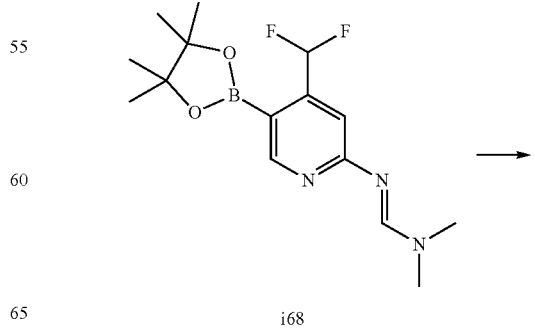

i68

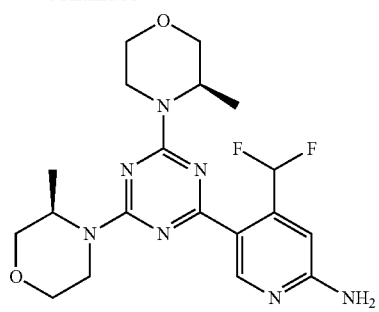

41

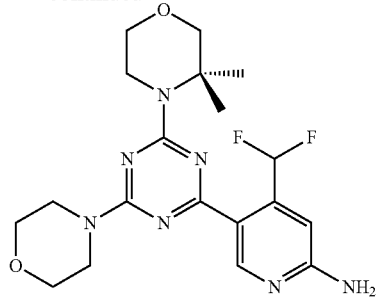

42

According to general procedure 1, compound 41 is obtained from starting materials i5 and i68 in 98% yield as a colorless solid. $^1$H NMR (400 MHz, CDCl$_3$): δ 9.04 (s, 1H), 7.70 (t, $^2J_{H,F}$=52.0 Hz, 1H), 6.84 (s, 1H), 4.88 (br s, 2H), 4.77-4.72 (m, 2H), 4.41 (d, $^2J_{H,H}$=12.0 Hz, 2H), 3.98 (dd, $^2J_{H,H}$=12.0 Hz, $^3J_{H,H}$=4.0 Hz, 2H), 3.78 (d, $^2J_{H,H}$=12.0 Hz, 2H), 3.68 (dd, $^2J_{H,H}$=12.0 Hz, $^3J_{H,H}$=4.0 Hz, 2H), 3.53 (dt, $^2J_{H,H}$=12.0 Hz, $^3J_{H,H}$=4.0 Hz, 2H), 3.28 (dt, $^2J_{H,H}$=12.0 Hz, $^3J_{H,H}$=4.0 Hz, 2H), 1.33 (d, $^2J_{H,H}$=8.0 Hz, 6H); $^{19}$F NMR (376 MHz, CDCl$_3$): δ−115.9 (s, 1F), −116.0 (s, 1F); MS (MALDI): m/z=421.7 ([M+H]$^+$).

Example 42: 4-(difluoromethyl)-5-[4-(3,3-dimethyl-morpholin-4-yl)-6-morpholino-1,3,5-triazin-2-yl]pyridin-2-amine (42)

According to general procedure 1, compound 42 is obtained from starting materials i16 and i68 in 35% yield as a colorless solid. $^1$H NMR (400 MHz, (CD$_3$)$_2$SO): δ 8.83 (s, 1H), 7.73 (t, $^2J_{H,F}$=55 Hz, 1H), 6.84 (br s, 2H), 6.76 (s, 1H), 3.85-3.76 (m, 4H), 3.76-3.63 (m, 8H), 3.45 (br s, 2H), 1.49 (s, 6H); $^{19}$F NMR (376 MHz, (CD$_3$)$_2$SO): δ−115.0/−116.3 (s, 2F); MS (MALDI): m/z=423.2 ([M+H]$^+$).

Example 43: 5-[4-[6-amino-4-(difluoromethyl)-3-pyridyl]-6-[(3R)-3-methylmorpholin-4-yl]-1,3,5-triazin-2-yl]-4-(difluoromethyl)pyridin-2-amine (43)

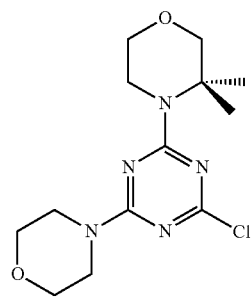

i16

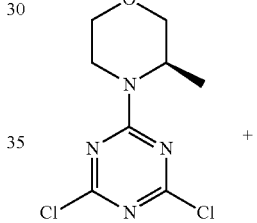

i33

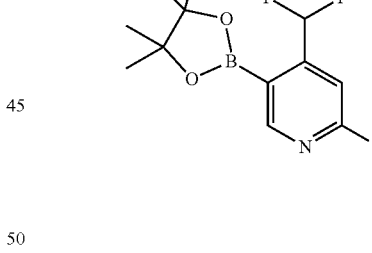

i68

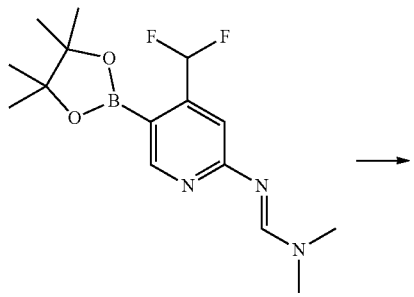

i68

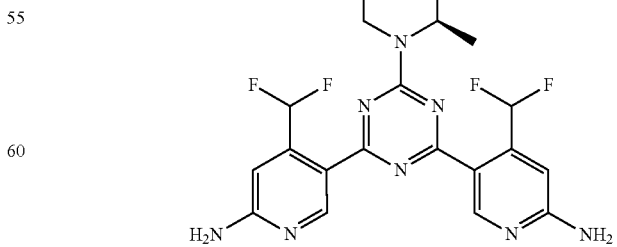

43

According to general procedure 1, compound 43 is obtained from starting materials i33 and i68 in 43% yield as a colorless solid. $^1$H NMR (400 MHz, (CD$_3$)$_2$SO): δ 9.01 (s, 2H), 7.81 (t, $^2J_{H,F}$=55 Hz, 2H), 7.00 (br s, 4H), 6.82 (s, 2H), 4.78-4.66 (m, 1H), 4.44-4.35 (m, 1H), 4.01-3.91 (m, 1H), 3.81-3.72 (m, 1H), 3.65-3.58 (m, 1H), 3.52-3.42 (m, 1H), 3.38-3.23 (m, 1H) 1.30 (d, $^3J_{H,H}$=6.7 Hz, 3H); $^{19}$F NMR (376 MHz, (CD$_3$)$_2$SO): δ−114.3-(−117.2) (m, 4F); MS (MALDI): m/z=465.1 ([M+H]$^+$).

Example 44: 4-(difluoromethyl)-5-[4-[(3R,5S)-3,5-dimethylmorpholin-4-yl]-6-[(3R)-3-methylmorpholin-4-yl]-1,3,5-triazin-2-yl]pyridin-2-amine (44)

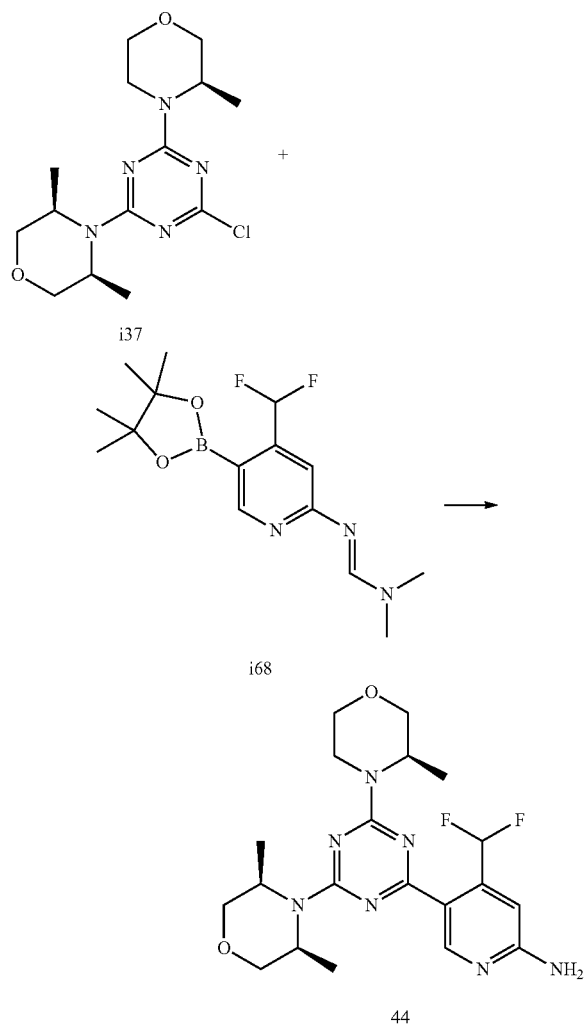

Example 45: 4-(difluoromethyl)-5-[4-(3,3-dimethylmorpholin-4-yl)-6-[(3R)-3-methylmorpholin-4-yl]-1,3,5-triazin-2-yl]pyridin-2-amine (45)

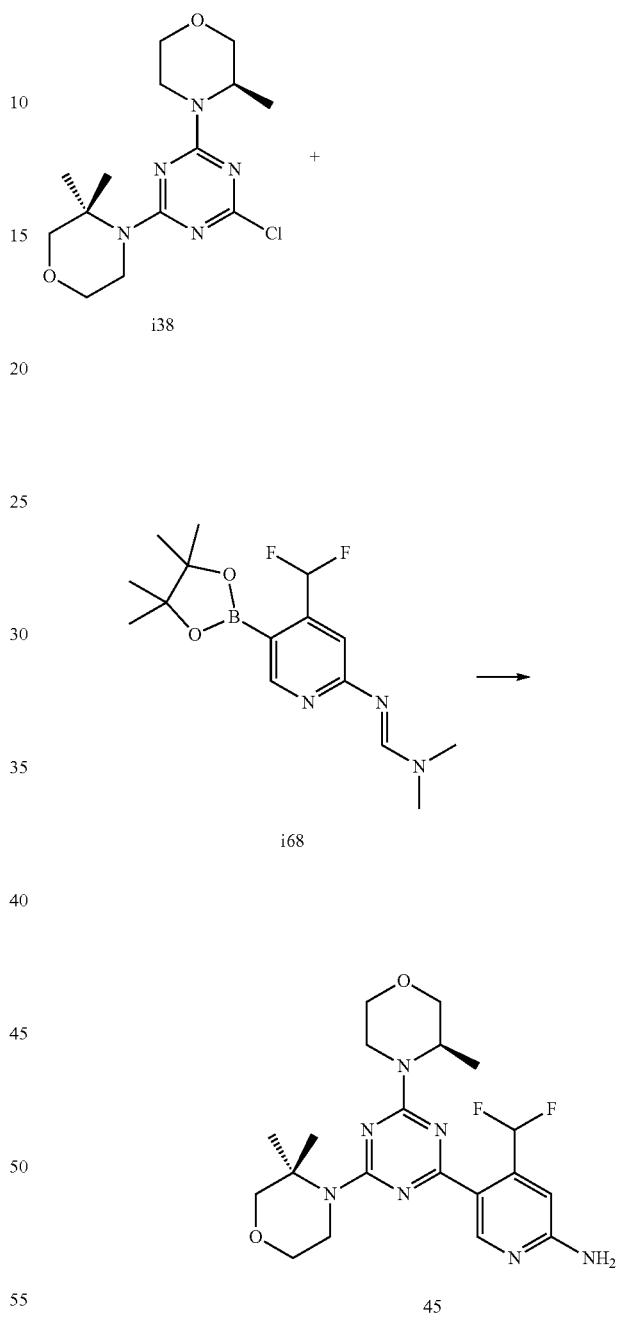

According to general procedure 1, compound 44 is obtained from starting materials i37 and i68 in 75% yield as a colorless solid. $^1$H NMR (400 MHz, (CD$_3$)$_2$SO): δ 8.89 (s, 1H), 7.79 (t, $^2J_{H,F}$=55 Hz, 1H), 6.83 (br s, 2H), 6.76 (s, 1H), 4.65 (br s, 1H), 4.50 (br s, 2H), 4.37-4.25 (m, 1H), 3.93 (dd, $^3J_{H,H}$=11 Hz, $^3J_{H,H}$=3.2 Hz, 1H), 3.79-3.67 (m, 3H), 3.59-3.51 (m, 3H), 3.45-3.36 (m, 1H), 3.22-3.11 (m, 1H), 1.30 (d, $^3J_{H,H}$=6.7 Hz, 6H), 1.24 (d, $^3J_{H,H}$=6.7 Hz, 3H); $^{19}$F NMR (376 MHz, (CD$_3$)$_2$SO): δ−115.0 (br s, 2F); MS (MALDI): m/z=436.1 ([M+H]$^+$).

According to general procedure 1, compound 45 is obtained from starting materials i38 and i68 in 71% yield as a colorless solid. $^1$H NMR (400 MHz, (CD$_3$)$_2$SO): δ 8.84 (s, 1H), 7.74 (t, $^2J_{H,F}$=55 Hz, 1H), 6.83 (br s, 2H), 6.76 (s, 1H), 4.58 (br s, 1H), 4.31-4.19 (m, 1H), 3.93 (dd, $^2J_{H,H}$=12 Hz, $^3J_{H,H}$=3.9 Hz, 1H), 3.84-3.81 (m, 4H), 3.76-3.69 (m, 1H), 3.58 (dd, $^2J_{H,H}$=11 Hz, $^3J_{H,H}$=3.2 Hz, 1H), 3.46-3.38 (m, 3H), 3.23-3.13 (m, 1H), 1.50 (br s, 6H), 1.23 (d, $^3J_{H,H}$=6.7 Hz, 3H); $^{19}$F NMR (376 MHz, (CD$_3$)$_2$SO): δ−114.8-(−115.5) (m, 2F); MS (MALDI): m/z=436.0 ([M+H]$^+$).

Example 46: 4-(difluoromethyl)-5-[4-[(3R)-3-(methoxymethyl)morpholin-4-yl]-6-[(3R)-3-methyl-morpholin-4-yl]-1,3,5-triazin-2-yl]pyridin-2-amine (46)

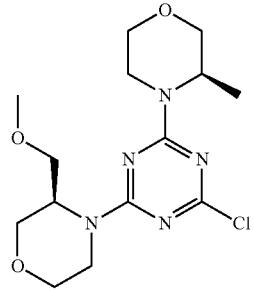

i39

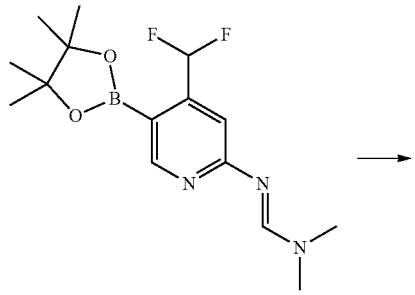

i68

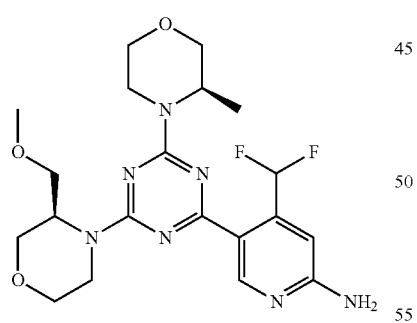

46

According to general procedure 1, compound 46 is obtained from starting materials i39 and i68 in 67% yield as a colorless solid. $^1$H NMR (400 MHz, (CD$_3$)$_2$SO): δ 8.87 (s, 1H), 7.77 (t, $^2J_{H,F}$=55 Hz, 1H), 6.84 (br s, 2H), 6.76 (s, 1H), 4.67 (br s, 2H), 4.44-4.24 (m, 2H), 3.96-3.83 (m, 3H), 3.75-3.63 (m, 2H), 3.60-3.36 (m, 5H), 3.31 (s, 3H), 3.21-3.04 (m, 2H), 1.23 (d, $^3J_{H,H}$=6.7 Hz, 3H); $^{19}$F NMR (376 MHz, (CD$_3$)$_2$SO): δ−115.0 (br s, 2F); MS (MALDI): m/z=452.3 ([M+H]$^+$).

Example 47: 4-(difluoromethyl)-5-[4-(3,7-dioxa-9-azabicyclo[3.3.1]nonan-9-yl)-6-[(3R)-3-methylmorpholin-4-yl]-1,3,5-triazin-2-yl]pyridin-2-amine (47)

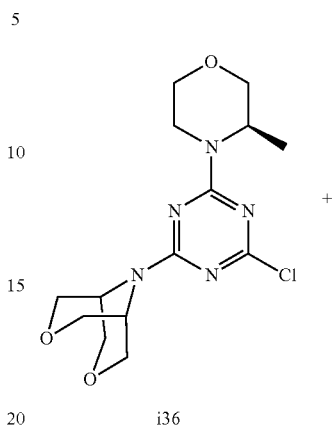

i36

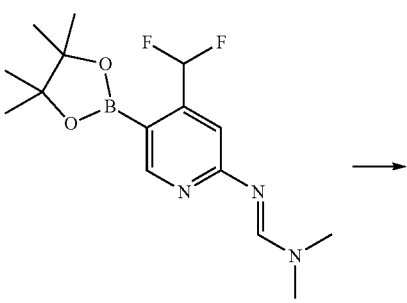

i68

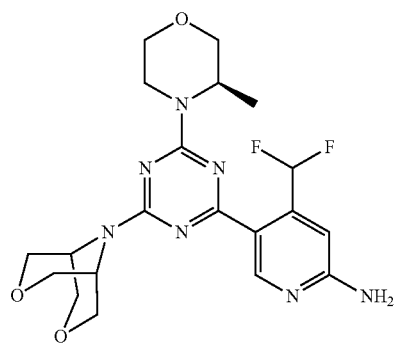

47

According to general procedure 1, compound 47 is obtained from starting materials i36 and i68 in 85% yield as a colorless solid. $^1$H NMR (400 MHz, (CD$_3$)$_2$SO): δ 8.86 (s, 1H), 7.72 (t, $^2J_{H,F}$=55 Hz, 1H), 6.84 (br s, 2H), 6.75 (s, 1H), 4.64 (br s, 1H), 4.53-4.42 (m, 2H), 4.37-4.25 (m, 1H), 4.05-3.96 (m, 4H), 3.92-3.84 (m, 1H), 3.77-3.66 (m, 5H), 3.60-3.52 (m, 1H), 3.44-3.35 (m, 1H), 3.22-3.10 (m, 1H), 1.23 (d, $^3J_{H,H}$=6.7 Hz, 3H); $^{19}$F NMR (376 MHz, (CD$_3$)$_2$SO): δ−114.9-(−117.1) (m, 2F); MS (MALDI): m/z=450.0 ([M+H]$^+$).

Example 48: (4S,5R)-3-[4-[2-amino-4-(difluoromethyl)pyrimidin-5-yl]-6-morpholino-1,3,5-triazin-2-yl]-4-(hydroxymethyl)-5-methyl-oxazolidin-2-one (48)

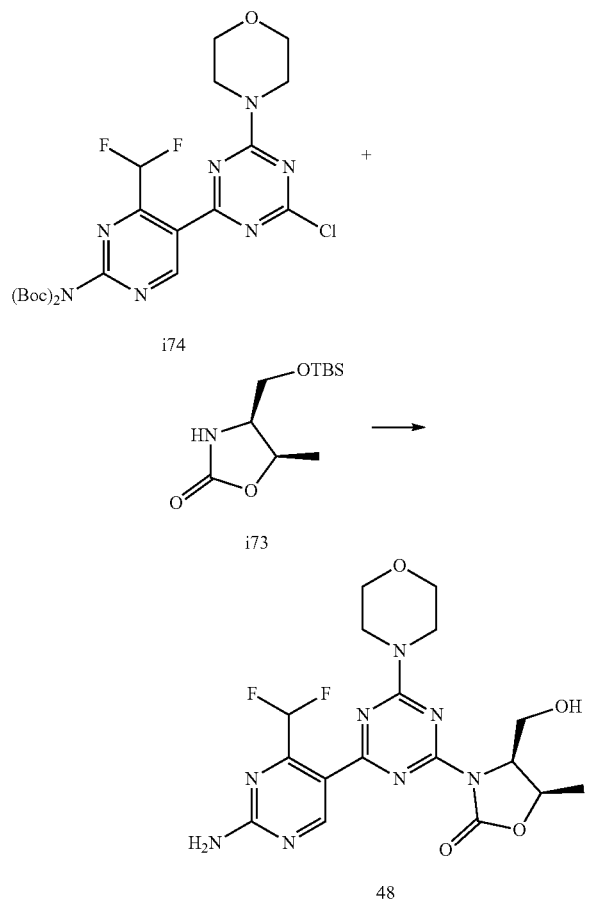

tert-Butyl N-tert-butoxycarbonyl-N-(5-(4-chloro-6-morpholino-1,3,5-triazin-2-yl)-4-(difluoromethyl)pyrimidin-2-yl)carbamate (i74, 350 mg, 643 μmol, 1.0 eq.), (4S,5R)-4-1.1 eq.), 4,5-bis(diphenylphosphino)-9,9-dimethylxanthene (22.3 mg, 38.5 μmol, 0.06 eq.), cesium carbonate (419 mg, 1.29 mmol, 2.0 eq.) and palladium(II) acetate (5.80 mg, 25.8 μmol, 0.04 eq.) are mixed in 1,4-dioxane (5 mL) under nitrogen atmosphere and heated at 95° C. for 2 hours. After this time, the reaction mixture is allowed to cool down to room temperature, deionized H₂O is added, and the aqueous layer is separated and extracted with ethyl acetate (3×). The combined organic layer is dried over anhydrous sodium sulfate, filtered and the solvent is evaporated under reduced pressure. The above residue is dissolved in tetrahydrofuran (5 mL) and aqueous HCl (3M, 2.00 mL, 6.00 mmol, 14 eq.) is added. The resulting mixture is heated at 60° C. overnight. Then, aqueous saturated sodium bicarbonate and ethyl acetate are added. The aqueous layer is separated and extracted with ethyl acetate (3×). The combined organic layer is dried over anhydrous sodium sulfate, filtered and concentrated und reduced pressure. Purification by column chromatography on silica gel (100% ethyl acetate) gives product 48 as a colorless solid (55% yield).

¹H NMR (400 MHz, (CD₃)₂SO): δ 9.23 (s, 1H), 8.23 (t, $^2J_{H,F}$ =54 Hz, 1H), 7.81-7.53 (m, 2H), 4.99 (t, $^2J_{H,F}$=5.2 Hz, 1H), 4.82 (q, $^2J_{H,F}$=6.5 Hz, 1H), 4.56-4.51 (m, 1H), 4.03-3.97 (m, 1H), 3.95-3.60 (m, 9H), 1.50 (d, $^2J_{H,F}$=6.5 Hz, 3H); ¹⁹F NMR (376 MHz, (CD₃)₂SO): δ –121.3 (s, 1F), –121.4 (s, 1F); MS (MALDI): m/z=439.1 ([M+H]⁺).

Example 49: (4S,5R)-3-[6-[2-amino-4-difluoromethyl)pyrimidin-5-yl]-2-morpholino-pyrimidin-4-yl]-4-(hydroxymethyl)-5-methyl-oxazolidin-2-one (49)

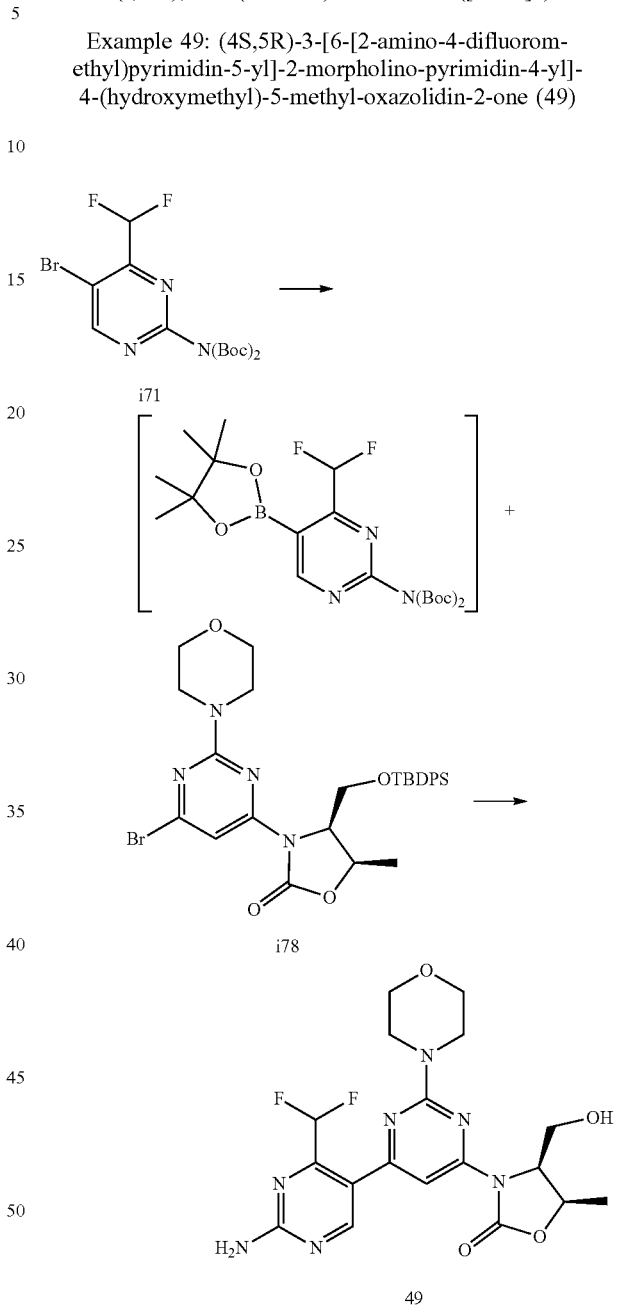

tert-Butyl N-[5-bromo-4-(difluoromethyl)pyrimidin-2-yl]-N-tert-butoxycarbonyl-carbamate (i71, 44.0 mg, 104 μmol, 1.0 eq.), bis(pinacolato)diboron (27.0 g, 106 μmol, 1.0 eq.), KOAc (31.0 mg, 316 μmol, 3.0 eq.) and [1,1'-bis(diphenylphosphino)ferrocene]-dichloropalladium(II) (7.70 mg, 10.5 μmol, 0.10 eq.) are mixed in 1,4-dioxane (2 mL) under nitrogen atmosphere and heated at 95° C. for 55 minutes.

After this time, the above reaction mixture is allowed to cool down to room temperature. Then, compound i78 (64.0 mg, 105 μmol, 1.0 eq.), potassium phosphate tribasic (44.0 mg, 207 μmol, 2.0 eq.), chloro(2-dicyclohexylphosphino-2', 4',6'-triisopropyl-1,1'-biphenyl) [2-(2'-amino-1,1'-biphenyl)]-palladium(II) (Sigma-Aldrich, product number 741825, 8.20 mg, 10.4 µmol, 0.10 eq.), 1,4-dioxane (2 mL) and deionized H$_2$O (0.5 mL) are added and the resulting dark mixture is placed in a pre-heated oil bath at 95° C. for 16 hours. After this time, aqueous saturated sodium bicarbonate and dichloromethane are added. The aqueous layer is separated and extracted with dichloromethane (3×). The combined organic layer is dried over anhydrous sodium sulfate, filtered and concentrated under reduced pressure. This intermediate is purified by column chromatography on silica gel (cyclohexane/ethyl acetate 1:0→1:1) to afford a colorless semisolid.

The semisolid obtained above is then dissolved in tetrahydrofuran (2 mL) and a solution of HCl in dioxane (1 M, 100 µL, 100 µmol, 1.0 eq) is added. The resulting mixture is stirred at room temperature overnight. After this time, the solvents are evaporated and the residue is dried in vacuo.

The above salt is then dissolved in tetrahydrofuran (2 mL) and a solution of tetrabutylammonium fluoride hydrate in tetrahydrofuran (1 M, 100 µL, 100 µmol, 1.0 eq.) is added. The reaction mixture is allowed to stir at room temperature for 2 days. After this time, aqueous saturated sodium bicarbonate is added and the product is extracted with ethyl acetate (3×). The combined organic layer is washed with an aqueous saturated NH$_4$Cl-solution (3×), dried over anhydrous sodium sulfate, filtered and concentrated under reduced pressure to afford a yellowish solid. This solid is triturated with diethyl ether (5×) and dried in vacuo. The desired product 49 is isolated as a colorless solid (5.5% yield). $^1$H NMR (400 MHz, CD$_3$OD): δ 8.64 (s, 1H), 7.69 (s, 1H), 7.15 (t, $^2J_{H,F}$=54 Hz, 1H), 4.82-4.76 (m, 1H), 4.66-4.61 (m, 1H), 4.17 (dd, $^2J_{H,H}$=12 Hz, $^3J_{H,H}$=4.1 Hz, 1H), 3.78 (dd, $^2J_{H,H}$=12 Hz, $^3J_{H,H}$=1.5 Hz, 1H), 3.72-3.61 (m, 8H), 1.61 (d, $^3J_{H,H}$=6.6 Hz, 3H); $^{19}$F NMR (376 MHz, CD$_3$OD): δ−121.4 (s, 1F), −121.5 (s, 1F); MS (MALDI): m/z=438.4 ([M+H]$^+$).

Example 50: 4-(difluoromethyl)-5-[4-[(3R)-3-methylmorpholin-4-yl]-6-(3-oxa-6-azabicyclo[3.1.1]heptan-6-yl)-1,3,5-triazin-2-yl]pyridin-2-amine (50)

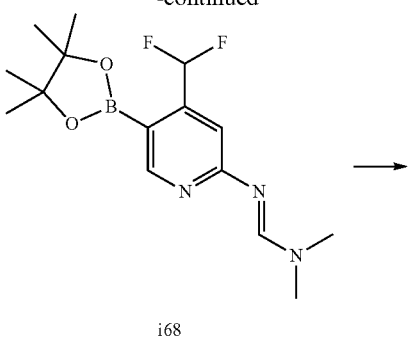

i68

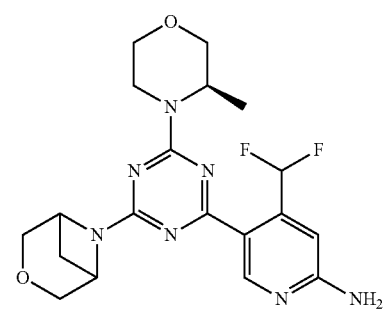

50

According to general procedure 1, compound 50 is obtained from starting materials i40 and i68 in 52% yield as a colorless solid. $^1$H NMR (400 MHz, (CD$_3$)$_2$SO): δ 8.90 (s, 1H), 7.82 (t, $^2J_{H,F}$=55 Hz, 1H), 6.87 (br s, 2H), 6.76 (s, 1H), 4.55-4.51 (m, 1H), 4.34-4.14 (m, 3H), 4.12-4.25 (m, 2H), 3.92-3.80 (m, 1H), 3.76-3.68 (m, 3H), 3.55-3.51 (m, 1H), 3.38 (m, 1H), 3.20-3.13 (m, 1H), 2.68 (m, 1H), 1.78 (m, 1H), 1.20 (d, $^3J_{H,H}$=6.9 Hz, 3H); $^{19}$F NMR (376 MHz, (CD$_3$)$_2$SO): δ−115.0 (br s, 2F); MS (MALDI): m/z=420.6 ([M+H]$^+$).

Example 51: 4-(difluoromethyl)-5-[4-[(3R)-3-methylmorpholin-4-yl]-6-(6-oxa-3-azabicyclo[3.1.1]heptan-3-yl)-1,3,5-triazin-2-yl]pyridin-2-amine (51)

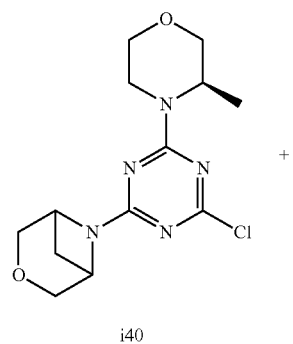

i40

+

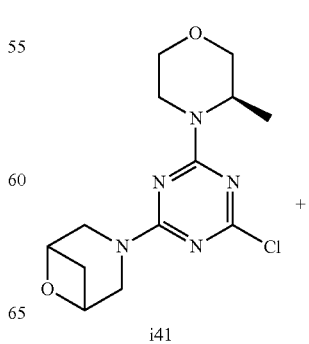

i41

+

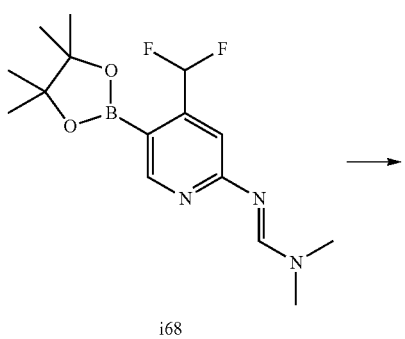

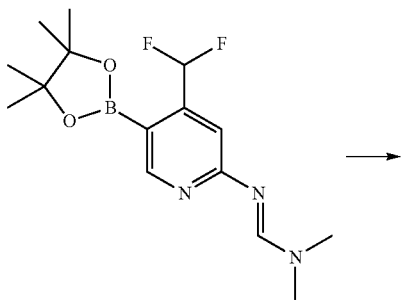

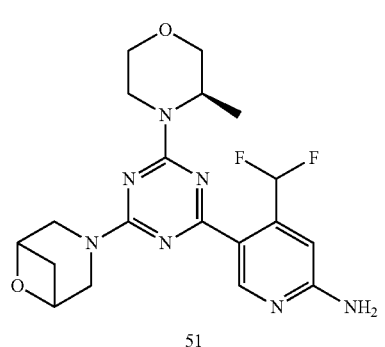

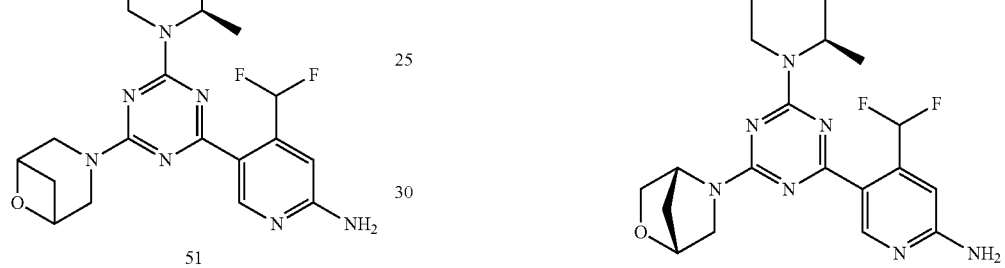

According to general procedure 1, compound 51 is obtained from starting materials i41 and i68 in 36% yield as a colorless solid. $^1$H NMR (400 MHz, (CD$_3$)$_2$SO): δ 8.99 (s, 1H), 7.89 (t, $^2$J$_{H,F}$=55 Hz, 1H), 6.84 (br s, 2H), 6.77 (s, 1H), 4.69 (m, 3H), 4.37 (m, 1H), 3.91-3.85 (m, 3H), 3.75-3.53 (m, 4H), 3.42-3.35 (m, 1H), 3.22-3.15 (m, 1H), 3.12-3.08 (m, 1H), 1.85 (m, 1H), 1.24 (d, $^3$J$_{H,H}$=6.9 Hz, 3H); $^{19}$F NMR (376 MHz, (CD$_3$)$_2$SO): δ−116.0 (br s, 2F); MS (MALDI): m/z=420.6 ([M+H]$^+$).

Example 52: 4-(difluoromethyl)-5-[4-[(3R)-3-methylmorpholin-4-yl]-6-[(1R,4R)-2-oxa-5-azabicyclo[2.2.1]heptan-5-yl]-1,3,5-triazin-2-yl]pyridin-2-amine (52)

According to general procedure 1, compound 52 is obtained from starting materials i42 and i68 in 44% yield as a colorless solid (1:1 mixture of rotamers). $^1$H NMR (400 MHz, (CD$_3$)$_2$SO): δ 8.89 (m, 1H), 7.77 (m, 1H), 6.84 (br s, 2H), 6.76 (s, 1H), 5.02-4.97 (m, 1H), 4.68-4.66 (m, 2H), 4.31 (m, 1H), 3.89-3.85 (m, 1H), 3.79-3.57 (m, 3H), 3.57-3.44 (m, 4H), 3.22 (m, 1H), 1.90-1.83 (m, 2H), 1.21 (d, $^3$J$_{H,H}$=6.9 Hz, 3H); $^{19}$F NMR (376 MHz, (CD$_3$)$_2$SO): δ−115.5 (br s, 2F); MS (MALDI): m/z=420.2 ([M+H]$^+$).

Example 53: 4-(difluoromethyl)-5-[4-[(3R)-3-methylmorpholin-4-yl]-6-[(1S,4S)-2-oxa-5-azabicyclo[2.2.1]heptan-5-yl]-1,3,5-triazin-2-yl]pyridin-2-amine (53)

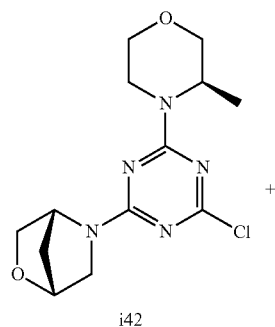

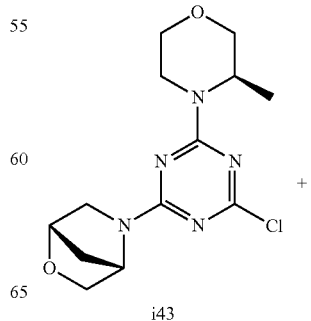

211

-continued

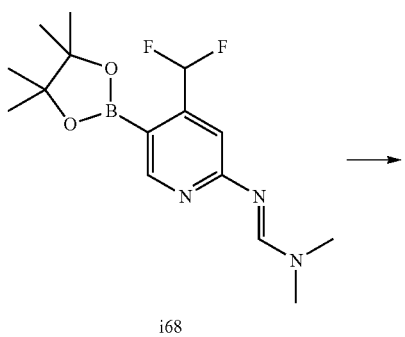

i68

→

212

-continued

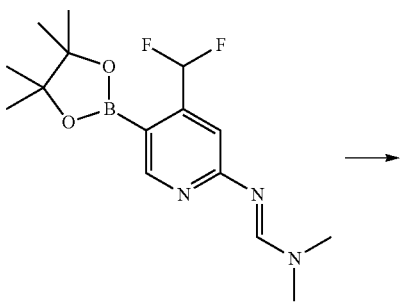

i68

→

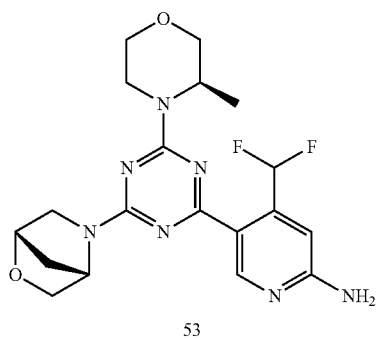

53

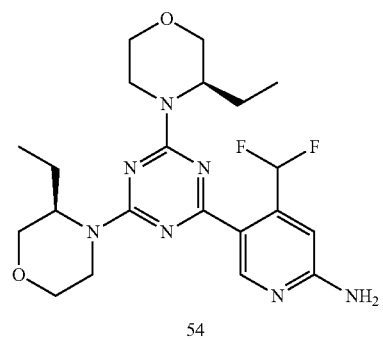

54

According to general procedure 1, compound 53 is obtained from starting materials i43 and i68 in 53% yield as a colorless solid (1:1 mixture of rotamers). $^1$H NMR (400 MHz, (CD$_3$)$_2$SO): δ 8.90 (m, 1H), 7.77 (m, 1H), 6.84 (brs, 2H), 6.76 (s, 1H), 5.02-4.96 (m, 1H), 4.68-4.62 (m, 2H), 3.90 (m, 1H), 3.80 (m, 1H), 3.70 (m, 2H), 3.57 (m, 2H), 3.45 (m, 3H), 3.20 (m, 1H), 1.90-1.83 (m, 2H), 1.21 (d, $^3J_{H,H}$=6.9 Hz, 3H); $^{19}$F NMR (376 MHz, (CD$_3$)$_2$SO): δ−115.0 (br s, 2F); MS (MALDI): m/z=420.2 ([M+H]$^+$).

Example 54: 5-[4,6-bis[(3R)-3-ethylmorpholin-4-yl]-1,3,5-triazin-2-yl]-4-(difluoromethyl)pyridin-2-amine (54)

According to general procedure 1, compound 54 is obtained from starting materials i8 and i68 in 61% yield as a colorless solid. $^1$H NMR (400 MHz, (CD$_3$)$_2$SO): δ 8.87 (s, 1H), 7.77 (t, $^2J_{H,F}$=55 Hz, 1H), 6.83 (br s, 2H), 6.76 (s, 1H), 4.47 (m, 4H), 3.89-3.81 (m, 4H), 3.51-3.34 (m, 4H), 3.12 (m, 2H), 1.71 (m, 4H), 0.86 (m, 6H). $^{19}$F NMR (376 MHz, (CD$_3$)$_2$SO): δ−115.0 (br s, 2F); MS (MALDI): m/z=450.3 ([M+H]$^+$).

Example 55: 5-[4,6-bis(8-oxa-5-azaspiro[3.5]nonan-5-yl)-1,3,5-triazin-2-yl]-4-(difluoromethyl)pyridin-2-amine (55)

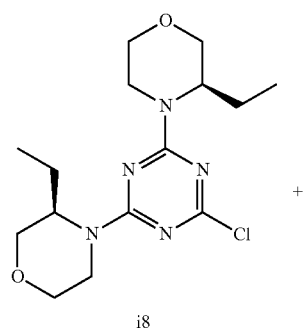

i8

+

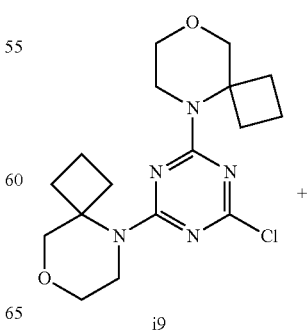

i9

+

213

-continued

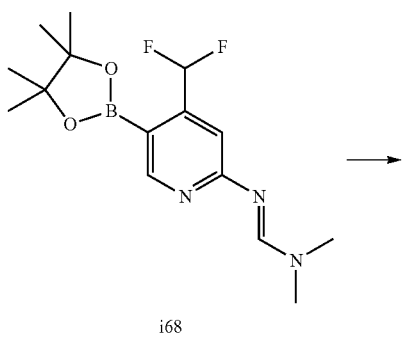

i68

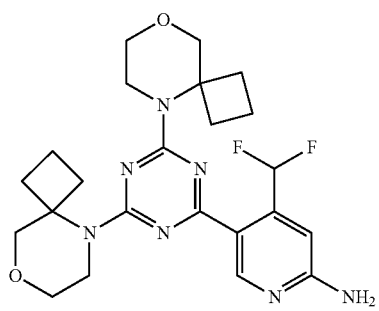

55

According to general procedure 1, compound 55 is obtained from starting materials i9 and i68 in 59% yield as a colorless solid. $^1$H NMR (400 MHz, (CD$_3$)$_2$SO): δ 8.74 (s, 1H), 7.65 (t, $^2J_{H,F}$=55 Hz, 1H), 6.81 (br s, 2H), 6.75 (s, 1H), 3.68 (m, 8H), 3.49 (m, 4H), 2.46-2.38 (m, 4H), 2.25-2.16 (m, 4H), 1.72-1.66 (m, 4H); $^{19}$F NMR (376 MHz, (CD$_3$)$_2$SO): δ−115.5 (br s, 2F); MS (MALDI): m/z=474.3 ([M+H]$^+$).

Example 56: 5-[4,6-bis[(3R)-3-isopropylmorpholin-4-yl]-1,3,5-triazin-2-yl]-4-(difluoromethyl)pyridin-2-amine (56)

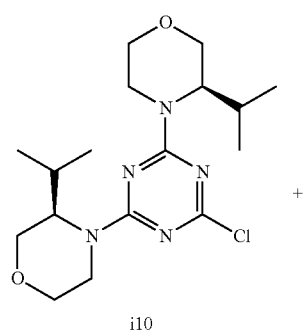

i10

214

-continued

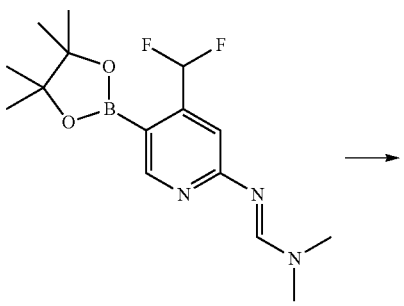

i68

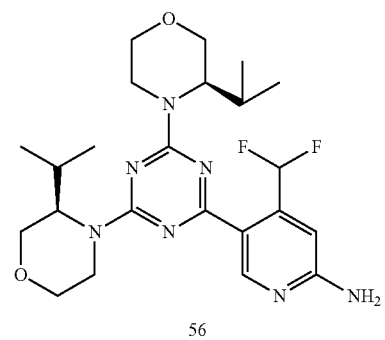

56

According to general procedure 1, compound 56 is obtained from starting materials i10 and i68 in 59% yield as a colorless solid. $^1$H NMR (400 MHz, (CD$_3$)$_2$SO): δ 8.87 (s, 1H), 7.76 (t, $^2J_{H,F}$=55 Hz, 1H), 6.82 (br s, 2H), 6.76 (s, 1H), 4.50 (m, 2H), 4.29 (m, 2H), 4.02-3.84 (m, 4H), 3.40 (m, 4H), 3.08 (m, 2H), 2.34 (m, 2H), 1.02 (m, 6H), 0.77 (m, 6H); $^{19}$F NMR (376 MHz, (CD$_3$)$_2$SO): δ−115.0 (br s, 2F); MS (MALDI): m/z=478.4 ([M+H]$^+$).

Example 57: 4-[6-amino-4-(difluoromethyl)-3-pyridyl]-N-methyl-6-[(3R)-3-methylmorpholin-4-yl]-N-(2,2,2-trifluoroethyl)-1,3,5-triazin-2-amine (57)

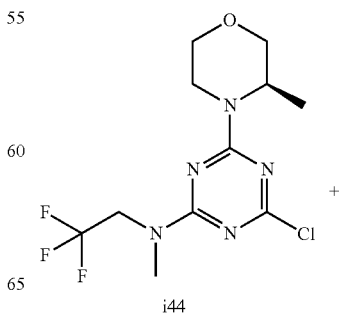

i44

-continued

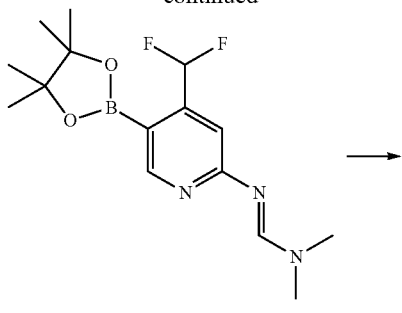

i68

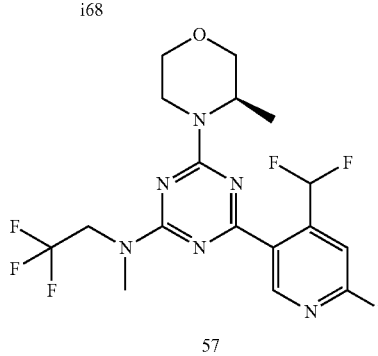

57

According to general procedure 1, compound 57 is obtained from starting materials i44 and i68 in 45% yield as a colorless solid (1:1 mixture of rotamers). $^1$H NMR (400 MHz, (CD$_3$)$_2$SO): δ 8.87 (m, 1H), 7.77 (m, 1H), 6.84 (brs, 2H), 6.76 (s, 1H), 4.71-4.35 (m, 4H), 3.92 (m, 1H), 3.72 (m, 1H), 3.56 (m, 1H), 3.42 (m, 1H), 3.23-3.18 (m, 4H), 1.24 (m, 3H); $^{19}$F NMR (376 MHz, (CD$_3$)$_2$SO): δ−69, −115.0 (br s, 2F); MS (MALDI): m/z=435.1 ([M+H]$^+$).

Example 58: 4-[6-amino-4-(difluoromethyl)-3-pyridyl]-6-[(3R)-3-methylmorpholin-4-yl]-N-(2,2,2-trifluoroethyl)-1,3,5-triazin-2-amine (58)

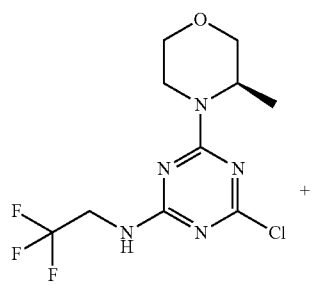

i45

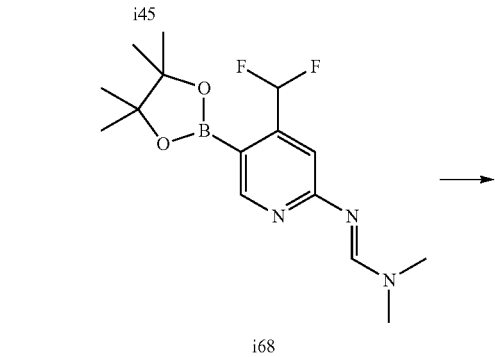

i68

-continued

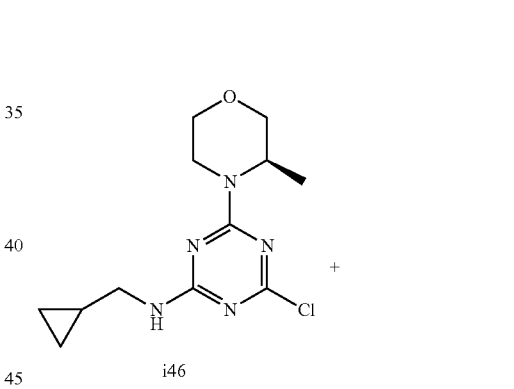

58

According to general procedure 1, compound 58 is obtained from starting materials i45 and i68 in 41% yield as a colorless solid (1:1 mixture of rotamers). $^1$H NMR (400 MHz, (CD$_3$)$_2$SO): δ 8.87 (m, 1H), 8.07 (m, 1H), 7.77 (m, 1H), 6.86 (br s, 2H), 6.76 (s, 1H), 4.65-4.77 (m, 1H), 4.36-4.01 (m, 3H), 3.83 (m, 1H), 3.62 (m, 1H), 3.52 (m, 1H), 3.35 (m, 1H), 3.10 (m, 1H), 1.18 (d, $^3J_{H,H}$=6.9 Hz, 3H); MS (MALDI): m/z=421.1 ([M+H]$^+$).

Example 59: 4-[6-amino-4-(difluoromethyl)-3-pyridyl]-N-(cyclopropylmethyl)-6-[(3R)-3-methyl-morpholin-4-yl]-1,3,5-triazin-2-amine (59)

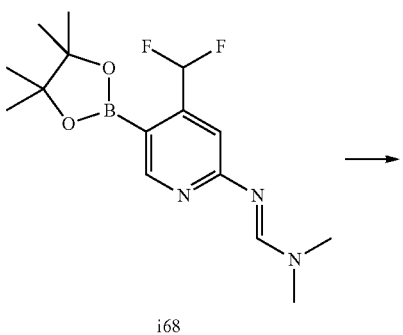

i46

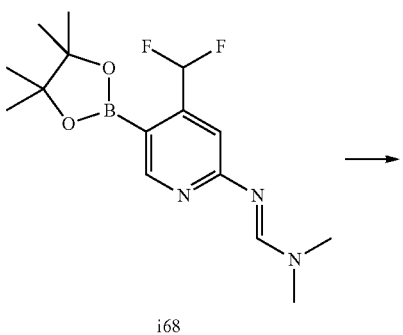

i68

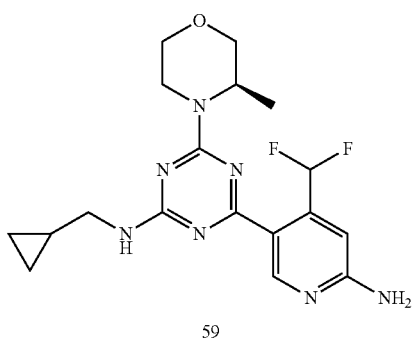

According to general procedure 1, compound 59 is obtained from starting materials i46 and i68 in 32% yield as a colorless solid (1:1 mixture of rotamers). $^1$H NMR (400 MHz, (CD$_3$)$_2$SO): δ 8.89-8.84 (m, 1H), 8.12-7.37 (m, 2H), 6.81-6.75 (m, 3H), 4.64 (m, 1H), 4.30 (m, 1H), 3.90 (m, 1H), 3.72 (m, 1H), 3.56 (m, 1H), 3.39 (m, 2H), 3.14 (m, 2H), 1.20 (d, $^3J_{H,H}$=6.9 Hz, 3H), 1.04 (m, 1H), 0.42 (m, 2H), 0.22 (m, 2H); $^{19}$F NMR (376 MHz, (CD$_3$)$_2$SO): δ−115.0 (br s, 2F); MS (MALDI): m/z=393.0 ([M+H]$^+$).

According to general procedure 1, compound 60 is obtained from starting materials i47 and i68 in 41% yield as a colorless solid. $^1$H NMR (400 MHz, (CD$_3$)$_2$SO): δ 8.96 (s, 1H), 7.75 (t, $^2J_{H,F}$=55 Hz, 1H), 7.07 (br s, 2H), 6.80 (s, 1H), 5.10-4.97 (m, 2H), 4.78-4.54 (m, 1H), 4.33 (m, 1H), 3.91 (m, 1H), 3.71 (m, 1H), 3.57 (m, 1H), 3.41 (m, 1H), 3.29 (m, 1H), 1.27 (d, $^3J_{H,H}$=6.9 Hz, 3H); $^{19}$F NMR (376 MHz, (CD$_3$)$_2$SO): δ−69, −115.0 (br s, 2F); MS (MALDI): m/z=422.3 ([M+H]$^+$).

Example 60: 4-(difluoromethyl)-5-[4-[(3R)-3-methylmorpholin-4-yl]-6-(2,2,2-trifluoroethoxy)-1,3,5-triazin-2-yl]pyridin-2-amine (60)

Example 61: 5-[4-(2,2-difluoroethoxy)-6-[(3R)-3-methylmorpholin-4-yl]-1,3,5-triazin-2-yl]-4-(difluoromethyl)pyridin-2-amine (61)

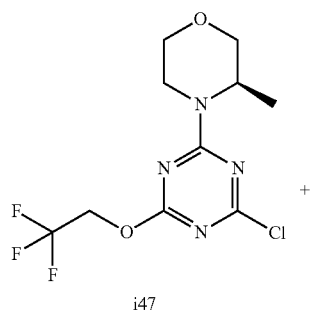

i47

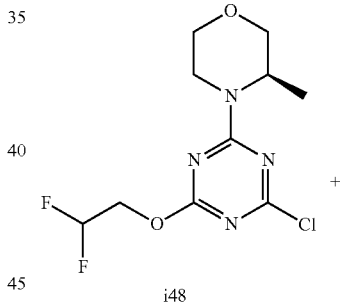

i48

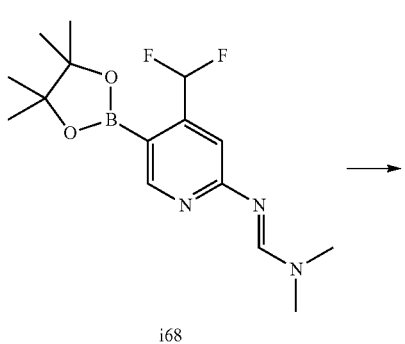

i68

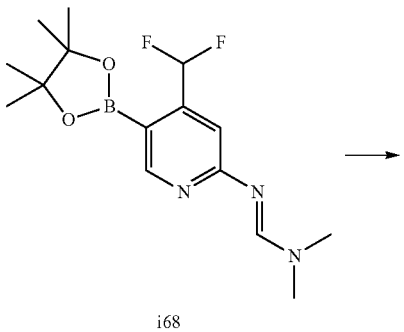

i68

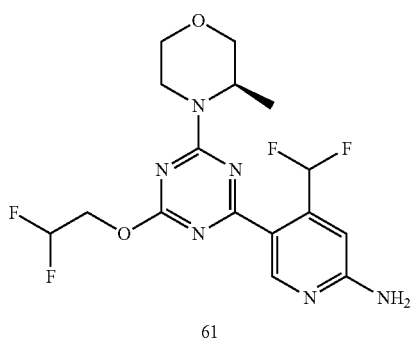

61

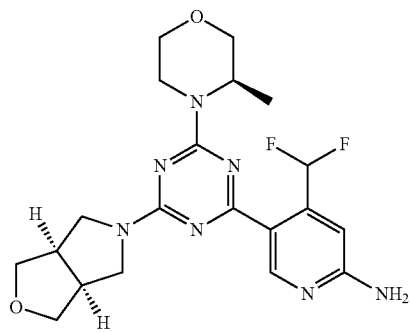

62

According to general procedure 1, compound 61 is obtained from starting materials i48 and i68 in 60% yield as a colorless solid. $^1$H NMR (400 MHz, (CD$_3$)$_2$SO): δ 8.95 (s, 1H), 7.89 (t, $^2J_{H,F}$=55 Hz, 1H), 7.04 (br s, 2H), 6.80 (s, 1H), 6.37 (m, 1H), 4.68-4.53 (m, 3H), 4.25 (m, 1H), 3.90 (m, 1H), 3.70 (m, 1H), 3.55 (m, 1H), 3.41 (m, 1H), 3.25 (m, 1H), 1.26 (d, $^3J_{H,H}$=6.9 Hz, 3H). $^{19}$F NMR (376 MHz, (CD$_3$)$_2$SO): δ−115.0 (br s, 2F), −126; MS (MALDI): m/z=404.1 ([M+H]$^+$).

Example 62: 5-[4-[(3aR,6aS)-1,3,3a,4,6,6a-hexahydrofuro[3,4-c]pyrrol-5-yl]-6-[(3R)-3-methylmorpholin-4-yl]-1,3,5-triazin-2-yl]-4-(difluoromethyl)pyridin-2-amine (62)

According to general procedure 1, compound 62 is obtained from starting materials i49 and i68 in 20% yield as a colorless solid. $^1$H NMR (400 MHz, (CD$_3$)$_2$SO): δ 8.90 (s, 1H), 7.86 (t, $^2J_{H,F}$=55 Hz, 1H), 6.82 (br s, 2H), 6.76 (s, 1H), 4.67 (m, 1H), 4.35 (m, 1H), 3.93-3.43 (m, 14H), 3.16 (m, 1H), 2.99 (m, 2H), 1.21 (d, $^3J_{H,H}$=6.9 Hz, 3H); $^{19}$F NMR (376 MHz, (CD$_3$)$_2$SO): δ−115.0 (br s, 2F); MS (MALDI): m/z=435.2 ([M+H]$^+$).

Example 63: 5-[4-[(4aS,7aR)-2,3,4a,5,7,7a-hexahydro-[1,4]dioxino[2,3-c]pyrrol-6-yl]-6-[(3R)-3-methylmorpholin-4-yl]-1,3,5-triazin-2-yl]-4-(difluoromethyl)pyridin-2-amine (63)

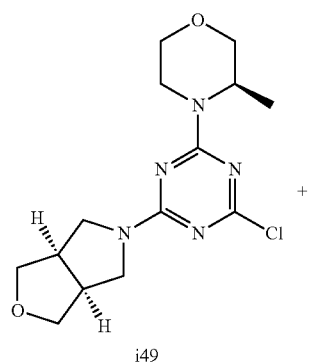

i49

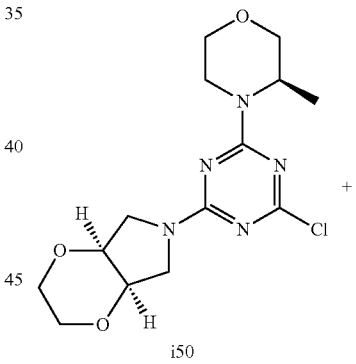

i50

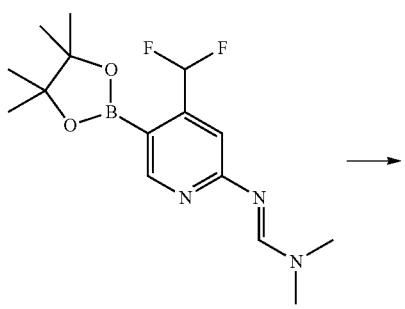

i68

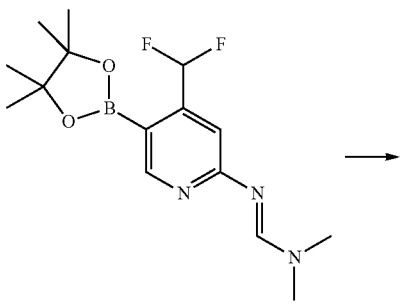

i68

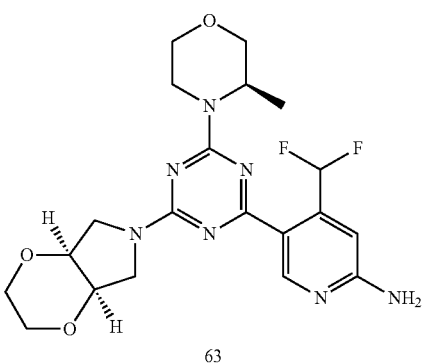

63

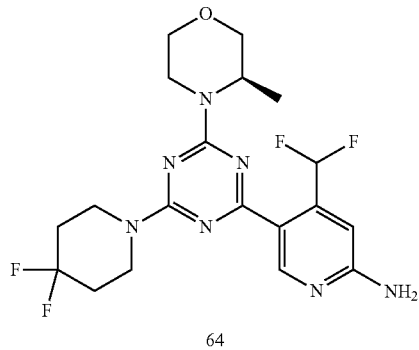

64

According to general procedure 1, compound 63 is obtained from starting materials i50 and i68 in 25% yield as a colorless solid. $^1$H NMR (400 MHz, (CD$_3$)$_2$SO): δ 8.92 (s, 1H), 7.88 (t, $^2J_{H,F}$=55 Hz, 1H), 6.84 (br s, 2H), 6.76 (s, 1H), 4.70 (m, 1H), 4.36-4.26 (m, 3H), 3.88 (m, 1H), 3.79-3.53 (m, 12H), 3.41 (m, 1H), 3.09 (m, 1H), 1.21 (d, $^3J_{H,H}$=6.9 Hz, 3H); $^{19}$F NMR (376 MHz, (CD$_3$)$_2$SO): δ−115.0 (br s, 2F); MS (MALDI): m/z=451.2 ([M+H]$^+$).

According to general procedure 1, compound 64 is obtained from starting materials i51 and i68 in 61% yield as a colorless solid. $^1$H NMR (400 MHz, (CD$_3$)$_2$SO): δ 8.88 (s, 1H), 7.74 (t, $^2J_{H,F}$=55 Hz, 1H), 6.85 (br s, 2H), 6.77 (s, 1H), 4.70 (m, 1H), 4.32 (m, 1H), 3.99 (m, 5H), 3.72 (m, 1H), 3.56 (m, 1H), 3.41 (m, 1H), 3.18 (m, 1H), 2.01 (m, 4H), 1.21 (d, $^3J_{H,H}$=6.9 Hz, 3H); $^{19}$F NMR (376 MHz, (CD$_3$)$_2$SO): δ−95.5, −115.0 (br s, 2F); MS (MALDI): m/z=442.0 ([M+H]$^+$).

Example 64: 4-(difluoromethyl)-5-[4-(4,4-difluoro-1-piperidyl)-6-[(3R)-3-methylmorpholin-4-yl]-1,3,5-triazin-2-yl]pyridin-2-amine (64)

Example 65: 4-(difluoromethyl)-5-[4-[(3R)-3-methylmorpholin-4-yl]-6-(2-oxa-7-azaspiro[3.5]nonan-7-yl)-1,3,5-triazin-2-yl]pyridin-2-amine (65)

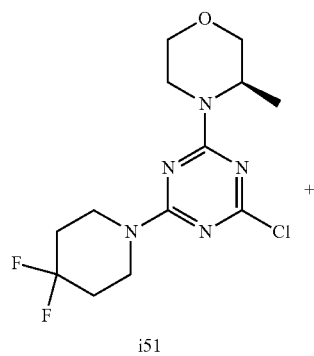

i51

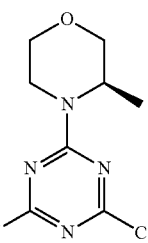

i52

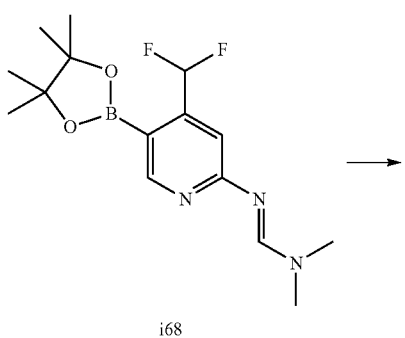

i68

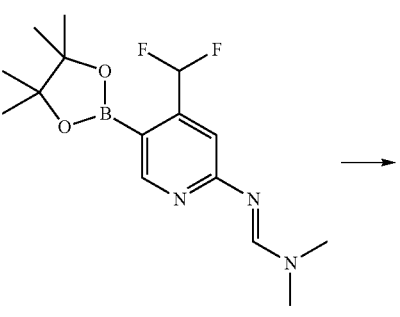

i68

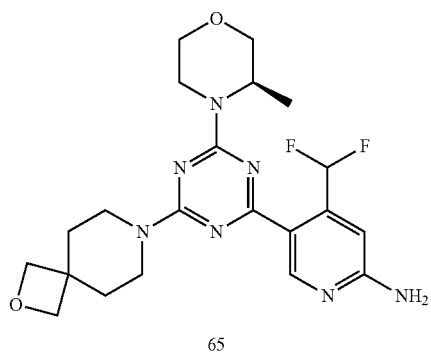

65

According to general procedure 1, compound 65 is obtained from starting materials i52 and i68 in 49% yield as a colorless solid. $^1$H NMR (400 MHz, (CD$_3$)$_2$SO): δ 8.86 (s, 1H), 7.75 (t, $^2J_{H,F}$=55 Hz, 1H), 6.83 (br s, 2H), 6.76 (s, 1H), 4.65 (m, 1H), 4.35 (m, 5H), 3.87 (m, 1H), 3.70 (m, 5H), 3.57 (m, 1H), 3.43 (m, 1H), 3.16 (m, 1H), 1.79 (m, 4H), 1.20 (d, $^3J_{H,H}$=6.9 Hz, 3H); $^{19}$F NMR (376 MHz, (CD$_3$)$_2$SO): δ −115.5 (br s, 2F); MS (MALDI): m/z=449.3 ([M+H]$^+$).

Example 66: 4-(difluoromethyl)-5-[4-(3,3-dimethyl-morpholin-4-yl)-6-[(3R,5S)-3,5-dimethylmorpholin-4-yl]-1,3,5-triazin-2-yl]pyridin-2-amine (66)

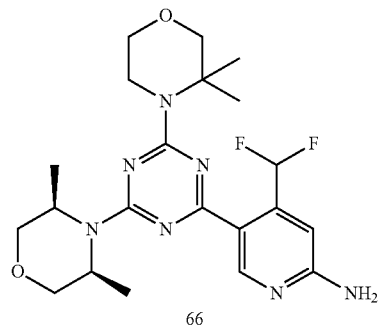

66

According to general procedure 1, compound 66 is obtained from starting materials i55 and i68 in 61% yield as a colorless solid. $^1$H NMR (400 MHz, (CD$_3$)$_2$SO): δ 8.87 (s, 1H), 7.77 (t, $^2J_{H,F}$=55 Hz, 1H), 6.83 (br s, 2H), 6.76 (s, 1H), 4.46 (m, 2H), 3.81-3.77 (m, 6H), 3.55 (m, 2H), 3.44 (m, 2H), 1.49 (s, 6H), 1.28 (d, $^3J_{H,H}$=6.9 Hz, 6H); $^{19}$F NMR (376 MHz, (CD$_3$)$_2$SO): δ −115.0 (br s, 2F); MS (MALDI): m/z=450.4 ([M+H]$^+$).

Example 67: 4-(difluoromethyl)-5-[4-(3,3-dimethyl-morpholin-4-yl)-6-[(3R)-3-(methoxymethyl)morpholin-4-yl]-1,3,5-triazin-2-yl]pyridin-2-amine (67)

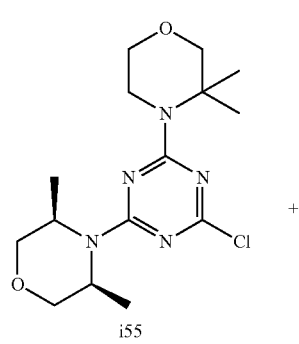

i55

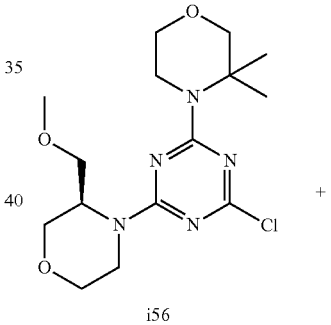

i56

+

+

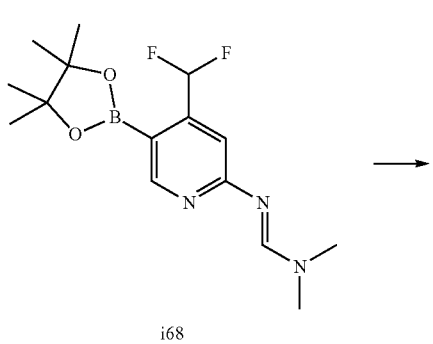

i68

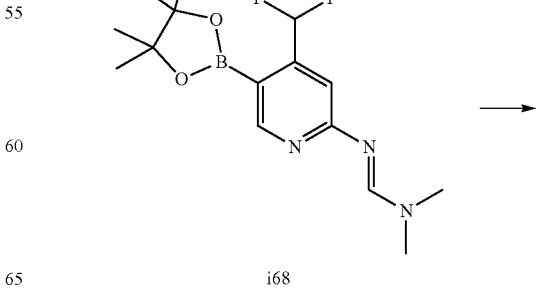

i68

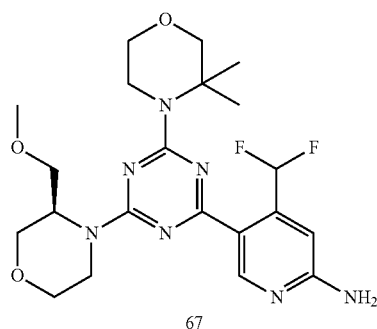

67

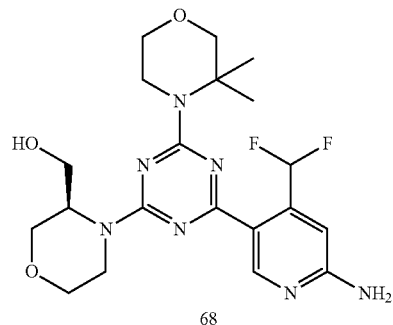

68

According to general procedure 1, compound 67 is obtained from starting materials i56 and i68 in 37% yield as a colorless solid. $^1$H NMR (400 MHz, (CD$_3$)$_2$SO): δ 8.84 (s, 1H), 7.89 (t, $^2J_{H,F}$=55 Hz, 1H), 6.85 (br s, 2H), 6.76 (s, 1H), 4.60 (m, 1H), 4.31 (m, 1H), 3.92 (m, 2H), 3.83 (m, 4H), 3.65 (m, 1H), 3.51-3.41 (m, 5H), 3.28 (s, 3H), 3.12 (m, 1H), 1.49 (s, 3H), 1.48 (s, 3H); $^{19}$F NMR (376 MHz, (CD$_3$)$_2$SO): δ−115.5 (br s, 2F); MS (MALDI): m/z=466.4 ([M+H]$^+$).

According to general procedure 1, compound 68 is obtained from starting materials i57 and i68 in 58% yield as a colorless solid. $^1$H NMR (400 MHz, (CD$_3$)$_2$SO): δ 8.83 (s, 1H), 7.77 (m, 1H), 6.84 (br s, 2H), 6.76 (s, 1H), 4.91 (m, 1H), 4.35 (m, 2H), 4.05 (m, 1H), 3.97-3.70 (m, 6H), 3.54-3.38 (m, 5H), 3.12 (m, 1H), 1.49 (s, 3H), 1.48 (s, 3H); $^{19}$F NMR (376 MHz, (CD$_3$)$_2$SO): δ−115.5 (br s, 2F); MS (MALDI): m/z=453.2 ([M+H]$^+$).

Example 68: [(3R)-4-[4-[6-amino-4-(difluoromethyl)-3-pyridyl]-6-(3,3-dimethylmorpholin-4-yl)-1,3,5-triazin-2-yl]morpholin-3-yl]methanol (68)

Example 69: 4-(difluoromethyl)-5-[4-(3,3-dimethylmorpholin-4-yl)-6-(3,7-dioxa-9-azabicyclo[3.3.1]nonan-9-yl)-1,3,5-triazin-2-yl]pyridin-2-amine (69)

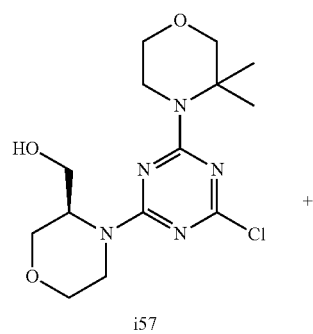

i57

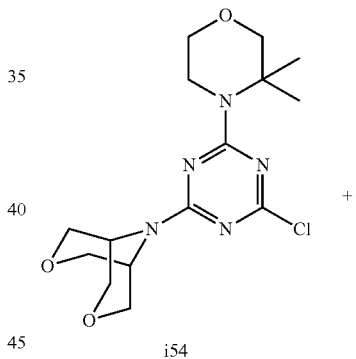

i54

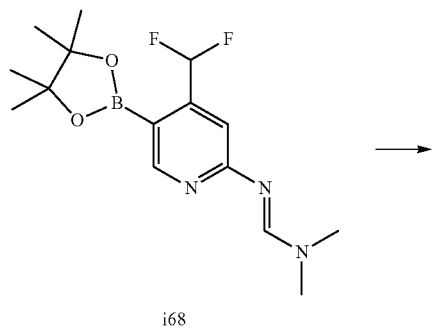

i68

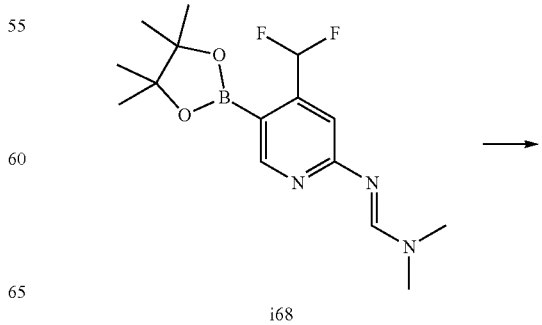

i68

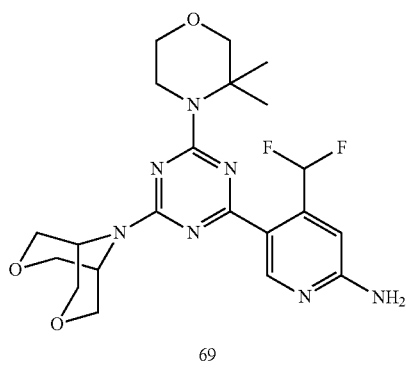

69

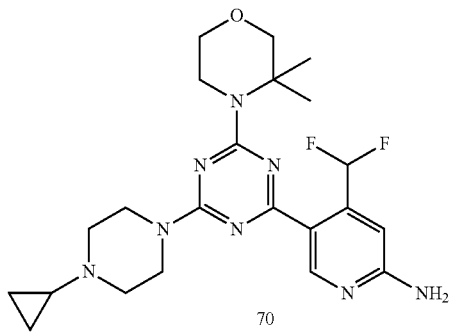

70

According to general procedure 1, compound 69 is obtained from starting materials i54 and i68 in 57% yield as a colorless solid. $^1$H NMR (400 MHz, (CD$_3$)$_2$SO): δ 8.83 (s, 1H), 7.69 (t, $^2J_{H,F}$=55 Hz, 1H), 6.85 (br s, 2H), 6.76 (s, 1H), 4.47-4.37 (m, 2H), 4.01 (m, 4H), 3.80-3.71 (m, 8H), 3.45 (m, 2H), 1.48 (s, 6H); $^{19}$F NMR (376 MHz, (CD$_3$)$_2$SO): δ−115.7 (br s, 2F); MS (MALDI): m/z=464.3 ([M+H]$^+$).

Example 70: 5-[4-(4-cyclopropylpiperazin-1-yl)-6-(3,3-dimethylmorpholin-4-yl)-1,3,5-triazin-2-yl]-4-(difluoromethyl)pyridin-2-amine (70)

According to general procedure 1, compound 70 is obtained from starting materials i58 and i68 in 12% yield as a colorless solid. $^1$H NMR (400 MHz, (CD$_3$)$_2$SO): δ 8.82 (s, 1H), 7.72 (t, $^2J_{H,F}$=55 Hz, 1H), 6.83 (br s, 2H), 6.76 (s, 1H), 3.82 (m, 4H), 3.71 (m, 4H), 3.44 (m, 2H), 2.58 (m, 4H), 1.64 (m, 1H), 1.44 (s, 6H), 0.45 (m, 2H), 0.36 (m, 2H); $^{19}$F NMR (376 MHz, (CD$_3$)$_2$SO): δ−115.4 (br s, 2F); MS (MALDI): m/z=460.4 ([M+H]$^+$).

Example 71: 4-(difluoromethyl)-5-[4-(3,3-dimethyl-morpholin-4-yl)-6-[4-(2-methoxyethyl)piperazin-1-yl]-1,3,5-triazin-2-yl]pyridin-2-amine (71)

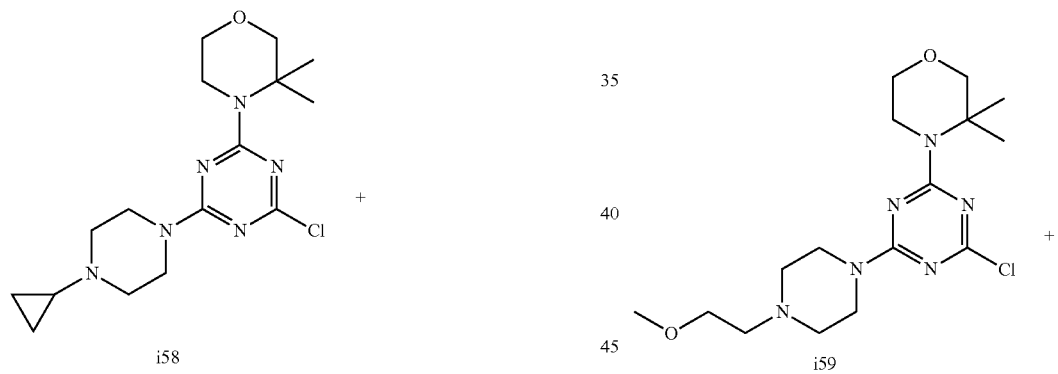

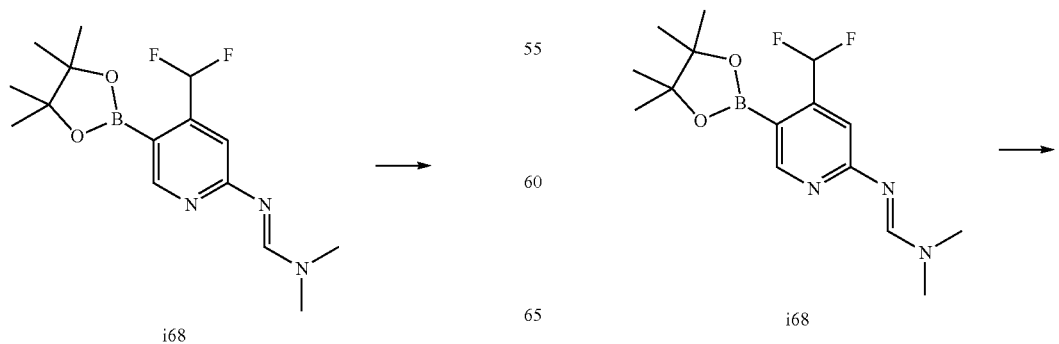

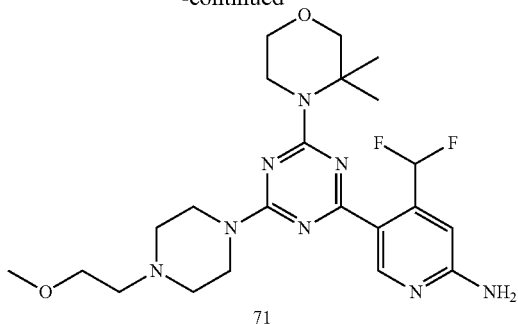

According to general procedure 1, compound 71 is obtained from starting materials i59 and i68 in 42% yield as a colorless solid. $^1$H NMR (400 MHz, (CD$_3$)$_2$SO): δ 8.82 (s, 1H), 7.73 (t, $^2J_{H,F}$=55 Hz, 1H), 6.83 (br s, 2H), 6.76 (s, 1H), 3.88-3.69 (m, 10H), 3.47-3.44 (m, 4H), 3.24 (m, 3H), 2.52-2.45 (m, 4H), 1.44 (s, 6H); $^{19}$F NMR (376 MHz, (CD$_3$)$_2$SO): δ−115.4 (br s, 2F); MS (MALDI): m/z=478.4 ([M+H]$^+$).

Example 72: 4-(difluoromethyl)-5-[4-(3,3-dimethyl-morpholin-4-yl)-6-(oxetan-3-yloxy)-1,3,5-triazin-2-yl]pyridin-2-amine (72)

According to general procedure 1, compound 72 is obtained from starting materials i60 and i68 in 41% yield as a colorless solid. $^1$H NMR (400 MHz, (CD$_3$)$_2$SO): δ 8.86 (s, 1H), 7.73 (t, $^2J_{H,F}$=55 Hz, 1H), 7.02 (br s, 2H), 6.78 (s, 1H), 5.62 (m, 1H), 4.90 (m, 2H), 4.63 (m, 2H), 3.85 (m, 4H), 3.49 (m, 2H), 3.13 (s, 6H); $^{19}$F NMR (376 MHz, (CD$_3$)$_2$SO): δ−115.7 (br s, 2F); MS (MALDI): m/z=409.3 ([M+H]$^+$).

Example 73: 4-(difluoromethyl)-5-[4-(3,3-dimethyl-morpholin-4-yl)-6-[(3S)-tetrahydrofuran-3-yl]oxy-1,3,5-triazin-2-yl]pyridin-2-amine (73)

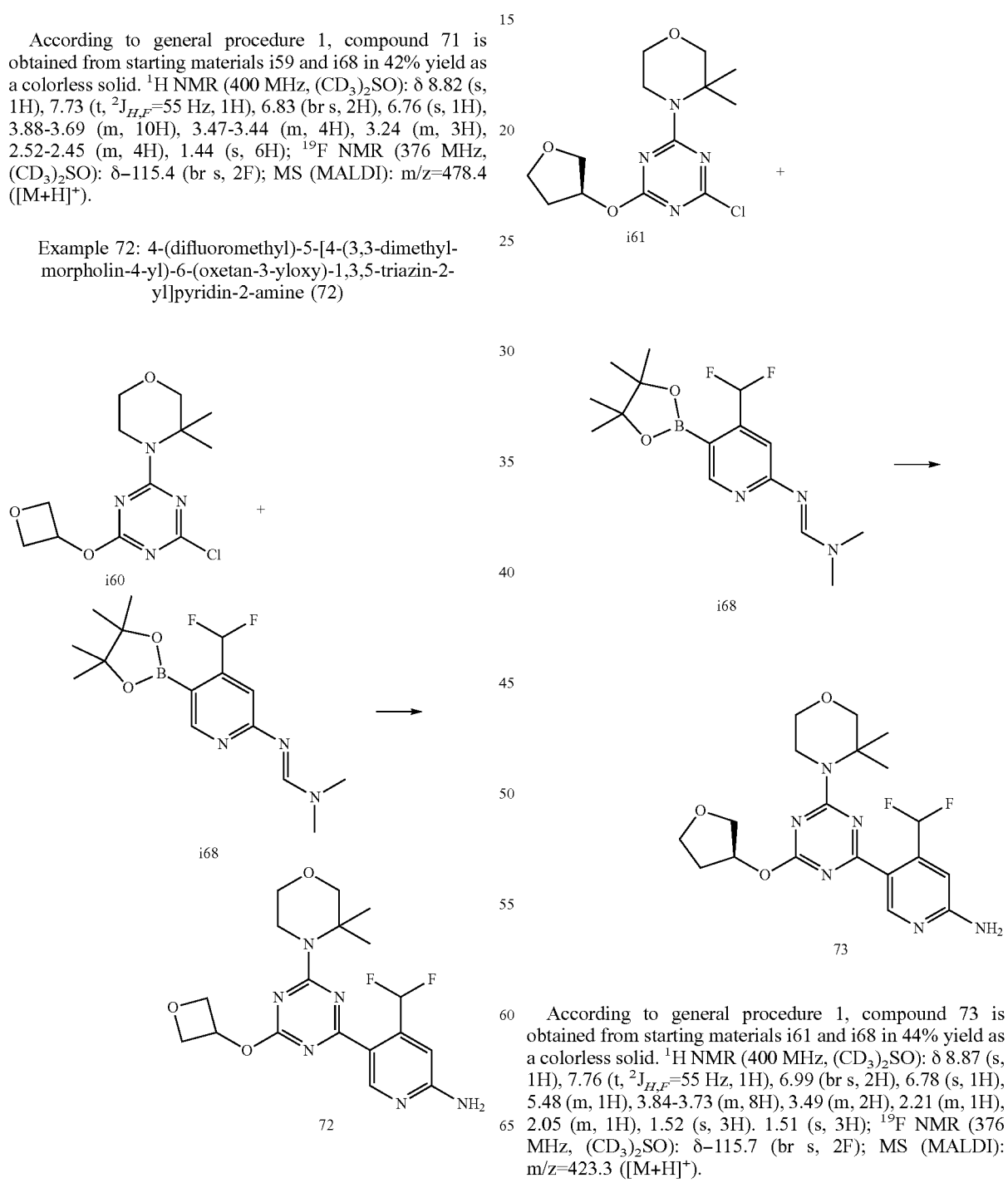

According to general procedure 1, compound 73 is obtained from starting materials i61 and i68 in 44% yield as a colorless solid. $^1$H NMR (400 MHz, (CD$_3$)$_2$SO): δ 8.87 (s, 1H), 7.76 (t, $^2J_{H,F}$=55 Hz, 1H), 6.99 (br s, 2H), 6.78 (s, 1H), 5.48 (m, 1H), 3.84-3.73 (m, 8H), 3.49 (m, 2H), 2.21 (m, 1H), 2.05 (m, 1H), 1.52 (s, 3H). 1.51 (s, 3H); $^{19}$F NMR (376 MHz, (CD$_3$)$_2$SO): δ−115.7 (br s, 2F); MS (MALDI): m/z=423.3 ([M+H]$^+$).

Example 74: 4-(difluoromethyl)-5-[4-(3,3-dimethyl-morpholin-4-yl)-6-[(3R)-tetrahydrofuran-3-yl]oxy-1,3,5-triazin-2-yl]pyridin-2-amine (74)

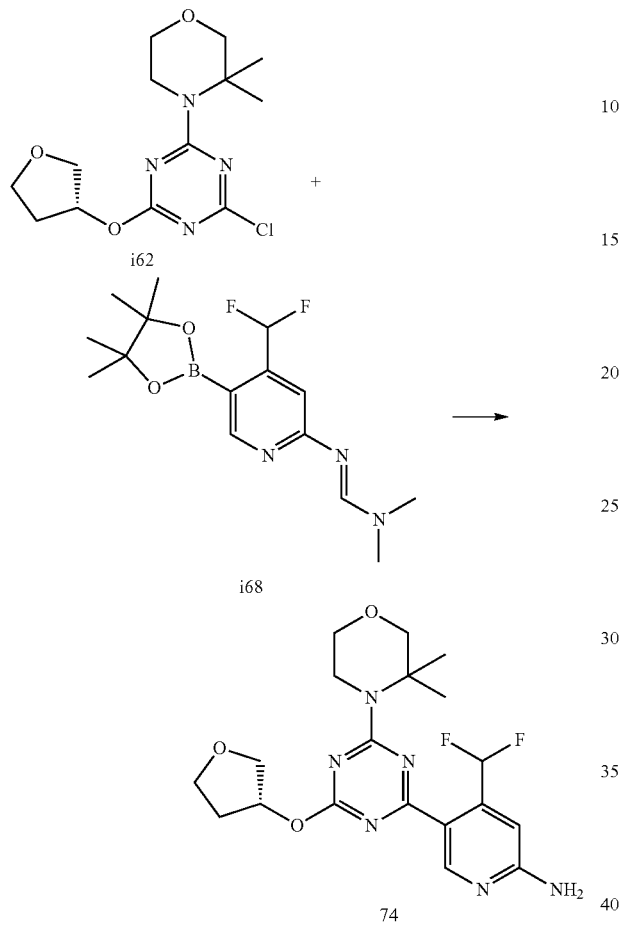

According to general procedure 1, compound 74 is obtained from starting materials i62 and i68 in 37% yield as a colorless solid. $^1$H NMR (400 MHz, (CD$_3$)$_2$SO): δ 8.87 (s, 1H), 7.76 (t, $^2J_{H,F}$=55 Hz, 1H), 6.99 (br s, 2H), 6.78 (s, 1H), 5.48 (m, 1H), 3.84-3.73 (m, 8H), 3.49 (m, 2H), 2.21 (m, 1H), 2.05 (m, 1H), 1.52 (s, 3H). 1.51 (s, 3H); $^{19}$F NMR (376 MHz, (CD$_3$)$_2$SO): δ−115.6 (br s, 2F); MS (MALDI): m/z=423.3 ([M+H]$^+$).

Example 75: 4-(difluoromethyl)-5-[4-(3,3-dimethyl-morpholin-4-yl)-6-tetrahydropyran-4-yloxy-1,3,5-triazin-2-yl]pyridin-2-amine (75)

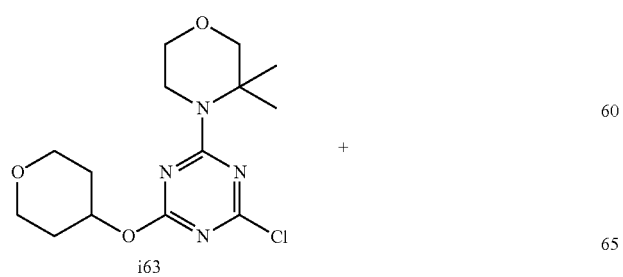

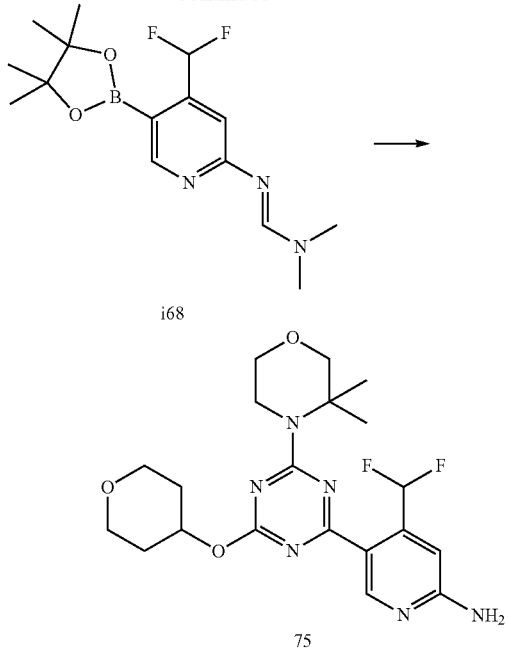

According to general procedure 1, compound 75 is obtained from starting materials i63 and i68 in 61% yield as a colorless solid. $^1$H NMR (400 MHz, (CD$_3$)$_2$SO): δ 8.87 (s, 1H), 7.76 (t, $^2J_{H,F}$=55 Hz, 1H), 6.99 (br s, 2H), 6.78 (s, 1H), 5.15 (m, 1H), 3.82 (m, 6H), 3.48 (m, 4H), 2.07-2.00 (m, 2H), 1.74 (m, 2H), 1.51 (s, 6H); $^{19}$F NMR (376 MHz, (CD$_3$)$_2$SO): δ−115.7 (br s, 2F); MS (MALDI): m/z=437.4 ([M+H]$^+$).

Example 76: 4-(difluoromethyl)-5-[4-(3,3-dimethyl-morpholin-4-yl)-6-(1,1-dioxo-1,4-thiazinan-4-yl)-1,3,5-triazin-2-yl]pyridin-2-amine (76)

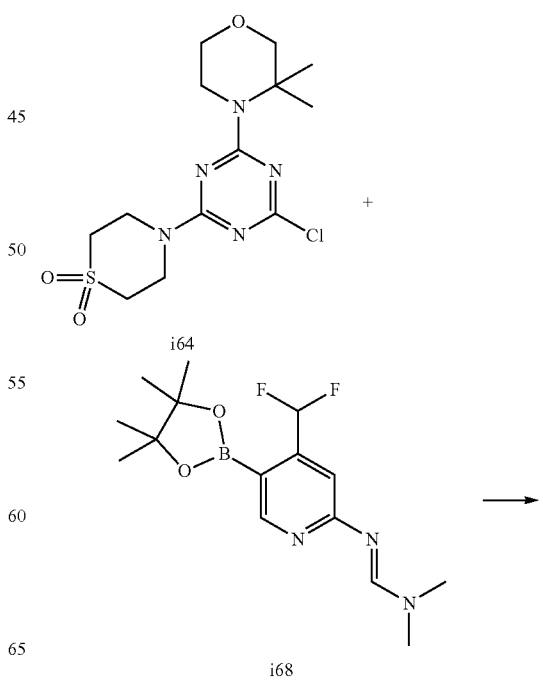

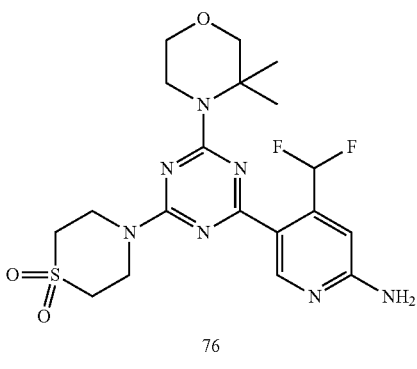

76

According to general procedure 1, compound 76 is obtained from starting materials i64 and i68 in 56% yield as a colorless solid. $^1$H NMR (400 MHz, $(CD_3)_2SO$): δ 8.83 (s, 1H), 7.68 (t, $^2J_{H,F}$=55 Hz, 1H), 6.88 (br s, 2H), 6.77 (s, 1H), 4.19 (m, 4H), 3.83 (m, 4H), 3.47 (m, 2H), 3.22 (m, 4H), 1.52 (s, 6H); $^{19}$F NMR (376 MHz, $(CD_3)_2SO$): δ −115.3 (br s, 2F); MS (MALDI): m/z=470.2 ([M+H]$^+$).

Example 77: [(3R)-4-[4-[6-amino-4-(difluoromethyl)-3-pyridyl]-6-[(3R)-3-methylmorpholin-4-yl]-1,3,5-triazin-2-yl]morpholin-3-yl]methanol (77)

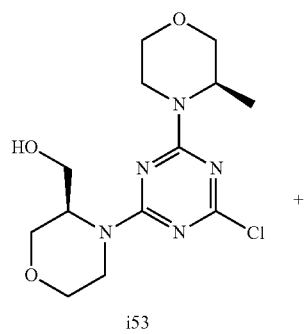

i53

+

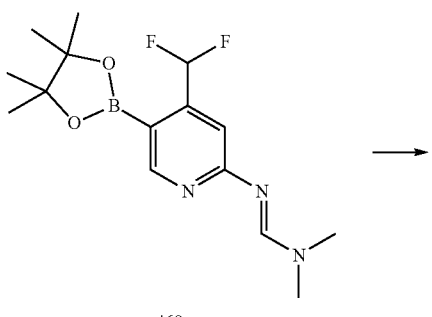

i68

→

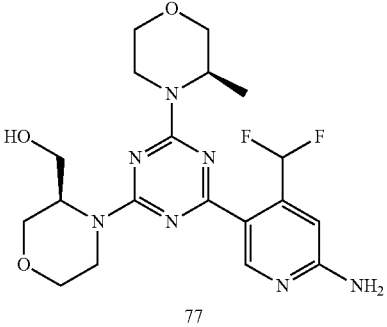

77

According to general procedure 1, compound 77 is obtained from starting materials i53 and i68 in 31% yield as a colorless solid. $^1$H NMR (400 MHz, $(CD_3)_2SO$): δ 8.88 (s, 1H), 7.78 (t, $^2J_{H,F}$=55 Hz, 1H), 6.84 (br s, 2H), 6.76 (s, 1H), 4.96 (m, 1H), 4.73 (m, 1H), 4.58-4.24 (m, 3H), 4.05 (m, 1H), 3.90 (m, 2H), 3.72 (m, 2H), 3.59 (m, 1H), 3.51-3.36 (m, 4H), 3.23-3.02 (m, 2H), 1.23 (d, $^3J_{H,H}$=6.9 Hz, 3H); MS (MALDI): m/z=438.3 ([M+H]$^+$).

In-Cell Western Blot

A2058 cells are plated at 20,000 cells/well in a 96-well plate (Perkin Elmer, Cat. No. 6005558) and 24 hours later treated with different compounds for 1 hour. For each compound 7 different concentrations are applied on cells (5 μM, 1.25 μM, 0.625 μM, 0.3125 μM, 0.155 μM, 0.08 μM and 0.04 μM). Cells are fixed with 4% paraformaldehyde for 30 minutes at room temperature, washed 2 times with 1% BSA in PBS, permeabilized with 0.1% Triton X-100 in PBS/1% BSA for 30 minutes at room temperature and blocked with 5% goat serum in PBS/1% BSA/0.1% Triton X-100 for 30 minutes at room temperature. Cells are stained with primary antibody either with rabbit anti-pPKB S473 (1:500; Cell Signaling Technology, Cat. No. 4058) combined with mouse anti-α-tubulin (1:2000; used for normalization; Sigma, Cat. No. T9026) or with rabbit anti-pS6 S235/S236 (1:500; Cell Signalling Technology, Cat. No. 4856) combined with mouse anti-α-tubulin (1:2000; used for normalization) over night at 4° C. After 3 times 5 minutes wash with PBS/1% BSA/0.1% triton cells are treated with the secondary antibodies goat-anti-mouse IRDye680 (LICOR, Cat. No. 926-68070) and goat-anti-rabbit IRDye800 (LICOR, 926-32211) (each diluted 1:500 in PBS/1% BSA/0.1% triton) for 1 hour while shaking in the dark. Cells are washed 3 times 5 minutes with PBS/1% BSA/0.1% triton and plate scanned with the Odyssey Infrared Scanning system using both 700 and 800 nm channels. As control for 0% inhibition vehicle (0.2% DMSO) is added to cells. To correct for background staining in the data analysis wells are treated only with secondary antibodies.

For data analysis the mean background signal from channel 700 nm and 800 nm are subtracted from each signal in channel 700 nm and 800 nm, respectively. The signals in each channel are normalized to the 0% inhibition and then signal ratio 800 nm over 700 nm is performed to obtain the values for either pPKB S473 or pS6 S235/S236 normalized to α-Tubulin.

IC$_{50}$ values of each compound are determined by plotting the normalized pPBK S473 and pS6 S235/S236 signals, respectively, versus the compound concentrations (in logarithmic scale) and then by fitting a sigmoidal dose-response curve with variable slope to the data using GraphPad™ Prism.

TABLE 1

Comparative biological activities

| | This invention Compound 1 | WO2010/052569 |
|---|---|---|
| | (structure) | (structure) |
| pPKB S473 IC$_{50}$ [nM] | 108 | 149 |
| pS6 S235/236 IC$_{50}$ [nM] | 196 | 340 |
| | This invention Compound 2 | WO2010/052569 |
| | (structure) | (structure) |
| pPKB S473 IC$_{50}$ [nM] | 34 | 64 |
| pS6 S235/236 IC$_{50}$ [nM] | 80 | 650 |

TABLE 2

Comparative biological activities

| | This invention Compound 6 | WO2010/052569 |
|---|---|---|
| | (structure) | (structure) |
| pPKB S473 IC$_{50}$ [nM] | 155 | 255 |

TABLE 2-continued
| Comparative biological activities | | |
|---|---|---|
| pS6 S235/236 IC$_{50}$ [nM] | 215 | 433 |
| This invention Compound 7 | WO2010/052569 |
|---|---|
| 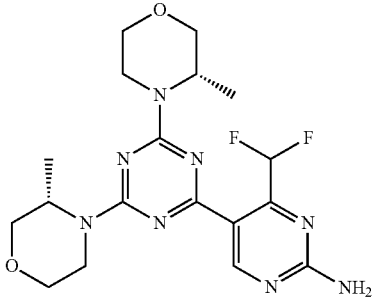 | 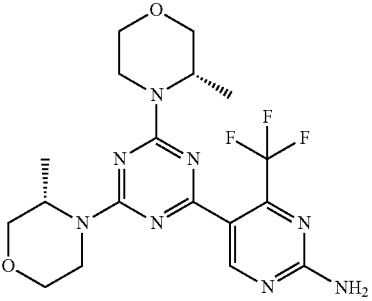 |
| pPKB S473 IC$_{50}$ [nM] | 59 | 118 |
|---|---|---|
| pS6 S235/236 IC$_{50}$ [nM] | 97 | 224 |
TABLE 3
| Comparative biological activities | | |
|---|---|---|
| This invention Compound 8 | | WO2010/052569 |
| 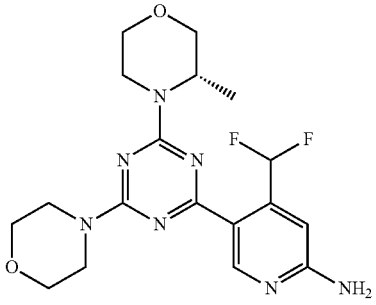 | | 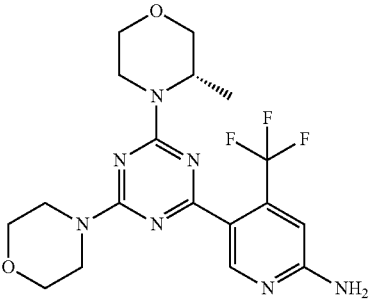 |
| pPKB S473 IC$_{50}$ [nM] | 74 | 196 |
| pS6 S235/236 IC$_{50}$ [nM] | 68 | 90 |
| This invention Compound 9 | | WO2010/052569 |
| 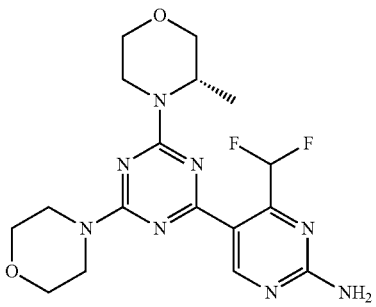 | | 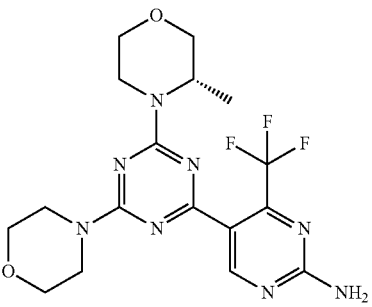 |

TABLE 3-continued
Comparative biological activities
| | | |
|---|---|---|
| pPKB S473 $IC_{50}$ [nM] | 35 | 91 |
| pS6 S235/236 $IC_{50}$ [nM] | 72 | 164 |
TABLE 4
Comparative biological activities
| This invention Compound 12 | WO2010052569 |
|---|---|
| 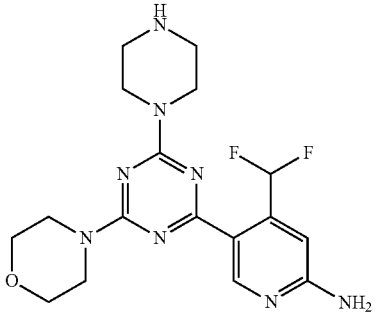 | 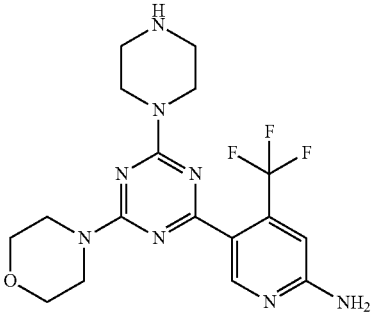 |
| | | |
|---|---|---|
| pPKB S473 $IC_{50}$ [nM] | 208 | 302 |
| pS6 S235/236 $IC_{50}$ [nM] | 515 | 743 |
| This invention Compound 13 | WO2010052569 |
|---|---|
| 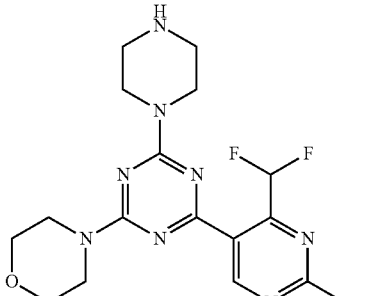 | 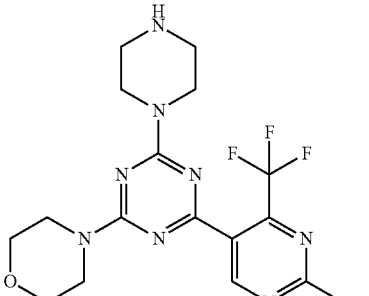 |
| | | |
|---|---|---|
| pPKB S473 $IC_{50}$ [nM] | 43 | 116 |
| pS6 S235/236 $IC_{50}$ [nM] | 150 | 416 |

TABLE 5
Comparative biological activities
| | This invention Compound 16 | WO2007/084786 |
|---|---|---|
| | 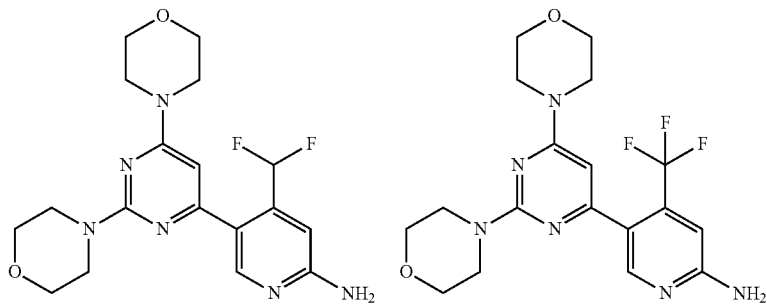 | |
| pPKB S473 IC$_{50}$ [nM] | 207 | 263 |
| pS6 S235/236 IC$_{50}$ [nM] | 184 | 277 |
| | This invention Compound 17 | WO2007/084786 |
| | 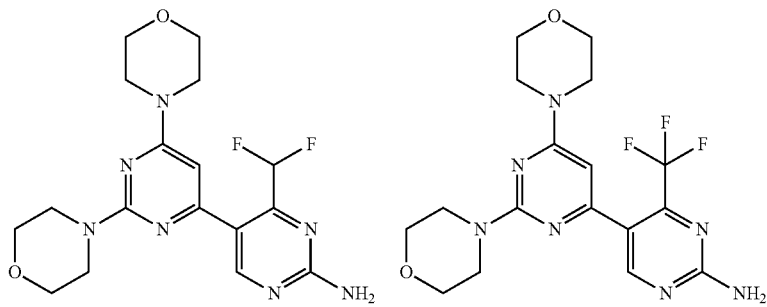 | |
| pPKB S473 IC$_{50}$ [nM] | 90 | 194 |
| pS6 S235/236 IC$_{50}$ [nM] | 149 | 384 |
TABLE 6
Comparative biological activities
| | This invention Compound 18 | WO2008/098058 |
|---|---|---|
| | 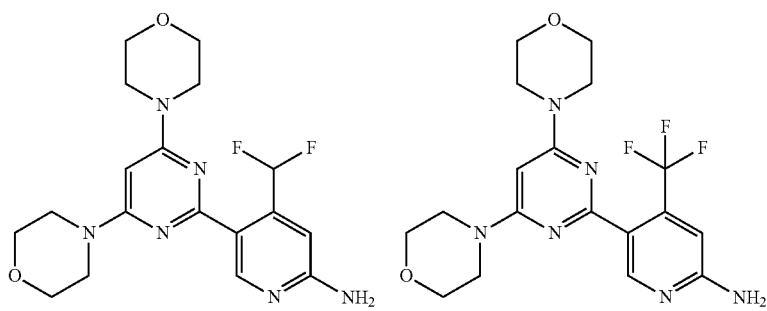 | |
| pPKB S473 IC$_{50}$ [nM] | 243 | 555 |

TABLE 6-continued
| Comparative biological activities | | |
|---|---|---|
| pS6 S235/236 IC$_{50}$ [nM] | 256 | 665 |
| | This invention Compound 19 | WO2008/098058 |
|---|---|---|
| | 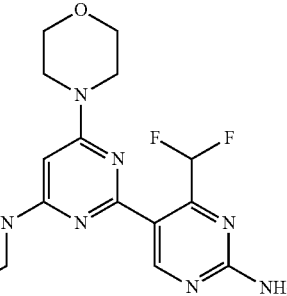 | 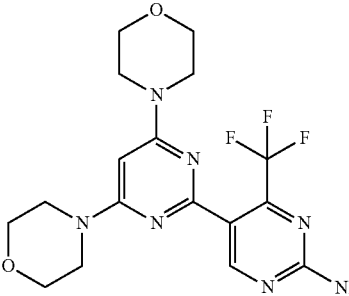 |
| pPKB S473 IC$_{50}$ [nM] | 78 | 175 |
| pS6 S235/236 IC$_{50}$ [nM] | 147 | 370 |
TABLE 7
| Comparative biological activities | | |
|---|---|---|
| | This invention Compound 20 | WO2010052569 |
| | 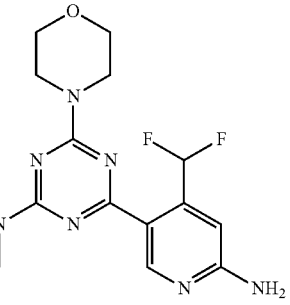 | 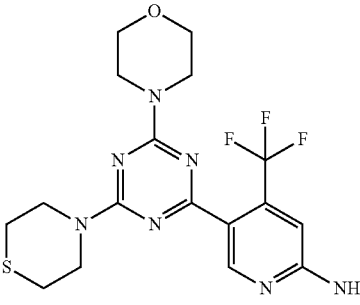 |
| pPKB S473 IC$_{50}$ [nM] | 146 | 311 |
| pS6 S235/236 IC$_{50}$ [nM] | 250 | 559 |
| | This invention Compound 21 | WO2010052569 |
| | 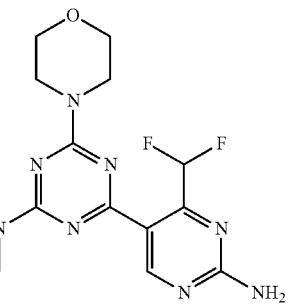 | 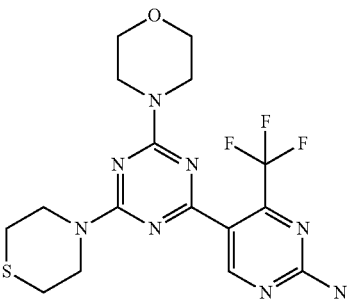 |

TABLE 7-continued
Comparative biological activities
| | | |
|---|---|---|
| pPKB S473 IC$_{50}$ [nM] | 57 | 343 |
| pS6 S235/236 IC$_{50}$ [nM] | 216 | 996 |
TABLE 8
Comparative biological activities
| This invention Compound 25 | WO2007/084786 |
|---|---|
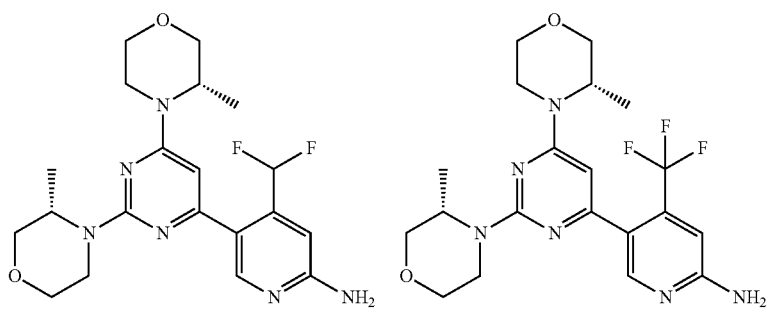
| | | |
|---|---|---|
| pPKB S473 IC$_{50}$ [nM] | 303 | 452 |
| pS6 S235/236 IC$_{50}$ [nM] | 294 | 553 |
| This invention Compound 26 | WO2007/084786 |
|---|---|
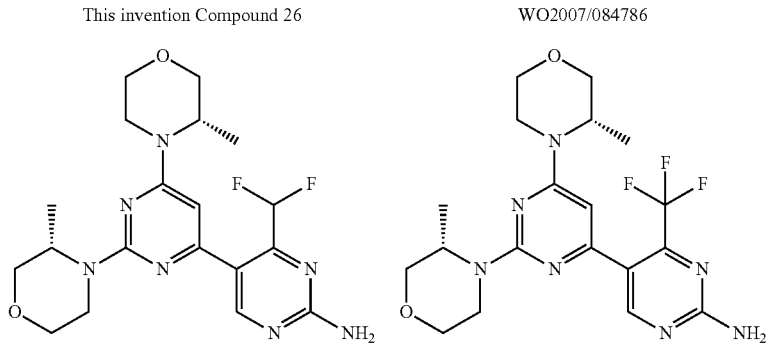
| | | |
|---|---|---|
| pPKB S473 IC$_{50}$ [nM] | 87 | 193 |
| pS6 S235/236 IC$_{50}$ [nM] | 191 | 617 |

TABLE 9
| Comparative biological activities | |
|---|---|
| This invention Compound 27 | WO2007/084786 |
| 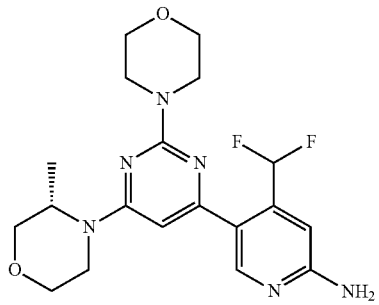 | 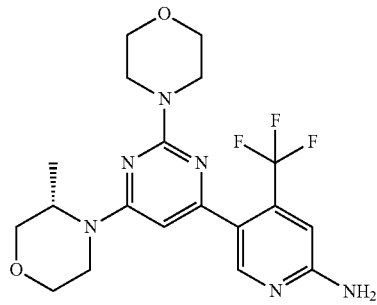 |
| pPKB S473 IC$_{50}$ [nM] | 614 | 883 |
| pS6 S235/236 IC$_{50}$ [nM] | 766 | 1100 |
| This invention Compound 28 | WO2007/084786 |
|---|---|
| 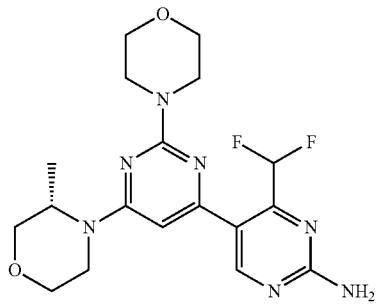 | 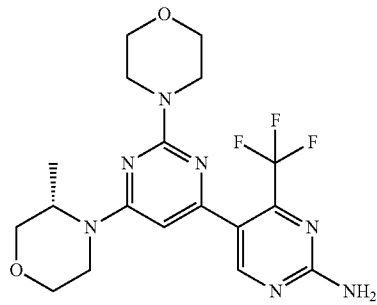 |
| pPKB S473 IC$_{50}$ [nM] | 77 | 290 |
| pS6 S235/236 IC$_{50}$ [nM] | 146 | 1027 |
TABLE 10
| Comparative biological activities | |
|---|---|
| This invention Compound 23 | WO2007/084786 |
| 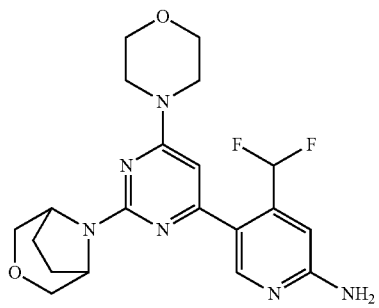 | 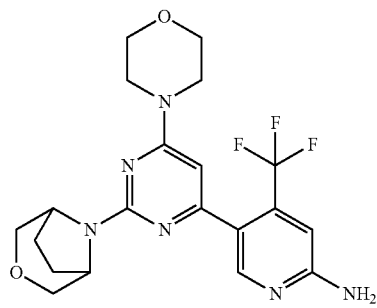 |
| pPKB S473 IC$_{50}$ [nM] | 285 | 564 |

TABLE 10-continued
Comparative biological activities
| | | |
|---|---|---|
| pS6 S235/236 IC$_{50}$ [nM] | 230 | 562 |
| This invention Compound 24 | WO2007/084786 |
|---|---|
| 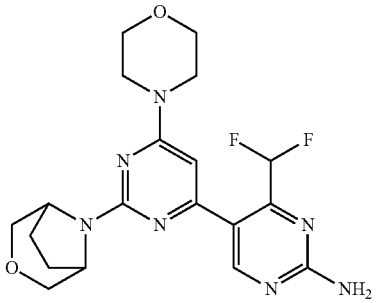 | 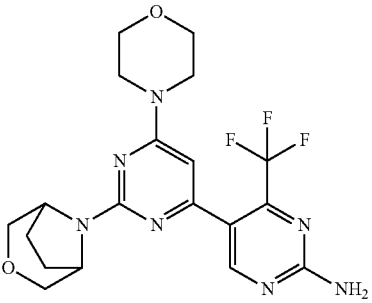 |
| | | |
|---|---|---|
| pPKB S473 IC$_{50}$ [nM] | 84 | 340 |
| pS6 S235/236 IC$_{50}$ [nM] | 167 | 740 |
TABLE 11
Comparative biological activities
| This invention Compound 31 | WO2007/084786 |
|---|---|
| 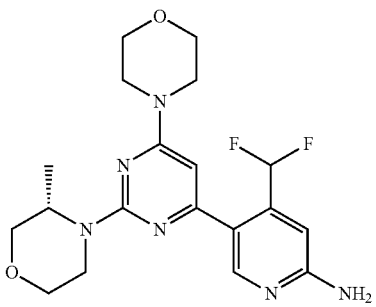 | 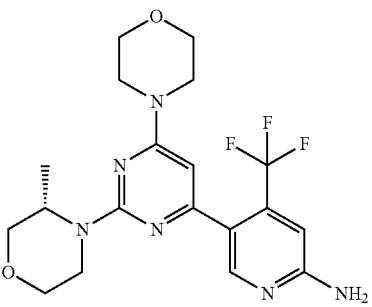 |
| | | |
|---|---|---|
| pPKB S473 IC$_{50}$ [nM] | 146 | 248 |
| pS6 S235/236 IC$_{50}$ [nM] | 124 | 228 |

TABLE 11-continued

Comparative biological activities

| This invention Compound 32 | WO2007/084786 |
|---|---|
| 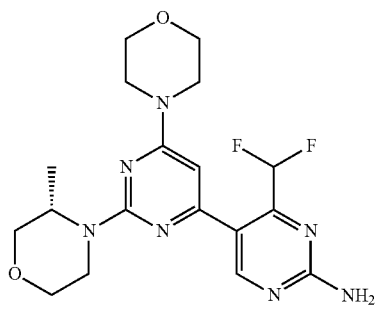 | 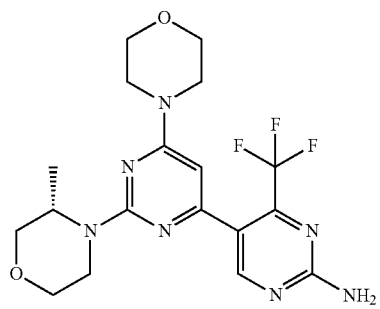 |
| pPKB S473 IC$_{50}$ [nM]: 100 | 191 |
| pS6 S235/236 IC$_{50}$ [nM]: 387 | 535 |

TABLE 12

Comparative biological activities

This invention Compound 48

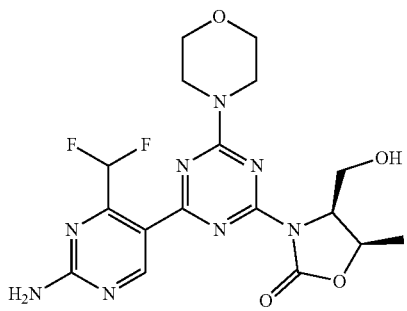 [SMILES: C[C@H]1OC(=O)N(c2nc(-c3cnc(N)nc3C(F)(F)F)nc(N3CCOCC3)n2)[C@H]1CO]

| pPKB S473 IC$_{50}$ [nM] | 100 | 689 |
| P110α IC$_{50}$ [nM] | 161 | 1864 |

TABLE 13

Results of in-cell Western Blot

| Compound | In-cell Western blot pPKB S473 IC$_{50}$ [nM] | pS6 S235/S236 IC$_{50}$ [nM] |
|---|---|---|
| 1 | 108 | 196 |
| 2 | 34 | 80 |
| 3 | 231 | 105 |
| 4 | 178 | 135 |
| 5 | 85 | 135 |
| 6 | 155 | 215 |
| 7 | 59 | 97 |
| 8 | 74 | 68 |
| 9 | 35 | 72 |
| 10 | 138 | 93 |
| 11 | 61 | 96 |

TABLE 13-continued

Results of in-cell Western Blot

| Compound | In-cell Western blot pPKB S473 IC$_{50}$ [nM] | pS6 S235/S236 IC$_{50}$ [nM] |
|---|---|---|
| 12 | 219 | 407 |
| 13 | 37 | 120 |
| 14 | 349.5 | 883 |
| 15 | 49 | 286 |
| 16 | 207 | 184 |
| 17 | 90 | 149 |
| 18 | 243 | 256 |
| 19 | 78 | 147 |
| 20 | 146 | 250 |
| 21 | 57 | 216 |
| 22 | 57 | 216 |

TABLE 13-continued

Results of in-cell Western Blot

| Compound | In-cell Western blot | |
|---|---|---|
| | pPKB S473 IC$_{50}$ [nM] | pS6 S235/S236 IC$_{50}$ [nM] |
| 23 | 285 | 230 |
| 24 | 84 | 167 |
| 25 | 303 | 294 |
| 26 | 87 | 191 |
| 27 | 614 | 766 |
| 28 | 77 | 146 |
| 31 | 146 | 124 |
| 32 | 100 | 387 |
| 35 | 207 | 229 |
| 36 | 99 | 153 |
| 37 | 533 | 268 |
| 38 | 219 | 79 |
| 39 | 106 | 47 |
| 40 | 252 | 160 |
| 41 | 436 | 261 |
| 42 | 54 | 45 |
| 43 | 383 | 154 |
| 44 | 197 | 87 |
| 45 | 234 | 93 |
| 46 | 956 | 426 |
| 47 | 469 | 176 |
| 48 | 100 | nd |

The invention claimed is:

1. A compound of formula (I),

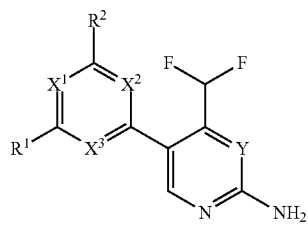

(I)

wherein
$X^1$ and $X^3$ are N, and
$X^2$ is CH;
Y is N or CH;
$R^1$ and $R^2$ are independently of each other
(i) a morpholinyl of formula (II)

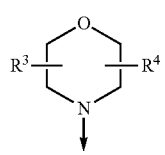

(II)

wherein the arrow denotes the bond in formula (I); and
wherein $R^3$ and $R^4$ are independently of each other H, $C_1$-$C_3$alkyl optionally substituted with one or two OH, $C_1$-$C_2$fluoroalkyl, $C_1$-$C_2$alkoxy, $C_1$-$C_2$alkoxyC$_1$-$C_3$alkyl, CN, or C(O)O—C$_1$-$C_2$alkyl; or $R^3$ and $R^4$ form together a bivalent residue —$R^5R^6$— selected from $C_1$-$C_3$alkylene optionally substituted with 1 to 4 F, —CH$_2$—O—CH$_2$—, —CH$_2$—NH—CH$_2$—, or any of the structures

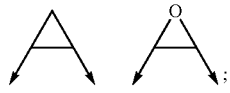

wherein the arrows denote the bonds in formula (II);
(ii) phenyl optionally substituted with 1 to 3 $R^7$, wherein $R^7$ is independently at each occurrence halogen, —OH, $C_1$-$C_3$alkyl optionally substituted with one or two OH, $C_1$-$C_2$fluoroalkyl, $C_1$-$C_2$alkoxy, $C_1$-$C_2$alkoxyC$_1$-$C_3$alkyl, $C_3$-$C_6$cycloalkyl, —NH$_2$, NHCH$_3$ or N(CH$_3$)$_2$;
(iii) a 5- to 6-membered heteroaryl ring W containing one to four heteroatoms independently selected from N, O and S, optionally substituted by 1 to 3 $R^8$, wherein $R^8$ is independently at each occurrence halogen, —OH, $C_1$-$C_3$alkyl optionally substituted with one or two OH, $C_1$-$C_2$fluoroalkyl, $C_1$-$C_2$alkoxy, $C_1$-$C_2$alkoxyC$_1$-$C_3$alkyl, $C_3$-$C_6$cycloalkyl, —NH$_2$, NHCH$_3$ or N(CH$_3$)$_2$;
(iv) a saturated 4- to 6-membered heterocyclic ring Z containing 1 to 3 heteroatoms independently selected from N, O and S, optionally substituted by 1 to 3 $R^9$; wherein $R^9$ is independently at each occurrence halogen, —OH, $C_1$-$C_3$alkyl optionally substituted with one or two OH, $C_1$-$C_2$fluoroalkyl, $C_1$-$C_2$alkoxy, $C_1$-$C_2$alkoxyC$_1$-$C_3$alkyl, $C_3$-$C_6$cycloalkyl, =O, —NH$_2$, NHCH$_3$ or N(CH$_3$)$_2$; or two $R^9$ substituents form together a bivalent residue —$R^{10}R^{11}$— selected from $C_1$-$C_3$alkylene optionally substituted with 1 to 4 F, —CH$_2$—O—CH$_2$— or —O—CH$_2$CH$_2$—O—;
(v) OR$^{12}$, wherein $R^{12}$ is $C_1$-$C_3$alkyl, $C_1$-$C_3$haloalkyl, $C_1$-$C_3$alkoxy, $C_3$-$C_6$cycloalkyl, $C_1$-$C_2$alkyleneC$_3$-$C_6$cycloalkyl; Cycle-P or $C_1$-$C_2$alkyleneCycle-P, wherein Cycle-P represents a saturated 4- to 6-membered heterocyclic ring containing 1 to 3 heteroatoms independently selected from N, O and S, optionally substituted by 1 to 3 $R^{13}$, wherein $R^{13}$ is independently at each occurrence halogen, —OH, $C_1$-$C_3$alkyl optionally substituted with one or two OH, $C_1$-$C_2$fluoroalkyl, $C_1$-$C_2$alkoxy, $C_1$-$C_2$alkoxyC$_1$-$C_3$alkyl, $C_3$-$C_6$cycloalkyl, —NH$_2$, NHCH$_3$ or N(CH$_3$); Cycle-Q or $C_1$-$C_2$alkyleneCycle-Q, wherein Cycle-Q represents 5- to 6-membered heteroaryl ring containing one to four heteroatoms independently selected from N, O and S, optionally substituted by 1 to 3 $R^{14}$, wherein $R^{14}$ is independently at each occurrence halogen, —OH, $C_1$-$C_3$alkyl optionally substituted with one or two OH, $C_1$-$C_2$fluoroalkyl, $C_1$-$C_2$alkoxy, $C_1$-$C_2$alkoxyC$_1$-$C_3$alkyl, $C_3$-$C_6$cycloalkyl, —NH$_2$, NHCH$_3$ or N(CH$_3$); or
(vi) NR$^{15}$R$^{16}$; wherein $R^{15}$ and $R^{16}$ are independently of each other H, $C_1$-$C_3$alkyl optionally substituted with one or two OH, $C_1$-$C_2$fluoroalkyl, $C_1$-$C_2$alkoxy, $C_1$-$C_2$alkoxyC$_1$-$C_3$alkyl; Cycle-P or $C_1$-$C_2$alkyleneCycle-P, wherein Cycle-P represents a saturated 4- to 6-membered heterocyclic ring containing 1 to 3 heteroatoms independently selected from N, O and S, optionally substituted by 1 to 3 $R^{13}$, wherein $R^{13}$ is independently at each occurrence halogen, —OH, $C_1$-$C_3$alkyl optionally substituted with one or two OH, $C_1$-$C_2$fluoroalkyl, $C_1$-$C_2$alkoxy, $C_1$-$C_2$alkoxyC$_1$-$C_3$alkyl, $C_3$-$C_6$cycloalkyl, —NH$_2$, NHCH$_3$ or N(CH$_3$); Cycle-Q or C₁-C₂alkyleneCycle-Q, wherein Cycle-Q represents 5- to 6-membered heteroaryl ring containing one to four heteroatoms independently selected from N, O and S, optionally substituted by 1 to 3 R¹⁴, wherein R¹⁴ is independently at each occurrence halogen, —OH, C₁-C₃alkyl optionally substituted with one or two OH, C₁-C₂fluoroalkyl, C₁-C₂alkoxy, C₁-C₂alkoxyC₁-C₃alkyl, C₃-C₆cycloalkyl, —NH₂, NHCH₃ or N(CH₃);

with the proviso that at least one of R¹ and R² is a morpholinyl of formula II;

or a tautomer, solvate, or a pharmaceutically acceptable salt thereof.

2. The compound of formula (I) according to claim 1, wherein said R¹ and said R² are independently of each other (i) a morpholinyl of formula (II); (ii) said 5- to 6-membered heteroaryl ring W; (iii) said saturated 4- to 6-membered heterocyclic ring Z; (iv) said OR¹²; or (v) said NR¹⁵R¹⁶.

3. The compound of formula (I) according to claim 1, wherein said R¹ and said R² are independently of each other selected from

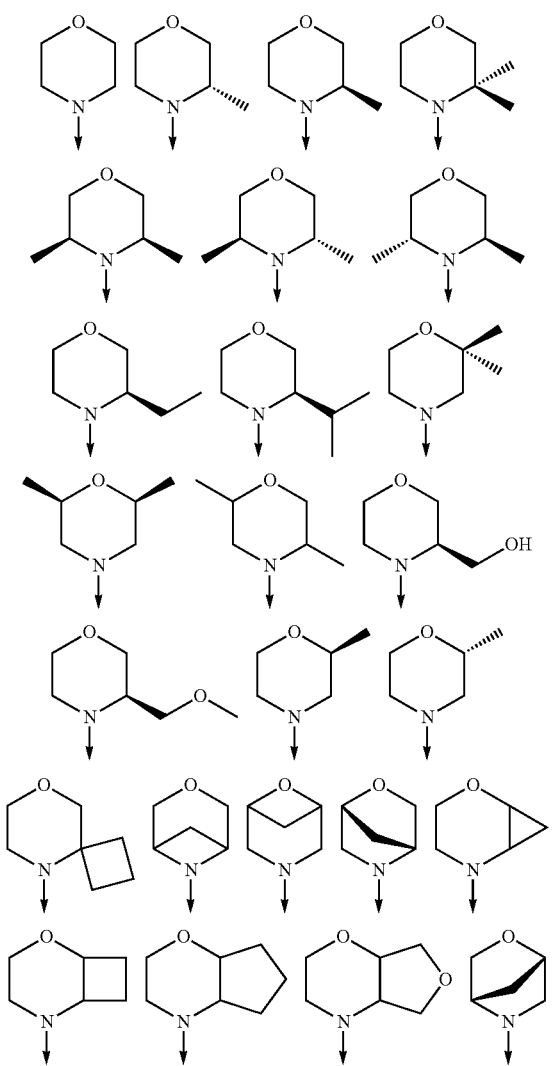

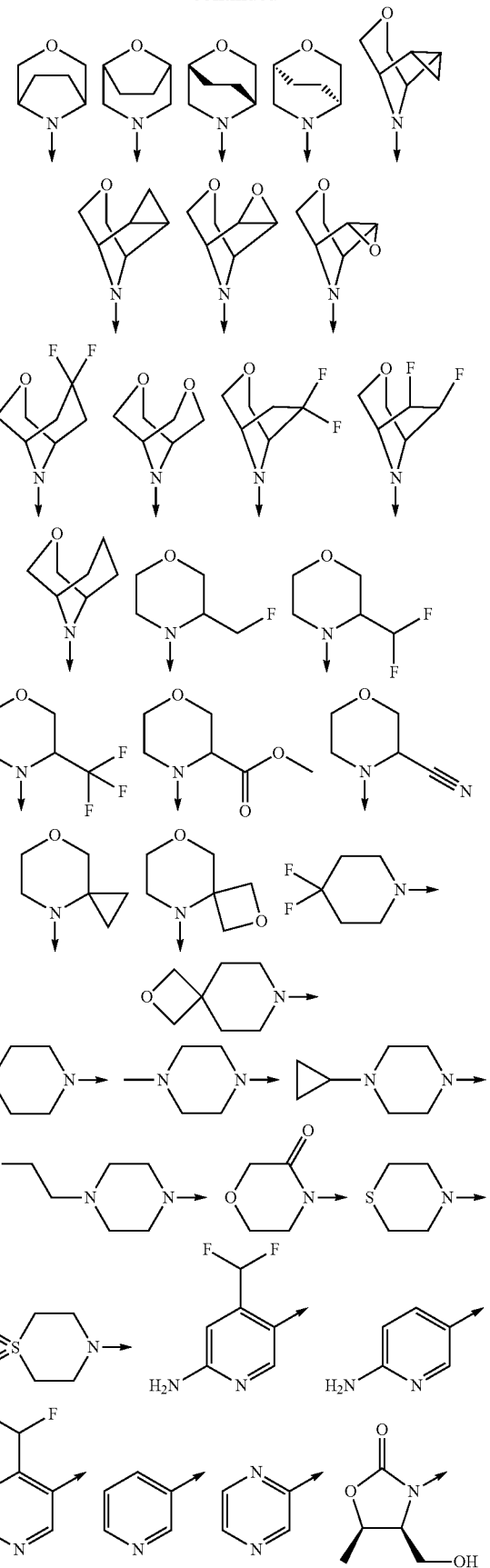

-continued

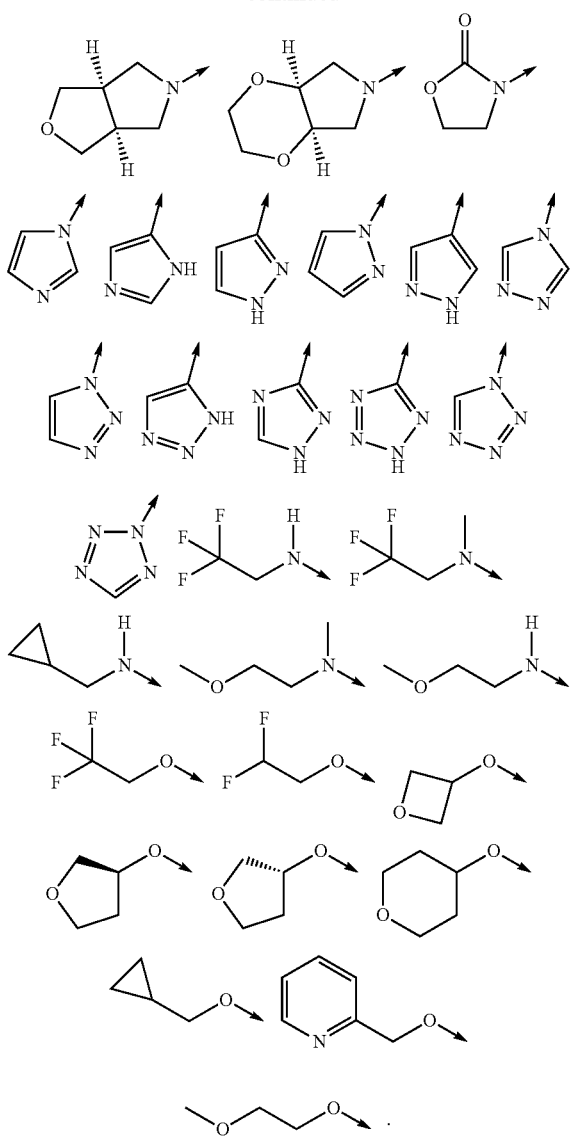

4. The compound of formula (I) according to claim 1, wherein $R^1$ and $R^2$ are independently of each other selected from

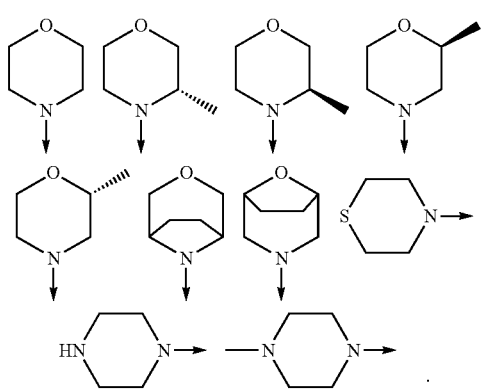

5. The compound of formula (I) according to claim 1, wherein $R^1$ and $R^2$ are independently of each other selected from

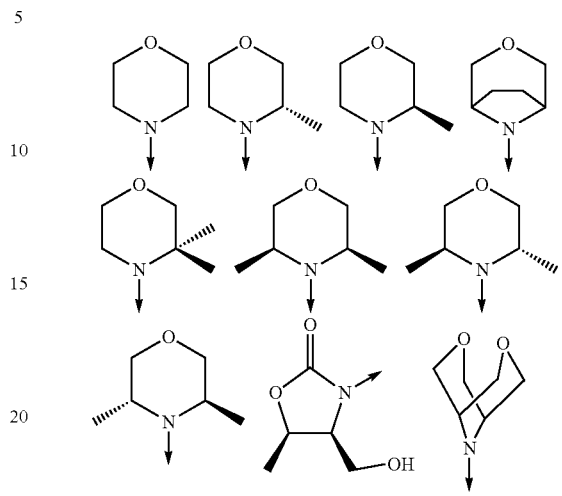

6. The compound of formula (I) according to claim 1, wherein said compound is selected from
  4-(difluoromethyl)-5-(2,6-dimorpholinopyrimidin-4-yl)pyridin-2-amine;
  4'-(difluoromethyl)-2,6-dimorpholino-[4,5'-bipyrimidin]-2'-amine;
  4-(difluoromethyl)-5-(4,6-dimorpholinopyrimidin-2-yl)pyridin-2-amine;
  4'-(difluoromethyl)-4,6-dimorpholino-[2,5'-bipyrimidin]-2'-amine;
  5-(6-(3-oxa-8-azabicyclo[3.2.1]octan-8-yl)-2-(3-oxa-8-azabicyclo[3.2.1]octan-8-yl)pyrimidin-4-yl)-4-(difluoromethyl)pyridin-2-amine;
  5-(2-(3-oxa-8-azabicyclo[3.2.1]octan-8-yl)-6-morpholinopyrimidin-4-yl)-4-(difluoromethyl)pyridin-2-amine;
  2-(3-oxa-8-azabicyclo[3.2.1]octan-8-yl)-4'-(difluoromethyl)-6-morpholino-[4,5'-bipyrimidin]-2'-amine;
  5-(2,6-bis((S)-3-methylmorpholino)pyrimidin-4-yl)-4-(difluoromethyl)pyridin-2-amine;
  4'-(difluoromethyl)-2,6-bis((S)-3-methylmorpholino)-[4,5'-bipyrimidin]-2'-amine;
  (S)-4-(difluoromethyl)-5-(6-(3-methylmorpholino)-2-morpholinopyrimidin-4-yl)pyridin-2-amine;
  (S)-4'-(difluoromethyl)-6-(3-methylmorpholino)-2-morpholino-[4,5'-bipyrimidin]-2'-amine;
  (S)-4-(difluoromethyl)-5-(2-(3-methylmorpholino)-6-morpholinopyrimidin-4-yl)pyridin-2-amine;
  (S)-4'-(difluoromethyl)-2-(3-methylmorpholino)-6-morpholino-[4,5'-bipyrimidin]-2'-amine;
  and
  (4S,5R)-3-[6-[2-amino-4-(difluoromethyl)pyrimidin-5-yl]-2-morpholino-pyrimidin-4-yl]-4-(hydroxymethyl)-5-methyl-oxazolidin-2-one.

7. The compound of formula (I) according to claim 1, wherein $R^1$ and $R^2$ are independently of each other a morpholinyl of formula (II).

8. The compound of formula (I) according to claim 7, wherein $R^1$ is equal to $R^2$.

9. The compound of formula (I) according to claim 7, wherein $R^1$ is not equal to $R^2$.

10. The compound of formula (I) according to claim 1, wherein $R^1$ and $R^2$ are independently of each other a morpholinyl of formula (II) and said 5- to 6-membered heteroaryl ring W.

11. The compound of formula (I) according to claim 1, wherein $R^1$ and $R^2$ are independently of each other a morpholinyl of formula (II) and said saturated 4- to 6-membered heterocyclic ring Z.

12. The compound of formula (I) according to claim 1, wherein $R^1$ and $R^2$ are independently of each other a morpholinyl of formula (II) and said $OR^{12}$.

13. The compound of formula (I) according to claim 1, wherein $R^1$ and $R^2$ are independently of each other a morpholinyl of formula (II) and said $NR^{15}R^{16}$.

14. A pharmaceutical composition comprising a compound of formula (I) according to claim 1 and a pharmaceutically acceptable carrier.

* * * * *